(12) United States Patent
Che et al.

(10) Patent No.: US 8,779,154 B2
(45) Date of Patent: Jul. 15, 2014

(54) FUSED RING COMPOUNDS FOR INFLAMMATION AND IMMUNE-RELATED USES

(76) Inventors: Qinglin Che, Foxboro, MA (US); Nha Huu Vo, Southborough, MA (US); Shoujun Chen, Bedford, MA (US)

(*) Notice: Subject to any disclaimer, the term of this patent is extended or adjusted under 35 U.S.C. 154(b) by 0 days.

(21) Appl. No.: 11/861,278

(22) Filed: Sep. 25, 2007

(65) Prior Publication Data

US 2008/0132513 A1 Jun. 5, 2008

Related U.S. Application Data

(60) Provisional application No. 60/847,325, filed on Sep. 26, 2006.

(51) Int. Cl.
| | |
|---|---|
| A61K 31/428 | (2006.01) |
| A61K 31/429 | (2006.01) |
| C07D 277/60 | (2006.01) |
| C07D 513/04 | (2006.01) |

(52) U.S. Cl.
USPC ........... 548/150; 548/151; 540/586; 540/578; 540/521; 544/344; 544/249; 544/124; 544/133; 546/270.1; 546/256; 546/84; 514/211.04; 514/211.1; 514/250; 514/267; 514/366; 514/333; 514/338; 514/232.8; 514/293

(58) Field of Classification Search
USPC ........................................................ 548/150
See application file for complete search history.

(56) References Cited

U.S. PATENT DOCUMENTS

| | | | |
|---|---|---|---|
| 4,421,670 A | 12/1983 | Deutscher et al. | |
| 5,480,874 A | 1/1996 | Shoji et al. | |
| 5,565,479 A * | 10/1996 | Iwaoka et al. | 514/366 |
| 7,026,334 B1 | 4/2006 | Takemoto et al. | |
| 7,087,761 B2 | 8/2006 | Spurr et al. | |
| 2003/0176454 A1 | 9/2003 | Yamada et al. | |
| 2005/0107436 A1 | 5/2005 | Xie et al. | |
| 2005/0148633 A1 | 7/2005 | Xie et al. | |
| 2006/0030589 A1 | 2/2006 | Cai et al. | |
| 2006/0173006 A1 | 8/2006 | Sun et al. | |
| 2006/0173021 A1 | 8/2006 | Sun et al. | |
| 2006/0199845 A1 | 9/2006 | Sun et al. | |
| 2007/0249050 A1 | 10/2007 | Chen et al. | |
| 2007/0249051 A1 | 10/2007 | Bohnert et al. | |
| 2007/0249609 A1 | 10/2007 | Chen et al. | |
| 2007/0249661 A1 | 10/2007 | Chen et al. | |
| 2007/0254363 A1 | 11/2007 | Chen et al. | |
| 2007/0254912 A1 | 11/2007 | Chen et al. | |
| 2007/0254925 A1 | 11/2007 | Vo et al. | |
| 2007/0254926 A1 | 11/2007 | Jiang et al. | |
| 2007/0275960 A1 | 11/2007 | Jiang et al. | |
| 2008/0207641 A1 | 8/2008 | Bohnert et al. | |

FOREIGN PATENT DOCUMENTS

| | | |
|---|---|---|
| JP | 57-81441 A | 5/1982 |
| JP | 11-240832 A | 9/1999 |
| JP | 2004-18489 | 1/2004 |
| WO | WO-01/87845 A2 * | 11/2001 |
| WO | WO 03/099827 A1 | 12/2003 |
| WO | WO 2005/005438 A1 | 1/2005 |
| WO | WO 2006/040279 A1 | 4/2006 |
| WO | WO 2006/040281 A1 | 4/2006 |
| WO | WO 2006/081389 A1 | 8/2006 |
| WO | WO-2008/103310 | 2/2008 |
| WO | PCT/US2009/030367 | 1/2009 |
| WO | WO-2009/017819 | 2/2009 |
| WO | WO-2009/017831 | 2/2009 |
| WO | WO-2009017818 | 2/2009 |
| WO | WO-2009/038775 | 3/2009 |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Chemical Abstracts Registry No. 380335-09-1, indexed in the Registry file on STN Jan. 3, 2002.*
Cernani, A., "Coloranti acidi per Ian a—Nota II—Mono-azoici e bis-azolci acidi da arilidi dell'acido salicilico e dell'acido 2-ossi-3-naftoico," Bollettino, vol. 27, pp. 313-321 (1969).
Chaudhuri, A., "Reactions of 2-Arylazo-Naphthalene-1-Sulphenylbrmide with "Carbon Acids:" Synthesis of 2-Substituted Naphtho-thiazoles and their U.V. and I.R. Spectra," J. Indian Chem. Soc., vol. LV, pp. 702-704 (1978).
Goblyos, A., "Synthesis and Biological Evaluation of 2-aminothiazoles and their Amide Derivatives on Human Adenosine Receptors. Lack of Effect of 2-aminothiazoles as Allosteric Enhancers," Bioorganic & Medicinal Chemistry, vol. 113, pp. 2079-2087 (2005).
Prasad, D.V., "Synthesis of N-4-Oxo-[1]-Benzopyrano[3,4-d] Thiazol-2-YL-p-Toluimides," Sulfur Letters, vol. 4(3), pp. 87-92 (1986).
International Search Report of PCT/US07/20864, Jun. 17, 2008.
Database Caplus on STN, CAS (Columbus, OH, USA), CA 106:84462, Prasad et aL 'Sulfer Letters' (1986).
Extended European Search Report for EP 07861381.7 mailed Nov. 21, 2011.

* cited by examiner

*Primary Examiner* — Laura L. Stockton
(74) *Attorney, Agent, or Firm* — Wolf, Greenfield & Sacks, P.C.

(57) ABSTRACT

The invention relates to certain fused ring compounds, or pharmaceutically acceptable salts, solvates, clathrates, or prodrugs thereof, that are useful as immunosuppressive agents and for treating and preventing inflammatory conditions, allergic disorders, and immune disorders.

29 Claims, No Drawings

FUSED RING COMPOUNDS FOR INFLAMMATION AND IMMUNE-RELATED USES

RELATED APPLICATIONS

This application claims the benefit of U.S. Provisional Application No. 60/847,325, filed Sep. 26, 2006, the entire teachings of which are incorporated herein by reference.

FIELD OF THE INVENTION

This invention relates to biologically active chemical compounds, that may be used for immunosuppression or to treat or prevent inflammatory conditions and immune disorders.

BACKGROUND OF THE INVENTION

Inflammation is a mechanism that protects mammals from invading pathogens. However, while transient inflammation is necessary to protect a mammal from infection, uncontrolled inflammation causes tissue damage and is the underlying cause of many illnesses. Inflammation is typically initiated by binding of an antigen to T-cell antigen receptor. Antigen binding by a T-cell initiates calcium influx into the cell via calcium ion channels, such as $Ca^{2+}$-release-activated $Ca^{2+}$ channels (CRAC). Calcium ion influx in turn initiates a signaling cascade that leads to activation of these cells and an inflammatory response characterized by cytokine production.

Interleukin 2 (IL-2) is a cytokine that is secreted by T cells in response to calcium ion influx into the cell. IL-2 modulates immunological effects on many cells of the immune system. For example, it is a potent T cell mitogen that is required for the T cell proliferation, promoting their progression from G1 to S phase of the cell cycle; it stimulates the growth of NK cells; and it acts as a growth factor to B cells and stimulates antibody synthesis.

IL-2, although useful in the immune response, can cause a variety of problems. IL-2 damages the blood-brain barrier and the endothelium of brain vessels. These effects may be the underlying causes of neuropsychiatric side effects observed under IL-2 therapy, e.g. fatigue, disorientation and depression. It also alters the electrophysiological behaviour of neurons.

Due to its effects on both T and B cells, IL-2 is a major central regulator of immune responses. It plays a role in inflammatory reactions, tumour surveillance, and hematopoiesis. It also affects the production of other cytokines, inducing IL-1, TNF-α and TNF-β secretion, as well as stimulating the synthesis of IFN-γ in peripheral leukocytes.

T cells that are unable to produce IL-2 become inactive (anergic). This renders them potentially inert to any antigenic stimulation they might receive in the future. As a result, agents which inhibit IL-2 production can be used for immunosupression or to treat or prevent inflammation and immune disorders. This approach has been clinically validated with immunosuppressive drugs such as cyclosporin, FK506, and RS61443. Despite this proof of concept, agents that inhibit IL-2 production remain far from ideal. Among other problems, efficacy limitations and unwanted side effects (including dose-dependant nephrotoxicity and hypertension) hinder their use.

Over production of proinflammatory cytokines other than IL-2 has also been implicated in many autoimmune diseases. For example, Interleukin 5 (IL-5), a cytokine that increases the production of eosinophils, is increased in asthma. Overproduction of IL-5 is associated with accumulation of eosinophils in the asthmatic bronchial mucosa, a hall mark of allergic inflammation. Thus, patients with asthma and other inflammatory disorders involving the accumulation of eosinophils would benefit from the development of new drugs that inhibit the production of IL-5.

Interleukin 4 (IL-4) and interleukin 13 (IL-13) have been identified as mediators of the hypercontractility of smooth muscle found in inflammatory bowel disease and asthma. Thus, patients with asthma and inflammatory bowel disease would benefit from the development of new drugs that inhibit IL-4 and IL-13 production.

Granulocyte macrophage-colony stimulating factor (GM-CSF) is a regulator of maturation of granulocyte and macrophage lineage population and has been implicated as a key factor in inflammatory and autoimmune diseases. Anti-GM-CSF antibody blockade has been shown to ameliorate autoimmune disease. Thus, development of new drugs that inhibit the production of GM-CSF would be beneficial to patients with an inflammatory or autoimmune disease.

There is therefore a continuing need for new drugs which overcome one or more of the shortcomings of drugs currently used for immunosuppression or in the treatment or prevention of inflammatory disorders, allergic disorders and autoimmune disorders. Desirable properties of new drugs include efficacy against diseases or disorders that are currently untreatable or poorly treatable, new mechanism of action, oral bioavailability and/or reduced side effects.

SUMMARY OF THE INVENTION

This invention meets the above-mentioned needs by providing certain compounds that inhibit the activity of CRAC ion channels and inhibit the production of IL-2, IL-4, IL-5, IL-13, GM-CSF, TNF-α, and IFNγ. These compounds are particularly useful for immunosuppression and/or to treat or prevent inflammatory conditions and immune disorders.

The invention relates to compounds of formula (X):

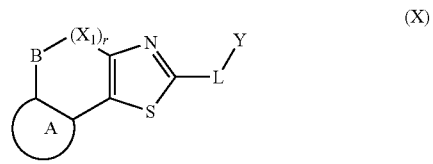

wherein:
Ring A is a 5 or 6 membered aryl or heteroaryl ring wherein the members of the ring are selected from the group consisting of —CZ—, —S—, —O— or —N—;
Y is an optionally substituted aryl or an optionally substituted heteroaryl;
B is —C($R^a$)$_2$—, —C(O)—; —O—, —S—, or —N($R^b$)—;
each $X_1$ is independently —C($R^a$)$_2$—, —C(O)—; —O—, —S—, or —N($R^b$)—;
Z is a substituent;
L is a linker;
each $R^a$ is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)N$R_1R_2$, —N$R_4$C(O)

$R_5$, halo, —$OR_4$, cyano, nitro, haloalkoxy, —$C(O)R_4$, —$NR_1R_2$, —$SR_4$, —$C(O)OR_4$, —$OC(O)R_4$, —$NR_4C(O)NR_1R_2$, —$OC(O)NR_1R_2$, —$NR_4C(O)OR_5$, —$S(O)_pR_4$, or —$S(O)_pNR_1R_2$;

each $R^b$ is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, halo, —$C(O)NR_1R_2$, —$C(O)R_4$, or —$C(O)OR_4$;

$R_1$ and $R_2$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_1$ and $R_2$ taken together with the nitrogen to which they are attached is optionally substituted heterocyclyl or optionally substituted heteroaryl;

$R_4$ and $R_5$, for each occurrence is, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

r is 1, 2, 3, or 4; and p is 0, 1, or 2;

or a pharmaceutically acceptable salt, solvate, clathrate, or prodrug thereof.

In one aspect of compounds of formula (X), when r is 1, $X_1$ is C(O) and L is —NHC(O)—, Y is not phenyl or methylphenyl.

In one aspect of compounds of formula (X), when $X_1$ is —$CH_2$—, r is 1, B is —$CH_2$— and ring A is an unsubstituted phenyl group, L is not —NH— or —CH=CH—.

In another embodiment, the invention relates to compounds of formula (XI):

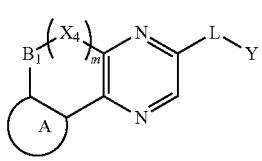

(XI)

wherein:

$X_4$ is —$C(R^a)_2$—;

$B_1$ is —$C(R^a)_2$—, —$C(O)$—; or —O—;

m is 1 or 2; and

Ring A, L and Y are defined as for formula (X);

or a pharmaceutically acceptable salt, solvate, clathrate, or prodrug thereof.

In another embodiment, the invention relates to compounds of formula (XII):

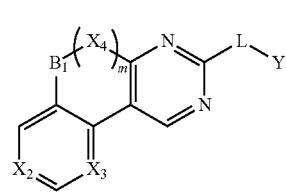

(XII)

wherein:

$X_2$ and $X_3$ are independently selected from the group consisting of —$CR^a$— or —N—; and Ring A, L and Y are defined as for formula (X) and $B_1$, $X_4$, and m are defined as for formula (XI);

or a pharmaceutically acceptable salt, solvate, clathrate, or prodrug thereof.

In another embodiment, the invention relates to compounds of formula (XIII):

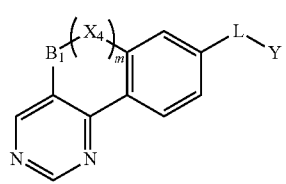

(XIII)

wherein:

L and Y are defined as for formula (X) and $B_1$, $X_4$, and m are defined as for formula (XI);

or a pharmaceutically acceptable salt, solvate, clathrate, or prodrug thereof.

In another embodiment, the invention relates to compounds of formula (XIV):

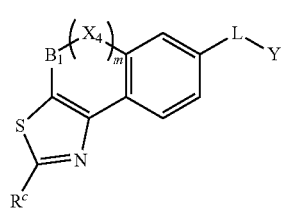

(XIV)

wherein:

$R^c$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —$C(O)NR_1R_2$, —$NR_4C(O)R_5$, halo, —$OR_4$, cyano, nitro, haloalkoxy, —$C(O)R_4$, —$NR_1R_2$, —$SR_4$, —$C(O)OR_4$, —$OC(O)R_4$, —$NR_4C(O)NR_1R_2$, —$OC(O)NR_1R_2$, —$NR_4C(O)OR_5$, —$S(O)_pR_4$, or —$S(O)_pNR_1R_2$;

L and Y are defined as for formula (X) and $B_1$, $X_4$, and m are defined as for formula (XI);

or a pharmaceutically acceptable salt, solvate, clathrate, or prodrug thereof.

In one embodiment of compounds of formula (XIV), when $X_5$ is —C(NH$_2$)— and m is 1, then Y is not an unsubstituted phenyl.

A compound of the invention or a pharmaceutically acceptable salt, solvate, clathrate, or prodrug thereof is particularly useful inhibiting immune cell (e.g., T-cells and/or B-cells) activation (e.g., activation in response to an antigen). In particular, a compound of the invention or a pharmaceutically acceptable salt, solvate, clathrate, or prodrug thereof can inhibit the production of certain cytokines that regulate immune cell activation. For example, a compound of the invention or a pharmaceutically acceptable salt, solvate, clathrate, or prodrug thereof can inhibit the production of IL-2, IL-4, IL-5, IL-13, GM-CSF, TNF-α, INF-γ or combinations thereof. Moreover, a compound of the invention or a pharmaceutically acceptable salt, solvate, clathrate, or prodrug thereof can modulate the activity of one or more ion channel involved in activation of immune cells, such as CRAC ion channels.

A compound of the invention or a pharmaceutically acceptable salt, solvate, clathrate, or prodrug thereof is particularly useful for immunosuppression or for treating or preventing inflammatory conditions, allergic disorders, and immune disorders.

The invention also encompasses pharmaceutical compositions comprising a compound of the invention or a pharmaceutically acceptable salt, solvate, clathrate, or prodrug thereof; and a pharmaceutically acceptable carrier or vehicle. These compositions may further comprise additional agents. These compositions are useful for immunosuppression and treating or preventing inflammatory conditions, allergic disorders and immune disorders.

The invention further encompasses methods for treating or preventing inflammatory conditions, allergic disorders, and immune disorders, comprising administering to a subject in need thereof an effective amount of a compound of the invention or a pharmaceutically acceptable salt, solvate, clathrate, or prodrug thereof, or a pharmaceutical composition comprising a compound of the invention or a pharmaceutically acceptable salt, solvate, clathrate, or prodrug thereof. These methods may also comprise administering to the subject an additional agent separately or in a combination composition with the compound of the invention or a pharmaceutically acceptable salt, solvate, clathrate, or prodrug thereof.

The invention further encompasses methods for suppressing the immune system of a subject, comprising administering to a subject in need thereof an effective amount of a compound of the invention or a pharmaceutically acceptable salt, solvate, clathrate, or prodrug thereof, or a pharmaceutical composition comprising a compound of the invention or a pharmaceutically acceptable salt, solvate, clathrate, or prodrug thereof. These methods may also comprise administering to the subject an additional agent separately or in a combination composition with the compound of the invention or a pharmaceutically acceptable salt, solvate, clathrate, or prodrug thereof.

The invention further encompasses methods for inhibiting immune cell activation, including inhibiting proliferation of T cells and/or B cells, in vivo or in vitro comprising administering to the cell an effective amount of a compound of the invention or a pharmaceutically acceptable salt, solvate, clathrate, or prodrug thereof or a pharmaceutical composition comprising a compound of the invention or a pharmaceutically acceptable salt, solvate, clathrate, or prodrug thereof.

The invention further encompasses methods for inhibiting cytokine production in a cell, (e.g., IL-2, IL-4, IL-5, IL-13, GM-CSF, TNF-α, and/or INF-γ production) in vivo or in vitro comprising administering to a cell an effective amount of a compound of the invention or a pharmaceutically acceptable salt, solvate, clathrate, or prodrug thereof or a pharmaceutical composition comprising a compound of the invention or a pharmaceutically acceptable salt, solvate, clathrate, or prodrug thereof.

The invention further encompasses methods for modulating ion channel activity (e.g., CRAC) in vivo or in vitro comprising administering an effective amount of a compound of the invention or a pharmaceutically acceptable salt, solvate, clathrate, or prodrug thereof or a pharmaceutical composition comprising a compound of the invention or a pharmaceutically acceptable salt, solvate, clathrate, or prodrug thereof.

All of the methods of this invention may be practice with a compound of the invention alone, or in combination with other agents, such as other immunosuppressive agents, anti-inflammatory agents, agents for the treatment of allergic disorders or agents for the treatment of immune disorders.

DETAILED DESCRIPTION OF THE INVENTION

Definitions

Unless otherwise specified, the below terms used herein are defined as follows:

As used herein, the term an "aromatic ring" or "aryl" means a monocyclic or polycyclic-aromatic ring or ring radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents (including without limitation alkyl (preferably, lower alkyl or alkyl substituted with one or more halo), hydroxy, alkoxy (preferably, lower alkoxy), alkylthio, cyano, halo, amino, and nitro. In certain embodiments, the aryl group is a monocyclic ring, wherein the ring comprises 6 carbon atoms.

As used herein, the term "alkyl" means a saturated straight chain or branched non-cyclic hydrocarbon typically having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more substituents, such as amino, alkylamino, alkoxy, alkylthio, oxo, halo, acyl, nitro, hydroxyl, cyano, aryl, alkylaryl, aryloxy, arylthio, arylamino, carbocyclyl, carbocyclyloxy, carbocyclylthio, carbocyclylamino, heterocyclyl, heterocyclyloxy, heterocyclylamino, heterocyclylthio, and the like. In addition, any carbon in the alkyl segment may be substituted with oxygen (=O), sulfur (=S), or nitrogen (=NR²³, wherein R²³ is —H, an alkyl, acetyl, or aralkyl). Lower alkyls are typically preferred for the compounds of this invention.

The term alkylene refers to an alkyl group that has two points of attachment to two moieties (e.g., {—CH₂—}, —{CH₂CH₂—},

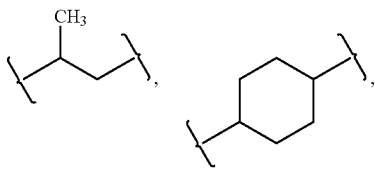

etc., wherein the brackets indicate the points of attachment). Alkylene groups may be substituted or unsubstituted.

An aralkyl group refers to an aryl group that is attached to another moiety via an alkylene linker. Aralkyl groups can be substituted or unsubstituted.

The term "alkoxy," as used herein, refers to an alkyl group which is linked to another moiety though an oxygen atom. Alkoxy groups can be substituted or unsubstituted.

The term "alkoxyalkoxy," as used herein, refers to an alkoxy group in which the alkyl portion is substituted with another alkoxy group.

The term "alkyl sulfanyl," as used herein, refers to an alkyl group which is linked to another moiety though a divalent sulfur atom. Alkyl sulfanyl groups can be substituted or unsubstituted.

The term "alkylamino," as used herein, refers to an amino group in which one hydrogen atom attached to the nitrogen has been replaced by an alkyl group. The term "dialkylamino," as used herein, refers to an amino group in which two hydrogen atoms attached to the nitrogen have been replaced by alkyl groups, in which the alkyl groups can be the same or different. Alkylamino groups and dialkylamino groups can be substituted or unsubstituted.

As used herein, the term "alkenyl" means a straight chain or branched, hydrocarbon radical typically having from 2 to 10 carbon atoms and having at least one carbon-carbon double bond. Representative straight chain and branched alkenyls include vinyl, allyl, 1-butenyl, 2-butenyl, isobutylenyl, 1-pentenyl, 2-pentenyl, 3-methyl-1-butenyl, 1-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups can be substituted or unsubstituted.

As used herein, the term "alkynyl" means a straight chain or branched, hydrocarbon radical typically having from 2 to 10 carbon atoms and having at lease one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl, -1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl and the like. Alkynyl groups can be substituted or unsubstituted.

As used herein, the term "cycloalkyl" means a saturated, mono- or polycyclic alkyl radical typically having from 3 to 10 carbon atoms. Representative cycloalkyls include cyclopropyl, cyclobutyl, cyclopentyl, cyclohexyl, cycloheptyl, cyclooctyl, cyclononyl, cyclodecyl, adamantly, decahydronaphthyl, octahydropentalene, bicycle[1.1.1]pentanyl, and the like. Cycloalkyl groups can be substituted or unsubstituted.

As used herein, the term "cycloalkenyl" means a cyclic non-aromatic alkenyl radical having at least one carbon-carbon double bond in the cyclic system and typically having from 5 to 10 carbon atoms. Representative cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like. Cycloalkenyl groups can be substituted or unsubstituted.

As used herein, the term "heterocycle" or "heterocyclyl" means a monocyclic or polycyclic heterocyclic ring (typically having 3- to 14-members) which is either a saturated ring or a unsaturated non-aromatic ring. A 3-membered heterocycle can contain up to 3 heteroatoms, and a 4- to 14-membered heterocycle can contain from 1 to about 8 heteroatoms. Each heteroatom is independently selected from nitrogen, which can be quaternized; oxygen; and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents (including without limitation a halogen atom, an alkyl radical, or aryl radical). Only stable isomers of such substituted heterocyclic groups are contemplated in this definition. Heterocyclyl groups can be substituted or unsubstituted.

As used herein, the term "heteroaromatic" or "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquniolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, indolyl, tetrahydroindolyl, azaindolyl, imidazopyridyl, qunizaolinyl, purinyl, pyrrolo[2,3]pyrimidyl, pyrazolo[3,4]pyrimidyl or benzo(b)thienyl and the like. These heteroaryl groups may be optionally substituted with one or more substituents A heteroaralkyl group refers to a heteroaryl group that is attached to another moiety via an alkylene linker. Heteroaralkyl groups can be substituted or unsubstituted.

As used herein, the term "halogen" or "halo" means —F, —Cl, —Br or —I.

As used herein, the term "haloalkyl" means an alkyl group in which one or more —H is replaced with a halo group. Examples of haloalkyl groups include —$CF_3$, —$CHF_2$, —$CCl_3$, —$CH_2CH_2Br$, —$CH_2CH(CH_2CH_2Br)CH_3$, —$CHICH_3$, and the like.

As used herein, the term "haloalkoxy" means an alkoxy group in which one or more —H is replaced with a halo group. Examples of haloalkoxy groups include —$OCF_3$ and —$OCHF_2$.

As used herein, the term "contiguous linear connectivity" means connected together so as to form an uninterrupted linear array or series of atoms. For example, a linker of the compounds described herein having a specified number of atoms in contiguous linear connectivity has at least that number of atoms connected together so as to form an uninterrupted chain, but may also include additional atoms that are not so connected (e.g., branches or atoms contained within a ring system).

As used herein, the term "linker" means a diradical having from 1-3 atoms in contiguous linear connectivity (i.e., as defined above and excluding atoms present in any side chains and branches), that covalently connects the isothiazole portion of a compound of this invention to the Y group of the compound, as illustrated in formula (I). The atoms of the linker in contiguous linear connectivity may be connected by saturated or unsaturated covalent bonds. Linkers include, but are not limited to, alkylidene, alkenylidene, alkynylidene and cycloalkylidene (such as lower alkylidene, cycloalkylidene, alkylycloalkylidene and alkyl-substituted alkylidene) linkers wherein one or more (e.g., between 1 and 3, (e.g., 1 or 2)) carbon atoms may be optionally replaced with O, S, or N and wherein two or more (e.g., 2-3 (e.g., 2 or 3)) adjacent atoms may be optionally linked together to form a carbocyclic or heterocyclic moiety within the linker (which may be monocyclic, polycyclic and/or fused, and which may be saturated, unsaturated, or aromatic). Examples of specific linkers useful in the compounds of the invention include (without limitation) diradicals of alkyl, alkenyl, alynyl, alkoxy, alkoxyalkyl, alkylaminoalkyl, cycloalkyl, alkylcycloalkyl, and alkyl-substituted alkylcycloalkyl (wherein one or more carbon atoms in any of these linkers may be optionally replaced with O, S, or N).

The terms "bioisostere" and "bioisosteric replacement" have the same meanings as those generally recognized in the art. Bioisosteres are atoms, ions, or molecules in which the peripheral layers of electrons can be considered substantially identical. The term bioisostere is usually used to mean a portion of an overall molecule, as opposed to the entire molecule itself. Bioisosteric replacement involves using one bioisostere to replace another with the expectation of maintaining or slightly modifying the biological activity of the first bioisostere. The bioisosteres in this case are thus atoms or groups of atoms having similar size, shape and electron density. Preferred bioisosteres of esters, amides or carboxylic acids are compounds containing two sites for hydrogen bond acceptance. In one embodiment, the ester, amide or carboxylic acid bioisostere is a 5-membered monocyclic heteroaryl ring, such as an optionally substituted 1H-imidazolyl, an optionally substituted oxazolyl, 1H-tetrazolyl, [1,2,4]triazolyl, or an optionally substituted [1,2,4]oxadiazolyl.

As used herein, the terms "subject", "patient" and "animal", are used interchangeably and include, but are not limited to, a cow, monkey, horse, sheep, pig, chicken, turkey, quail, cat, dog, mouse, rat, rabbit, guinea pig and human. The preferred subject, patient or animal is a human.

As used herein, the term "lower" refers to a group having up to four carbon atoms. For example, a "lower alkyl" refers to an alkyl radical having from 1 to 4 carbon atoms, and a "lower alkenyl" or "lower alkynyl" refers to an alkenyl or alkynyl radical having from 2 to 4 carbon atoms, respectively. A lower alkoxy or a lower alkyl sulfanyl refers to an alkoxy or a alkyl sulfanyl having from 1 to 4 carbon atoms. Lower substituents are typically preferred.

Where a particular substituent, such as an alkyl substituent, occurs multiple times in a given structure or moeity, the identity of the substitutent is independent in each case and may be the same as or different from other occurrences of that substituent in the structure or moiety. Furthermore, individual substituents in the specific embodiments and exemplary compounds of this invention are preferred in combination with other such substituents in the compounds of this invention, even if such individual substituents are not expressly noted as being preferred or not expressly shown in combination with other substituents.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Suitable substituents for an alkyl, alkoxy, alkyl sulfanyl, alkylamino, dialkylamino, alkylene, alkenyl, alkynyl, cycloalkyl, cycloalkenyl, heterocyclyl, aryl, aralkyl, heteroaryl, and heteroarylalkyl groups include any substituent which will form a stable compound of the invention. Examples of substituents for an alkyl, alkoxy, alkylsulfanyl, alkylamino, dialkylamino, alkylene, alkenyl, alkynyl, cycloalkyl, cycloalkenyl, heterocyclyl, aryl, aralkyl, heteroaryl, and heteroarylalkyl include an alkyl, alkoxy, alkyl sulfanyl, alkylamino, dialkylamino, an alkenyl, an alkynyl, an cycloalkyl, an cycloalkenyl, an heterocyclyl, an aryl, an heteroaryl, an aralkyl, an heteraralkyl, a haloalkyl, —$C(O)NR_{13}R_{14}$, —$NR_{15}C(O)R_{16}$, halo, —$OR_{15}$, cyano, nitro, haloalkoxy, —$C(O)R_{15}$, —$NR_{13}R_{14}$, —$SR_{15}$, —$C(O)OR_{15}$, —$OC(O)R_{15}$, —$NR_{15}C(O)NR_{13}R_{14}$, —$OC(O)NR_{13}R_{14}$, —$NR_{15}C(O)OR_{16}$, —$S(O)_pR_{15}$, or —$S(O)_pNR_{13}R_{14}$, wherein $R_{13}$ and $R_{14}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{13}$ and $R_{14}$ taken together with the nitrogen to which they are attached is optionally substituted heterocyclyl or optionally substituted heteroaryl; and $R_{15}$ and $R_{16}$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

In addition, alkyl, cycloalkyl, alkylene, a heterocyclyl, and any saturated portion of a alkenyl, cycloalkenyl, alkynyl, aralkyl, and heteroaralkyl groups, may also be substituted with =O, =S, =N—$R_{15}$.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

Choices and combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject). Typically, such compounds are stable at a temperature of 40° C. or less, in the absence of excessive moisture, for at least one week. Such choices and combinations will be apparent to those of ordinary skill in the art and may be determined without undue experimentation.

Unless indicated otherwise, the compounds of the invention containing reactive functional groups (such as, without limitation, carboxy, hydroxy, and amino moieties) also include protected derivatives thereof. "Protected derivatives" are those compounds in which a reactive site or sites are blocked with one or more protecting groups. Suitable protecting groups for carboxy moieties include benzyl, tert-butyl, and the like. Suitable protecting groups for amino and amido groups include acetyl, tert-butoxycarbonyl, benzyloxycarbonyl, and the like. Suitable protecting groups for hydroxy include benzyl and the like. Other suitable protecting groups are well known to those of ordinary skill in the art and include those found in T. W. Greene, Protecting Groups in Organic Synthesis, John Wiley & Sons, Inc. 1981, the entire teachings of which are incorporated herein by reference.

As used herein, the term "compound(s) of this invention" and similar terms refers to a compound of any one of formulas (I) through (XIV), or Table 1, or a pharmaceutically acceptable salt, solvate, clathrate, or prodrug thereof and also include protected derivatives thereof.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, but they may have activity in their unreacted forms. Examples of prodrugs contemplated in this invention include, but are not limited to, analogs or derivatives of compounds of any one of formulas (I) through (XIV), or Table 1 that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of formulas (I) through (XIV), or of Table 1 that comprise —NO, —NO$_2$, —ONO, or —ONO$_2$ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed), the entire teachings of which are incorporated herein by reference.

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the term "pharmaceutically acceptable salt," is a salt formed from an acid and a basic group of one of the compounds of any one of formulas (I) through (XIV) or of Table 1. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of any one of formulas (I) through (XIV) or Table 1 having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)-amine, 2-hydroxy-tert-butylamine, or tris-(hydroxymethyl)methylamine, N, N,-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like. The term "pharmaceutically acceptable salt" also refers to a salt prepared from a compound of any one of formulas (I) through (XIV) or Table 1 having a basic functional group, such as an amino functional group, and a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

As used herein, the term "pharmaceutically acceptable solvate," is a solvate formed from the association of one or more solvent molecules to one or more molecules of a compound of any one of formulas (I) through (XIV) or Table 1. The term solvate includes hydrates (e.g., hemi-hydrate, mono-hydrate, dihydrate, trihydrate, tetrahydrate, and the like).

As used herein, the term "clathrate" means a compound of the present invention or a salt thereof in the form of a crystal lattice that contains spaces (e.g., channels) that have a guest molecule (e.g., a solvent or water) trapped within.

As used herein, the term "asthma" means a pulmonary disease, disorder or condition characterized by reversible airway obstruction, airway inflammation, and increased airway responsiveness to a variety of stimuli.

"Immunosuppression" refers to impairment of any component of the immune system resulting in decreased immune function. This impairment may be measured by any conventional means including whole blood assays of lymphocyte function, detection of lymphocyte proliferation and assessment of the expression of T cell surface antigens. The antisheep red blood cell (SRBC) primary (IgM) antibody response assay (usually referred to as the plaque assay) is one specific method. This and other methods are described in Luster, M. I., Portier, C., Pait, D. G., White, K. L., Jr., Gennings, C., Munson, A. E., and Rosenthal, G. J. (1992). "Risk Assessment in Immunotoxicology I: Sensitivity and Predictability of Immune Tests." Fundam. Appl. Toxicol., 18, 200-210. Measuring the immune response to a T-cell dependent immunogen is another particularly useful assay (Dean, J. H., House, R. V., and Luster, M. I. (2001). "Immunotoxicology: Effects of, and Responses to, Drugs and Chemicals." In Principles and Methods of Toxicology: Fourth Edition (A. W. Hayes, Ed.), pp. 1415-1450, Taylor & Francis, Philadelphia, Pa.).

The compounds of this invention can be used to treat subjects with immune disorders. As used herein, the term "immune disorder" and like terms means a disease, disorder or condition caused by the immune system of an animal, including autoimmune disorders. Immune disorders include those diseases, disorders or conditions that have an immune component and those that are substantially or entirely immune system-mediated. Autoimmune disorders are those wherein the animal's own immune system mistakenly attacks itself, thereby targeting the cells, tissues, and/or organs of the animal's own body. For example, the autoimmune reaction is directed against the nervous system in multiple sclerosis and the gut in Crohn's disease. In other autoimmune disorders such as systemic lupus erythematosus (lupus), affected tissues and organs may vary among individuals with the same disease. One person with lupus may have affected skin and joints whereas another may have affected skin, kidney, and lungs. Ultimately, damage to certain tissues by the immune system may be permanent, as with destruction of insulin-producing cells of the pancreas in Type 1 diabetes mellitus. Specific autoimmune disorders that may be ameliorated using the compounds and methods of this invention include without limitation, autoimmune disorders of the nervous system (e.g., multiple sclerosis, myasthenia gravis, autoimmune neuropathies such as Guillain-Barré, and autoimmune uveitis), autoimmune disorders of the blood (e.g., autoimmune hemolytic anemia, pernicious anemia, and autoimmune thrombocytopenia), autoimmune disorders of the blood vessels (e.g., temporal arteritis, anti-phospholipid syndrome, vasculitides such as Wegener's granulomatosis, and Behcet's disease), autoimmune disorders of the skin (e.g., psoriasis, dermatitis herpetiformis, pemphigus vulgaris, and vitiligo), autoimmune disorders of the gastrointestinal system (e.g., Crohn's disease, ulcerative colitis, primary biliary cirrhosis, and autoimmune hepatitis), autoimmune disorders of the endocrine glands (e.g., Type 1 or immune-mediated diabetes mellitus, Grave's disease. Hashimoto's thyroiditis, autoimmune oophoritis and orchitis, and autoimmune disorder of the adrenal gland); and autoimmune disorders of multiple organs (including connective tissue and musculoskeletal system diseases) (e.g., rheumatoid arthritis, systemic lupus erythematosus, scleroderma, polymyositis, dermatomyositis, spondyloarthropathies such as ankylosing spondylitis, and Sjogren's syndrome). In addition, other immune system mediated diseases, such as graft-versus-host disease and allergic disorders, are also included in the definition of immune disorders herein. Because a number of immune disorders are caused by inflammation, there is some overlap between disorders that are considered immune disorders and inflammatory disorders. For the purpose of this invention, in the case of such an overlapping disorder, it may be considered either an immune disorder or an inflammatory disorder. "Treatment of an immune disorder" herein refers to administering a compound or a composition of the invention to a subject, who has an immune disorder, a symptom of such a disease or a predisposition towards such a disease, with the purpose to cure, relieve, alter, affect, or prevent the autoimmune disorder, the symptom of it, or the predisposition towards it.

As used herein, the term "allergic disorder" means a disease, condition or disorder associated with an allergic response against normally innocuous substances. These substances may be found in the environment (such as indoor air pollutants and aeroallergens) or they may be non-environmental (such as those causing dermatological or food allergies). Allergens can enter the body through a number of routes, including by inhalation, ingestion, contact with the skin or injection (including by insect sting). Many allergic disorders are linked to atopy, a predisposition to generate the allergic antibody IgE. Because IgE is able to sensitize mast cells anywhere in the body, atopic individuals often express disease in more than one organ. For the purpose of this invention, allergic disorders include any hypersensitivity that occurs upon re-exposure to the sensitizing allergen, which in turn causes the release of inflammatory mediators. Allergic disorders include without limitation, allergic rhinitis (e.g., hay fever), sinusitis, rhinosinusitis, chronic or recurrent otitis media, drug reactions, insect sting reactions, latex reactions, conjunctivitis, urticaria, anaphylaxis and anaphylactoid reactions, atopic dermatitis, asthma and food allergies.

The compounds of this invention can be used to prevent or to treat subjects with inflammatory disorders. As used herein, an "inflammatory disorder" means a disease, disorder or condition characterized by inflammation of body tissue or having an inflammatory component. These include local inflammatory responses and systemic inflammation. Examples of such inflammatory disorders include: transplant rejection, including skin graft rejection; chronic inflammatory disorders of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gums, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune disorders, immune-complex vasculitis, systemic lupus and erythematodes; systemic lupus erythematosus (SLE); and inflammatory diseases of the heart such as cardiomyopathy, ischemic heart disease hypercholesterolemia, atherosclerosis); as well as various other diseases with significant inflammatory components, including preeclampsia; chronic liver failure, brain and spinal cord trauma, cancer). There may also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent used in cancer chemotherapy. "Treatment of an inflammatory disorder" herein refers to administering a compound or a composition of the invention to a subject, who has an inflammatory disorder, a symptom of such a disorder or a predisposition towards such a disorder, with the purpose to cure, relieve, alter, affect, or prevent the inflammatory disorder, the symptom of it, or the predisposition towards it.

An "effective amount" is the quantity of compound in which a beneficial outcome is achieved when the compound is administered to a subject or alternatively, the quantity of compound that possess a desired activity in-vivo or in-vitro. In the case of inflammatory disorders and autoimmune disorders, a beneficial clinical outcome includes reduction in the extent or severity of the symptoms associated with the disease or disorder and/or an increase in the longevity and/or quality of life of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of inflammatory disorder or autoimmune disorder or the degree of immunosuppression sought. The skilled artisan will be able to determine appropriate dosages depending on these and other factors. Effective amounts of the disclosed compounds typically range between about 1 mg/m$^2$ per day and about 10 grams/m$^2$ per day, and preferably between 10 mg/m$^2$ per day and about 1 gram/m$^2$.

The compounds of the invention may contain one or more chiral centers and/or double bonds and, therefore, exist as stereoisomers, such as double-bond isomers (i.e., geometric isomers), enantiomers, or diastereomers. According to this invention, the chemical structures depicted herein, including the compounds of this invention, encompass all of the corresponding compounds' enantiomers and stereoisomers, that is, both the stereomerically pure form (e.g., geometrically pure, enantiomerically pure, or diastereomerically pure) and enantiomeric, diastereomeric, and geometric isomeric mixtures. In some cases, one enantiomer, diastereomer, or geometric isomer will possess superior activity or an improved toxicity or kinetic profile compared to others. In those cases, such enantiomers, diastereomers, and geometric isomers of a compound of this invention are preferred.

The term "inhibit production of IL-2" and like terms means inhibiting IL-2 synthesis (e.g. by inhibiting transcription (mRNA expression), or translation (protein expression)) and/or inhibiting IL-2 secretion in a cell that has the ability to produce and/or secrete IL-2 (e.g., T lymphocyte). Likewise, the term "inhibiting production of IL-4, IL-5, IL-13, GM-CSF, TNF-α or INF-γ means inhibiting the synthesis (e.g. by inhibiting transcription, or translation) and/or inhibiting the secretion in a cell that has the ability to produce and/or secrete these cytokines.

As used herein, a composition that "substantially" comprises a compound means that the composition contains more than about 80% by weight, more preferably more than about 90% by weight, even more preferably more than about 95% by weight, and most preferably more than about 97% by weight of the compound.

As used herein, a composition that is "substantially free" of a compound means that the composition contains less than about 20% by weight, more preferably less than about 10% by weight, even more preferably less than about 5% by weight, and most preferably less than about 3% by weight of the compound.

As used herein, a reaction that is "substantially complete" means that the reaction contains more than about 80% by weight of the desired product, more preferably more than about 90% by weight of the desired product, even more preferably more than about 95% by weight of the desired product, and most preferably more than about 97% by weight of the desired product.

As used herein, a racemic mixture means about 50% of one enantiomer and about 50% of is corresponding enantiomer relative to all chiral centers in the molecule. The invention encompasses all enantiomerically-pure, enantiomerically-enriched, diastereomerically pure, diastereomerically enriched, and racemic mixtures of the compounds of any one of formulas (I) through (XIV) or Table 1.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When administered to a patient, e.g., to a non-human animal for veterinary use or for improvement of livestock, or to a human for clinical use, the compounds of the invention are typically administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least 95%, preferably at least 98%, of a single compound of the invention by weight of the isolate.

Only those choices and combinations of substituents that result in a stable structure are contemplated. Such choices and combinations will be apparent to those of ordinary skill in the art and may be determined without undue experimentation.

The invention can be understood more fully by reference to the following detailed description and illustrative examples, which are intended to exemplify non-limiting embodiments of the invention.

SPECIFIC EMBODIMENTS

The invention relates to compounds and pharmaceutical compositions that are particularly useful for immunosuppression or to treat or prevent inflammatory conditions, immune disorders, and allergic disorders.

One embodiment of the invention relates to compounds of formula (X):

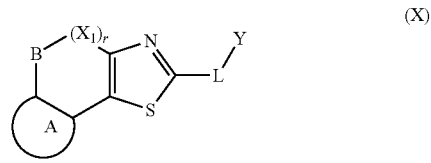

wherein:
Ring A is a 5 or 6 membered aryl or heteroaryl ring wherein the members of the ring are selected from the group consisting of —CZ—, —S—, —O— or —N—;
Y is an optionally substituted aryl or an optionally substituted heteroaryl;
B is —C(R$^a$)$_2$—, —C(O)—; —O—, —S—, or —N(R$^b$)—;

each $X_1$ is independently —C($R^a$)$_2$—, —C(O)—; —O—, —S—, or —N($R^b$)—;

Z is a substituent;

L is a linker;

each $R^a$ is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —SR$_4$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_p$NR$_1$R$_2$;

each $R^b$ is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, halo, —C(O)NR$_1$R$_2$, —C(O)R$_4$, or —C(O)OR$_4$;

$R_1$ and $R_2$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_1$ and $R_2$ taken together with the nitrogen to which they are attached is optionally substituted heterocyclyl or optionally substituted heteroaryl;

$R_4$ and $R_5$, for each occurrence is, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

r is 1, 2, 3, or 4; and p is 0, 1, or 2;

or a pharmaceutically acceptable salt, solvate, clathrate, or prodrug thereof.

In one aspect of compounds of formula (X), when r is 1, $X_1$ is C(O) and L is —NHC(O)—, Y is not phenyl or methylphenyl.

In one aspect of compounds of formula (X), when $X_1$ is —CH$_2$—, r is 1, B is —CH$_2$— and ring A is an unsubstituted phenyl group, L is not —NH— or —CH=CH—.

Another embodiment of the invention relates to compounds of formula (I):

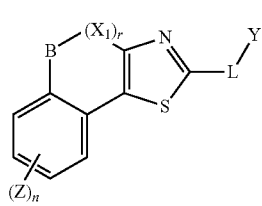

wherein:

Y is an optionally substituted aryl or an optionally substituted heteroaryl;

B is —C($R^a$)$_2$—, —C(O)—; —O—, —S—, or —N($R^b$)—;

each $X_1$ is independently —C($R^a$)$_2$—, —C(O)—; —O—, —S—, or —N($R^b$)—;

Z is a substituent;

L is a linker;

each $R^a$ is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —SR$_4$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_p$NR$_1$R$_2$;

each $R^b$ is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, halo, —C(O)NR$_1$R$_2$, —C(O)R$_4$, or —C(O)OR$_4$;

$R_1$ and $R_2$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_1$ and $R_2$ taken together with the nitrogen to which they are attached is optionally substituted heterocyclyl or optionally substituted heteroaryl;

$R_4$ and $R_5$, for each occurrence is, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

r is 1, 2, 3, or 4;

n is 0, 1, 2, 3 or 4; and p is 0, 1, or 2;

or a pharmaceutically acceptable salt, solvate, clathrate, or prodrug thereof.

In one aspect of compounds of formula (I), when r is 1, $X_1$ is C(O) and L is —NHC(O)—, Y is not phenyl or methylphenyl.

In one aspect of compounds of formula (I), when r is 1 and n is 0, L is not —NH—.

Another embodiment of the invention relates to compounds of formula (II):

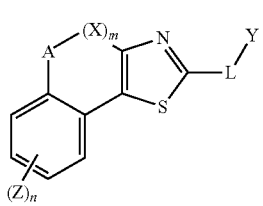
(II)

wherein:

A is —C(R$^a$)$_2$— or —O—;

each X is independently —C(R$^a$)$_2$— or —C(O)—;

m is 1 or 2; and

Z, L, and Y are defined as for formula (I);

or a pharmaceutically acceptable salt, solvate, clathrate, or prodrug thereof.

In one aspect of compounds of formula (II), when m is 1, X is C(O) and L is —NHC(O)—, Y is not phenyl or methylphenyl.

In another aspect of compounds of formula (II), when m is 1 and n is 0, L is not —NH—.

Another embodiment of the invention relates to compounds of formula (III):

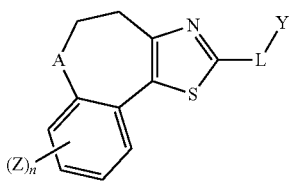
(III)

wherein Z, Y, L and n are defined as for formula (I) and A is defined as for formula (II);

or a pharmaceutically acceptable salt, solvate, clathrate, or prodrug thereof.

Another embodiment of the invention relates to compounds of formula (IV):

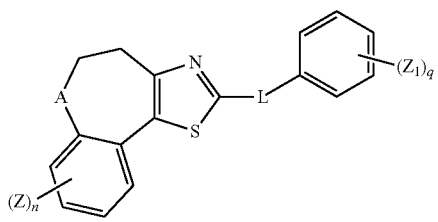
(IV)

wherein $Z_1$ is a substituent; q is 0, 1, 2, 3, 4, or 5; Z, n, and L are defined as for formula (I); and A is defined as for formula (II);

or a pharmaceutically acceptable salt, solvate, clathrate, or prodrug thereof.

Another embodiment of the invention relates to compounds of formula (V):

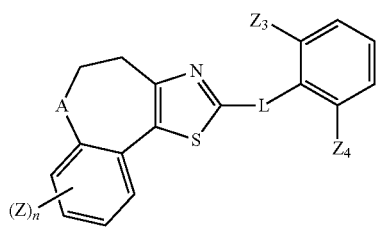
(V)

wherein $Z_3$ and $Z_4$ are each independently substituents; Z, n, and L are defined as for formula (I); and A is defined as for formula (II);

or a pharmaceutically acceptable salt, solvate, clathrate, or prodrug thereof.

Another embodiment of the invention relates to compounds of formula (VI):

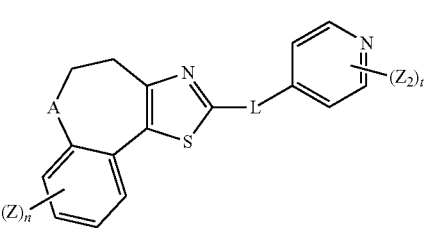
(VI)

wherein $Z_2$ is a substituent; t is 0, 1, 2, 3 or 4; Z, n, and L are defined as for formula (I); and A is defined as for formula (II);

or a pharmaceutically acceptable salt, solvate, clathrate, or prodrug thereof.

Another embodiment of the invention relates to compounds of formula (VII):

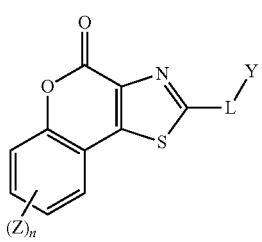
(VII)

wherein Z, n, L, and Y are defined as for formula (I);

or a pharmaceutically acceptable salt, solvate, clathrate, or prodrug thereof.

In one aspect of compounds of formula (VII), when L is —NHC(O)—, Y is not phenyl or methylphenyl.

In one aspect of compounds of formula (VII), when n is 0, L is not —NH—.

Another embodiment of the invention relates to compounds of formula (VIII):

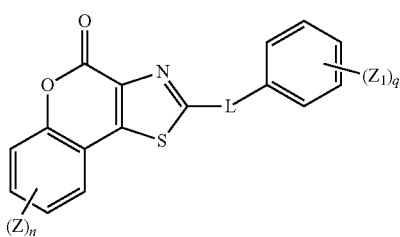

(VIII)

wherein $Z_1$ is a substituent; q is 0, 1, 2, 3, 4, or 5; and Z, n and L are defined as for formula (I).

or a pharmaceutically acceptable salt, solvate, clathrate, or prodrug thereof.

In one aspect of compounds of formula (VIII), when L is —NHC(O)—, Y is not phenyl or methylphenyl.

In one aspect of compounds of formula (VIII), when n is 0, L is not —NH—.

Another embodiment of the invention relates to compounds of formula (IX):

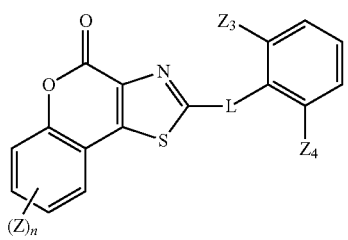

(IX)

wherein $Z_3$ and $Z_4$ are each independently substituents; and Z, n, and L are defined as for formula (I);

or a pharmaceutically acceptable salt, solvate, clathrate, or prodrug thereof.

In one aspect of compounds of formula (IX), when n is 0, L is not —NH—.

Another embodiment of the invention relates to compounds of formula (XI):

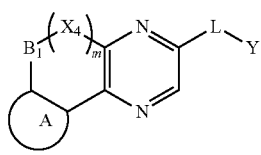

(XI)

wherein:

$X_4$ is —C(R$^a$)$_2$—;

$B_1$ is —C(R$^a$)$_2$—, —C(O)—; or —O—;

m is 1 or 2; and

Ring A, L and Y are defined as for formula (X);

or a pharmaceutically acceptable salt, solvate, clathrate, or prodrug thereof.

Another embodiment of the invention relates to compounds of formula (XII):

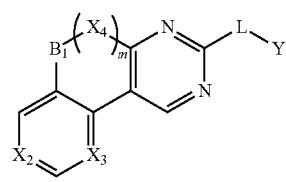

(XII)

wherein:

$X_2$ and $X_3$ are independently selected from the group consisting of —CR$^a$— or —N—; and Ring A, L and Y are defined as for formula (X) and $B_1$, $X_4$, and m are defined as for formula (XI);

or a pharmaceutically acceptable salt, solvate, clathrate, or prodrug thereof.

Another embodiment of the invention relates to compounds of formula (XIII):

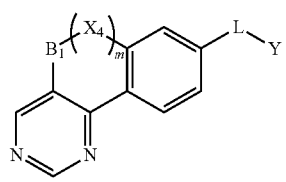

(XIII)

wherein:

L and Y are defined as for formula (X) and $B_1$, $X_4$, and m are defined as for formula (XI);

or a pharmaceutically acceptable salt, solvate, clathrate, or prodrug thereof.

Another embodiment of the invention relates to compounds of formula (XIV):

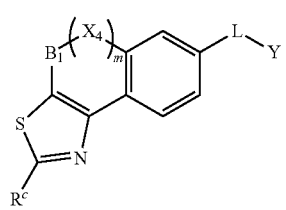

(XIV)

wherein:

$R^c$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —SR$_4$, —C(O)OR$_4$, —OC(O), —NR$_4$C(O)NR$_1$R$_2$, —OC(O)NR$_1$R$_2$, —NR$_4$C(O)OR$_5$, —S(O)$_p$R$_4$, or —S(O)$_p$NR$_1$R$_2$; and L and Y are defined as for formula (X) and $B_1$, $X_4$, and m are defined as for formula (XI);

or a pharmaceutically acceptable salt, solvate, clathrate, or prodrug thereof.

In one embodiment of compounds of formula (XIV), when $X_5$ is —C(NH$_2$)— and m is 1, then Y is not an unsubstituted phenyl.

In one embodiment, in compounds represented by formula (I)-(XIV), L is —NRCH$_2$—, —CH$_2$NR—, —C(O)—, —NR—C(O)—, —C(O)—NR—, —OC(O)—, —C(O)O—, —C(S)—, —NR—C(S)—, —C(S)—NR—, —NRC(NR$_9$)— or —C(NR$_9$)NR—;

R, for each occurrence, is independently —H, alkyl, —C(O)—R$_7$, or —C(O)OR$_7$;

R$_9$, for each occurrence, is independently —H, halo, an alkyl, —OR$_7$, —NR$_{11}$R$_{12}$, —C(O)R$_7$, —C(O)OR$_7$, or —C(O)R$_{11}$R$_{12}$;

R$_7$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; and R$_{11}$ and R$_{12}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_{11}$ and R$_{12}$ taken together with the nitrogen to which they are attached are an optionally substituted heterocyclyl or optionally substituted heteroaryl.

In one aspect, in compounds represented by formula (I)-(XIV), L is —NRCH$_2$—, —CH$_2$NR—, —NR—C(O)—, or —C(O)—NR—. In another aspect, R is —H. In a further aspect, L is —NH—C(O)— or —C(O)—NH—. In another aspect, L is —NH—C(O)—. In another aspect, L is —C(O)—NH—.

In one embodiment, in compounds represented by formula (I)-(XIV), L is —NRS(O)$_2$—, —S(O)$_2$NR—, —NRS(O)$_2$NR—, —NRC(O)NR—, —NRC(NR)NR—, —NRC(S)NR—, —NRCH$_2$NR—, —NRN=CR$_6$—, —C(NR)—, or —CR$_6$=NNR—;

R, for each occurrence, is independently —H, alkyl, —C(O)—R$_7$, or —C(O)OR$_7$;

R$_6$, for each occurrence, is —H or alkyl; and

R$_7$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl.

In one aspect, in compounds represented by formula (I)-(XIV), R is —H; and R$_6$ is —H. In another aspect, L is —NHS(O)$_2$—, —NHC(O)NH—, —NHC(S)NH—, or —NHN=CH—. In one aspect, L is —NHC(O)NH—.

In one aspect, in compounds represented by formula (I)-(XIV), L is —C(=NR$_{20}$)NR—. R$_{20}$ is —H, alkyl, —C(O)—R$_7$, —OR$_7$, or —C(O)OR$_7$. In one aspect, R is —H.

In one embodiment, in compounds represented by formula (I)-(X), Z is an optionally substituted phenyl, an optionally substituted oxazolyl, an optionally substituted thiazolyl, an optionally substituted imidazolyl, an optionally substituted pyridinyl, an optionally substituted pyrazolyl, an optionally substituted pyrrolyl, an optionally substituted thiophenyl, an optionally substituted furanyl, an optionally substituted thiadiazolyl, an optionally substituted oxadiazolyl, or an optionally substituted tetrazolyl. In one aspect, Z is an optionally substituted oxazolyl, an optionally substituted thiazolyl, an optionally substituted pyridinyl, or an optionally substituted tetrazolyl. In another aspect, Z is thiazol-2-yl, pyridin-2-yl, tetrazol-5-yl, oxadiazol-3-yl, or oxazol-5-yl. In one aspect, Z is thiazol-2-yl. In one aspect, Z is pyridin-2-yl. In one aspect, Z is tetrazol-5-yl. In one aspect, Z is oxadiazol-3-yl. In one aspect, Z is oxazol-5-yl.

In one embodiment, in compounds represented by formula (I)-(X), Z is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteralkyl, halo, cyano, —NO$_2$, —C(O)NR$_1$R$_2$, —NR$_4$C(O)R$_5$, —OR$_4$, haloalkoxy, —C(O)R$_4$, —NR$_1$R$_2$, —SR$_4$, —C(O)OR$_4$, —OC(O), —NR$_4$C(O)NR$_1$R$_2$, —OC(O)NR$_1$R$_2$, —NR$_4$C(O)OR$_5$, —S(O)$_p$R$_4$, or —S(O)$_p$NR$_1$R$_2$. In one aspect, Z is halo, cyano, —NO$_2$, —OR$_4$, —C(O)OR$_4$, or an optionally substituted alkyl. In another aspect, Z is —Br, —Cl, —F, —OCH$_3$, —C(O)OCH$_3$, or CF$_3$. In one aspect, Z is —OH, —OCH$_3$, or —C(O)OCH$_3$. In another aspect, Z is cyano or —NO$_2$.

In one embodiment, in compounds represented by formula (I)-(IX), n is 1 or 0. In one aspect, n is 1. In another aspect n is 0.

In one embodiment, in compounds represented by formula (I)-(IX), n is 3.

In one embodiment, in compounds represented by formula (I), (II), (III), (VII), (X), (XI), (XII), (XIII), or (XIV), Y is an optionally substituted phenyl, an optionally substituted oxazolyl, an optionally substituted furanyl, an optionally substitute pyrazolyl, an optionally substituted pyridinyl, an optionally substituted pyridazinyl, an optionally substituted thiadiazolyl, an optionally substituted pyrimidinyl, or an optionally substituted thiophenyl. In one aspect, Y is unsubstituted. In another aspect, Y is an optionally substituted phenyl or an optionally substituted pyridinyl. In a further aspect, Y is substituted with one to two substituents. In another aspect, the one to two substituents on Y are each independently a lower alkyl or a halo. In one aspect, Y is difluorophenyl. In a further aspect, Y is an optionally substituted thiadiazolyl. In another aspect, Y is an optionally substituted thiophenyl. In one aspect, Y is an optionally substituted pyridazinyl. In another aspect, Y is an optionally substituted pyrimidinyl. In another aspect, Y is thiadiazolyl substituted with one methyl group. In another aspect, Y is thiophenyl substituted with one methyl group. In another aspect, Y is pyridazinyl substituted with one methyl group.

In one embodiment, in compounds represented by formula (I) or (X), r is 3.

In one embodiment, in compounds represented by formula (I) or (X), r is 4.

In one embodiment, in compounds represented by formula (I) or (X), r is 2.

In one embodiment, in compounds represented by formula (I) or (X), B is —C(R$^a$)$_2$— or —O— and each X$_1$ is —C(R$^a$)$_2$—.

In one embodiment, in compounds represented by formula (I) or (X), r is 3; B is —C(R$^a$)$_2$— or —O—; and each X$_1$ is —C(R$^a$)$_2$—.

In one embodiment, in compounds represented by formula (II)-(VI), A is —O—.

In one embodiment, in compounds represented by formula (II)-(VI), A is —$CH_2$—.

In one embodiment, in compounds represented by formula (II), X is —$C(R^a)_2$— and m is 1.

In one embodiment, in compounds represented by formula (II), X is —$C(R^a)_2$— and m is 2.

In one embodiment, in compounds represented by formula (II), X is —C(O)— and m is 1.

In one embodiment, in compounds represented by formula (II), X is —C(O)— and m is 2.

In one embodiment, in compounds represented by formula (II), (XI), (XII), or (XIII), m is 1.

In one embodiment, in compounds represented by formula (II), (XI), (XII), or (XIII), m is 2.

In one embodiment, in compounds represented by formula (IV) or formula (VIII), $Z_1$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, —$NO_2$, —$C(O)NR_1R_2$, —$NR_4C(O)R_5$, —$OR_4$, haloalkoxy, —$C(O)R_4$, —$NR_1R_2$, —$SR_4$, —$C(O)OR_4$, —OC(O), —$NR_4C(O)NR_1R_2$, —$OC(O)NR_1R_2$, —$NR_4C(O)OR_5$, —$S(O)_pR_4$, or —$S(O)_pNR_1R_2$. In one aspect, $Z_1$ is halo.

In one embodiment, in compounds represented by formula (IV) or formula (VIII), q is 2.

In one embodiment, in compounds represented by formula (IV) or formula (VIII), q is 3.

In one embodiment, in compounds represented by formula (IV) or formula (VIII), q is 1.

In one embodiment, in compounds represented by formula (V) or formula (IX), $Z_3$ and $Z_4$ are each independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, —$C(O)NR_1R_2$, —$NR_4C(O)R_5$, —$OR_4$, haloalkoxy, —C(O), —$NR_1R_2$, —$SR_4$, —$C(O)OR_4$, —$OC(O)R_4$, —$NR_4C(O)NR_1R_2$, —$OC(O)NR_1R_2$, —$NR_4C(O)OR_5$, —$S(O)_pR_4$, or —$S(O)_pNR_1R_2$. In one aspect, $Z_3$ and $Z_4$ are the same. In another aspect, $Z_3$ and $Z_4$ are each —F.

In one embodiment, in compounds represented by formula (V) or formula (IX), Z is —Br, —Cl, —F, —$OCH_3$, —C(O)$OCH_3$, or $CF_3$; $Z_3$ and $Z_4$ are each —F; and L is —NH—C(O)— or —C(O)—NH—.

In one embodiment, in compounds represented by formula (V), Z is —Br, —Cl, —F, —$OCH_3$, —C(O)$OCH_3$, or $CF_3$; $Z_3$ and $Z_4$ are each —F; A is —$CH_2$—; and L is —NH—C(O)— or —C(O)—NH—.

In one embodiment, in compounds represented by formula (V), Z is —Br, —Cl, —F, —$OCH_3$, —C(O)$OCH_3$, or $CF_3$; $Z_3$ and $Z_4$ are each —F; A is —$CH_2$—; n is 1; and L is —NH—C(O)— or —C(O)—NH—.

In one embodiment, in compounds represented by formula (VI), $Z_2$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, —$C(O)NR_1R_2$, —$NR_4C(O)R_5$, —$OR_4$, haloalkoxy, —$C(O)R_4$, —$NR_1R_2$, —$SR_4$, —$C(O)OR_4$, —OC(O), —$NR_4C(O)NR_1R_2$, —$OC(O)NR_1R_2$, —$NR_4C(O)OR_5$, —$S(O)_pR_4$, or —$S(O)_pNR_1R_2$. In one aspect, $Z_2$ is halo or optionally substituted lower alkyl. In another aspect, $Z_2$ is —F or —$CH_3$. In one aspect, $Z_2$ is —$CH_3$, —$NH_2$, —$OCH_3$, Cl, or F.

In one embodiment, in compounds represented by formula (VI), t is 1.

In one embodiment, in compounds represented by formula (VI), $Z_2$ is —F or —$CH_3$ and t is 1.

In one embodiment, in compounds represented by formula (X) or (XI), Ring A is a 5-membered heteroaromatic ring containing one heteroatom. In one aspect, that one heteroatom is —S—.

In one embodiment, in compounds represented by formula (X) or (XI), Ring A is a 6-membered aromatic ring, containing no heteroatoms.

In one embodiment, in compounds represented by formula (XI) or (XII), (XIII), or (XIV), $B_1$ is —$C(R^a)_2$— or —O—. In one aspect, $B_1$ is —$C(R^a)_2$—. In one aspect, $B_1$ is —$CH_2$—.

In one embodiment, in compounds represented by formula (XI) or (XII), (XIII), or (XIV), $X_4$ is —$CH_2$—. In one aspect, m is 2.

In one embodiment, in compounds represented by formula (XI) or (XII), (XIII), or (XIV), m is 1.

In one embodiment, in compounds represented by formula (XI) or (XII), (XIII), or (XIV), m is 2.

In one embodiment, in compounds represented by formula (XI) or (XII), (XIII), or (XIV), $B_1$ is —$C(R^a)_2$— or —O— and each $X_4$ is —$CH_2$—.

In one embodiment, in compounds represented by formula (XI) or (XII), (XIII), or (XIV), $B_1$ is —$C(R^a)_2$— and each $X_4$ is —$CH_2$—.

In one embodiment, in compounds represented by formula (XII), at least one of $X_2$ and $X_3$ is —N—. In one aspect, $X_2$ and $X_3$ are both —N—.

In one embodiment, in compounds represented by formula (XII), $X_2$ and $X_3$ are both —CH—.

In one embodiment, in compounds represented by formula (XIV), $R_c$ is an optionally substituted aryl or an optionally substituted heteroaryl. In one aspect, $R_c$ is an optionally substituted heteroaryl. In one aspect, $R_c$ is an optionally substituted pyridyl.

In one embodiment, in compounds represented by formula (XIV), $R_c$ is an optionally substituted phenyl, an optionally substituted oxazolyl, an optionally substituted thiazolyl, an optionally substituted imidazolyl, an optionally substituted pyridinyl, an optionally substituted pyrazolyl, an optionally substituted pyrrolyl, an optionally substituted thiophenyl, an optionally substituted furanyl, an optionally substituted thiadiazolyl, an optionally substituted oxadiazolyl, or an optionally substituted tetrazolyl. In one aspect, $R_c$ is an optionally substituted oxazolyl, an optionally substituted thiazolyl, an optionally substituted pyridinyl, or an optionally substituted tetrazolyl. In another aspect, $R_c$ is thiazol-2-yl, pyridin-2-yl, tetrazol-5-yl, oxadiazol-3-yl, or oxazol-5-yl. In one aspect, $R_c$ is thiazol-2-yl. In one aspect, $R_c$ is pyridin-2-yl. In one aspect, $R_c$ is tetrazol-5-yl. In one aspect, $R_c$ is oxadiazol-3-yl. In one aspect, $R_c$ is oxazol-5-yl.

In one embodiment, in compounds represented by formula (XIV), $R_c$ is halo, cyano, —$NO_2$, —$OR_4$, —$C(O)OR_4$, or an optionally substituted alkyl. In another aspect, $R_c$ is —Br, —Cl, —F, —$OCH_3$, —C(O)$OCH_3$, or $CF_3$. In one aspect, $R_c$ is —OH, —$OCH_3$, or —C(O)$OCH_3$. In another aspect, $R^c$ is cyano or —$NO_2$.

All of the features, specific embodiments and particular substituents disclosed herein may be combined in any combination. Each feature, embodiment or substituent disclosed in this specification may be replaced by an alternative feature, embodiment or substituent serving the same, equivalent, or similar purpose. In the case of chemical compounds, specific values for variables (e.g., values shown in the exemplary compounds disclosed herein) in any chemical formula disclosed herein can be combined in any combination resulting in a stable structure. Furthermore, specific values (whether preferred or not) for substituents in one type of chemical structure may be combined with values for other substituents (whether preferred or not) in the same or different type of chemical structure. Thus, unless expressly stated otherwise, each feature, embodiment or substituent disclosed is only an example of a generic series of equivalent or similar features, embodiments or substituents.

In another embodiment, the invention relates to pharmaceutical compositions that comprise a compound of any one of formulas (I) through (XIV), or Table 1, or a pharmaceutically acceptable salt, solvate, clathrate, or prodrug thereof, as an active ingredient, and a pharmaceutically acceptable carrier or vehicle. The compositions are useful for immunosuppression or to treat or prevent inflammatory conditions, allergic conditions and immune disorders.

In another embodiment, the invention relates to methods for immunosuppression or for treating or preventing inflammatory conditions, immune disorders, or allergic disorders in a patient in need thereof comprising administering an effective amount of a compound represented by any one of formulas (I) through (XIV), or Table 1, or a pharmaceutically acceptable salt, solvate, clathrate, or prodrug thereof.

In another embodiment, the invention relates to methods for immunosuppression or for treating or preventing inflammatory conditions, immune disorders, or allergic disorders in a patient in need thereof comprising administering an effective amount of a pharmaceutical composition that comprises a compound represented by any one of formulas (I) through (XIV), or in or Table 1, or a pharmaceutically acceptable salt, solvate, clathrate, or prodrug thereof.

In another embodiment, compounds of any one of formulas (I) through (XIV), or Table 1, or a pharmaceutically acceptable salt, solvate, clathrate, or prodrug thereof, are particularly useful inhibiting immune cell (e.g., T-cells and/or B-cells) activation (e.g., activation in response to an antigen) and/or T cell and/or B cell proliferation. Indicators of immune cell activation include secretion of IL-2 by T cells, proliferation of T cells and/or B cells, and the like. In one embodiment, a compound of any one of formulas (I) through (XIV) or Table 1, inhibits immune cell activation and/or T cell and/or B cell proliferation in a mammal (e.g., a human).

In another embodiment, compounds of any one of formula (I) through (XIV), or Table 1, or a pharmaceutically acceptable salt, solvate, clathrate, or prodrug thereof, can inhibit the production of certain cytokines that regulate immune cell activation. For example, compounds of any one of formulas (I) through (XIV), or Table 1, or a pharmaceutically acceptable salt, solvate, clathrate, or prodrug thereof, can inhibit the production of IL-2, IL-4, IL-5, IL-13, GM-CSF, IFN-γ, TNF-α and combinations thereof. In one embodiment, a compound of any one of formulas (I) through (XIV), or Table 1, inhibits cytokine production in a mammal (e.g., a human).

In another embodiment, compounds of any one of formulas (I) through (XIV), or Table 1, or a pharmaceutically acceptable salt, solvate, clathrate, or prodrug thereof, can modulate the activity of one or more ion channel involved in activation of immune cells, such as CRAC ion channels. In one embodiment, a compound of any one of formulas (I) through (XIV) or Table 1 can inhibit the influx of calcium ions into an immune cell (e.g., T cells and/or B cells) by inhibiting the action of CRAC ion channels. In general, a decrease in $I_{CRAC}$ current upon contacting a cell with a compound is one indicator that the compound inhibitions CRAC ion channels. $I_{CRAC}$ current can be measured, for example, using a patch clamp technique, which is described in more detail in the examples below. In one embodiment, a compound of any one of formulas (I) through (XIV) or Table 1 modulates an ion channel in a mammal (e.g., a human).

Exemplary Compounds of the Invention

Exemplary compounds of the invention are depicted in Table 1 below.

TABLE 1

| Compound No. | Structure |
|---|---|
| 1 | 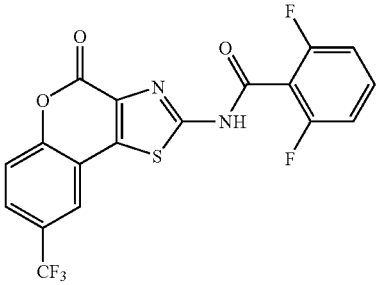 [SMILES: O=C(Nc1nc2c(=O)oc3ccc(C(F)(F)F)cc3c2s1)c1c(F)cccc1F] |
| 2 | 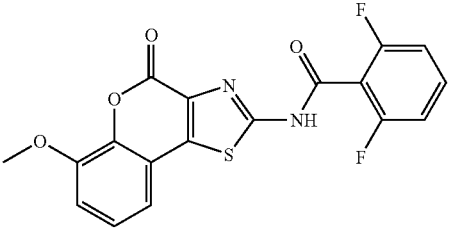 [SMILES: COc1cccc2c1oc(=O)c1nc(NC(=O)c3c(F)cccc3F)sc12] |
| 3 | 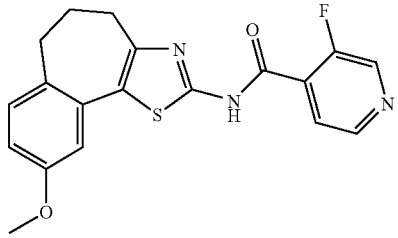 [SMILES: COc1ccc2c(c1)-c1sc(NC(=O)c3ccncc3F)nc1CCC2] |
| 4 | 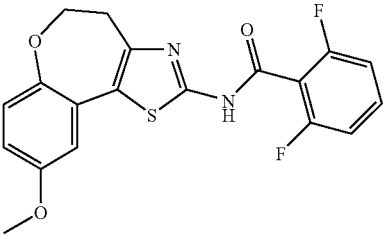 [SMILES: COc1ccc2c(c1)-c1sc(NC(=O)c3c(F)cccc3F)nc1CCO2] |
| 5 | 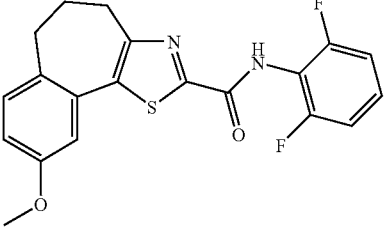 |

TABLE 1-continued

| Compound No. | Structure |
|---|---|
| 6 | (structure) |
| 7 | (structure) |
| 8 | (structure) |
| 9 | (structure) |
| 10 | (structure) |
| 11 | (structure) |
| 12 | (structure) |
| 13 | (structure) |
| 14 | (structure) |
| 15 | (structure) |
| 16 | (structure) |
| 17 | (structure) |
| 18 | (structure) |

TABLE 1-continued
| Compound No. | Structure |
|---|---|
| 19 | 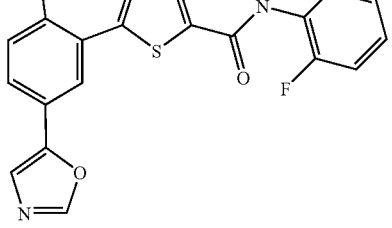 |
| 20 | 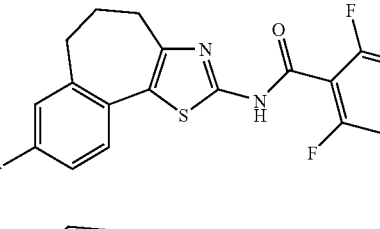 |
| 21 | 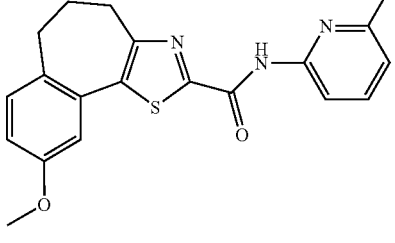 |
| 22 | 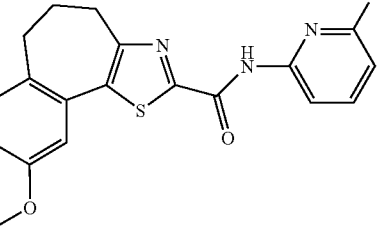 |
| 23 | 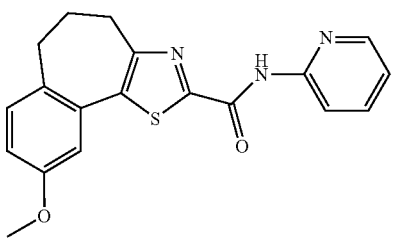 [SMILES: COc1ccc2c(c1)-c1sc(C(=O)Nc3ccccn3)nc1CCC2] |
| 24 | 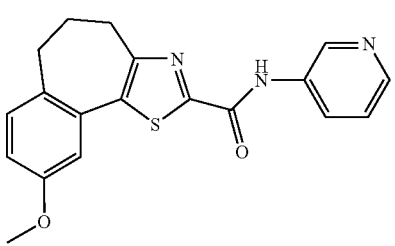 [SMILES: COc1ccc2c(c1)-c1sc(C(=O)Nc3cccnc3)nc1CCC2] |
| 25 | 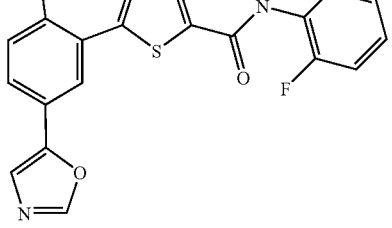 |
| 26 | 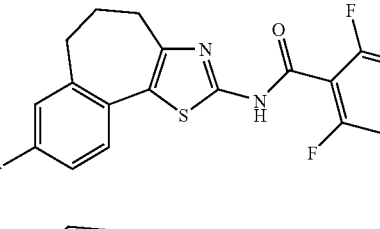 |
| 27 | 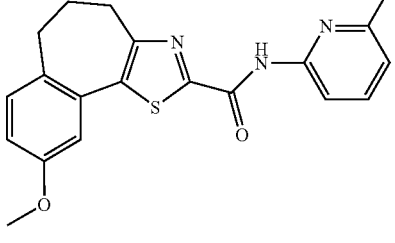 |
| 28 | 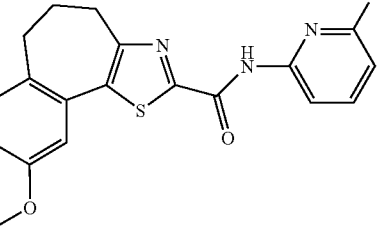 |
| 29 | 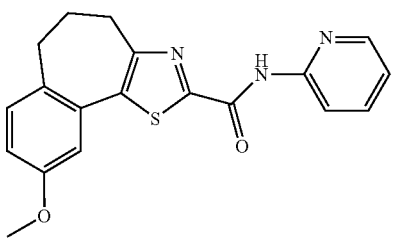 [SMILES: COc1ccc2c(c1)-c1sc(C(=O)Nc3ccccn3)nc1CCC2] |

TABLE 1-continued
| Compound No. | Structure |
|---|---|
| 30 | 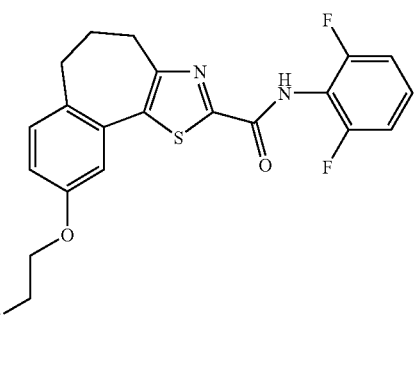 |
| 31 | 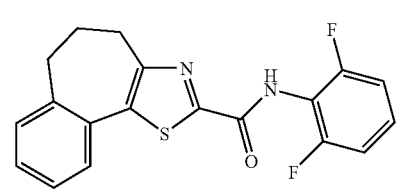 [SMILES: O=C(Nc1c(F)cccc1F)c1nc2c(s1)-c1ccccc1CCC2] |
| 32 | 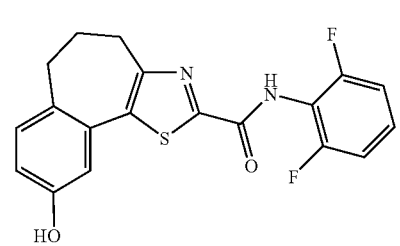 |
| 33 | 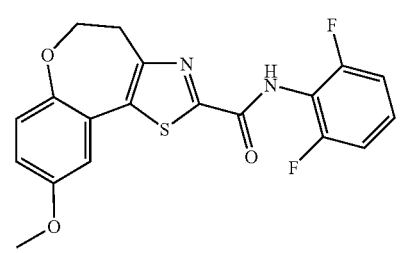 [SMILES: COc1ccc2c(c1)-c1sc(C(=O)Nc3c(F)cccc3F)nc1CCO2] |
| 34 | 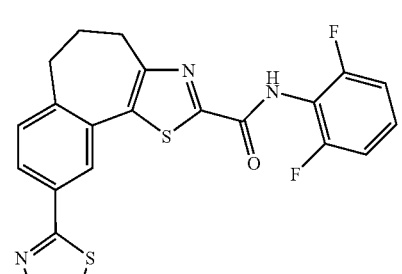 |
| 35 | 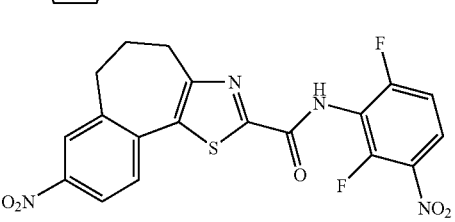 |
| 36 | 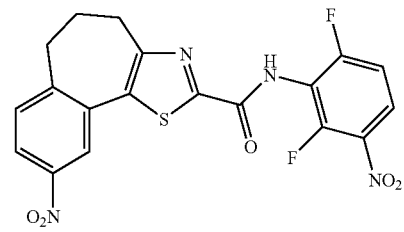 [SMILES: O=C(Nc1c(F)ccc([N+](=O)[O-])c1F)c1nc2c(s1)-c1cc([N+](=O)[O-])ccc1CCC2] |
| 37 | 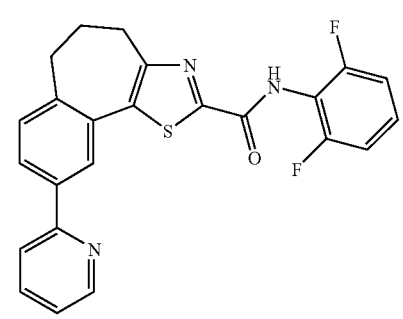 [SMILES: O=C(Nc1c(F)cccc1F)c1nc2c(s1)-c1cc(-c3ccccn3)ccc1CCC2] |
| 38 | 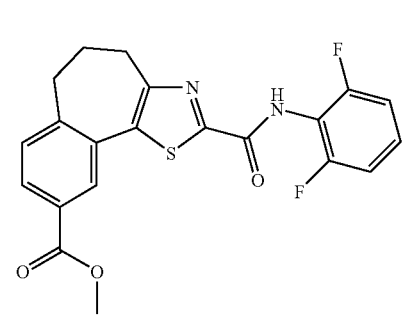 [SMILES: COC(=O)c1ccc2c(c1)-c1sc(C(=O)Nc3c(F)cccc3F)nc1CCC2] |
| 39 | 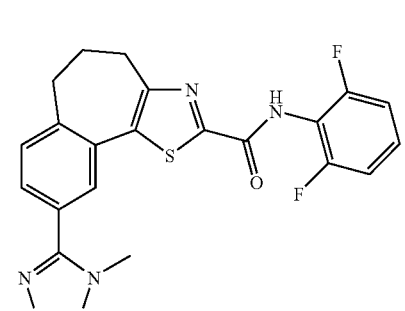 |
| 40 | 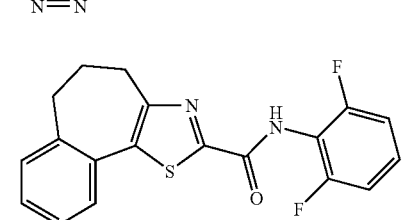 |

TABLE 1-continued

| Compound No. | Structure |
|---|---|
| 41 | (structure) |
| 42 | (structure) |
| 43 | (structure) |
| 44 | (structure) |
| 45 | (structure) |
| 46 | (structure) |
| 47 | (structure) |
| 48 | (structure) |
| 49 | (structure) |
| 50 | (structure) |
| 51 | (structure) |
| 52 | (structure) |
| 53 | (structure) |
| 54 | (structure) |

TABLE 1-continued

| Compound No. | Structure |
|---|---|
| 55 | 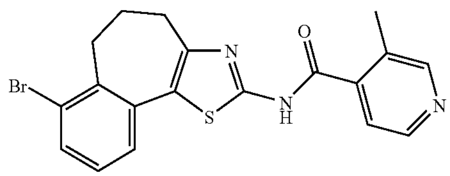 [SMILES: Cc1cnccc1C(=O)Nc1nc2c(s1)-c1cccc(Br)c1CCC2] |
| 56 | 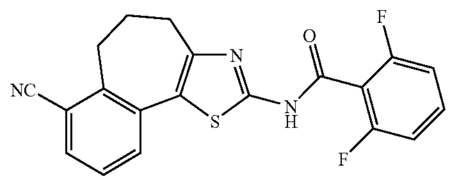 [SMILES: N#Cc1cccc2c1CCCc1nc(NC(=O)c3c(F)cccc3F)sc1-2] |
| 57 | 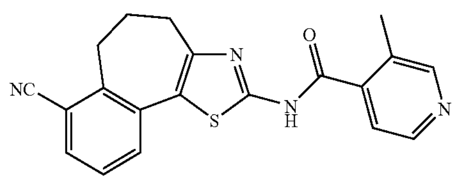 [SMILES: Cc1cnccc1C(=O)Nc1nc2c(s1)-c1cccc(C#N)c1CCC2] |
| 58 | 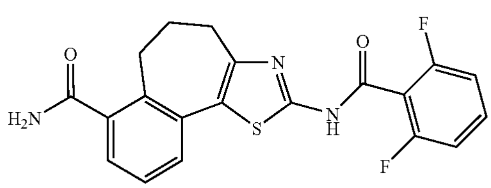 [SMILES: NC(=O)c1cccc2c1CCCc1nc(NC(=O)c3c(F)cccc3F)sc1-2] |
| 59 | 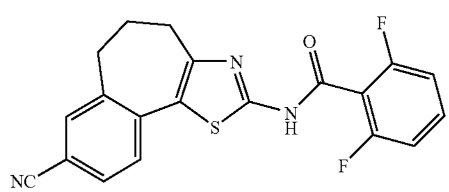 [SMILES: N#Cc1ccc2c(c1)CCCc1nc(NC(=O)c3c(F)cccc3F)sc1-2] |
| 60 | 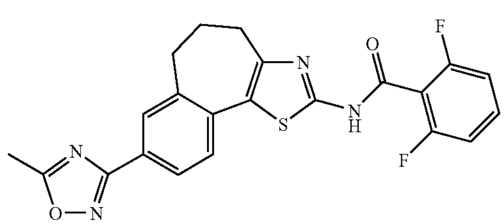 [SMILES: Cc1nc(-c2ccc3c(c2)CCCc2nc(NC(=O)c4c(F)cccc4F)sc2-3)no1] |
| 61 | 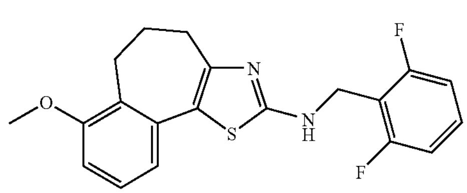 [SMILES: COc1cccc2c1CCCc1nc(NCc3c(F)cccc3F)sc1-2] |

TABLE 1-continued

| Compound No. | Structure |
|---|---|
| 62 | |
| 63 | |
| 64 | |
| 65 | |
| 66 | |
| 67 | |

TABLE 1-continued

| Compound No. | Structure |
|---|---|
| 68 | (oxazol-5-yl-substituted tricyclic benzothiazole 2,6-difluorobenzamide) |
| 69 | (oxazol-5-yl-substituted tricyclic benzothiazole 2,6-difluorobenzylamine) |
| 70 | (thiazol-2-yl-substituted tricyclic benzothiazole 2,6-difluorobenzamide) |
| 71 | (4-methylthiazol-2-yl-substituted tricyclic benzothiazole 2,6-difluorobenzamide) |
| 72 | (iodo-substituted tricyclic benzothiazole 2,6-difluorobenzamide) |
| 73 | (methyl ester-substituted tricyclic benzothiazole 2,6-difluorobenzamide) |
| 74 | (imidazol-1-yl-substituted tricyclic benzothiazole 2,6-difluorobenzamide) |
| 75 | (thiazol-2-yl-substituted tricyclic benzothiazole 2,6-difluorobenzamide) |
| 76 | (oxazol-2-yl-substituted tricyclic benzothiazole 2,6-difluorobenzamide) |
| 77 | (tetrazol-5-yl-substituted tricyclic benzothiazole 2,6-difluorobenzamide) |
| 78 | (1-methyltetrazol-5-yl-substituted tricyclic benzothiazole 2,6-difluorobenzamide) |
| 79 | (hydroxy-substituted tricyclic benzothiazole 2,6-difluorobenzamide) |
| 80 | (cyano-substituted tricyclic benzothiazole 2,6-difluorobenzamide) |

TABLE 1-continued

| Compound No. | Structure |
|---|---|
| 81 | (structure) |
| 82 | (structure) |
| 83 | (structure) |
| 84 | (structure) |
| 85 | (structure) |
| 86 | (structure) |
| 87 | (structure) |
| 88 | (structure) |
| 89 | (structure) |
| 90 | (structure) |
| 91 | (structure) |

TABLE 1-continued

| Compound No. | Structure |
|---|---|
| 92 | (structure) |
| 93 | (structure) |
| 94 | (structure) |
| 95 | (structure) |
| 96 | (structure) |
| 97 | (structure) |
| 98 | (structure) |
| 99 | (structure) |
| 100 | (structure) |
| 101 | (structure) |
| 102 | (structure) |

TABLE 1-continued
| Compound No. | Structure |
|---|---|
| 103 | 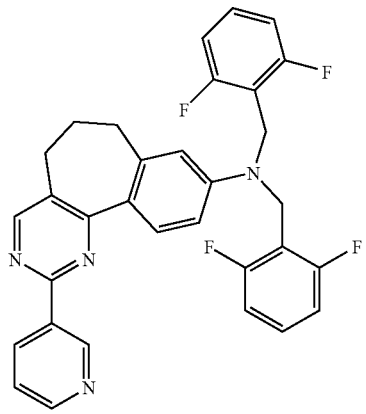 [SMILES: Fc1cccc(F)c1CN(Cc1c(F)cccc1F)c1ccc2c(c1)CCCc1cnc(-c3cccnc3)nc1-2] |
| 104 | 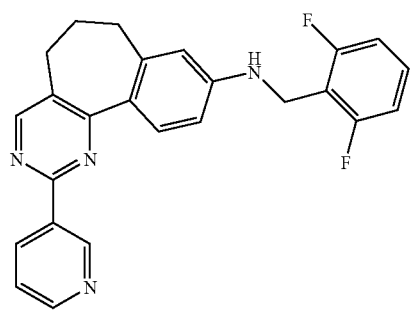 [SMILES: Fc1cccc(F)c1CNc1ccc2c(c1)CCCc1cnc(-c3cccnc3)nc1-2] |
| 105 | 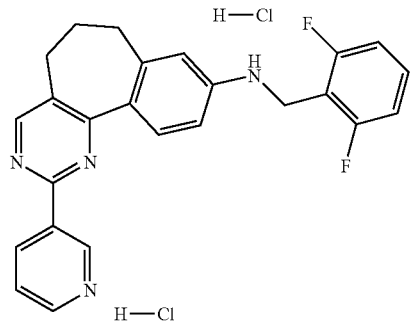 |
| 106 | 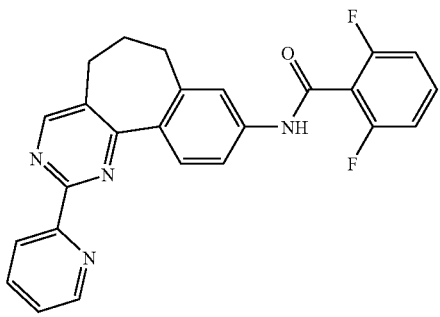 [SMILES: O=C(Nc1ccc2c(c1)CCCc1cnc(-c3ccccn3)nc1-2)c1c(F)cccc1F] |
| 107 | 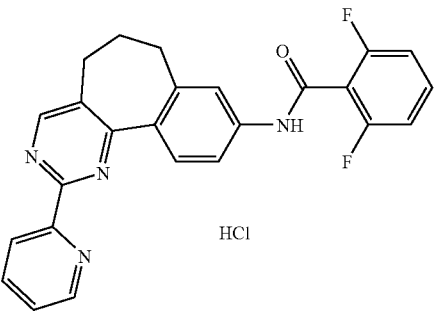 [SMILES: O=C(Nc1ccc2c(c1)CCCc1cnc(-c3ccccn3)nc1-2)c1c(F)cccc1F ; Cl] |
| 108 | 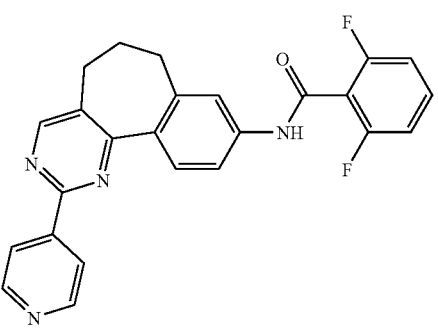 [SMILES: O=C(Nc1ccc2c(c1)CCCc1cnc(-c3ccncc3)nc1-2)c1c(F)cccc1F] |
| 109 | 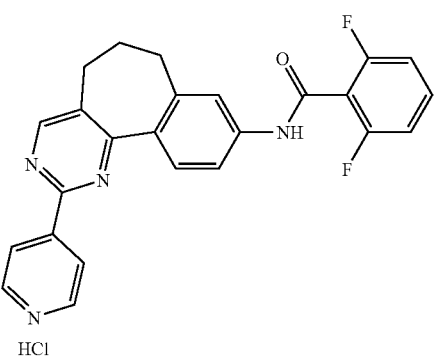 [SMILES: O=C(Nc1ccc2c(c1)CCCc1cnc(-c3ccncc3)nc1-2)c1c(F)cccc1F ; Cl] |
| 110 | 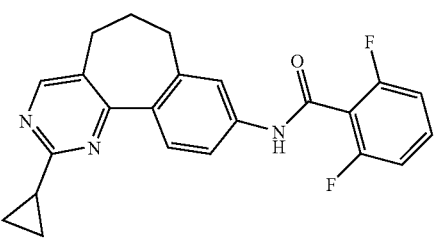 [SMILES: O=C(Nc1ccc2c(c1)CCCc1cnc(C3CC3)nc1-2)c1c(F)cccc1F] |

TABLE 1-continued
| Compound No. | Structure |
|---|---|
| 111 | 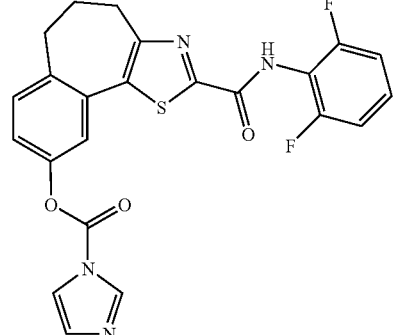 [SMILES: O=C(Nc1c(F)cccc1F)c1nc2c(s1)-c1cc(OC(=O)n3ccnc3)ccc1CCC2] |
| 112 | 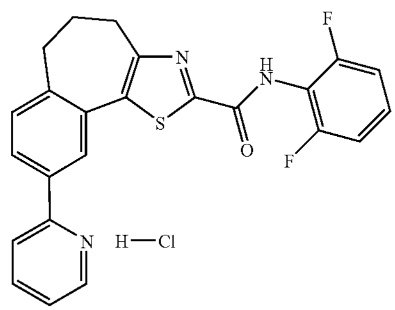 |
| 113 | 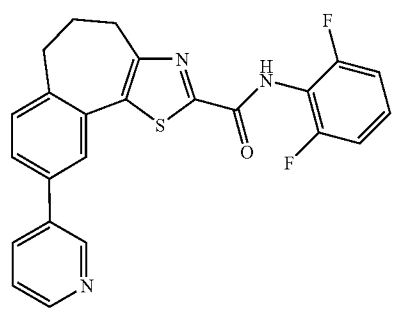 [SMILES: O=C(Nc1c(F)cccc1F)c1nc2c(s1)-c1cc(-c3cccnc3)ccc1CCC2] |
| 114 | 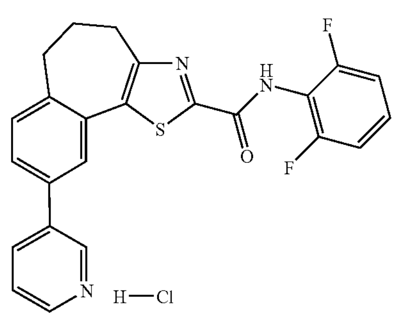 |
| 115 | 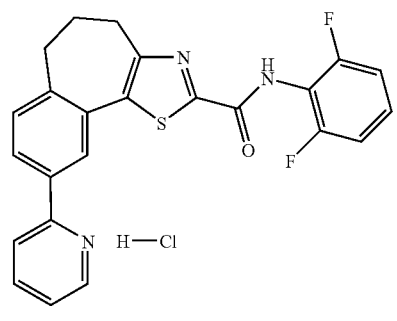 |
| 116 | |
| 117 | |
| 118 | |

TABLE 1-continued

| Compound No. | Structure |
|---|---|
| 119 | 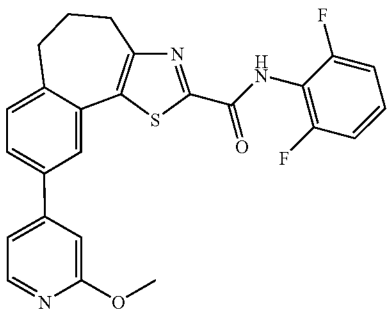 [SMILES: COc1cc(-c2ccc3c(c2)-c2sc(C(=O)Nc4c(F)cccc4F)nc2CCC3)ccn1] |
| 120 | 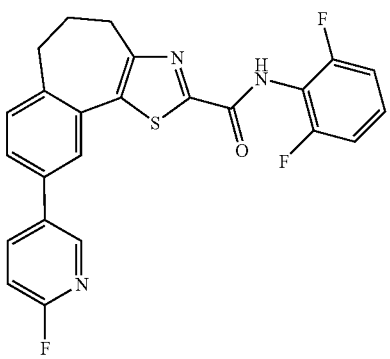 [SMILES: O=C(Nc1c(F)cccc1F)c1nc2c(s1)-c1cc(-c3ccc(F)nc3)ccc1CCC2] |
| 121 | 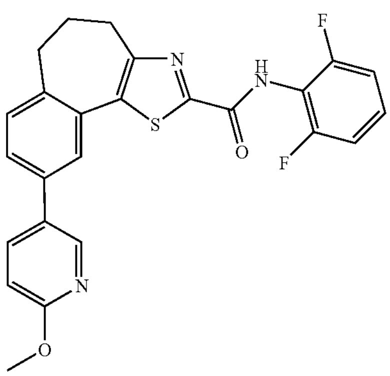 [SMILES: COc1ccc(-c2ccc3c(c2)-c2sc(C(=O)Nc4c(F)cccc4F)nc2CCC3)cn1] |
| 122 | 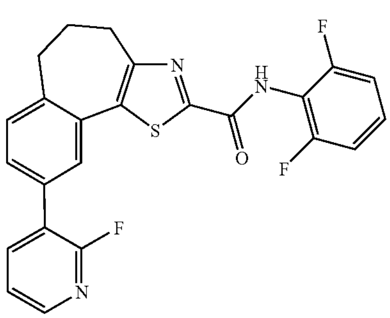 [SMILES: O=C(Nc1c(F)cccc1F)c1nc2c(s1)-c1cc(-c3cccnc3F)ccc1CCC2] |
| 123 | |
| 124 | |
| 125 | |
| 126 | H—Cl |

TABLE 1-continued
| Compound No. | Structure |
|---|---|
| 127 | 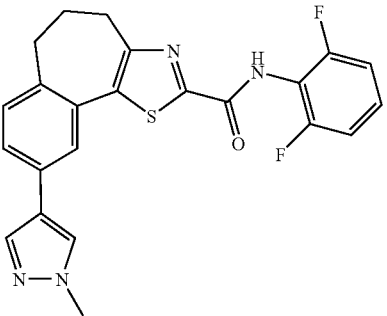 [SMILES: Cn1cc(-c2ccc3c(c2)-c2sc(C(=O)Nc4c(F)cccc4F)nc2CCC3)cn1] |
| 128 | 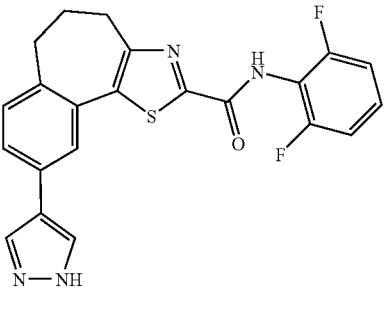 [SMILES: O=C(Nc1c(F)cccc1F)c1nc2c(s1)-c1cc(-c3cn[nH]c3)ccc1CCC2] |
| 129 | 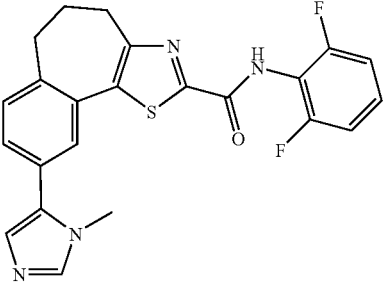 [SMILES: Cn1cncc1-c1ccc2c(c1)-c1sc(C(=O)Nc3c(F)cccc3F)nc1CCC2] |
| 130 | 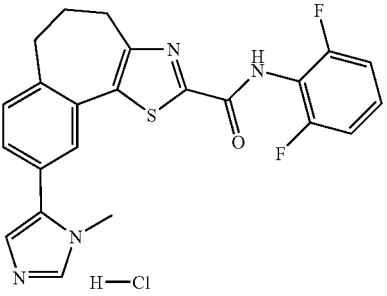 |
| 131 | 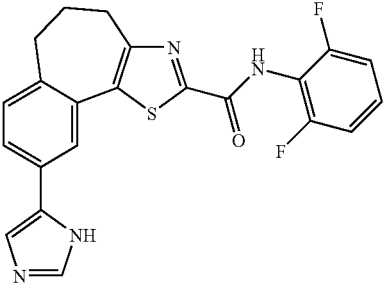 [SMILES: O=C(Nc1c(F)cccc1F)c1nc2c(s1)-c1cc(-c3cnc[nH]3)ccc1CCC2] |
| 132 | 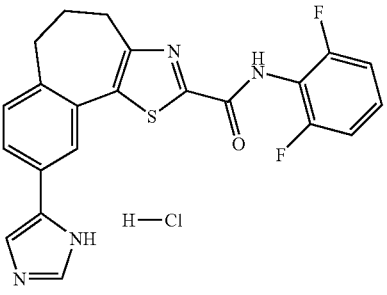 |
| 133 | 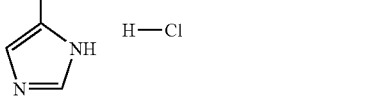 |
| 134 | 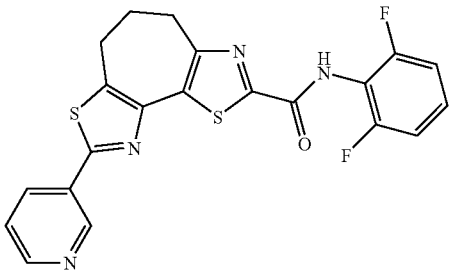 [SMILES: O=C(Nc1c(F)cccc1F)c1nc2c(s1)-c1nc(-c3cccnc3)sc1CCC2] |

TABLE 1-continued
| Compound No. | Structure |
|---|---|
| 135 | 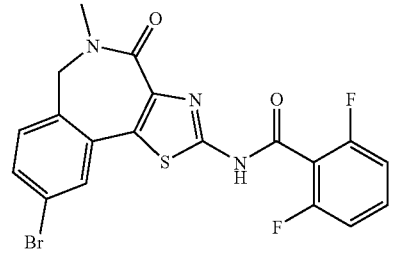 [SMILES: CN1Cc2ccc(Br)cc2-c2sc(NC(=O)c3c(F)cccc3F)nc2C1=O] |
| 136 | 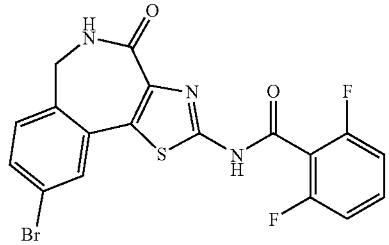 [SMILES: O=C1NCc2ccc(Br)cc2-c2sc(NC(=O)c3c(F)cccc3F)nc21] |
| 137 | 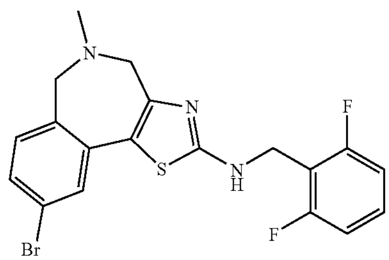 [SMILES: CN1Cc2ccc(Br)cc2-c2sc(NCc3c(F)cccc3F)nc2C1] |
| 138 | 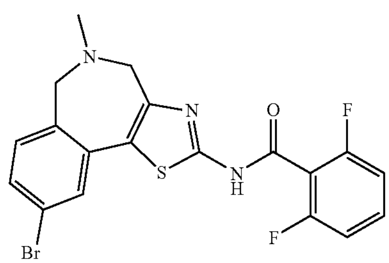 [SMILES: CN1Cc2ccc(Br)cc2-c2sc(NC(=O)c3c(F)cccc3F)nc2C1] |
| 139 | 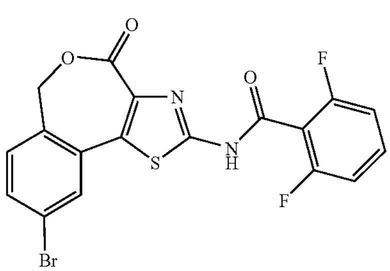 [SMILES: O=C1OCc2ccc(Br)cc2-c2sc(NC(=O)c3c(F)cccc3F)nc21] |
| 140 | 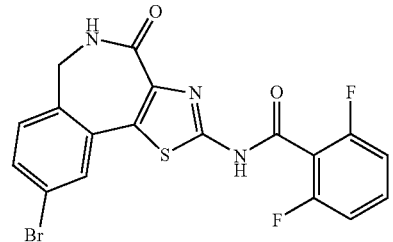 |
| 141 | 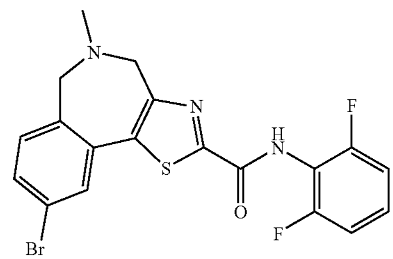 [SMILES: CN1Cc2ccc(Br)cc2-c2sc(C(=O)Nc3c(F)cccc3F)nc2C1] |
| 142 | 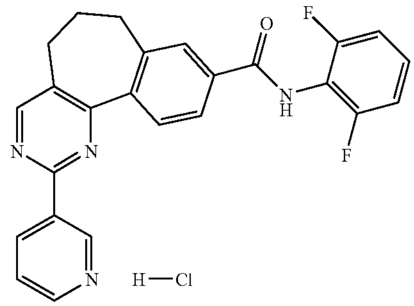 |
| 143 | 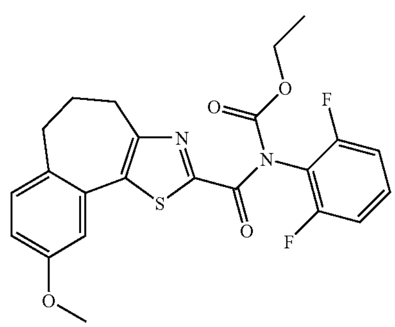 [SMILES: CCOC(=O)N(C(=O)c1nc2c(s1)-c1cc(OC)ccc1CCC2)c1c(F)cccc1F] |
| 144 | 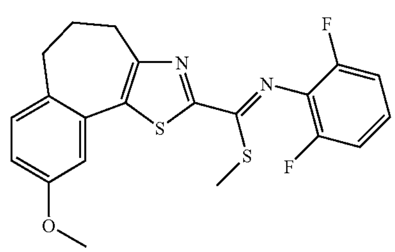 [SMILES: COc1ccc2c(c1)-c1sc(/C(=N/c3c(F)cccc3F)SC)nc1CCC2] |

TABLE 1-continued
| Compound No. | Structure |
|---|---|
| 145 | 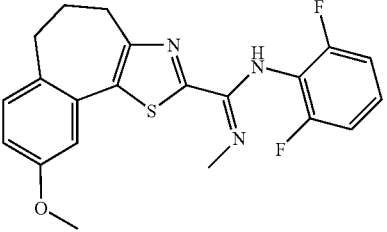 [SMILES: C/N=C(/Nc1c(F)cccc1F)c1nc2c(s1)-c1cc(OC)ccc1CCC2] |
| 146 | 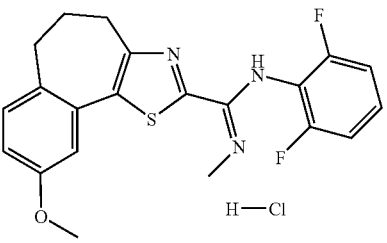 |
| 147 | 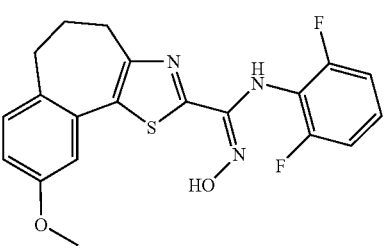 [SMILES: COc1ccc2c(c1)-c1sc(/C(=N\O)Nc3c(F)cccc3F)nc1CCC2] |
| 148 | 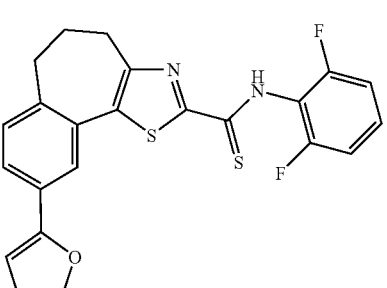 |
| 149 | 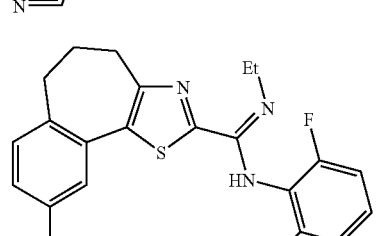 |
| 150 | 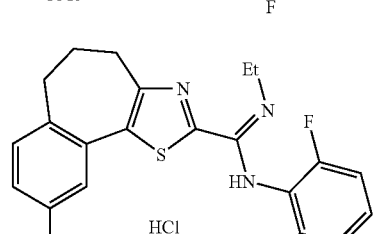 |
| 151 | 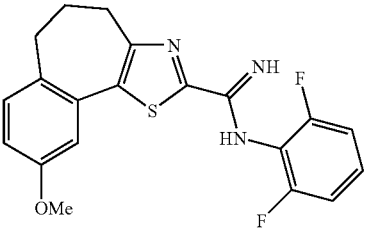 [SMILES: COc1ccc2c(c1)-c1sc(C(=N)Nc3c(F)cccc3F)nc1CCC2] |
| 152 | 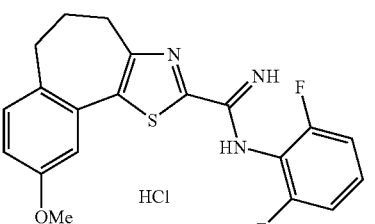 |
| 153 | 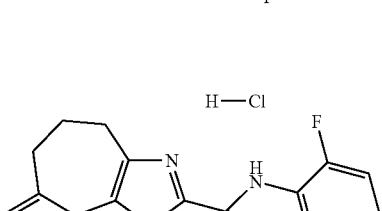 |
| 154 | 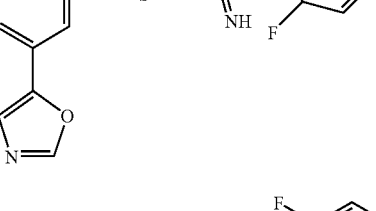 |
| 155 | 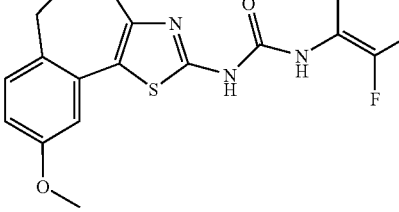 |

TABLE 1-continued

| Compound No. | Structure |
|---|---|
| 156 | |
| 157 | |
| 158 | |
| 159 | 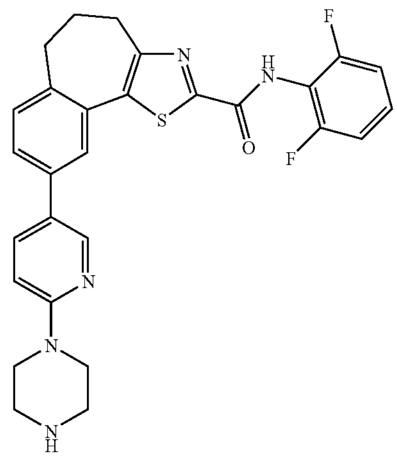 [SMILES: O=C(Nc1c(F)cccc1F)c1nc2c(s1)-c1cc(-c3ccc(N4CCNCC4)nc3)ccc1CCC2] |
| 160 | 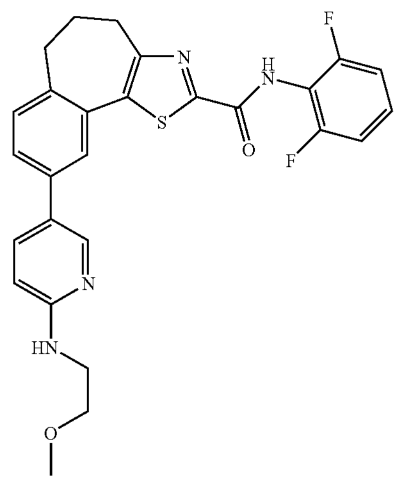 [SMILES: COCCNc1ccc(-c2ccc3c(c2)-c2sc(C(=O)Nc4c(F)cccc4F)nc2CCC3)cn1] |
| 161 | 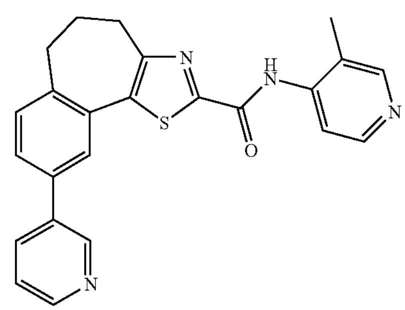 [SMILES: Cc1cnccc1NC(=O)c1nc2c(s1)-c1cc(-c3cccnc3)ccc1CCC2] |
| 162 | 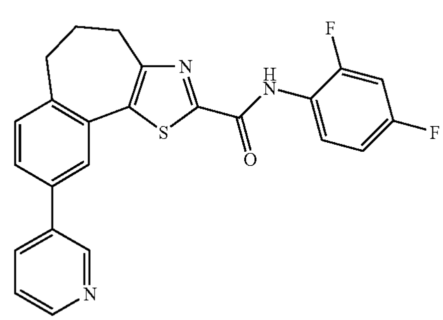 [SMILES: O=C(Nc1ccc(F)cc1F)c1nc2c(s1)-c1cc(-c3cccnc3)ccc1CCC2] |

TABLE 1-continued
| Compound No. | Structure |
|---|---|
| 163 | 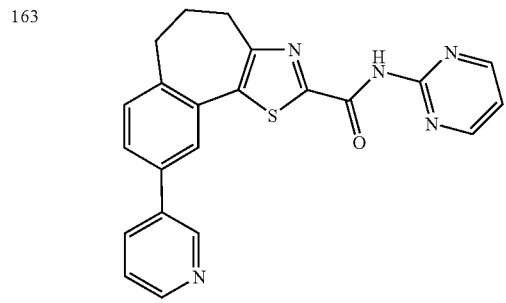 |
| 164 | 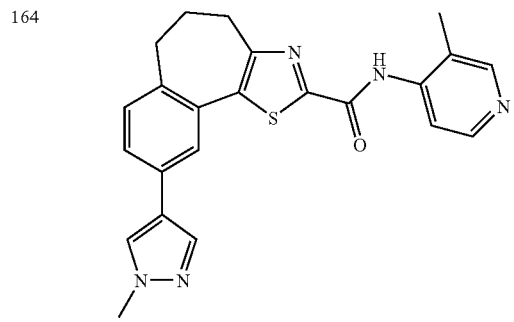 |
| 165 | 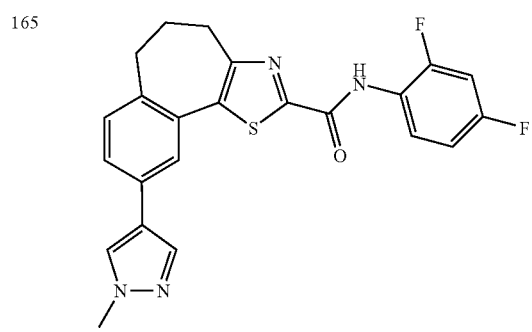 |
| 166 | 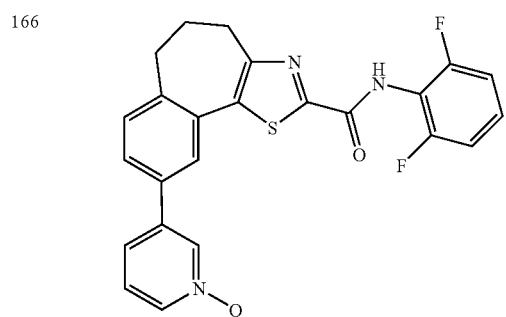 |
| 167 | 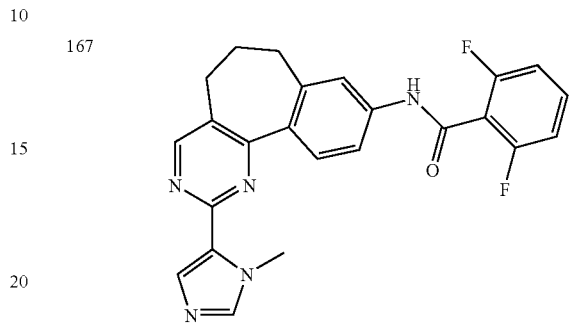 |
| 168 | 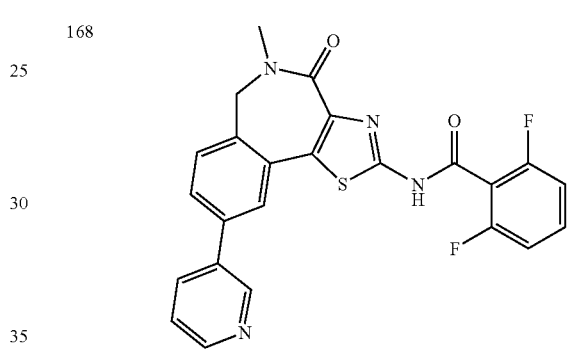 |
| 169 | 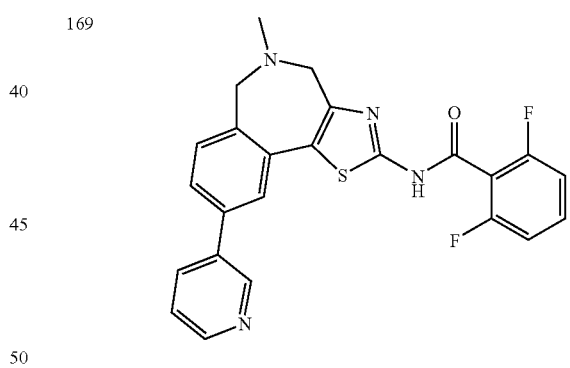 |
| 170 | 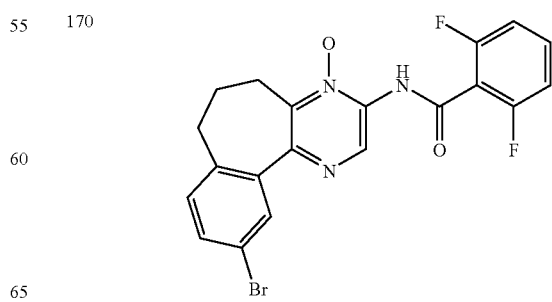 |

TABLE 1-continued

| Compound No. | Structure |
|---|---|
| 171 | 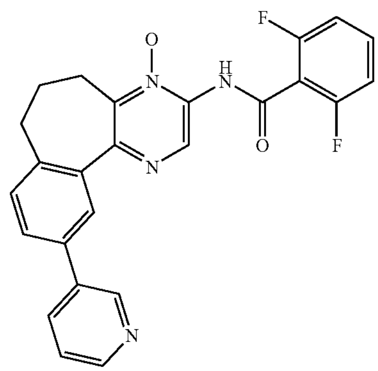 |
| 172 | 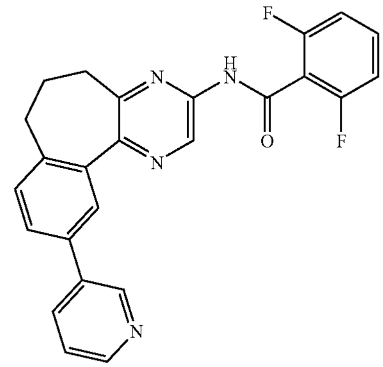 [SMILES: O=C(Nc1cnc2c(n1)CCCc1ccc(-c3cccnc3)cc1-2)c1c(F)cccc1F] |

Methods for Making Compounds of the Invention

Compounds of the invention can be obtained via standard, well-known synthetic methodology, see e.g., March, J. Advanced Organic Chemistry; Reactions Mechanisms, and Structure, 4th ed., 1992. In particular, compounds of the invention can be obtained by the following reaction schemes.

Scheme 1:

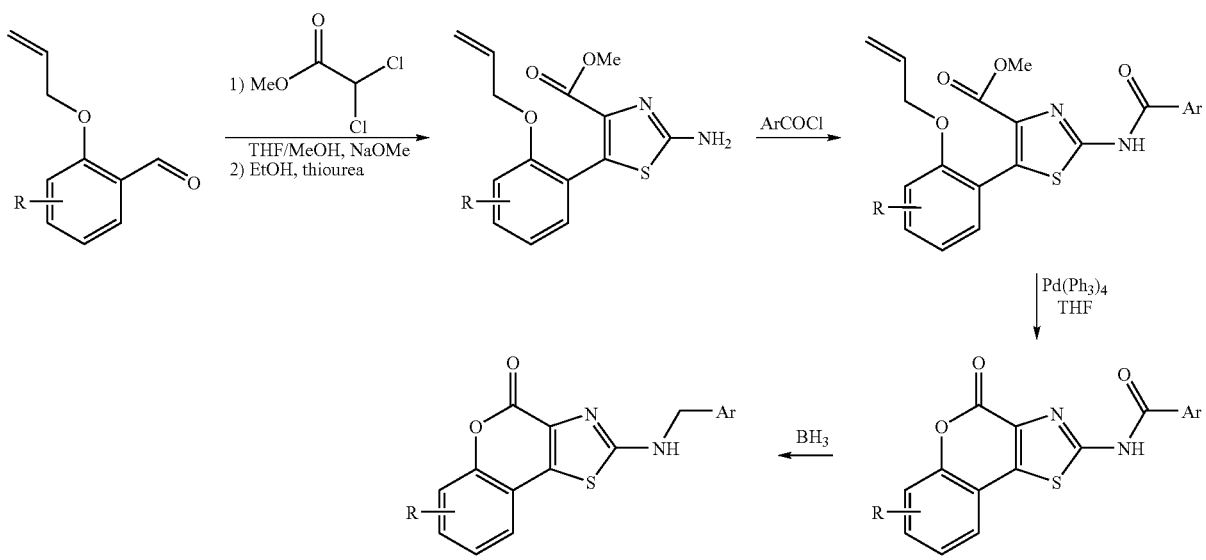

Scheme 2:

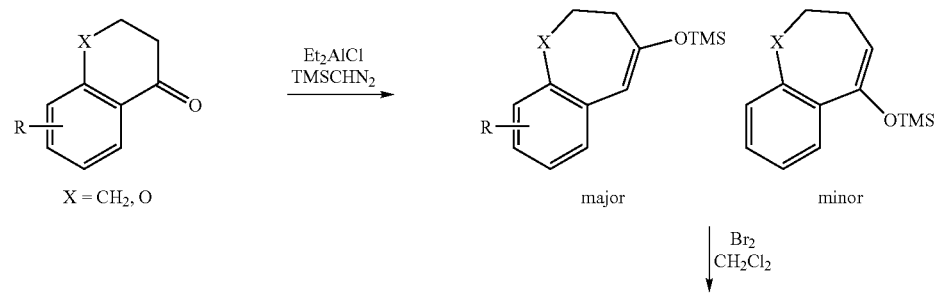

X = CH$_2$, O

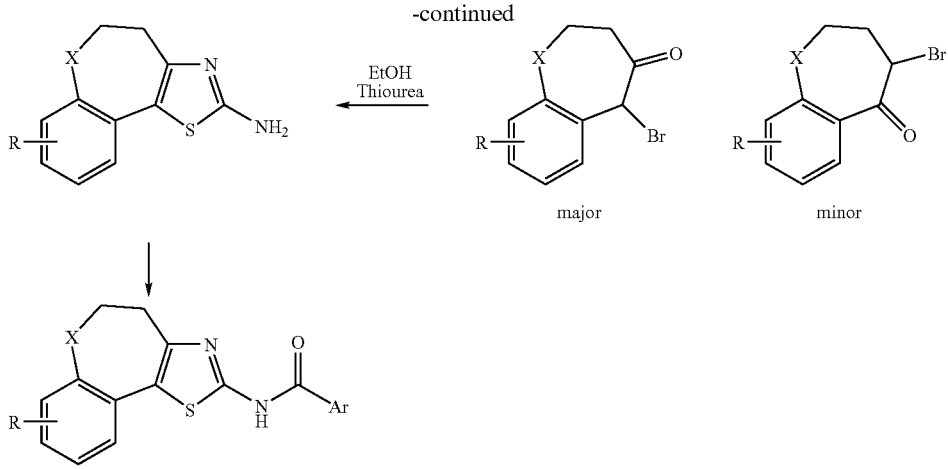

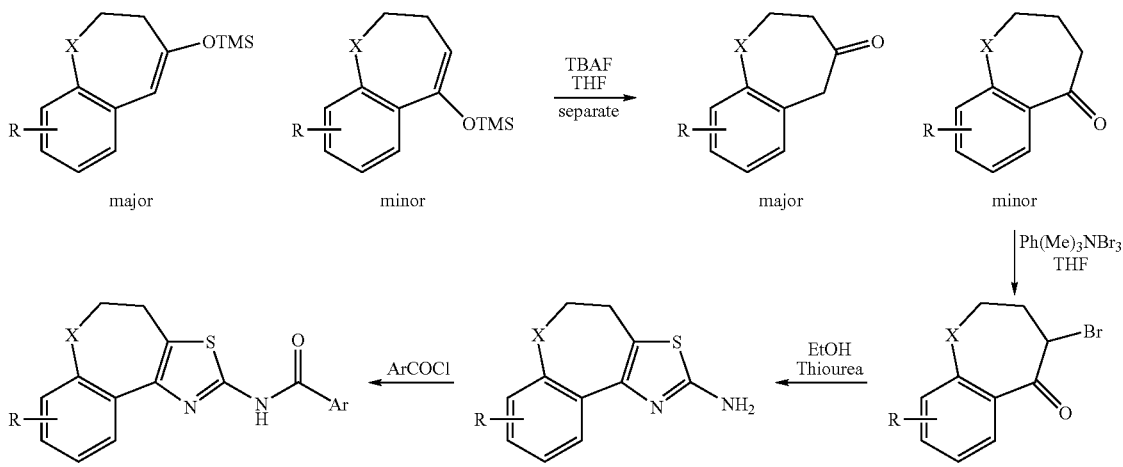

Scheme 3:

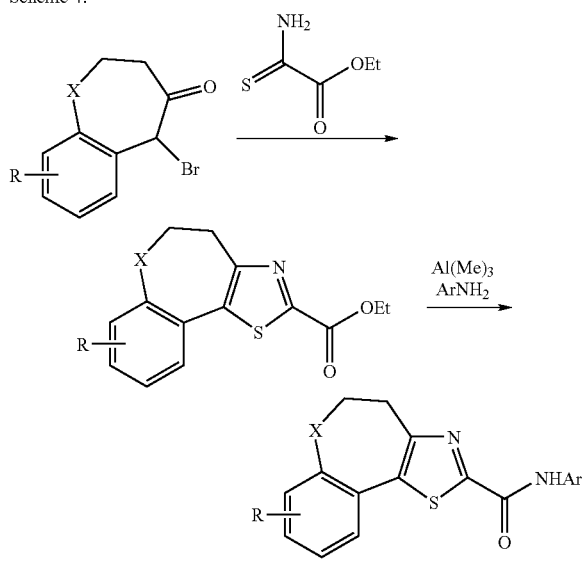

Scheme 4:

Mechanism of Action

Activation of T-lymphocytes in response to an antigen is dependent on calcium ion oscillations. Calcium ion oscillations in T-lymphocytes are triggered through stimulation of the T-cell antigen receptor, and involve calcium ion influx through the stored-operated $Ca^{2+}$-release-activated $Ca^{2+}$ (CRAC) channel. Although the molecular structure of the CRAC ion channel has not been identified, a detailed electrophysiological profile of the channel exist. Thus, inhibition of CRAC ion channels can be measured by measuring inhibition of the $I_{CRAC}$ current. Calcium ion oscillations in T-cells have been implicated in the activation of several transcription factors (e.g., NFAT, Oct/Oap and NFκB) which are critical for T-cell activation (Lewis, *Biochemical Society Transactions* (2003), 31:925-929, the entire teachings of which are incorporated herein by reference). Without wishing to be bound by any theory, it is believed that because the compounds of the invention inhibit the activity of CRAC ion channels, they inhibit immune cell activation.

Methods of Treatment and Prevention

In accordance with the invention, an effective amount of a compound of any one of formulas (I) through (XIV) or Table 1, or a pharmaceutically acceptable salt, solvate, clathrate, and prodrug thereof, or a pharmaceutical composition comprising a compound of any one of formulas (I) through (XIV) or Table 1, or a pharmaceutically acceptable salt, solvate, clathrate, and prodrug thereof, is administered to a patient in need of immunosuppression or in need of treatment or prevention of an inflammatory condition, an immune disorder, or an allergic disorder. Such patients may be treatment naïve or may experience partial or no response to conventional therapies.

Responsiveness of a particular inflammatory condition, immune disorder, or allergic disorder in a subject can be measured directly (e.g., measuring blood levels of inflammatory cytokines (such as IL-2, IL-4, IL-5, IL-13, GM-CSF, TNF-$\alpha$, IFN-$\gamma$ and the like) after administration of a compound of this invention), or can be inferred based on an understanding of disease etiology and progression. The compounds of any one of formulas (I) through (XIV), or Table 1, or pharmaceutically acceptable salts, solvates, clathrates, and prodrugs thereof can be assayed in vitro or in vivo, for the desired therapeutic or prophylactic activity, prior to use in humans. For example, known animal models of inflammatory conditions, immune disorders, or allergic disorders can be used to demonstrate the safety and efficacy of compounds of this invention.

Pharmaceutical Compositions and Dosage Forms

Pharmaceutical compositions and dosage forms of the invention comprise one or more active ingredients in relative amounts and formulated in such a way that a given pharmaceutical composition or dosage form can be used for immunosuppression or to treat or prevent inflammatory conditions, immune disorders, and allergic disorders. Preferred pharmaceutical compositions and dosage forms comprise a compound of any one of formulas (I) through (XIV), or Table 1, or a pharmaceutically acceptable prodrug, salt, solvate, or clathrate thereof, optionally in combination with one or more additional active agents.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form suitable for mucosal administration may contain a smaller amount of active ingredient(s) than an oral dosage form used to treat the same indication. This aspect of the invention will be readily apparent to those skilled in the art. See, e.g., Remington's Pharmaceutical Sciences (1990) 18th ed., Mack Publishing, Easton Pa.

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms.

The suitability of a particular excipient may also depend on the specific active ingredients in the dosage form. For example, the decomposition of some active ingredients can be accelerated by some excipients such as lactose, or when exposed to water. Active ingredients that comprise primary or secondary amines (e.g., N-desmethylvenlafaxine and N,N-didesmethylvenlafaxine) are particularly susceptible to such accelerated decomposition. Consequently, this invention encompasses pharmaceutical compositions and dosage forms that contain little, if any, lactose. As used herein, the term "lactose-free" means that the amount of lactose present, if any, is insufficient to substantially increase the degradation rate of an active ingredient. Lactose-free compositions of the invention can comprise excipients that are well known in the art and are listed, for example, in the U.S. Pharmocopia (USP) SP (XXI)/NF (XVI). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen (1995) Drug Stability: Principles & Practice, 2d. Ed., Marcel Dekker, NY, N.Y., 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizer" include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise a compound of any one of formulas (I) through (XIV), or Table 1, or a pharmaceutically acceptable salt, solvate, clathrate, or prodrug thereof in an amount of from about 1 mg to about 1000 mg, preferably in an amount of from about 50 mg to about 500 mg, and most preferably in an amount of from about 75 mg to about 350 mg. The typical total daily dosage of a compound of any one of formulas (I) through (XIV), or Table 1, or a pharmaceutically acceptable salt, solvate, clathrate, or prodrug thereof can range from about 1 mg to about 5000 mg per day, preferably in an amount from about 50 mg to about 1500 mg per day, more preferably from about 75 mg to about 1000 mg per day. It is within the skill of the art to determine the appropriate dose and dosage form for a given patient.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences (1990) 18th ed., Mack Publishing, Easton Pa.

Typical oral dosage forms of the invention are prepared by combining the active ingredient(s) in an admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. One specific binder is a mixture of microcrystalline cellulose and sodium carboxymethyl cellulose sold as AVICEL RC-581. Suitable anhydrous or low moisture excipients or additives include AVICEL-PH-103J and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pregelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Controlled Release Dosage Forms

Active ingredients of the invention can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

A particular extended release formulation of this invention comprises a therapeutically or prophylactically effective amount of a compound of formula (I) through (XIV), or Table 1, or a pharmaceutically acceptable salt, solvate, hydrate, clathrate, or prodrug thereof, in spheroids which further comprise microcrystalline cellulose and, optionally, hydroxypropylmethyl-cellulose coated with a mixture of ethyl cellulose and hydroxypropylmethylcellulose. Such extended release formulations can be prepared according to U.S. Pat. No. 6,274,171, the entire teachings of which are incorporated herein by reference.

A specific controlled-release formulation of this invention comprises from about 6% to about 40% a compound of any one of formulas (I) through (XIV), or Table 1 by weight, about 50% to about 94% microcrystalline cellulose, NF, by weight, and optionally from about 0.25% to about 1% by weight of hydroxypropyl-methylcellulose, USP, wherein the spheroids are coated with a film coating composition comprised of ethyl cellulose and hydroxypropylmethylcellulose.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences (1980 & 1990) 16th and 18th eds., Mack Publishing, Easton Pa. and Introduction to Pharmaceutical Dosage Forms (1985) 4th ed., Lea & Febiger, Philadelphia. Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences (1980 & 1990) 16th and 18th eds., Mack Publishing, Easton Pa.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Combination Therapy

The methods for immunosuppression or for treating or preventing inflammatory conditions and immune disorders in a patient in need thereof can further comprise administering to the patient being administered a compound of this invention, an effective amount of one or more other active agents. Such active agents may include those used conventionally for immunosuppression or for inflammatory conditions or immune disorders. These other active agents may also be those that provide other benefits when administered in combination with the compounds of this invention. For example, other therapeutic agents may include, without limitation, steroids, non-steroidal anti-inflammatory agents, antihistamines, analgesics, immunosuppressive agents and suitable mixtures thereof. In such combination therapy treatment, both the compounds of this invention and the other drug agent(s) are administered to a subject (e.g., humans, male or female) by conventional methods. The agents may be administered in a single dosage form or in separate dosage forms. Effective amounts of the other therapeutic agents and dosage forms are well known to those skilled in the art. It is well within the skilled artisan's purview to determine the other therapeutic agent's optimal effective-amount range.

In one embodiment of the invention where another therapeutic agent is administered to a subject, the effective amount of the compound of this invention is less than its effective amount when the other therapeutic agent is not administered. In another embodiment, the effective amount of the conventional agent is less than its effective amount when the compound of this invention is not administered. In this way, undesired side effects associated with high doses of either agent may be minimized. Other potential advantages (including without limitation improved dosing regimens and/or reduced drug cost) will be apparent to those of skill in the art.

In one embodiment relating to autoimmune and inflammatory conditions, the other therapeutic agent may be a steroid or a non-steroidal anti-inflammatory agent. Particularly useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For a more detailed description of the NSAIDs, see Paul A. Insel, *Analgesic-Antipyretic and Antiinflammatory Agents and Drugs Employed in the Treatment of Gout*, in *Goodman & Gilman's The Pharmacological Basis of Therapeutics* 617-57 (Perry B. Molinhoff and Raymond W. Ruddon eds., 9$^{th}$ ed 1996) and Glen R. Hanson, *Analgesic, Antipyretic and Anti-Inflammatory Drugs in Remington: The Science and Practice of Pharmacy Vol II* 1196-1221 (A. R. Gennaro ed. 19th ed. 1995) which are hereby incorporated by reference in their entireties.

Of particular relevance to allergic disorders, the other therapeutic agent may be an antihistamine. Useful antihistamines include, but are not limited to, loratadine, cetirizine, fexofenadine, desloratadine, diphenhydramine, chlorpheniramine, chlorcyclizine, pyrilamine, promethazine, terfenadine, doxepin, carbinoxamine, clemastine, tripelennamine, brompheniramine, hydroxyzine, cyclizine, meclizine, cyproheptadine, phenindamine, acrivastine, azelastine, levocabastine, and mixtures thereof. For a more detailed description of anthihistamines, see Goodman & Gilman's The Pharmacological Basis of Therapeutics (2001) 651-57, 10$^{th}$ ed).

Immunosuppressive agents include glucocorticoids, corticosteroids (such as Prednisone or Solumedrol), T cell blockers (such as cyclosporin A and FK506), purine analogs (such as azathioprine (Imuran)), pyrimidine analogs (such as cytosine arabinoside), alkylating agents (such as nitrogen mustard, phenylalanine mustard, buslfan, and cyclophosphamide), folic acid antagonists (such as aminopterin and methotrexate), antibiotics (such as rapamycin, actinomycin D, mitomycin C, puramycin, and chloramphenicol), human IgG, antilymphocyte globulin (ALG), and antibodies (such as anti-CD3 (OKT3), anti-CD4 (OKT4), anti-CD5, anti-CD7, anti-IL-2 receptor, anti-alpha/beta TCR, anti-ICAM-1, anti-CD20 (Rituxan), anti-IL-12 and antibodies to immunotoxins).

The foregoing and other useful combination therapies will be understood and appreciated by those of skill in the art. Potential advantages of such combination therapies include a different efficacy profile, the ability to use less of each of the individual active ingredients to minimize toxic side effects, synergistic improvements in efficacy, improved ease of administration or use and/or reduced overall expense of compound preparation or formulation.

Other Embodiments

The compounds of this invention may be used as research tools (for example, as a positive control for evaluating other potential CRAC inhibitors, or IL-2, IL-4, IL-5, IL-13, GM-CSF, TNF-α, and/or INF-α inhibitors). These and other uses and embodiments of the compounds and compositions of this invention will be apparent to those of ordinary skill in the art.

The invention is further defined by reference to the following examples describing in detail the preparation of compounds of the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Experimental Rationale

Without wishing to be bound by theory, it is believed that the compounds of this invention inhibit CRAC ion channels, thereby inhibiting production of IL-2 and other key cytokines involved with inflammatory and immune responses. The examples that follow demonstrate these properties.

Materials and General Methods

Reagents and solvents used below can be obtained from commercial sources such as Aldrich Chemical Co. (Milwaukee, Wis., USA). $^1$H-NMR and $^{13}$C-NMR spectra were recorded on a Varian 300 MHz NMR spectrometer. Significant peaks are tabulated in the order: δ (ppm): chemical shift, multiplicity (s, singlet; d, doublet; t, triplet; q, quartet; m, multiplet; br s, broad singlet), coupling constant(s) in Hertz (Hz) and number of protons.

Patch clamp experiments were performed in the tight-seal whole-cell configuration at 21-25° C. High resolution current recordings were acquired by a computer-based patch clamp amplifier system (EPC-9, HEKA, Lambrecht, Germany). Patch pipettes had resistances between 2-4 MΩ after filling with the standard intracellular solution. Immediately following establishment of the whole-cell configuration, voltage ramps of 50-200 ms duration spanning the voltage range of −100 to +100 mV were delivered at a rate of 0.5 Hz over a period of 300-400 seconds. All voltages were corrected for a liquid junction potential of 10 mV between external and internal solutions when using glutamate as the intracellular anion. Currents were filtered at 2.9 kHz and digitized at 10 μs intervals. Capacitive currents and series resistance were determined and corrected before each voltage ramp using the automatic capacitance compensation of the EPC-9. The low resolution temporal development of membrane currents was assessed by extracting the current amplitude at −80 mV or +80 mV from individual ramp current records.

Example 1

Synthesis of Representative Exemplary Compounds of this Invention

Compound 1:

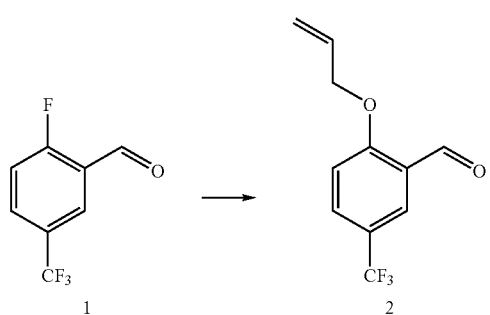 [SMILES: O=Cc1cc(C(F)(F)F)ccc1F ; C=CCOc1ccc(C(F)(F)F)cc1C=O]

Into a solution of 1 (3.00 g, 15.6 mmol) in allyl alcohol was added $K_2CO_3$ (2.80 g, 20.0 mmol). The mixture was heated to 60° C. for 5 hours, cooled to room temperature, taken up in ethyl acetate, washed with water, then with brine and dried ($Na_2SO_4$), filtered and concentrated. The residue was purified on silica (eluted with a solution of ethyl acetate:hexane, 1:19) to give 2 (2.15 g, 60% yield).

$^1$H NMR (300 MHz, CDCl$_3$) δ 10.52 (s, 1H), 8.12 (d, J=1.5 Hz, 1H), 7.76 (dd, J=1.5, 8 Hz, 1H), 7.07 (d, J=8 Hz, 1H), 6.18-5.84 (m, 1H), 5.36-5.16 (m, 2H), 4.75 (d, J=6 Hz, 2H).

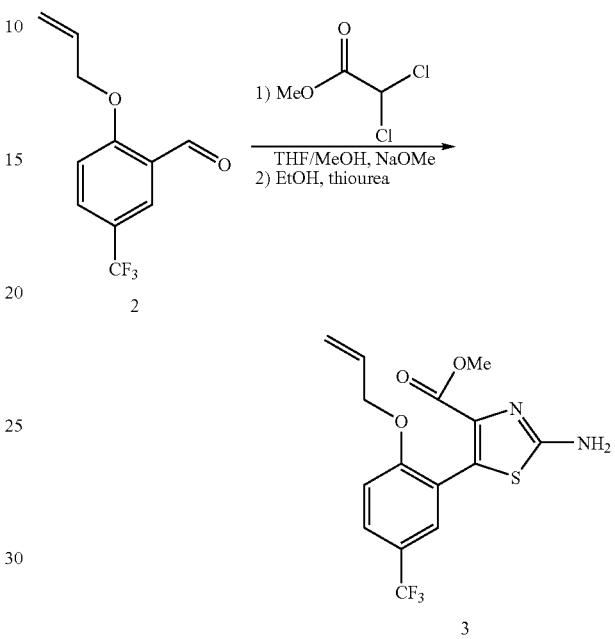

Into a mixture of 25% NaOMe in MeOH (2.30 mL, 10.0 mmol) and THF (40 mL) at

−78° C. was added dropwised a solution of 2 (2.15 g, 9.34 mmol) and methyl dichloroacetate (1.43 g, 10.0 mmol) in THF (10 mL). The mixture was stirred at −78° C. for 3 hours, then at room temperature overnight. The reaction mixture was quenched with the addition of ice, extracted with methylene chloride. The extract was washed with water, dried (Na$_2$SO$_4$), filtered and concentrated to give 3 (2.05 g, 61% yield).

$^1$H NMR (300 MHz, CDCl$_3$) δ 7.58 (d, J=8 Hz, 1H), 7.57 (s, 1H), 6.96 (d, J=8 Hz, 1H), 5.92 (tdd, J=5.4, 10.5, 17 Hz, 1H), 5.31 (d, J=17 Hz, 1H), 5.23 (d, J=10.5 Hz, 1H), 4.58 (d, J=5.4, 2H), 3.70 (s, 3H).

MS (ESI) [M+H$^+$]: 359

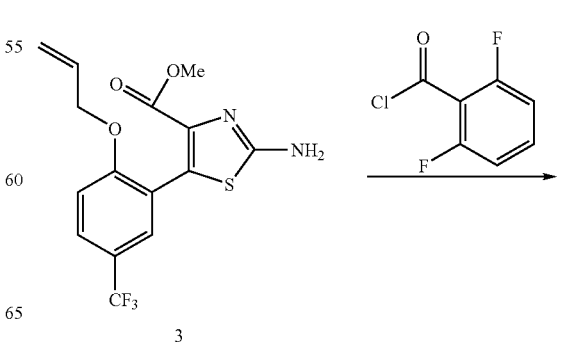

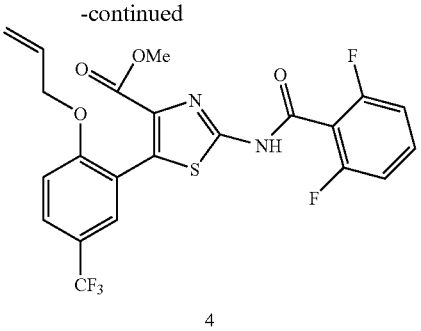

4

Into a solution of 3 (2.00 g, 5.60 mmol), triethylamine (1.01 g, 10.0 mmol), and catalytic amount of DMAP (20.0 mg, 0.16 mmol) in methylene chloride (20.0 mL) at room temperature was added 2,6-difluorobenzoylchloride. The mixture was stirred at room temperature overnight, concentrated under reduced pressure. The residue was taken up in MeOH (20.0 mL). $K_2CO_3$ (1.38 g, 10.0 mmol) was added. The mixture was stirred at room temperature for 1 hour, diluted with methylene chloride, washed with water, dried ($Na_2SO_4$), filtered and concentrated. The residue was purified on silica (eluted with methylene chloride) to give 4 (2.21 g, 79% yield).

$^1$H NMR (300 MHz, $CDCl_3$) δ 10.07 (bs, 1H), 7.63 (d, J=8.4 Hz, 1H), 7.60 (s, 1H), 7.56-7.46 (m, 1H), 7.07-7.01 (m, 3H), 5.94 (tdd, J=5.4, 10, 17 Hz, 1H), 5.32 (d, J=17 Hz, 1H), 5.26 (d, J=10 Hz, 1H), 4.61 (d, J=5.4, 2H), 3.71 (s, 3H).

MS (ESI) [M+H$^+$]: 499

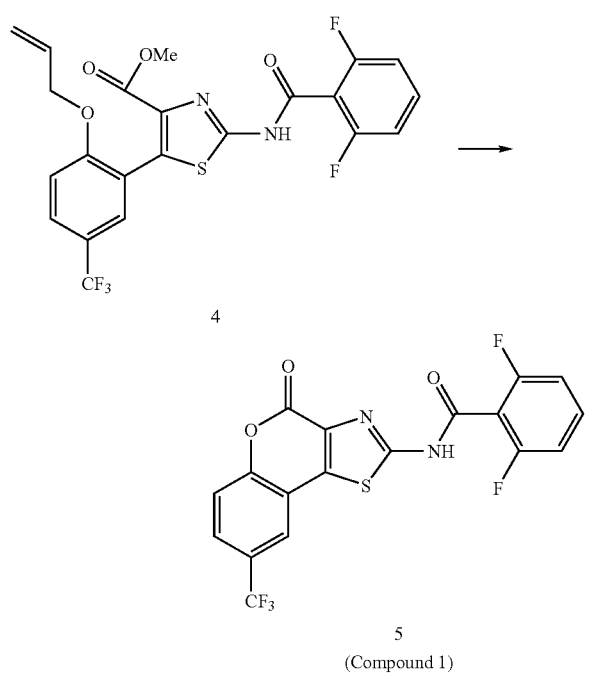

Into a solution of 4 (100 mg, 0.20 mmol) and pyrrolidine (36 mg, 0.5 mmol) in THF (2.0 mL) at room temperature was added palladium-tetrakis(triphenylphosphine) (20 mg, 0.02 mmol). The mixture was degassed by vacuum/nitrogen-fill method (3×) then heated to 65° C. for 2 hours, cooled to room temperature, concentrated under reduced pressure. Into the residue, trifluoroacetic acid (1.0 mL) was added. The mixture was heated to 65° C. for 2 hours, cooled to room temperature, concentrated under reduced pressure. The residue was taken up in methylene chloride. The resulting solution was washed with a solution of saturated $NaHCO_3$, dried ($Na_2SO_4$), filtered and concentrated. The residue was purified on silica (eluted with methylene chloride) to give 5 (Compound 1) (67 mg, 79% yield).

$^1$H NMR (300 MHz, $CDCl_3$) δ 7.96 (s, 1H), 7.78 (dd, J=1.9, 8.7 Hz, 1H), 7.60 (d, J=8.7 Hz, 1H), 7.60-7.50 (m, 1H), 7.12-7.06 (m, 2H).

MS (ESI) [M+H$^+$]: 427

Compound 7:

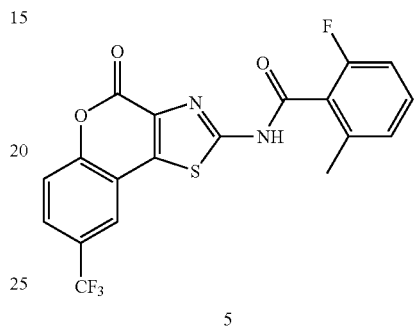

5

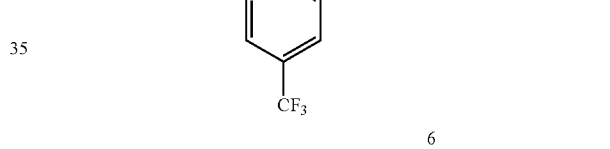

6
(Compound 7)

Into a solution of 5 (50.0 mg, 0.12 mmol) in THF at room temperature was added 1M borane-methyl sulfide complex in THF (0.5 mL, 0.5 mmol). The mixture was stirred at 60° C. overnight, cooled to room temperature, quenched with ice, extracted with methylene chloride. The extract was washed with water, dried ($Na_2SO_4$), filtered and concentrated. The residue was purified on silica (eluted with methylene chloride then with ethyl acetate) to give 6 (Compound 7) (11.0 mg).

$^1$H NMR (300 MHz, $CDCl_3$) δ 7.67 (s, 1H), 7.66 (d, J=8.7 Hz, 1H), 7.49 (d, J=8.7 Hz, 1H), 7.34-7.26 (m, 1H), 7.15-6.93 (m, 2H), 6.20 (bs, 1H), 4.76 (d, J=5.7 Hz, 2H).

MS (ESI) [M+H$^+$]: 413

Compound 2:

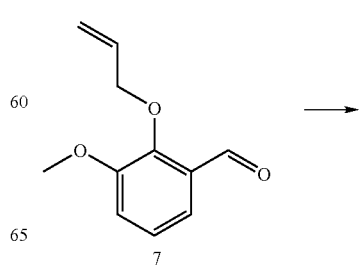

7

-continued

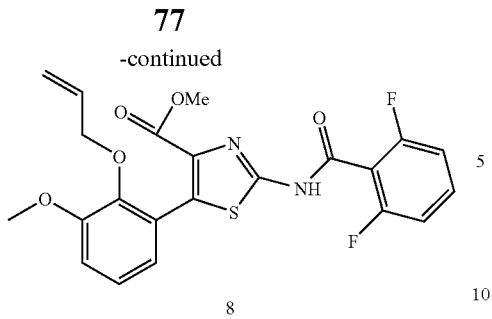
8

8 was prepared from aldehyde 7 as described for the preparation of 4.

$^1$H NMR (300 MHz, CDCl$_3$) δ 10.29 (bs, 1H), 7.54-7.44 (m, 1H), 7.13-6.91 (series of m, 5H), 5.84 (tdd, J=6.0, 9.0, 17.1 Hz, 1H), 5.15 (d, J=17.1 Hz, 1H), 5.18 (d, J=9.0 Hz, 1H), 4.40 (d, J=6.0 Hz, 2H), 3.84 (s, 3H), 3.68 (s, 3H).

MS (ESI) [M+H$^+$]: 461

9 (Compound 2) was prepared from 8 as described for the preparation of 5.

$^1$H NMR (300 MHz, CDCl$_3$) δ 7.60-6.90 (series of m, 6H), 4.95 (s, 3H).

MS (ESI) [M+H$^+$]: 389

Compound 15:

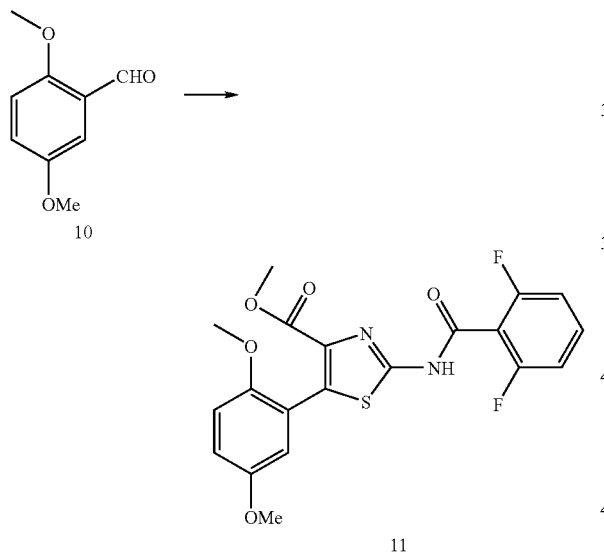

11 was prepared from 2,5-dimethoxybenzaldehyde as described for the preparation of 4.

$^1$H NMR (300 MHz, CDCl3+CD$_3$OD) δ 7.75-7.65 (m, 1H), 7.32 (t, J=8.0 Hz, 2H), 7.05 (br, 2H), 6.99 (s, 1H), 3.79 (s, 3H), 3.77 (s, 3H), 3.75 (s, 3H).

MS (ESI) [M+H$^+$]: 435.

-continued

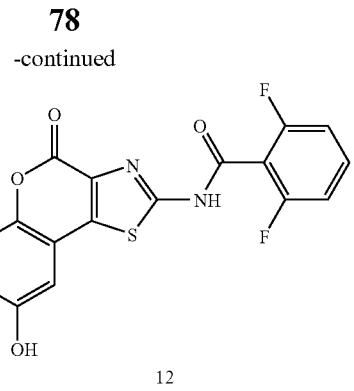
12
(Compound 15)

12 (Compound 15)

Into a solution of 11 (434 mg, 1 mmol) in CH$_2$Cl$_2$ (15.0 mL) at −78° C. under N$_2$ was added dropwised BBr$_3$ (1M solution in CH$_2$Cl$_2$, 2.0 mmol). The solution was stirred at −78° C. for 1 hour, warmed to room temperature for overnight. The reaction mixture was quenched with ice water, acidified with 1N HCl and extracted with methylene chloride (2×). The solution was treated with 0.1 mL of TFA and stirred at room temperature for 30 minutes. The solution was evaporated under reduced pressure. The residue was recrystallized in MeOH to give 12 (Compound 15) (230 mg, 61%) as a white solid.

$^1$H NMR (300 MHz, DMSO-d$_6$) δ 9.90 (brs, 1H, NH), 7.75-7.65 (m, 1H), 7.38 (d, J=9.1 Hz, 1H), 7.33 (t, J=8.2 Hz, 2H), 7.14 (d, J=2.2 Hz, 1H), 7.03 (dd, J=9.1, 2.2 Hz, 1H). MS (ESI) [M+H$^+$]: 375.

Compound 8:

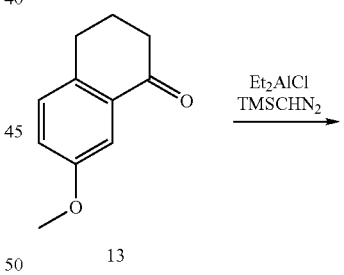
13

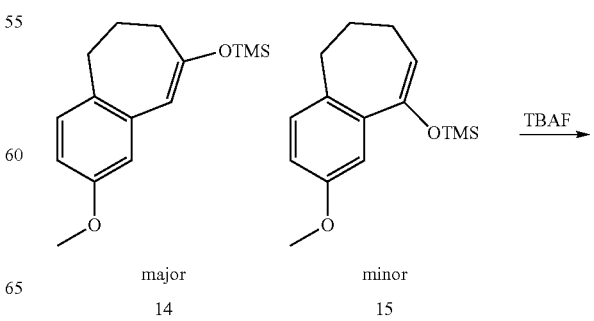
major
14 minor
15

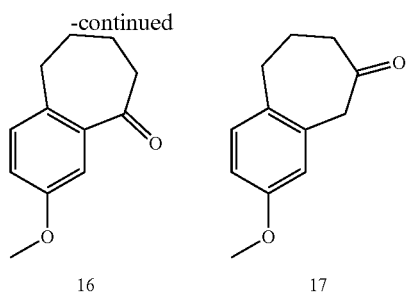

16          17

Into a solution of 13 (1.76 g, 10.0 mmol) in methylene chloride (20.0 mL) at 0° C. was added dropwised a solution of 1 M diethylaluminum chloride in hexane (15.0 mL, 15.0 mmol), followed by a solution of 2M (trimethylsilyl)diazomethane in diethyl ether (7.50 mL, 15.0 mmol). The mixture was stirred at 0° C. for 10 minutes, quenched by addition of ice, acidified with 1N HCl, extracted with methylene chloride (2×). The combined extracts were washed with water, dried (Na$_2$SO$_4$), filtered and concentrated. The residue was filtered through a short plug of silica (eluted with a solution of ethyl acetate:hexane, 1:9) to give a crude 9:1 mixture of 14:15 respectively (2.91 g). The mixture was taken up in THF (40 mL), cooled to 0° C. Into the mixture, a solution of 1M TBAF in THF was added (12.0 mL, 12.0 mmol). The resulting solution was stirred at 0° C. for 10 minutes, quenched with ice, extracted with methylene chloride (2×). The combined extracts were washed with water, dried (Na$_2$SO$_4$), filtered and concentrated. The residue was purified on silica (eluted with a solution of ethyl acetate:hexane, 1:9) to give 16 (168 mg) followed by 17 (1.12 g).

16: $^1$H NMR (300 MHz, CDCl$_3$) δ 7.26 (d, J=2.5 Hz, 1H), 7.10 (d, J=8.4 Hz, 1H), 3.78 (s, 3H), 3.69 (s, 2H), 2.90-2.84 (m, 2H), 2.58-2.52 (m, 2H), 2.00-1.91 (m, 2H).

17: $^1$H NMR (300 MHz, CDCl$_3$) δ 7.07 (d, J=8.4 Hz, 1H), 6.74-6.66 (m, 2H), 6.73 (dd, J=2.7, 8.4 Hz, 1H), 3.83 (s, 3H), 2.83-2.75 (m, 4H), 2.13-2.04 (m, 2H).

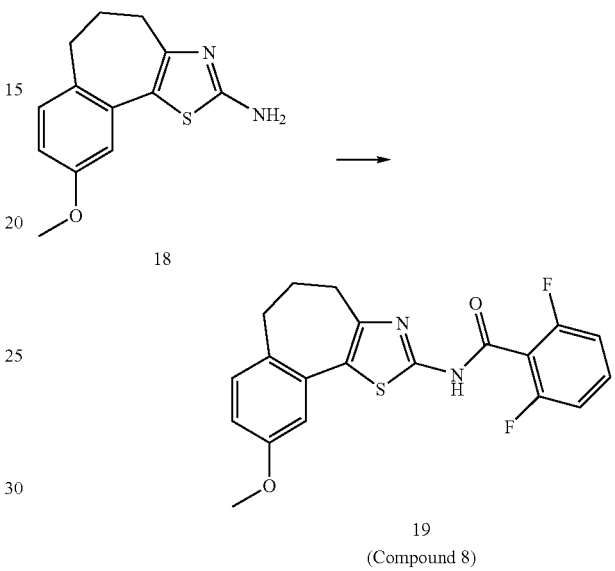

Into a solution of 17 (1.12 g, 5.86 mmol) in THF (20 mL) at 0° C. was added phenyltrimethylammonium tribromide (2.20 g, 5.86 mmol). The mixture was stirred at 0° C. for 1 hour, quenched by ice addition, extracted with methylene chloride (2×). The combined extracted was dried (Na$_2$SO$_4$), filtered and concentrated. The residue was purified on silica (eluted with methylene chloride) to give 18 (780 mg).

18 can also be prepared by direct bromination of the mixture of the enol silyl ether 14 and 15, followed by cyclization with thiourea.

$^1$H NMR (300 MHz, CDCl$_3$) δ 6.98 (d, J=8.4 Hz, 1H), 6.75 (d, J=2.7 Hz, 1H), 6.60 (dd, J=2.7, 8.4 Hz, 1H), 3.75 (s, 3H), 2.87-2.62 (m, 4H), 2.02-1.90 (m, 2H).

MS (ESI) [M+H$^+$]: 247

19 (Compound 8) was prepared from 18 as described for the preparation of 4.

$^1$H NMR (300 MHz, CDCl$_3$) δ 7.48-7.39 (m, 1H), 7.06-6.94 (m, 4H), 6.73 (dd, J=2.4, 8.4 Hz, 1H), 3.83 (s, 3H), 2.65-2.47 (m, 4H), 1.95-1.82 (m, 2H).

MS (ESI) [M+H$^+$]: 387

Compound 3:

(Compound 3) was prepared from 18 as described for the preparation of 4 using the corresponding acid chloride.

$^1$H NMR (300 MHz, CDCl$_3$) δ 8.71 (d, J=2.7 Hz, 1H), 8.67 (d, J=4.8 Hz, 1H), 8.05 (dd, J=5.4, 6.0 Hz, 1H), 7.09 (d, J=8.4 Hz, 1H), 7.05 (d, J=2.7 Hz, 1H), 6.74 (dd, J=2.7, 8.4 Hz, 1H), 3.82 (s, 3H), 3.00 (dd, J=6.6, 7.2 Hz, 2H), 2.78-2.74 (m, 2H), 2.20-2.10 (m, 2H).

MS (ESI) [M+H$^+$]: 370

Compound 17:

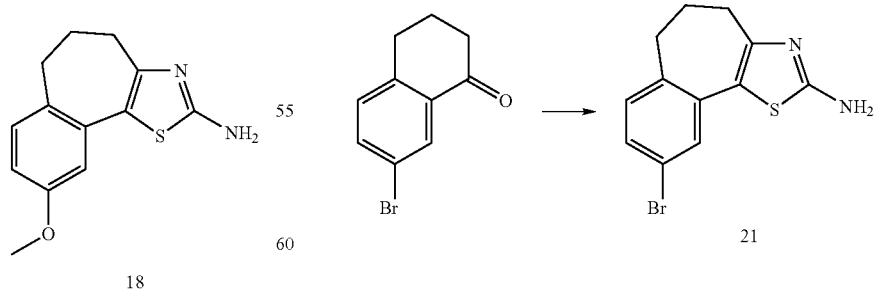

21 was prepared from 7-bromo-1-tetralone as described for the preparation of 18.

$^1$H NMR (300 MHz, CDCl$_3$) δ 7.37 (d, J=1.9 Hz, 1H), 7.19 (dd, J=8.0, 1.9 Hz, 1H), 6.98 (d, J=8.0 Hz, 1H), 2.90 (t, J=6.9 Hz, 2H), 2.83-2.74 (m, 2H), 2.02-1.94 (m, 2H).

MS (ESI) [M+H$^+$]: 297, 295.

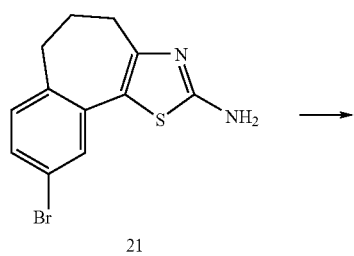

21

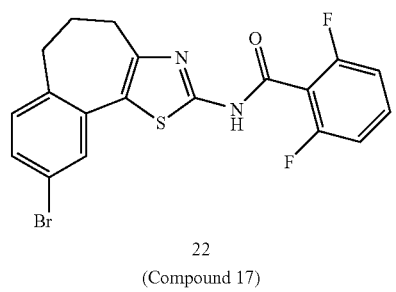

22
(Compound 17)

22 (Compound 17) was prepared from 21 as described for the preparation of 4.

$^1$H NMR (300 MHz, CDCl$_3$) δ 10.5 (brs, 1H, NH), 7.68 (d, J=1.9 Hz, 1H), 7.53-7.43 (m, 1H), 7.28 (dd, J=8.0, 1.9 Hz, 1H), 7.03 (d, J=8.0 Hz, 1H), 7.02 (t, J=8.0 Hz, 2H), 2.77-2.69 (m, 2H), 2.07-1.94 (m, 2H).

MS (ESI) [M+H$^+$]: 437, 435.

Compound 59:

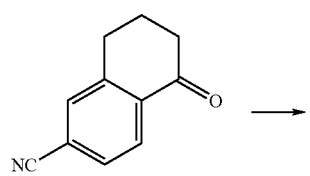

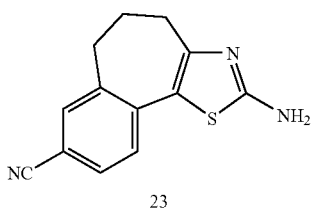

23

23 was prepared from 6-nitrile-1-tetralone as described for the preparation of 18.

$^1$H NMR (300 MHz, CDCl$_3$+CD$_3$OD) δ 7.58 (dd, J=8.0, 1.6 Hz, 1H), 7.52 (s, 1H), 7.39 (d, J=8.0 Hz, 1H) 3.04 (t, J=7.0 Hz, 2H), 2.96-2.92 (m, 2H), 2.13-2.05 (m, 2H).

MS (ESI) [M+H$^+$]: 242.

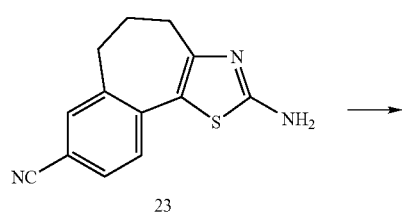

23

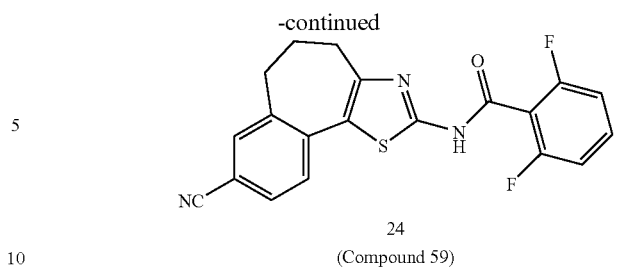

24
(Compound 59)

24 (Compound 59) was prepared from 23 as described for the preparation of 4.

$^1$H NMR (300 MHz, CDCl$_3$) δ 7.61 (d, J=8.0 Hz, 1H), 7.54-7.45 (m, 3H), 7.01 (t, J=8.2 Hz, 2H), 2.78-2.74 (m, 2H), 2.66 (t, J=7.2 Hz, 2H), 1.99-1.91 (m, 2H).

MS (ESI) [M+H$^+$]: 382.

Compound 60:

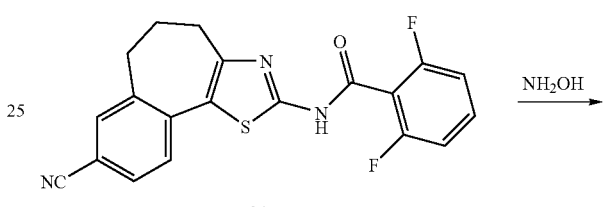

24

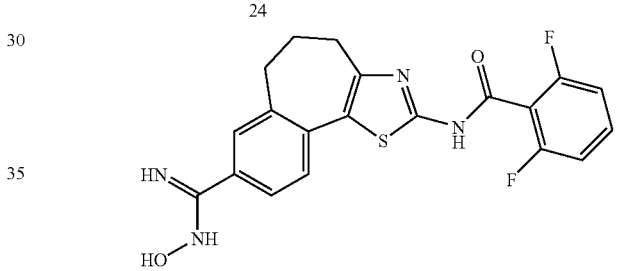

25

Into a solution of 24 (38.1 mg, 0.1 mmol) in 5 mL of MeOH was added hydroxyamine hydrochloride (21 mg, 0.3 mmol) and NaHCO$_3$ (50 mg, 0.6 mmol). The mixture was heated to reflux for 5 hours. After the reaction was cooled to room temperature, the reaction mixture was concentrated under reduced pressure. The residue was taken up with 20 mL of Et$_2$O. The solution was washed with a solution of saturated NH$_4$Cl, dried (Na$_2$SO$_4$), filtered and concentrated. The residue was purified by flash chromatography on silica gel (eluted with ethyl acetate-hexane mixtures) to give 25 (36 mg) as a white solid.

MS (ESI) [M+H$^+$]: 415.

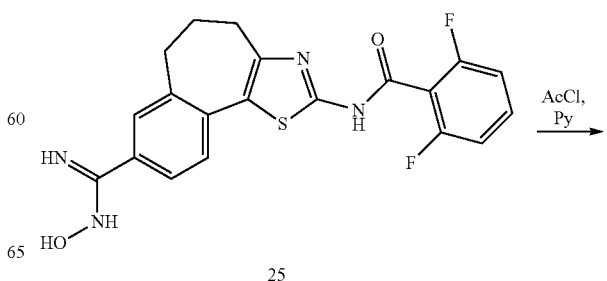

25

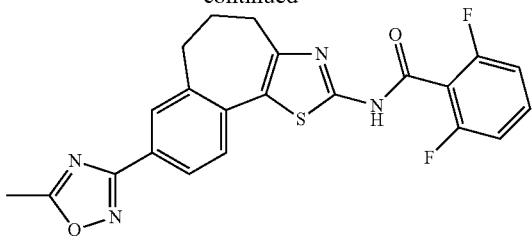

26
(Compound 60)

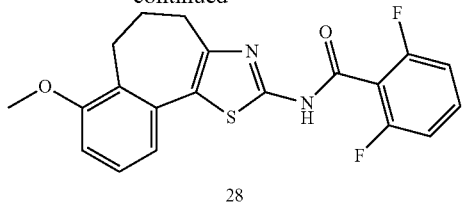

28
(Compound 12)

Into a solution of 25 (21 mg, 0.05 mmol) in 1 mL of AcCl was added 0.1 mL of pyridine. The mixture was heated at 100° C. for 3 hours under $N_2$. The reaction was concentrated under reduced pressure. The residue was taken up with 10 mL of $Et_2O$, the solution was washed with a saturated solution of $NaHCO_3$ then with a saturated solution of $NH_4Cl$. The organic solution was dried ($Na_2SO_4$), filtered and concentrated under reduced pressure. The residue was purified by flash chromatography on silica gel (eluted with ethyl acetate-hexane mixtures) to give 26 (Compound 60) (12 mg, 55%) as a white solid.

$^1$H NMR (300 MHz, $CDCl_3$) δ 10.20 (br s, 1H, NH), 7.91 (dd, J=8.2, 1.8 Hz, 1H), 7.89 (d, J=1.9 Hz, 1H), 7.64 (d, J=8.2 Hz, 1H), 7.54-7.45 (m, 1H), 7.04 (t, J=8.2 Hz, 2H), 2.92-2.81 (m, 4H), 2.68 (s, 3H), 2.09-2.01 (m, 2H).

MS (ESI) [M+H$^+$]: 439.

Compound 12:

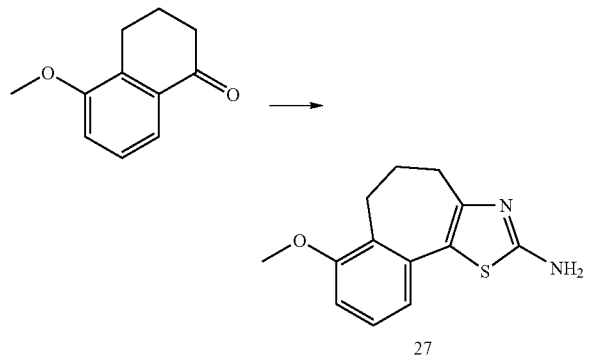

27 was prepared from 5-methoxy-1-tetralone as described for the preparation of 18.

$^1$H NMR (300 MHz, $CDCl_3$) δ 8.42 (br s, 2H, $NH_2$), 7.20 (t, J=8.0 Hz, 1H), 6.82 (d, J=8.0 Hz, 1H), 6.79 (d, J=8.0 Hz, 1H), 3.85 (s, 3H), 3.00-2.92 (m, 4H), 2.04-1.96 (m, 2H).

MS (ESI) [M+H$^+$]: 247.

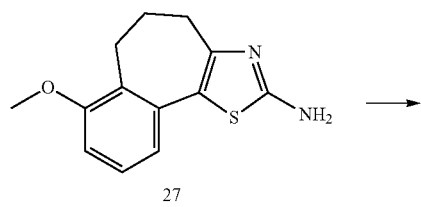

27

28 (Compound 12) was prepared from 27 as described for the preparation of 4.

$^1$H NMR (300 MHz, $CDCl_3$) δ 7.50-7.40 (m, 1H), 7.20 (t, J=7.7 Hz, 1H), 7.14 (d, J=7.7 Hz, 1H), 7.00 (t, d=8.2 Hz, 2H), 6.82 (d, J=7.7 Hz, 1H), 3.85 (s, 3H), 2.81-2.77 (m, 2H), 2.65 (t, J=7.2 Hz, 2H), 2.02-1.94 (m, 2H).

MS (ESI) [M+H$^+$]: 387.

29 to 38 were prepared similarly from 27 as described for the preparation of 4 using the corresponding acid chloride.

Compound 13:
$^1$H NMR (300 MHz, $CDCl_3$) δ 8.58 (s, 1H), 8.54 (d, J=5.0 Hz, 1H), 7.36 (d, J=5.0 Hz, 1H), 7.21 (t, J=7.7 Hz, 1H), 7.14 (dd, J=7.7, 1.1 Hz, 1H), 6.82 (d, J=7.7 Hz, 1H), 3.85 (s, 3H), 2.80-2.76 (m, 2H), 2.52 (s, 3H), 2.49 (t, J=7.3 Hz, 2H), 2.03-1.94 (m, 2H).

MS (ESI) [M+H$^+$]: 366.

Compound 14:
$^1$H NMR (300 MHz, $CDCl_3$) 6.8.62 (d, J=2.4 Hz, 1H), 8.58 (d, J=4.9 Hz, 1H), 7.93 (dd, J=6.1, 5.2 Hz, 1H), 7.12 (dd, J=7.9, 7.7 Hz, 1H), 7.04 (d, J=7.7 Hz, 1H), 6.75 (d, J=7.9 Hz, 1H), 3.77 (s, 3H), 2.85 (t, J=7.1 Hz, 2H), 2.80-2.76 (m, 2H), 2.04-1.94 (m, 2H). MS (ESI) [M+H$^+$]: 370.

Compound 43:
$^1$H NMR (300 MHz, $CDCl_3$) δ 8.99 (d, J=4.2 Hz, 1H), 9.40 (d, J=8.6 Hz, 1H), 8.17 (d, J=8.6 Hz, 1H), 7.81 (dt, J=1.1, 8.6 Hz, 1H), 7.65 (dt, J=1.1, 8.6 Hz, 1H), 7.23 (d, J=4.2 Hz, 1H), 7.23 (t, J=8.0 Hz, 1H), 7.15 (d, J=8.0 Hz, 1H), 6.84 (d, J=8.0 Hz, 1H), 3.86 (s, 3H), 2.79-2.75 (m, 2H), 2.51 (t, J=7.2 Hz, 2H), 1.94-1.86 (m, 1H). MS (ESI) [M+H$^+$]: 402.

Compound 46:
$^1$H NMR (300 MHz, $CDCl_3$) δ 8.55 (dd, J=4.7, 1.9 Hz, 1H), 8.21 (dd, J=6.7, 1.9 Hz, 1H), 7.42 (dd, J=6.7, 4.7 Hz, 1H), 7.20 (dd, J=8.0, 7.7 Hz, 1H), 7.14 (dd, J=7.7, 1.1 Hz, 1H), 6.83 (dd, J=8.0, 1.1 Hz, 1H), 3.86 (s, 3H), 2.84-2.80 (m, 2H), 2.72 (t, J=7.4 Hz, 2H), 2.10-2.00 (m, 2H). MS (ESI) [M+H$^+$]: 386.

Compound 49:
$^1$H NMR (300 MHz, $CDCl_3$) δ 8.48 (d, J=2.5 Hz, 1H), 8.21 (d, J=2.5 Hz, 1H), 7.21 (dd, J=8.0, 7.9 Hz, 1H), 7.13 (dd, J=8.0, 1.1 Hz, 1H), 6.83 (dd, J=7.9, 1.1 Hz, 1H), 3.86 (s, 3H), 2.85-2.81 (m, 2H), 2.73 (t, J=7.1 Hz, 2H), 2.09-2.00 (m, 2H). MS (ESI) [M+H$^+$]: 420.

Compound 47:
$^1$H NMR (300 MHz, $CDCl_3$) δ 9.17 (br s, 1H), 8.82 (d, J=2.2 Hz, 1H), 8.44 (dd, J=2.2, 1.9 Hz, 1H), 7.22 (dd, J=8.0, 7.7 Hz, 1H), 7.16 (d, J=7.7 Hz, 1H), 6.84 (d, J=8.0 Hz, 1H), 3.86 (s, 3H), 2.91-2.86 (m, 4H), 2.12-2.02 (m, 2H). MS (ESI) [M+H$^+$]: 432, 430.

Compound 50:
$^1$H NMR (300 MHz, $CDCl_3$) δ 8.07 (d, J=7.2 Hz, 1H), 7.21 (t, J=8.0 Hz, 1H), 7.11 (dd, J=8.0, 1.1 Hz, 1H), 6.83 (d, J=8.0 Hz, 1H), 3.85 (s, 3H), 2.86-2.84 (m, 2H), 2.79 (t, J=7.3 Hz, 2H), 2.10-2.02 (m, 2H).

MS (ESI) [M+H$^+$]: 438.

Compound 48:

¹H NMR (300 MHz, CDCl₃) δ 8.15 (s, 1H), 7.19 (dd, J=8.0, 7.7 Hz, 1H), 7.11 (dd, J=7.7, 1.1 Hz, 1H), 6.82 (dd, J=8.0, 1.1 Hz, 1H), 3.93 (s, 3H), 3.86 (s, 3H), 2.92 (t, J=7.3 Hz, 1H), 2.89-2.84 (m, 2H), 2.13-2.05 (m, 2H).

MS (ESI) [M+H⁺]: 389.

Compound 45:

¹H NMR (300 MHz, CDCl₃) δ 9.95 (br s, 1H, NH), 7.20 (dd, J=8.0, 7.7 Hz, 1H), 7.13 (d, J=7.7 Hz, 1H), 6.83 (d, J=8.0 Hz, 1H), 3.86 (s, 3H), 2.87-2.80 (m, 4H), 2.69 (s, 3H), 2.53 (s, 3H), 2.12-2.04 (m, 2H).

MS (ESI) [M+H⁺]: 370.

Compound 44:

¹H NMR (300 MHz, CDCl₃) δ 9.40 (br s, 1H, NH), 7.22 (dd, J=8.0, 7.7 Hz, 1H), 7.11 (d, J=7.7 Hz, 1H), 6.81 (d, J=8.0 Hz, 1H), 6.42 (s, 1H), 3.85 (s, 3H), 2.91-2.83 (m, 4H), 2.40 (s, 3H), 2.14-2.06 (m, 2H).

MS (ESI) [M+H⁺]: 423.

Compound 51:

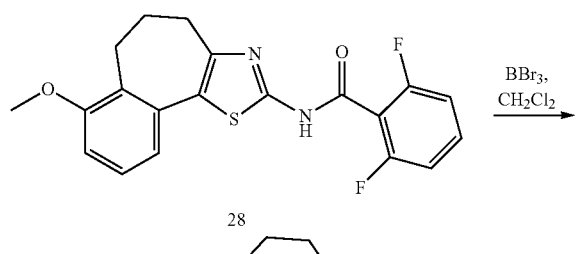

28

BBr₃, CH₂Cl₂ →

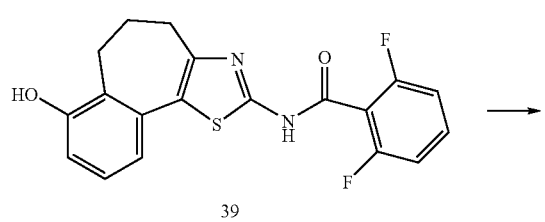

39
(Compound 51)

To a solution of 28 (386 mg, 1 mmol) in CH₂Cl₂ (10 mL) at −78° C. was added a solution of 1 M BBr₃ in CH₂Cl₂ (2.0 mL, 2.0 mmol). The mixture was kept at −78° C. for 30 minutes then to 0° C. for 1.5 hours. The mixture was quenched by addition of a saturated solution of NaHCO₃, diluted with ethyl acetate. The organic layer was washed with H₂O, brine, dried (MgSO₄), filtered and concentrated. The residue was purified by a flash chromatography on silica gel (eluted with ethyl acetate-hexane mixtures) to give 39 (Compound 51) (353 mg) as a white solid.

¹H NMR (300 MHz, CDCl₃) δ 7.48-7.40 (m, 1H), 7.08-6.84 (m, 4H), 6.75 (dd, J=6.4, 2.8 Hz, 1H), 2.76-2.72 (m, 2H), 2.57 (t, J=6.9 Hz, 2H), 2.00-1.92 (m, 2H). MS (ESI) [M+H⁺]: 373.

Compound 52:

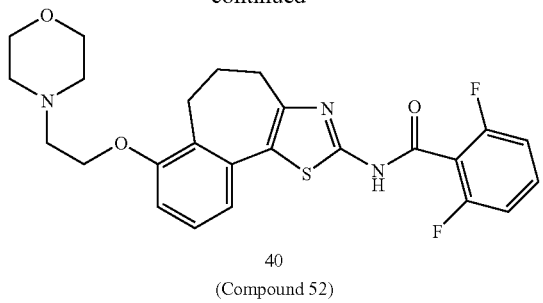

40
(Compound 52)

40

Into a solution of 39 (18.2 mg, 0.05 mmol) in THF (3.0 mL) at room temperature was added 4-(2-chloroethyl)morpholine hydrochloride (18.6 mg, 0.1 mmol) and K₂CO₃ (20 mg, 0.14 mmol), the solution was stirred at reflux for 3 hours, cooled to room temperature, diluted with 10 mL of Et₂O and washed with water. The organic phase was dried (Na₂SO₄), filtered and evaporated. The residue was purified on silica (eluted with ethyl acetate-hexane mixtures) to give 40 (Compound 52) (15.0 mg, 62%) as a white solid.

¹H NMR (300 MHz, CDCl₃) δ 7.49-7.42 (m, 1H), 7.13 (t, J=7.2 Hz, 1H), 7.06 (d, J=7.2 Hz, 1H), 7.04 (t, J=8.2 Hz, 2H), 6.70 (d, J=7.2 Hz, 1H), 4.21 (t, J=6.6 Hz, 2H), 3.58 (br, 4H), 2.97 (t, J=7.2 Hz, 2H), 2.86-2.82 (m, 2H), 2.65 (t, J=6.6 Hz, 2H), 2.31 (br, 4H), 2.20-2.12 (m, 2H).

MS (ESI) [M+H⁺]: 486.

Compound 61:

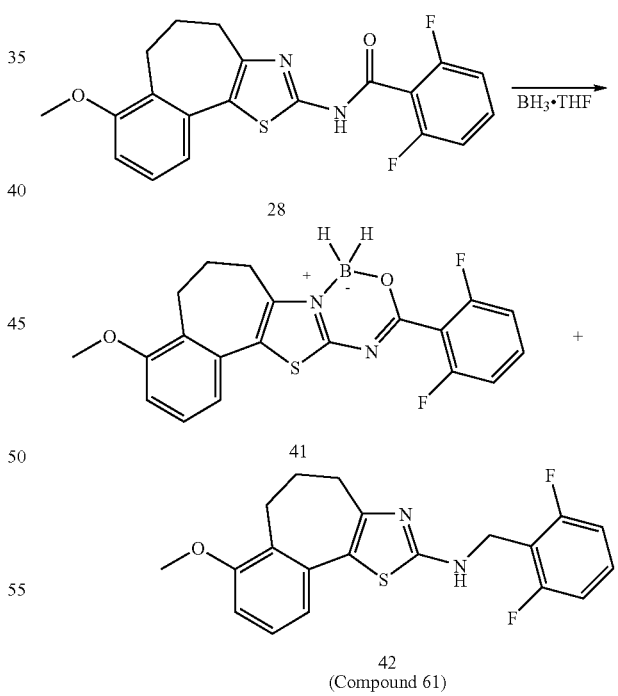

Into a solution of 28 (38.6 mg, 0.10 mmol) in THF at room temperature was added a solution of 1M borane-THF complex in THF (0.5 mL, 0.5 mmol). The mixture was stirred at reflux for 2 hours. The reaction was cooled to room temperature, quenched with ice, extracted with methylene chloride. The extracted was washed with water, dried (Na₂SO₄), filtered and evaporated. The residue was purified by flash chromatography on silica (eluted with ethyl acetate-hexane mixtures) to give 41 (32.0 mg) as a white solid, followed by 42 (Compound 61) (3.8 mg).

41: ¹H NMR (300 MHz, CDCl₃) δ 7.44-7.35 (m, 1H), 7.22 (t, J=8.0 Hz, 1H), 6.99 (t, J=7.7 Hz, 2H), 6.95 (d, J=8.0 Hz, 1H), 6.88 (d, J=8.0 Hz, 1H), 3.86 (s, 3H), 2.93-2.86 (m, 4H), 2.16-2.07 (m, 2H).

MS (ESI) [M+H⁺]: 399.

42: ¹H NMR (300 MHz, CDCl₃) δ 7.32-7.22 (m, 1H), 7.11 (t, J=8.0 Hz, 1H), 6.96-6.88 (m, 3H), 6.73 (d, J=8.0 Hz, 1H), 5.37 (br s, 1H, NH), 4.57 (s, 2H), 3.82 (s, 3H), 2.89-2.84 (m, 4H), 2.05-1.96 (m, 2H).

MS (ESI) [M+H⁺]: 373.

Compound 63:

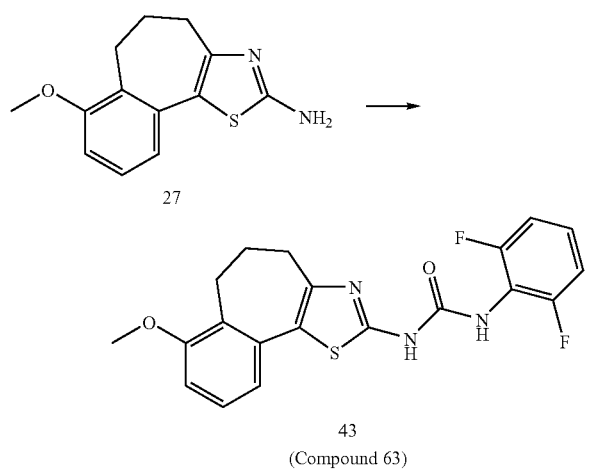

43
(Compound 63)

A solution of 27 (50 mg, 0.2 mmol) and 2,6-difluorophenyl isocyanate (32 mg, 0.2 mmol) in 3 mL of toluene was heated to 60° C. for 3 hours. The mixture was concentrated under reduced pressure. The residue was purified by flash chromatography on silica (eluted with ethyl acetate-hexane mixtures) to give 43 (Compound 63) (61 mg, 76%) as a white solid.

¹H NMR (300 MHz, CDCl₃) δ 7.22-7.14 (m, 1H), 7.16 (t, J=8.0 Hz, 1H), 7.00 (d, J=8.0 Hz, 1H), 6.94 (t, J=8.0 Hz, 2H), 6.79 (d, J=8.0 Hz, 1H), 2.93 (t, J=7.1 Hz, 2H), 2.89-2.86 (m, 2H), 2.13-2.05 (m, 2H).

MS (ESI) [M+H⁺]: 402.

Compound 54:

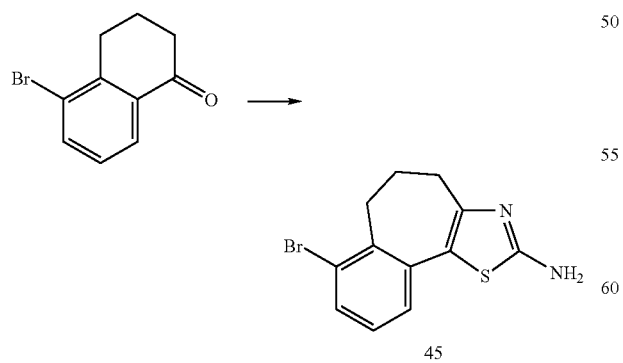

45

45 was prepared from 5-bromo-1-tetralone similarly as described for the preparation of 18.

MS (ESI) [M+H⁺]: 295, 297.

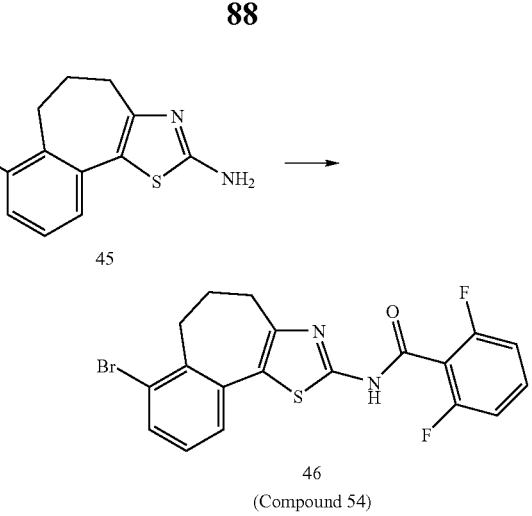

46
(Compound 54)

46 (Compound 54) was prepared from 45 as described for the preparation of 4.

¹H NMR (300 MHz, CDCl₃) δ 11.70 (br s, 1H, NH), 7.50-7.39 (m, 3H), 7.10 (t, J=8.0 Hz, 1H), 6.96 (t, J=8.2 Hz, 2H), 2.88-2.84 (m, 2H), 2.36 (dd, J=7.3 Hz, 2H), 1.99-1.90 (m, 2H).

MS (ESI) [M+H⁺]: 437, 435.

Compound 55:

(Compound 55) was prepared as described for the preparation of 4 using the corresponding acid chloride.

¹H NMR (300 MHz, CDCl₃) δ 8.60 (s, 1H), 8.55 (d, J=5.0 Hz, 1H), 7.50 (d, J=8.0 Hz, 1H), 7.43-7.40 (m, 2H), 7.09 (t, J=8.0 Hz, 1H), 2.97-2.93 (m, 2H), 2.63 (t, J=7.3 Hz, 2H), 2.53 (s, 3H), 2.05-1.97 (m, 2H).

MS (ESI) [M+H⁺]: 416, 414.

Compound 56:

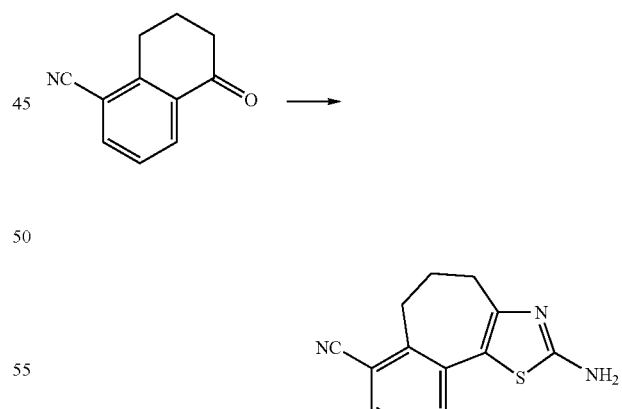

48

48 was prepared from 5-nitrile-1-tetralone as described for the preparation of 18.

¹H NMR (300 MHz, CDCl₃) δ 7.48-7.43 (m, 2H), 7.26 (t, J=8.0 Hz, 1H), 3.12-3.28 (m, 2H), 2.93 (t, J=7.2 Hz, 2H), 2.08-2.00 (m, 2H).

MS (ESI) [M+H⁺]: 242.

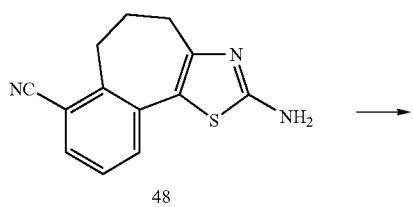

48

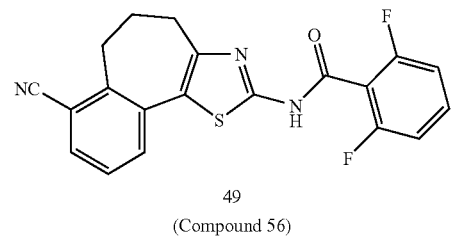

49
(Compound 56)

49 (Compound 56) was prepared from 48 as described for the preparation of 4.

$^1$H NMR (300 MHz, CDCl$_3$) δ 10.3 (br s, 1H, NH), 7.72 (dd, J=7.7, 1.1 Hz, 1H), 7.56-7.48 (m, 2H), 7.35 (t, J=7.7 Hz, 1H), 7.05 (t, J=8.5 Hz, 2H), 3.02-3.06 (m, 2H), 2.80 (t, J=7.2 Hz, 2H), 2.15-2.06 (m, 2H).

MS (ESI) [M+H$^+$]: 382.

Compound 57:

(Compound 57) was prepared from 48 similarly as described for the preparation of 4 using the corresponding acid chloride.

$^1$H NMR (300 MHz, CDCl$_3$) δ 11.6 (br s, 1H, NH), 8.59 (s, 1H), 8.52 (d, J=5.2 Hz, 1H), 7.74 (d, J=8.0 Hz, 1H), 7.55 (d, J=8.0 Hz, 1H), 7.41 (d, J=5.2 Hz, 1H), 7.36 (t, J=8.0 Hz, 1H), 3.05-3.01 (m, 2H), 2.67 (t, J=7.2 Hz, 2H), 2.54 (s, 3H), 2.10-2.00 (m, 2H).

MS (ESI) [M+H$^+$]: 361.

Compounds 58 and 64:

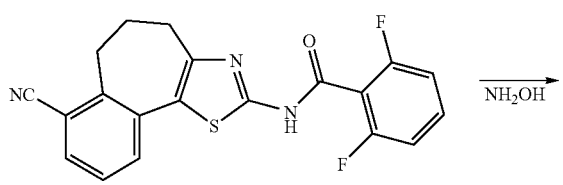

49

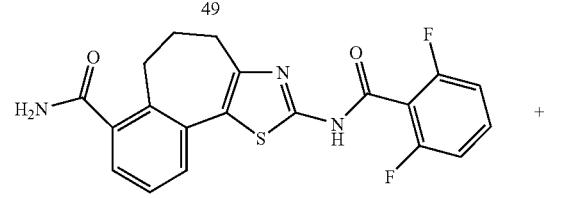

51
(Compound 58)

+

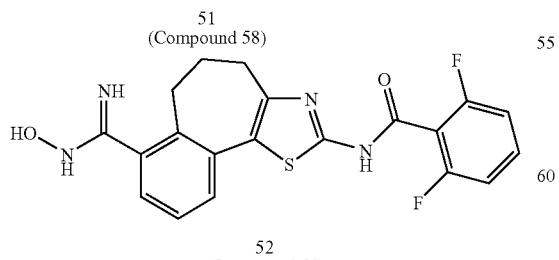

52
(Compound 64)

Into a solution of 49 (38.1 mg, 0.1 mmol) in 5 mL of MeOH was added hydroxyamine hydrochloride (21 mg, 0.3 mmol) and NaHCO$_3$ (50 mg, 0.6 mmol). The mixture was heated to reflux for 5 hours. After the reaction was cooled to room temperature, the reaction mixture was concentrated under reduced pressure to remove the solvent. The residue was taken up with 20 mL of Et$_2$O, the solution was washed with NH$_4$Cl, dried (Na$_2$SO$_4$), filtered and concentrated. The residue was purified by flash chromatography on silica gel (eluted with ethyl acetate-hexane mixtures) to give 51 (Compound 58) (8.0 mg) as a white solid followed by benamidoxime 52 (Compound 64) (25 mg) as a white solid.

51: $^1$H NMR (300 MHz, CDCl$_3$+CD$_3$OD) δ 7.73 (br s, NH), 7.59-7.47 (m, 3H), 7.36-7.27 (m, 2H), 7.07 (t, J=8.2 Hz, 2H), 2.94-2.85 (m, 4H), 2.30-2.21 (m, 2H).

MS (ESI) [M+H$^+$]: 400.

52: MS (ESI) [M+H$^+$]: 415.

Compound 16:

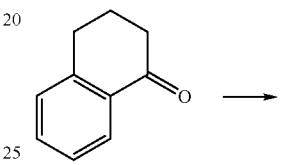

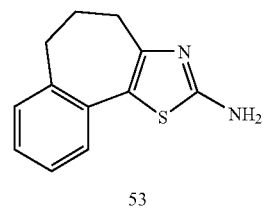

53

53 was prepared from 1-tetralone as described for the preparation of 18.

$^1$H NMR (300 MHz, CDCl$_3$) δ 7.30-7.10 (m, 4H), 2.95-2.80 (m, 4H), 2.05-1.98 (m, 2H).

MS (ESI) [M+H$^+$]: 217

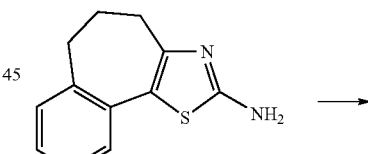

53

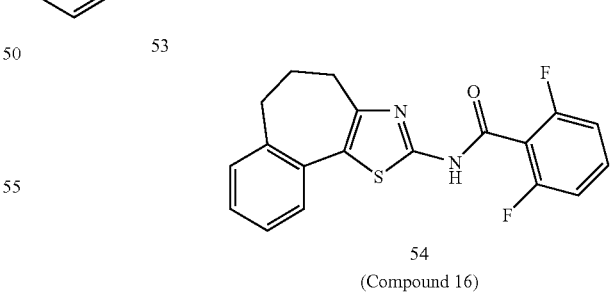

54
(Compound 16)

54 (Compound 16) was prepared from 53 as described for the preparation of 4.

$^1$H NMR (300 MHz, CDCl$_3$) δ 7.56-7.46 (m, 2H), 7.29-7.20 (m, 3H), 7.06 (t, J=8.0 Hz, 2H), 3.03-2.98 (t, J=7.2, 2H), 2.86-2.82 (m, 2H), 2.18-2.10 (m, 2H).

MS (ESI) [M+H$^+$]: 357.

Compound 20:

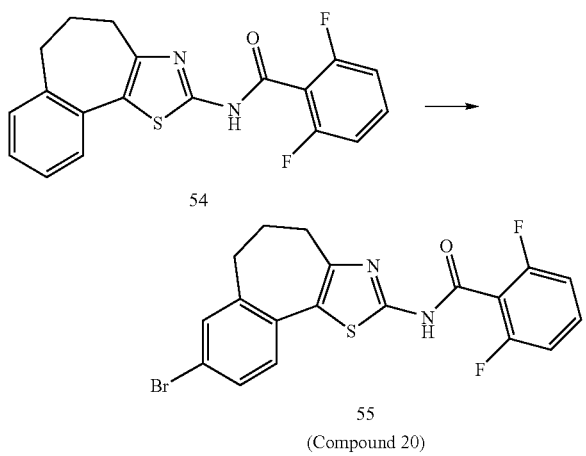

54

55
(Compound 20)

Into a solution of 54 (500 mg, 1.40 mmol) in methylene chloride (6.0 mL) at room temperature was added dropwise a solution of bromine (320 mg, 2.00 mmol) in methylene chloride (1.0 mL). The mixture was stirred at room temperature overnight, taken up in additional methylene chloride, washed with an aqueous solution of 10% $NaHSO_3$, then with a solution of saturated $NaHCO_3$, dried ($Na_2SO_4$), filtered and concentrated under reduced pressure to give 55 (Compound 20) (584 mg).

$^1$H NMR (300 MHz, $CDCl_3$) δ 7.54-7.37 (m, 4H), 7.06-7.00 (m, 2H), 2.85-2.70 (m, 4H), 2.10-2.00 (m, 2H).

MS (ESI) [M+H$^+$]: 437

Compound 4:

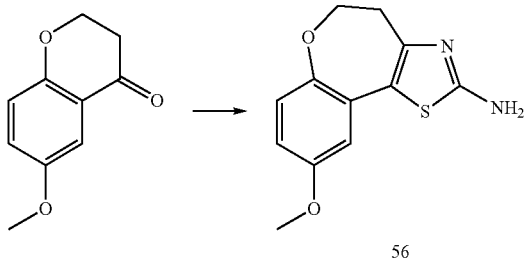 [SMILES: COc1ccc2c(c1)C(=O)CCO2 ; COc1ccc2c(c1)-c1sc(N)nc1CCO2]

56

56 was prepared from 6-methoxychroman-4-one as described for the preparation of 18.

$^1$H NMR (300 MHz, $CDCl_3$) δ 6.90 (d, J=8.7 Hz, 1H), 6.73 (d, J=3.0 Hz, 1H), 6.61 (dd, J=3.0, 8.7 Hz, 1H), 4.21 (dd, J=5.5, 5.5 Hz, 2H), 3.76 (s, 3H), 3.14 (dd, J=5.5, 5.5 Hz, 2H).

MS (ESI) [M+H$^+$]: 249

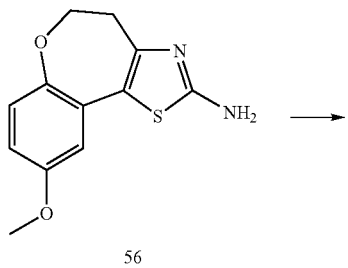

56

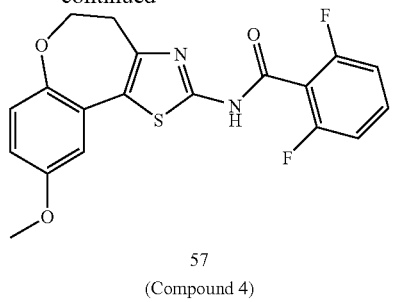

57
(Compound 4)

57 (Compound 4) was prepared from 56 as described for the preparation of 4.

$^1$H NMR (300 MHz, $CDCl_3$) δ 7.54-7.45 (m, 1H), 7.06-6.99 (m, 4H), 6.94 (d, J=8.7 Hz, 1H), 6.72 (dd, J=2.4, 8.7 Hz, 1H), 4.20-4.15 (m, 2H), 3.82 (s, 3H), 3.05-2.95 (m, 2H).

MS (ESI) [M+H$^+$]: 389.

Compound 9:

(Compound 9) was prepared from 56 as described for the preparation of 4 using the corresponding acid chloride.

$^1$H NMR (300 MHz, $CDCl_3$) δ 8.73 (d, J=2.7 Hz, 1H), 8.70 (dd, J=1.5, 4.8 Hz, 1H), 8.08 (dd, J=4.8, 6.3 Hz, 1H), 7.07 (d, J=3.0 Hz, 1H), 6.97 (d, J=8.7 Hz, 1H), 6.73 (dd, J=3.0, 8.7 Hz, 1H), 4.32 (dd, J=5.4, 5.4 Hz, 2H), 3.83 (s, 3H), 3.33 (dd, J=5.4, 5.4 Hz, 2H).

MS (ESI) [M+H$^+$]: 372.

Compound 5:

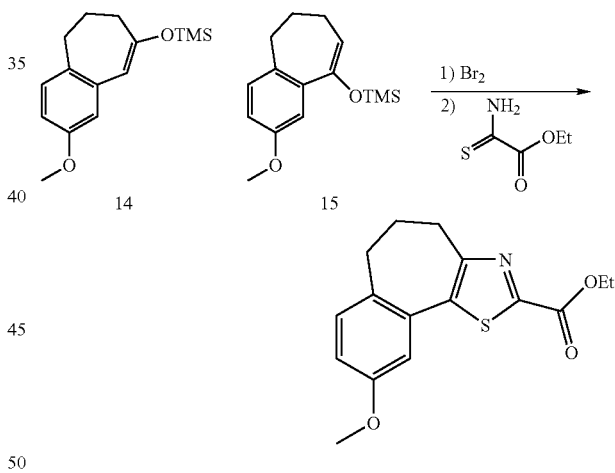

14    15

59

Into a 9:1 crude mixture of 14 and 15 respectively (995 mg, 3.80 mmol) in methylene chloride (50 mL) at 0° C. was added dropwise solution of bromine (800 mg, 5.0 mmol) in methylene chloride (10.0 mL). The bromine addition was stopped whence brownish color of the reaction mixture ceased to disappear. The mixture was concentrated under reduced pressure. The residue was taken up in ethanol (20.0 ml). Ethyl thiooxamate (670 mg, 5.0 mmol) was added. The mixture was stirred at room temperature overnight. An aqueous solution of saturated $NaHCO_3$ was added. The resulting mixture was extracted with methylene chloride (2×). The combined extracts were dried ($Na_2SO_4$), filtered and concentrated. The residue was purified on silica (eluted with a solution of ethyl acetate:hexane, 1:9) to give 59 (520 mg).

¹H NMR (300 MHz, CDCl₃) δ 7.09 (d, J=8 Hz, 1H), 7.00 (d, J=2 Hz, 1H), 6.83 (dd, J=2, 8 Hz, 1H), 4.45 (q, J=7.0 Hz, 2H), 3.83 (s, 3H), 3.04 (dd, J=7.2, 7.4 Hz, 2H), 2.65-2.60 (m, 2H), 2.26-2.18 (m, 2H), 1.42 (t, J=7.0 Hz, 3H).

MS (ESI) [M+H⁺]: 304

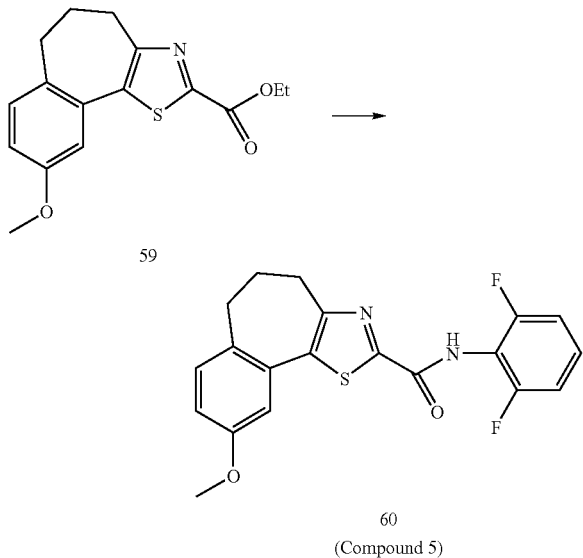

60
(Compound 5)

Into a solution of 59 (100 mg, 0.33 mmol) and 2,6-difluoro aniline (65.0 mg, 0.50 mmol) in anhydrous toluene (3.0 mL) at room temperature was added a solution 2M trimethylaluminum in toluene (0.5 mL, 1.0 mmol). The resulting solution was heated to 80° C. for 2 hours, cooled to room temperature, poured over ice, acidified with 2N HCl, extracted with methylene chloride (2×). The combined extracts were washed with water, dried (Na₂SO₄), filtered and concentrated. The residue was purified on silica (eluted with a solution of ethyl acetate:hexane, 1:9) to give 60 (Compound 5) (65 mg).

¹H NMR (300 MHz, CDCl₃) δ 8.60 (s, 1H), 7.31-7.22 (m, 1H), 7.18 (d, J=8.2 Hz, 1H), 7.05-6.99 (m, 3H), 6.84 (dd, J=2.5, 8.2 Hz, 1H), 3.84 (s, 3H), 3.06 (dd, J=7.2, 7.2 Hz, 2H), 2.75-2.71 (m, 2H), 2.27-2.18 (m, 2H).

MS (ESI) [M+H⁺]: 387.

Compound 21:

(Compound 21) was prepared from 59 similarly as described for the preparation of 60 using the corresponding amine.

¹H NMR (300 MHz, CDCl₃) δ 9.60 (s, 1H), 8.14 (d, J=8 Hz, 1H), 7.65 (dd, J=8, 8 Hz, 1H), 7.16 (d, J=8 Hz, 1H), 7.04 (d, J=2.5 Hz, 1H), 6.95 (d, J=8 Hz, 1H), 6.82 (dd, J=2.5, 8 Hz, 1H), 3.83 (s, 3H), 3.05 (dd, J=7.1, 7.2 Hz, 2H), 2.74-2.70 (m, 2H), 2.51 (s, 3H), 2.24-2.15 (m, 2H).

MS (ESI) [M+H⁺]: 366.

Compound 22:

(Compound 22) was prepared from 59 similarly as described for the preparation of 60 using the corresponding amine.

¹H NMR (300 MHz, CDCl₃) δ 9.36 (s, 1H), 7.67 (d, J=8.0 Hz, 1H), 7.51 (dd, J=8.0, 8.0 Hz, 1H), 7.16 (d, J=8.5 Hz, 1H), 7.04 (d, J=2.5 Hz, 1H), 6.83 (dd, J=2.5, 8.5 Hz, 1H), 6.31 (d, J=8.0 Hz, 1H), 4.37 (bs, 2H), 3.83 (s, 3H), 3.05 (dd, J=7.1, 7.1 Hz, 2H), 2.74-2.70 (m, 2H), 2.24-2.15 (m, 2H).

MS (ESI) [M+H⁺]: 367

Compound 23:

(Compound 23) was prepared from 59 similarly as described for the preparation of 60 using the corresponding amine.

¹H NMR (300 MHz, CDCl₃) δ 9.69 (s, 1H), 8.38-8.33 (m, 2H), 7.80-7.74 (m, 1H), 7.17 (d, J=8.2 Hz, 1H), 7.12-7.08 (m, 1H), 7.04 (d, J=2.7 Hz, 1H), 6.84 (dd, J=2.7, 8.2 Hz, 1H), 3.84 (s, 3H), 3.06 (dd, J=7.2, 7.4 Hz, 2H), 2.75-2.71 (m, 2H), 2.25-2.16 (m, 2H).

MS (ESI) [M+H⁺]: 352

Compound 24:

(Compound 24) was prepared from 59 similarly as described for the preparation of 60 using the corresponding amine.

¹H NMR (300 MHz, CDCl₃) δ 9.13 (s, 1H), 8.79 (d, J=2.5 Hz, 1H), 8.41 (dd, J=1.5, 5.0 Hz, 1H), 8.35 (dd, J=1.5, 8.4 Hz, 1H), 7.35 (dd, J=5.0, 8.4 Hz, 1H), 7.18 (d, J=8.3 Hz, 1H), 7.04 (d, J=2.5 Hz, 1H), 6.84 (dd, J=2.5, 8.3 Hz, 1H), 3.84 (s, 3H), 3.06 (dd, J=7.1, 7.4 Hz, 2H), 2.74-2.70 (m, 2H), 2.26-2.18 (m, 2H).

MS (ESI) [M+H⁺]: 352.

Compound 25:

(Compound 25) was prepared from 59 similarly as described for the preparation of 60 using the corresponding amine.

¹H NMR (300 MHz, CDCl₃) δ 8.95 (s, 1H), 8.40 (d, J=2.7 Hz, 1H), 8.11 (dd, J=2.7, 8.9 Hz, 1H), 7.17 (d, J=8.5 Hz, 1H), 7.03 (d, J=2.5 Hz, 1H), 6.83 (dd, J=2.5, 8.9 Hz, 1H), 6.80 (d, J=8.5 Hz, 1H), 3.95 (s, 3H), 3.84 (s, 3H), 3.05 (dd, J=7.1, 7.4 Hz, 2H), 2.74-2.70 (m, 2H), 2.26-2.17 (m, 2H).

MS (ESI) [M+H⁺]: 382

Compound 26:

(Compound 26) was prepared from 59 similarly as described for the preparation of 60 using the corresponding amine.

¹H NMR (300 MHz, CDCl₃) δ 9.72 (s, 1H), 8.89 (dd, J=2.6, 8.1 Hz, 1H), 8.17 (dd, J=1.6, 4.7 Hz, 1H), 7.33 (dd, J=4.7, 8.1 Hz, 1H), 7.19 (d, J=8.5 Hz, 1H), 7.04 (d, J=2.6 Hz, 1H), 6.85 (dd, J=1.6, 8.5 Hz, 1H), 3.84 (s, 3H), 3.09 (dd, J=7.1, 7.2 Hz, 2H), 2.75-2.70 (m, 2H), 2.28-2.19 (m, 2H).

MS (ESI) [M+H⁺]: 386.

Compound 10:

(Compound 10) was prepared from 59 similarly as described for the preparation of 60 using the corresponding amine.

¹H NMR (300 MHz, CDCl₃) δ 8.40 (d, J=5.4 Hz, 1H), 8.36 (s, 1H), 8.31 (d, J=5.4 Hz, 1H), 7.16 (d, J=8.4 Hz, 1H), 7.01 (d, J=2.7 Hz, 1H), 6.83 (dd, J=2.7, 8.4 Hz, 1H), 3.84 (s, 3H), 3.08 (dd, J=7, 7 Hz, 2H), 2.74-2.59 (m, 2H), 2.37 (s, 3H), 2.26-2.17 (m, 2H).

MS (ESI) [M+H⁺]: 366

Compound 27:

(Compound 27) was prepared from 59 similarly as described for the preparation of 60 using the corresponding amine.

¹H NMR (300 MHz, CDCl₃) δ 9.24 (s, 1H), 8.34 (d, J=5.5 Hz, 1H), 7.80 (d, J=2.0 Hz, 1H), 7.57 (dd, J=2.0, 5.7 Hz, 1H), 7.18 (d, J=8.2 Hz, 1H), 7.03 (d, J=2.7 Hz, 1H), 6.85 (dd, J=2.7, 8.2 Hz, 1H), 3.84 (s, 3H), 3.05 (dd, J=7.2, 7.4 Hz, 2H), 2.74-2.70 (m, 2H), 2.27-2.18 (m, 2H).

MS (ESI) [M+H⁺]: 386

Compound 29:

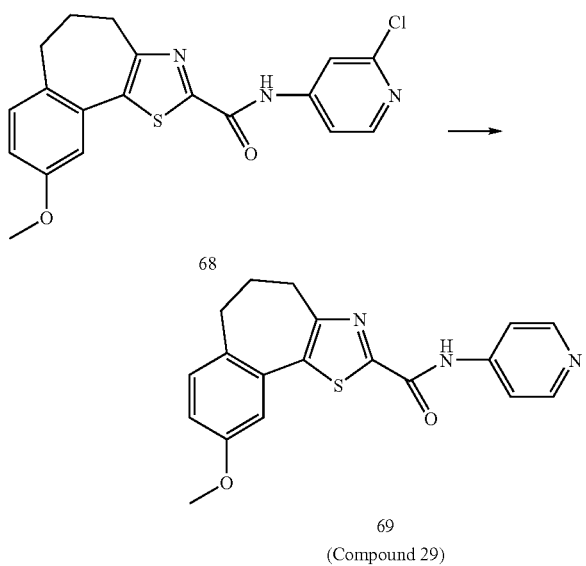

Into a solution of 68 (20.0 mg, 0.05 mmol) in ethanol (2.0 mL) was added 10% Pd/C (10.0 mg). The mixture was stirred under 3 atmosphere of hydrogen for 2 days. The mixture was filtered through a short plug of silica to give 69 (Compound 29) (12.0 mg).

$^1$H NMR (300 MHz, CDCl$_3$) δ 9.19 (s, 1H), 8.63-8.51 (m, 2H), 7.71-7.60 (m, 2H), 7.19 (d, J=8.5 Hz, 1H), 7.04 (d, J=2.5 Hz, 1H), 6.85 (dd, J=2.5, 8.5 Hz, 1H), 3.84 (s, 3H), 3.06 (dd, J=7.2, 7.4 Hz, 2H), 2.74-2.70 (m, 2H), 2.27-2.18 (m, 2H).

MS (ESI) [M+H$^+$]: 352

Compound 28:

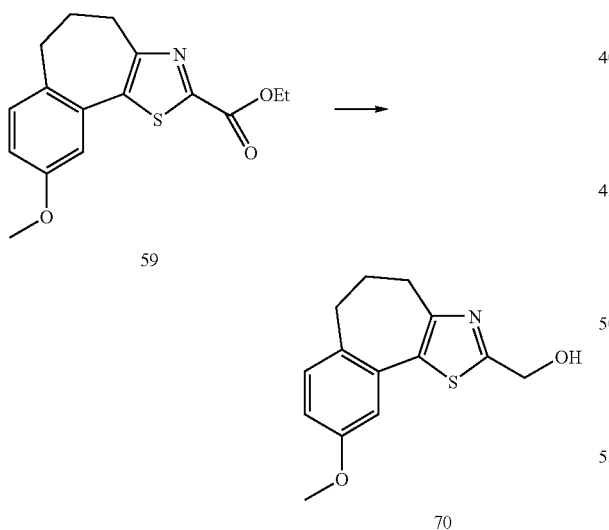

Into a solution of 59 (300 mg, 1.0 mmol) in THF (5.0 mL) at 0° C. was added dropwise a solution of 1M aluminum hydride in THF (2.0 mL, 2.0 mmol). The mixture was stirred at room temperature for 1 hour, cooled to 0° C. Into the mixture ice was added followed by 2N NaOH. The mixture was extracted with methylene chloride (2×). The extracts were washed with water, dried (Na$_2$SO$_4$), filtered and concentrated to give 70 (248 mg).

$^1$H NMR (300 MHz, CDCl$_3$) δ 7.11 (d, J=8.5 Hz, 1H), 6.99 (d, J=2.7 Hz, 1H), 6.76 (dd, J=2.7, 8.5 Hz, 1H), 4.92 (bd, J=5.5 Hz, 2H), 3.82 (s, 3H), 3.06 (dd, J=7.2, 7.2 Hz, 2H), 2.75-2.71 (m, 2H), 2.17-2.10 (m, 2H).

MS (ESI) [M+H$^+$]: 262

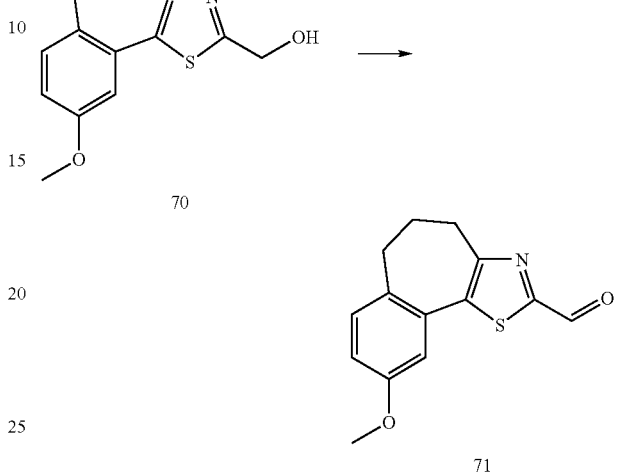

Into a solution of 70 (248 mg, 0.95 mmol) in methylene chloride (10.0 mL) at room temperature was added pyridinium dichromate (564 mg, 1.50 mmol). The mixture was stirred at room temperature overnight, filtered through a short plug of silica gel to give 71 (205 mg).

$^1$H NMR (300 MHz, CDCl$_3$) δ 9.93 (s, 1H), 7.19 (d, J=8.2 Hz, 1H), 7.03 (d, J=2.5 Hz, 1H), 6.87 (dd, J=2.5, 8.2 Hz, 1H), 3.84 (s, 3H), 3.06 (dd, J=7.2, 7.5 Hz, 2H), 2.72-2.68 (m, 2H), 2.29-2.20 (m, 2H).

MS (ESI) [M+H$^+$]: 260

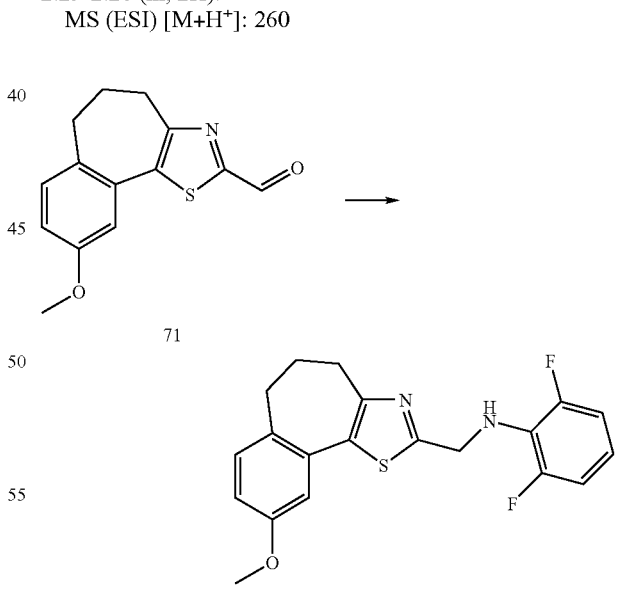

Into a solution of 71 (20.0 mg, 0.077 mmol) and 2,6-difluoroaniline (13.0 mg, 0.10 mmol) in CH$_2$Cl$_2$ (1.0 mL) at room temperature was added TFA (2 drops). The mixture was stirred at room temperature for 1 hour. Into the mixture Na(OAc)$_3$BH (42.0 mg, 0.20 mmol). The resulting solution was stirred at room temperature overnight, taken up in CH₂Cl₂, washed with saturated NaHCO₃, dried (Na₂SO₄), filtered and concentrated. The residue was purified on silica to give 72 (compound 28). ¹H NMR (300 MHz, CDCl₃) δ 7.09 (d, J=8.5 Hz, 1H), 6.95 (d, J=2.5 Hz, 1H), 6.87-6.69 (series of m, 4H), 4.75 (d, J=6.9 Hz, 2H), 3.80 (s, 3H), 3.06 (dd, J=6.9, 7.1 Hz, 2H), 2.74-2.70 (m, 2H), 2.16-2.07 (m, 2H).

MS (ESI) [M+H⁺]: 373

Compound 30:

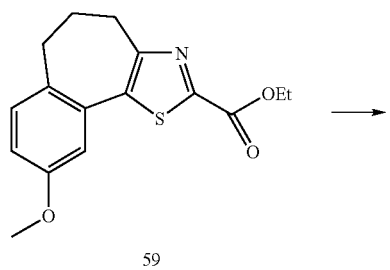

59

Into a solution of 59 (300 mg, 1.0 mmol) in methylene chloride (5.00 mL) at −78° C. was added a solution of 1M BBr₃ (2.0 mL, 2.0 mmol). The mixture was gradually warmed to room temperature over 2 hours, poured over ice, extracted with methylene chloride (2×). The extracts were washed with water and dried (Na₂SO₄), filtered and concentrated under reduced pressure. The residue was purified on silica to give 73 (210 mg).

MS (ESI) [M+H⁺]: 290

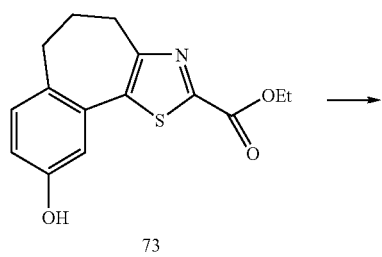

73

Into a solution of 73 (58.0 mg, 0.20 mmol), 4-(2-chloroethyl)morpholine hydrochloride (56 mg, 0.30 mmol) and NaI (3 mg, 0.02 mmol) in DMF (4.0 mL) at room temperature was added K₂CO₃ (83.0 mg, 0.60 mmol). The mixture was stirred at 60° C. overnight, cooled to room temperature, diluted with ethyl acetate, washed with water (3×) then with brine and dried (Na₂SO₄), filtered and concentrated under reduced pressure to give crude 74 (65 mg).

¹H NMR (300 MHz, CDCl₃) δ 7.14 (d, J=8 Hz, 1H), 7.02 (d, J=2 Hz, 1H), 6.83 (dd, J=2, 8 Hz, 1H), 4.48 (q, J=7 Hz, 2H), 4.12 (t, J=5.7 Hz, 2H), 3.77-3.73 (m, 4H), 3.07 (dd, J=7, 7 Hz, 2H).

MS (ESI) [M+H⁺]: 403

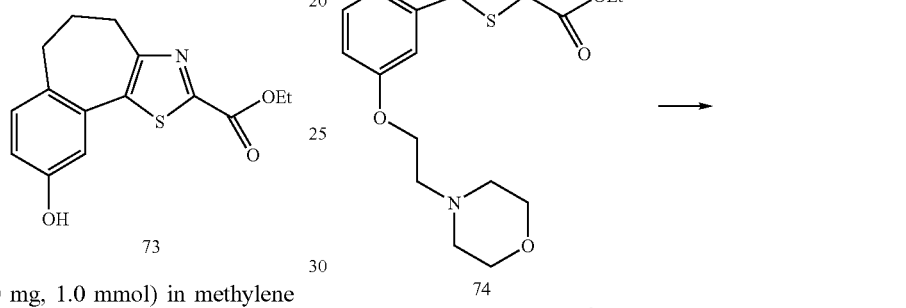

74

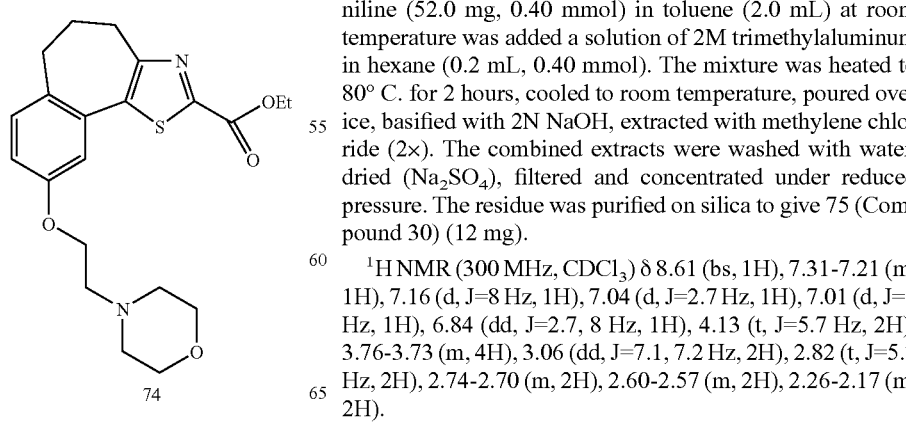

75
(Compound 30)

Into a solution of the crude 74 (65 mg) and 2,6-difluoroaniline (52.0 mg, 0.40 mmol) in toluene (2.0 mL) at room temperature was added a solution of 2M trimethylaluminum in hexane (0.2 mL, 0.40 mmol). The mixture was heated to 80° C. for 2 hours, cooled to room temperature, poured over ice, basified with 2N NaOH, extracted with methylene chloride (2×). The combined extracts were washed with water, dried (Na₂SO₄), filtered and concentrated under reduced pressure. The residue was purified on silica to give 75 (Compound 30) (12 mg).

¹H NMR (300 MHz, CDCl₃) δ 8.61 (bs, 1H), 7.31-7.21 (m, 1H), 7.16 (d, J=8 Hz, 1H), 7.04 (d, J=2.7 Hz, 1H), 7.01 (d, J=8 Hz, 1H), 6.84 (dd, J=2.7, 8 Hz, 1H), 4.13 (t, J=5.7 Hz, 2H), 3.76-3.73 (m, 4H), 3.06 (dd, J=7.1, 7.2 Hz, 2H), 2.82 (t, J=5.7 Hz, 2H), 2.74-2.70 (m, 2H), 2.60-2.57 (m, 2H), 2.26-2.17 (m, 2H).

MS (ESI) [M+H⁺]: 486

Compound 32:

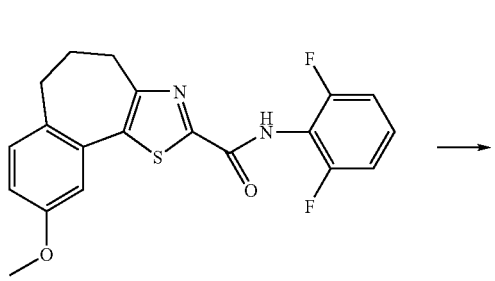

60

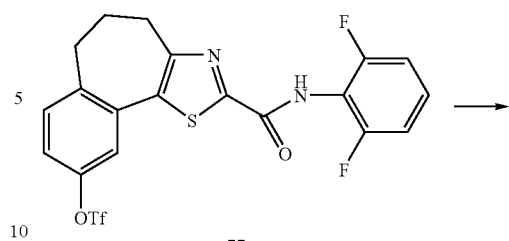

77

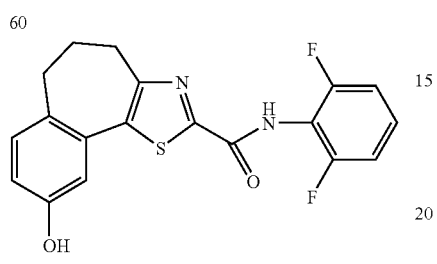

76
(Compound 32)

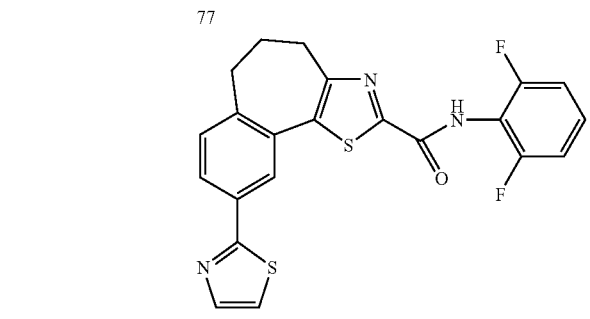

78
(Compound 34)

Into a solution of 60 (450 mg, 1.16 mmol) in methylene chloride (5.00 mL) at −78° C. was added a solution of 1M BBr$_3$ (2.0 mL, 2.0 mmol). The mixture was gradually warmed to room temperature over 2 hours, poured over ice, extracted with methylene chloride (2×). The extracts were washed with water and dried (Na$_2$SO$_4$), filtered and concentrated under reduced pressure. The residue was purified on silica to give 76 (Compound 32) (398 mg).

$^1$H NMR (300 MHz, CDCl$_3$) δ 8.72 (bs, 1H), 7.33-7.24 (m, 1H), 7.13-7.00 (m, 4H), 6.77 (dd, J=2, 8 Hz, 1H), 3.05 (dd, J=7, 7 Hz, 2H), 2.73-2.68 (m, 2H), 2.26-2.18 (m, 2H).

MS (ESI) [M+H$^+$]: 373

Compound 34:

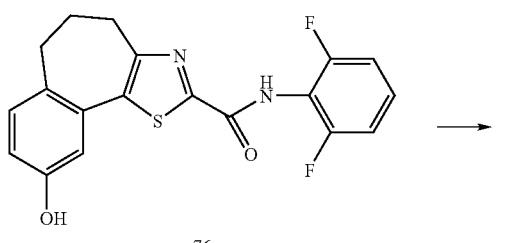

76

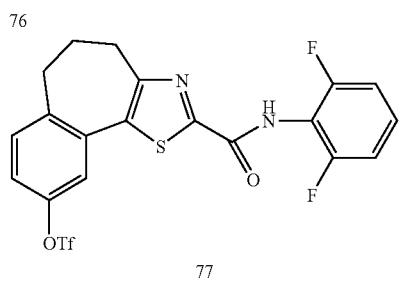

77

Into a solution of 76 (398 mg, 1.07 mmol) and pyridine (277 mg, 3.50 mmol) in methylene chloride (5.0 mL) at 0° C. was added triflic anhydride (1.00 g, 3.50 mmol). The mixture was stirred at room temperature for 4 hours, diluted with methylene chloride, washed with a solution of saturated NaHCO$_3$, dried (Na$_2$SO$_4$), filtered and concentrated under reduced pressure to give 77 (541 mg), which was used without purification.

MS (ESI) [M+H$^+$]: 505

Into a solution of 77 (50.0 mg, 0.10 mmol) in THF (2.0 mL) at room temperature was added tetrakis(triphenylphosphine) palladium (23.0 mg, 0.02 mmol) followed by a solution of 0.5M 2-thiazolzinc bromide in THF (0.6 mL, 0.3 mmol). The mixture was degassed by vacuum/N$_2$-fill method (3×). The degassed solution was heated to 60° C. overnight, cooled to room temperature, quenched with ice, extracted with methylene chloride (2×). The combined extracts were washed with water, dried (Na$_2$SO$_4$), filtered and concentrated under reduced pressure. The residue was purified on silica gel to give 78 (Compound 34) (31.0 mg).

$^1$H NMR (300 MHz, CDCl$_3$) δ 8.63 (bs, 1H), 8.10 (d, J=1.7 Hz, 1H), 7.88 (d, J=3.3 Hz, 1H), 7.86 (dd, J=1.7, 8.2 Hz, 1H), 7.36-7.22 (m, 3H), 7.05-6.99 (m, 2H), 3.10 (dd, J=7.2, 7.5 Hz, 2H), 2.85-2.81 (m, 2H), 2.31-2.23 (m, 2H).

MS (ESI) [M+H$^+$]: 440

Compound 37:

(Compound 37) was prepared from 77 similarly as described for the preparation of 78 using a solution of 0.5M 2-pyridylzinc bromide in THF.

$^1$H NMR (300 MHz, CDCl$_3$) δ 8.72-8.61 (m, 2H), 8.15 (bs, 1H), 7.94-7.73 (m, 3H), 7.38 (d, J=7.8 Hz, 1H), 7.30-7.22 (m, 1H), 7.05-7.00 (m, 2H), 3.11 (dd, J=6.9, 7.2 Hz, 2H), 2.87-2.83 (m, 2H), 2.31-2.24 (m, 2H).

MS (ESI) [M+H$^+$]: 434

Compound 38:

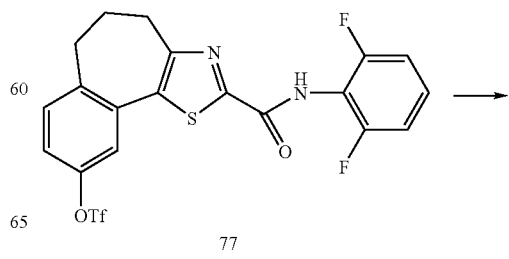

77

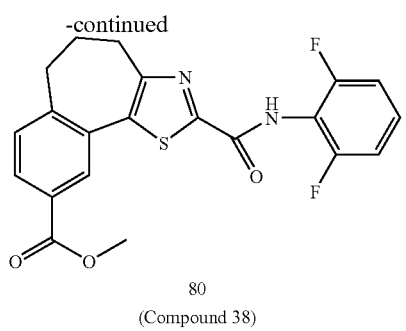

80
(Compound 38)

Into a solution of 77 (50.0 mg, 0.10 mmol) in MeOH (2.0 mL) at room temperature was added Pd(OAc)$_2$ (11.0 mg, 0.05 mmol), 1,3-bis(diphenylphosphino)propane (21.0 mg, 0.05 mmol) and triethylamine (50.0 mg, 0.5 mmol). A slow stream of CO gas was bubbling through the solution, which was heated to 50° C. for 2 days. The mixture was cooled to room temperature, concentrated under reduced pressure. The residue was purified on silica to give 80 (Compound 38) (30.0 mg).

$^1$H NMR (300 MHz, CDCl$_3$) δ 8.61 (bs, 1H), 8.17 (d, J=1.5 Hz, 1H), 7.95 (dd, J=1.5, 7.6 Hz, 1H), 7.35 (d, J=7.6 Hz, 1H), 7.30-7.23 (m, 1H), 7.05-7.00 (m, 2H), 3.94 (s, 3H), 3.10 (dd, J=6.9, 7.2 Hz, 2H), 2.87-2.83 (m, 2H), 2.30-2.22 (m, 2H).

MS (ESI) [M+H$^+$]: 415

Compound 65:

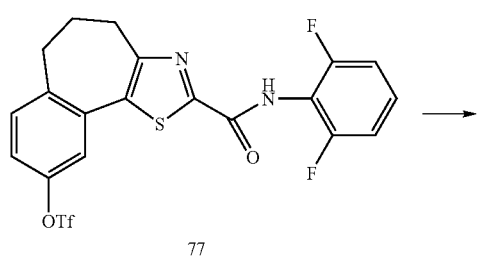

77

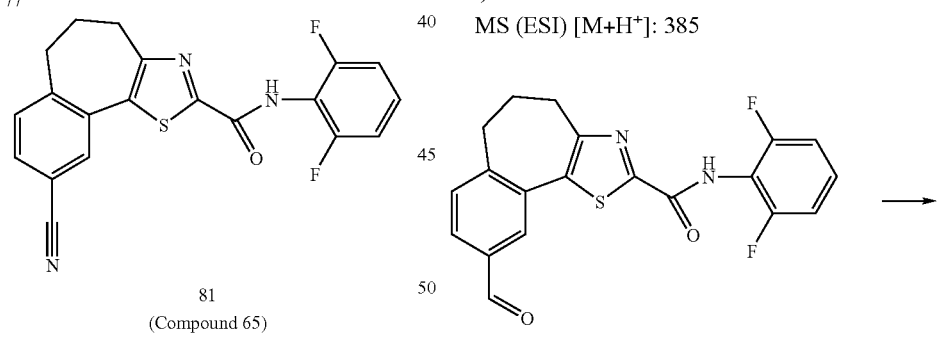

81
(Compound 65)

Into a solution of 77 (200 mg, 0.4 mmol) in DMF (4.0 mL) at room temperature were added Zinc cyanide (117 mg, 1.00 mmol) and tetrakis(triphenylphosphine)palladium (92.0 mg, 0.08 mmol). The mixture was degassed by vacuum/N$_2$-fill method (3×). The degassed solution was heated to 110° C. overnight, cooled to room temperature, diluted with methylene chloride, washed with water (3×). The organic solution was dried (Na$_2$SO$_4$), filtered and concentrated under reduced pressure. The residue was purified on silica gel to give 81 (Compound 65) (132 mg).

$^1$H NMR (300 MHz, CDCl$_3$) δ 8.59 (bs, 1H), 7.78 (d, J=1.7 Hz, 1H), 7.52 (dd, J=1.7, 7.7 Hz, 1H), 7.39 (d, J=7.7 Hz, 1H), 7.33-7.23 (m, 1H), 7.05-7.00 (m, 2H), 3.11 (dd, J=7.1, 7.5 Hz, 2H), 2.87-2.83 (m, 2H), 2.32-2.23 (m, 2H).

MS (ESI) [M+H$^+$]: 382

Compound 19:

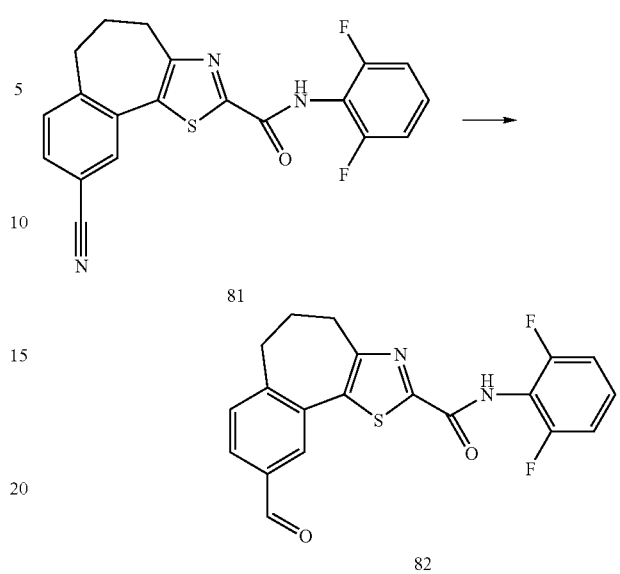

Into a solution of 81 (58 mg, 0.15 mmol) in THF (2.0 mL) at 0° C. was added dropwise a solution of 1M di-isobutyla-luminum hydride in THF (0.5 mL, 0.5 mmol). The mixture was stirred at room temperature for 1 hour, cooled to 0° C., poured over an ice-cooled solution of 1N HCl. The mixture was extracted with methylene chloride (2×). The combined extract was washed with water, dried (Na$_2$SO$_4$), filtered and concentrated under reduced pressure. The residue was purified on silica gel to give 82 (42 mg).

$^1$H NMR (300 MHz, CDCl$_3$) δ 10.02 (s, 1H), 8.61 (bs, 1H), 7.99 (d, J=1.7 Hz, 1H), 7.80 (dd, J=1.7, 7.5 Hz, 1H), 7.44 (d, J=7.5 Hz, 1H), 7.32-7.23 (m, 1H), 7.06-6.99 (m, 2H), 3.12 (dd, J=7.2, 7.2 Hz, 2H), 2.90-2.83 (m, 2H), 2.32-2.23 (m, 2H).

MS (ESI) [M+H$^+$]: 385

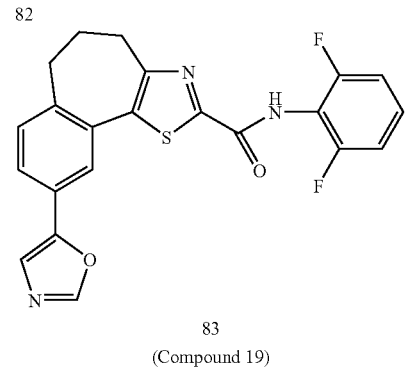

83
(Compound 19)

Into a solution of 82 (15 mg, 0.04 mmol) and p-toluene-sulfonylmethyl isocyanide (20 mg, 0.1 mmol) in MeOH (1.0 mL) at room temperature was added potassium carbonate (14 mg, 0.1 mmol). The mixture was stirred at 50° C. overnight. The mixture was cooled to room temperature, diluted with methylene chloride, washed with water, dried (Na$_2$SO$_4$), filtered and concentrated under reduced pressure. The residue was purified on silica gel to give 83 (Compound 19) (12 mg).

$^1$H NMR (300 MHz, CDCl$_3$) δ 8.61 (bs, 1H), 7.94 (s, 1H), 7.79 (d, J=1.7 Hz, 1H), 7.56 (dd, J=1.7, 8.0 Hz, 1H), 7.39 (s, 1H), 7.34 (d, J=8.0 Hz, 1H), 7.30-7.23 (m, 1H), 7.06-7.00 (m, 2H), 3.11 (dd, J=7.4, 8.3 Hz, 2H), 2.85-2.81 (m, 2H), 2.31-2.23 (m, 2H).

MS (ESI) [M+H$^+$]: 424

Compound 42:

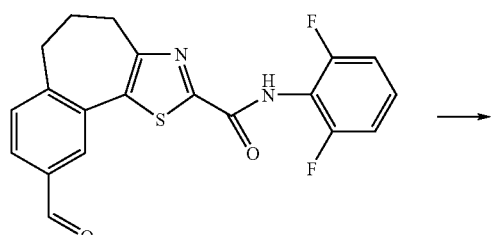

82

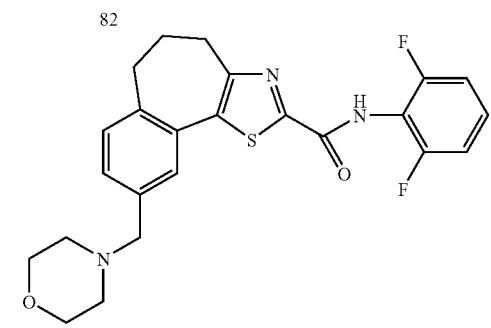

84
(Compound 42)

Into a solution of 82 (15 mg, 0.04 mmol) and morpholine (9.0 mg, 0.1 mmol) in methylene chloride at room temperature was added Na(OAc)$_3$BH (21 mg, 0.1 mmol). The mixture was stirred at room temperature overnight, diluted with methylene chloride, washed with water, dried (Na$_2$SO$_4$), filtered and concentrated under reduced pressure. The residue was purified on silica gel to give 84 (Compound 42) (9 mg).

$^1$H NMR (300 MHz, CDCl$_3$) δ 8.62 (s, 1H), 7.48 (s, 1H), 7.34-7.19 (m, 3H), 7.06-6.98 (m, 2H), 3.86-3.70 (m, 4H), 3.51 (s, 2H), 3.08 (dd, J=7.0, 7.2 Hz, 2H), 2.80-2.76 (m, 2H), 2.48-2.45 (m, 4H), 2.27-2.19 (m, 2H).

MS (ESI) [M+H$^+$]: 456

Compound 40:

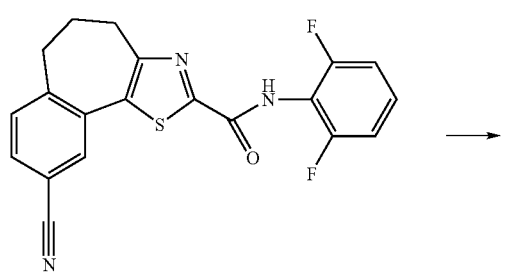

81

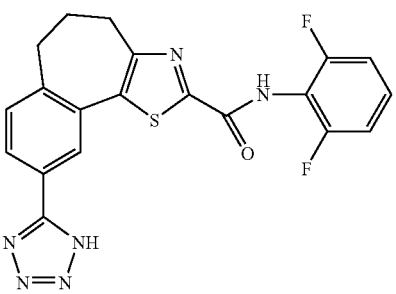

85
(Compound 40)

A solution of 81 (48 mg, 0.13 mmol), sodium azide (25 mg, 0.38 mmol) and ammonium chloride (21 mg, 0.38 mmol) in DMF (2.0 mL) was heated at 110° C. overnight. The mixture was cooled to room temperature, diluted with methylene chloride, washed with water (3×), dried (Na$_2$SO$_4$), filtered and concentrated under reduced pressure. The residue was purified on silica to give 85 (Compound 40) (35 mg).

$^1$H NMR (300 MHz, CDCl$_3$) δ 8.76 (bs, 1H), 8.19 (d, J=1.8 Hz, 1H), 8.13 (dd, J=1.8, 7.8 Hz, 1H), 7.45 (d, J=7.8 Hz, 1H), 7.16-7.07 (m, 1H), 6.81-6.76 (m, 2H), 3.12 (dd, J=7.2, 7.5 Hz, 2H), 2.90-2.85 (m, 2H), 2.35-2.26 (m, 2H).

MS (ESI) [M+H$^+$]: 425

Compounds 39 and 41:

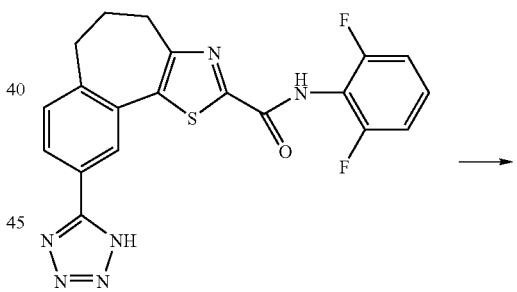

85

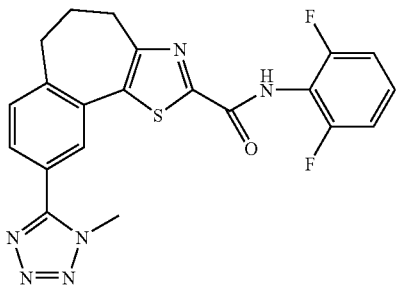

86
(Compound 39)

-continued

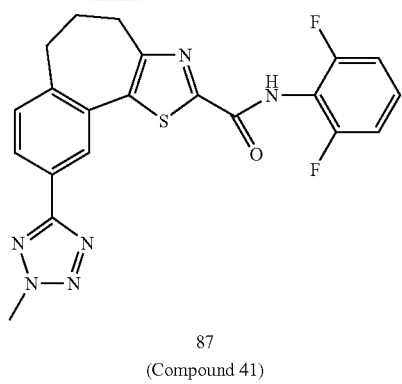

87
(Compound 41)

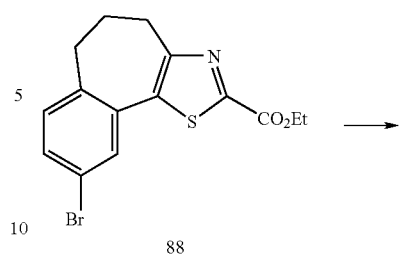

88

Into a solution of 85 (35 mg) in methylene chloride (2 mL) was added a solution of 2M trimethylsilyldiazomethane in ether (0.5 mL, 1.0 mmol). The mixture was concentrated under reduced pressure. The residue was purified on silica to give 86 (Compound 39) (32 mg) followed by 87 (Compound 41) (3 mg).

86: $^1$H NMR (300 MHz, CDCl$_3$) δ 8.64 (bs, 1H), 8.27 (d, J=1.5 Hz, 1H), 8.05 (dd, J=1.5, 7.8 Hz, 1H), 7.39 (d, J=7.8 Hz, 1H), 7.33-7.23 (m, 1H), 7.05-6.98 (m, 2H), 4.41 (s, 3H), 3.11 (dd, J=7.2, 7.2 Hz, 2H), 2.87-2.83 (m, 2H), 2.32-2.23 (m, 2H).

MS (ESI) [M+H$^+$]: 439

87: $^1$H NMR (300 MHz, CDCl$_3$) δ 8.63 (bs, 1H), 7.86 (d, J=1.5 Hz, 1H), 7.67 (dd, J=1.5, 7.8 Hz, 1H), 7.48 (d, J=7.8 Hz, 1H), 7.33-7.23 (m, 1H), 7.06-6.98 (m, 2H), 4.23 (s, 3H), 3.14 (dd, J=7.2, 7.2 Hz, 2H), 2.90-2.86 (m, 2H), 2.35-2.27 (m, 2H).

MS (ESI) [M+H$^+$]: 439

Compound 18:

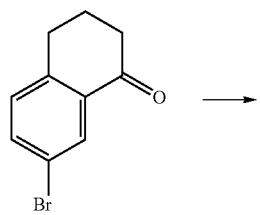

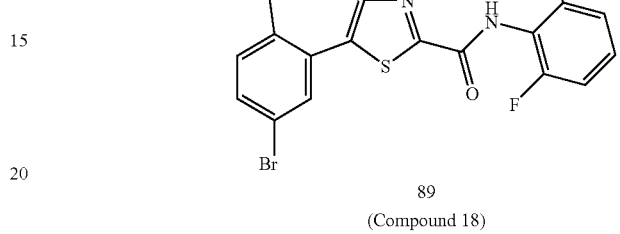

89
(Compound 18)

89 (Compound 18) was prepared from 88 similarly as described for the preparation of 60.

$^1$H NMR (300 MHz, CDCl$_3$) δ 8.61 (br s, 1H, NH), 7.64 (d, J=2.1 Hz, 1H), 7.40 (dd, J=8.0, 2.1 Hz, 1H), 7.32-7.22 (m, 1H), 7.14 (d, J=8.0 Hz, 1H), 7.02 (t, J=8.0 Hz, 2H), 3.08 (t, J=7.0 Hz, 2H), 2.77-2.73 (m, 2H), 2.28-2.21 (m, 2H).

MS (ESI) [M+H$^+$]: 437, 435.

Compound 62:

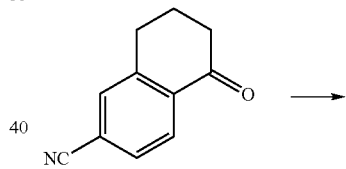

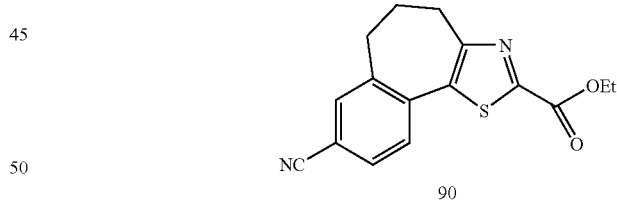

90

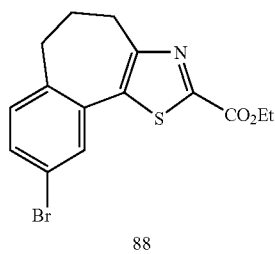

88

88 was prepared from 5-bromo-1-tetralone similarly as described for the preparation of 59.

MS (ESI) [M+H$^+$]: 354, 352.

90 was prepared from 6-nitrile-1-tetralone similarly as described for the preparation of 59.

MS (ESI) [M+H$^+$]: 299.

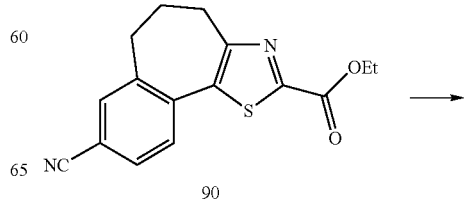

90

-continued

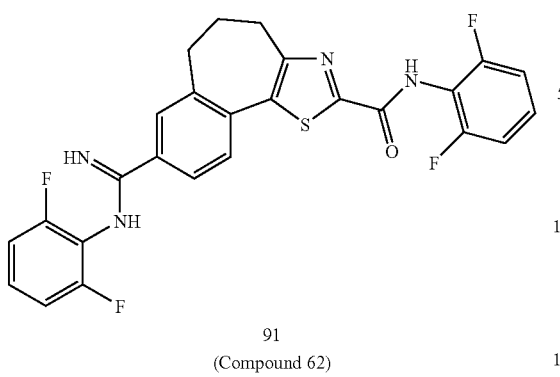

91
(Compound 62)

Into a solution of 90 (50 mg, 0.17 mmol) in toluene (2.0 mL) at room temperature was added a solution of 2M trimethylalluminum in toluene (0.5 mL, 1.0 mmol). The mixture was heated to 60° C. overnight, cooled to room temperature, poured over ice, basified with 2N NaOH, extracted with methylene chloride (2×). The combined extracts was washed with water, dried ($Na_2SO_4$), filtered and concentrated under reduced pressure. The residue was purified on silica to give 91 (Compound 62) (15 mg).

MS (ESI) [M+H$^+$]: 511.

Compound 6:

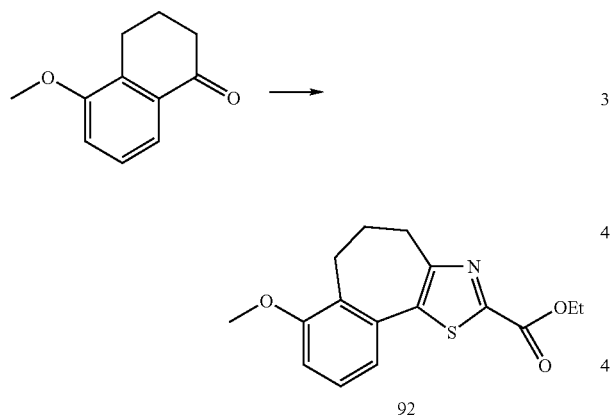

92

92 was prepared from 5-methoxy-1-tetralone as described for the preparation of 59.

$^1$H NMR (300 MHz, CDCl$_3$) δ 7.23 (dd, J=8, 8 Hz, 1H), 7.05 (d, J=8 Hz, 1H), 6.89 (d, J=8 Hz, 1H), 4.48 (q, J=7.2 Hz, 2H), 3.86 (s, 3H), 3.00 (dd, J=7.2, 7.5 Hz, 2H), 2.78-2.74 (m, 2H), 2.26-2.21 (m, 2H), 1.44 (t, J=7.2 Hz, 3H).

MS (ESI) [M+H$^+$]: 304

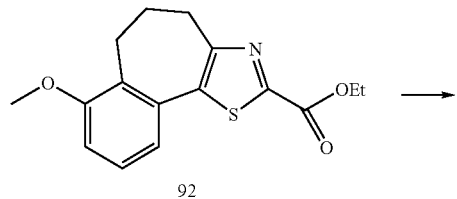

92

-continued

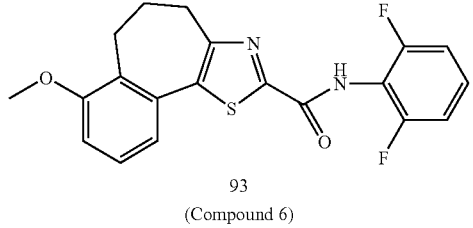

93
(Compound 6)

93 (Compound 6) was prepared from 92 similarly as described for the preparation of 60.

$^1$H NMR (300 MHz, CDCl$_3$) δ 8.63 (s, 1H), 7.28-7.02 (series of m, 5H), 6.91 (d, J=8.4 Hz, 1H), 3.88 (s, 3H), 2.98 (dd, J=7.2, 7.5 Hz, 2H), 2.84-2.79 (m, 2H), 2.30-2.21 (m, 2H).

MS (ESI) [M+H$^+$]: 387

Compound 11:

(Compound 11) was prepared from 92 similarly as described for the preparation of 60 using the corresponding amine.

$^1$H NMR (300 MHz, CDCl$_3$) δ 9.28 (s, 1H), 8.47 (d, J=5.5 Hz, 1H), 8.43 (s, 1H), 8.33 (d, J=5.5 Hz, 1H), 7.26 (dd, J=8, 8 Hz, 1H), 7.09 (d, J=8 Hz, 1H), 6.91 (dd, J=8, 8 Hz, 1H), 3.88 (s, 3H), 2.97 (dd, J=7.2, 7.5 Hz, 2H), 2.83-2.79 (m, 2H), 2.41 (s, 3H), 2.35-2.20 (m, 2H).

MS (ESI) [M+H$^+$]: 366

Compound 53:

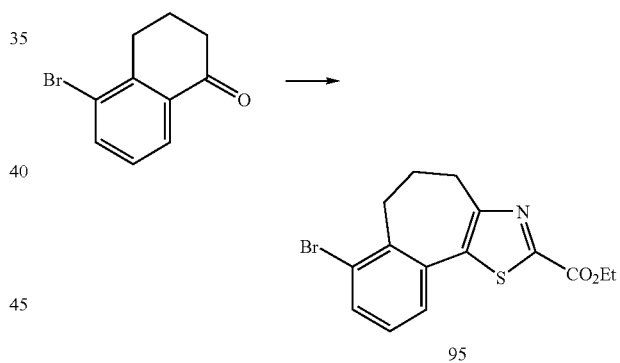

95

95 was prepared from 5-bromo-1-tetralone as described for the preparation of 59.

$^1$H NMR (300 MHz, CDCl$_3$) δ 7.56 (d, J=8.0 Hz, 1H), 7.34 (d, J=7.7 Hz, 1H), 7.12 (dd, J=8.0, 7.7 Hz, 1H), 4.98 (q, J=7.2 Hz, 2H), 2.95-2.85 (m, 4H), 2.34-2.25 (m, 2H), 1.44 (t, J=7.2 Hz, 3H).

MS (ESI) [M+H$^+$]: 354, 352.

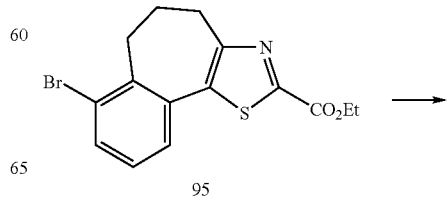

95

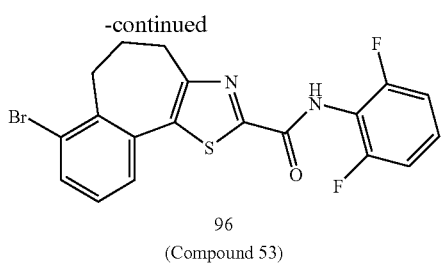

96
(Compound 53)

96 (Compound 53) was prepared from 95 as described for the preparation of 60.

$^1$H NMR (300 MHz, CDCl$_3$) δ 8.62 (br s, 1H, NH), 7.61-7.47 (m, 2H), 7.40 (d, J=8.0 Hz, 1H), 7.15 (t, J=8.0 Hz, 1H), 7.03 (t, J=8.2 Hz, 2H), 2.98-2.90 (m, 4H), 2.39-2.30 (m, 2H).

MS (ESI) [M+H$^+$]: 437, 435.

Compound 31:

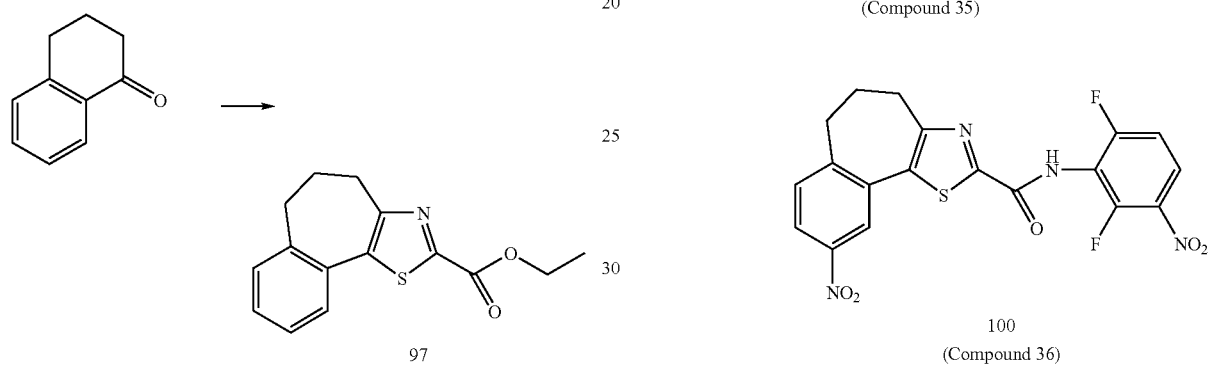

97

97 was prepared from 1-tetralone as described for the preparation of 59.

$^1$H NMR (300 MHz, CDCl$_3$) δ 7.50-7.47 (m, 1H), 7.31-7.26 (m, 3H), 4.50 (q, J=7 Hz, 2H), 3.11 (dd, J=7.2, 7.5 Hz, 2H), 2.78-2.74 (m, 2H), 2.26-2.22 (m, 2H), 1.45 (t, J=7 Hz, 3H).

MS (ESI) [M+H$^+$]: 274

97

98
(Compound 31)

98 (Compound 31) was prepared from 97 as described for the preparation of 60.

$^1$H NMR (300 MHz, CDCl$_3$) δ 8.62 (s, 1H), 7.53-7.49 (m, 1H), 7.29-7.22 (m, 4H), 7.05-6.99 (m, 2H), 3.09 (dd, J=7.1, 7.1 Hz, 2H), 2.82-2.71 (m, 2H), 2.30-2.21 (m, 2H).

MS (ESI) [M+H$^+$]: 357

Compounds 35 and 36:

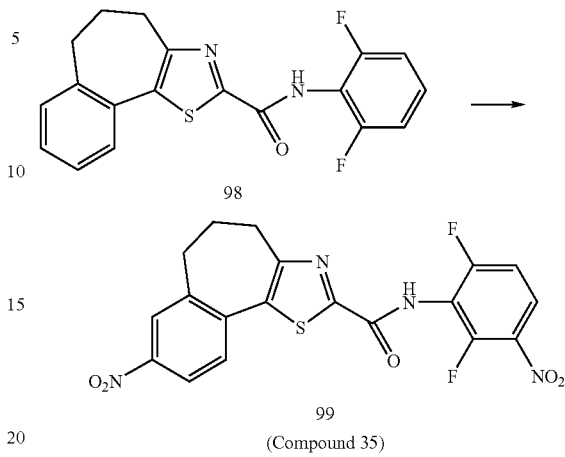

98

99
(Compound 35)

100
(Compound 36)

Into a solution of 98 (50 mg) in concentrated sulfuric acid (1.0 mL) at 0° C. was added dropwise a solution of concentrated nitric acid (0.1 mL). The mixture was stirred at 0° C. for 30 minutes, poured over ice, extracted with methylene chloride (2×). The combined extracts was washed with water, dried (Na$_2$SO$_4$), filtered and concentrated under reduced pressure. The residue was purified on silica to give 99 (Compound 35) (14 mg) and 100 (Compound 36) (13 mg).

99: $^1$H NMR (300 MHz, CDCl$_3$) δ 8.19-8.14 (m, 3H), 7.68 (d, J=10 Hz, 1H), 7.24-7.18 (m, 1H), 3.18 (dd, J=7.2, 7.4 Hz, 2H), 2.96-2.92 (m, 2H), 2.37-2.27 (m, 2H).

MS (ESI) [M+H$^+$]: 447

100: $^1$H NMR (300 MHz, CDCl$_3$) δ 8.34 (d, J=2.1 Hz, 3H), 8.15-8.07 (m, 2H), 7.44 (d, J=11 Hz, 1H), 7.20-7.14 (m, 1H), 3.11 (dd, J=7.2, 7.5 Hz, 2H), 2.90-2.86 (m, 2H), 2.33-2.26 (m, 2H).

MS (ESI) [M+H$^+$]: 447

Compound 66:

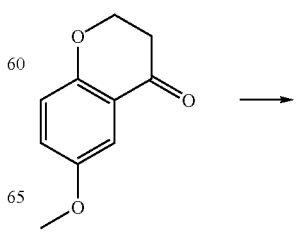

-continued

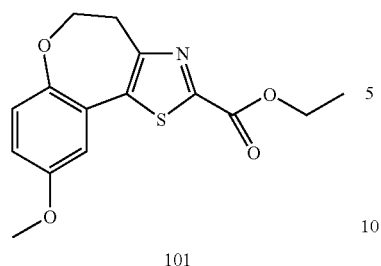

101

101 was prepared from 6-methoxychroman-4-one as described for the preparation of 59.

¹H NMR (300 MHz, CDCl₃) δ 7.08 (d, J=3.0 Hz, 1H), 7.00 (d, J=8.8 Hz, 1H), 6.81 (dd, J=3.0, 8.8 Hz, 1H), 4.50 (q, J=7.0 Hz, 2H) 4.33 (dd, J=5.1, 5.7 Hz, 2H), 3.82 (s, 3H), 3.52 (dd, J=5.1, 5.7 Hz, 2H), 1.45 (t, J=7.0 Hz, 3H).

MS (ESI) [M+H⁺]: 306

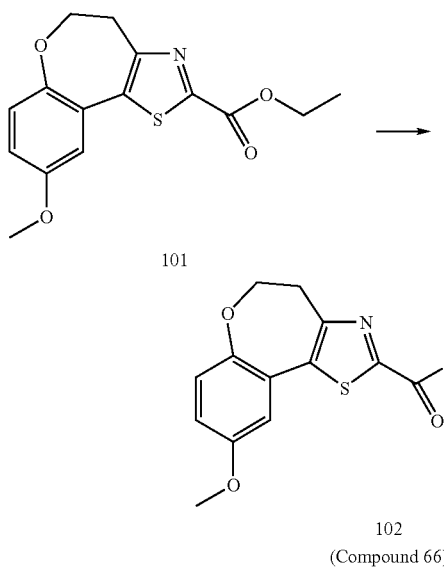

102
(Compound 66)

102 (Compound 66) was prepared from 101 as described for the preparation of 60.

¹H NMR (300 MHz, CDCl₃) δ 8.56 (bs, 1H), 7.32-7.22 (m, 1H), 7.10 (d, J=2.7 Hz, 1H), 7.06-6.99 (m, 3H), 6.81 (dd, J=2.7, 8 Hz, 1H), 4.35 (dd, J=5.2, 5.5 Hz, 2H), 3.82 (s, 3H), 3.47 (dd, J=5.1, 5.7 Hz, 2H).

MS (ESI) [M+H⁺]: 389

Compound 67:

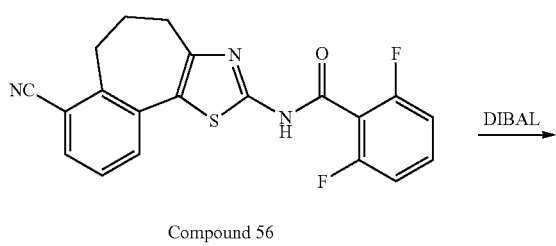

Compound 56

-continued

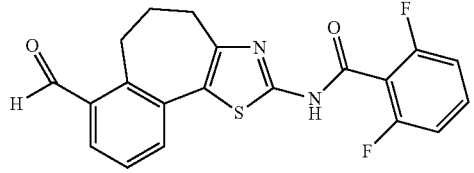

Compound 67

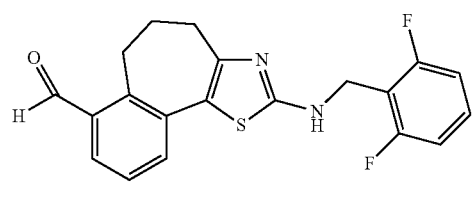

1a

Into the solution of Compound 56 (762 mg, 2 mmol) in 20 mL of CH₂Cl₂ at 0° C. was added dropwise a 1M solution of DIBAl-H in THF (6.0 mL, 6.0 mmol). The mixture was stirred at room temperature for 1 hour, cooled to 0° C., poured over an ice-cooled solution of 1N HCl. The mixture was extracted with methylene chloride. The combined extracts were washed with water, dried (Na₂SO₄), filtered and concentrated under reduced pressure. The residue was purified by column chromatography on silica gel to give 1a (110 mg, 15% yield) followed by Compound 67 (443 mg, 56% yield).

1a: ¹H NMR (300 MHz, CDCl₃) δ 10.35 (s, 1H), 7.67 (dd, J=1.1, 7.7 Hz, 1H), 7.53 (dd, J=1.4, 7.7 Hz, 1H), 7.37-7.27 (m, 2H), 6.95 (t, J=8.0 Hz, 2H), 4.59 (s, 2H), 3.11-3.07 (m, 2H), 2.82-2.75 (m, 2H), 2.22-2.10 (m, 2H).

MS (ESI) [M+H⁺]: 371.

Compound 67: ¹H NMR (300 MHz, CDCl₃) δ 11.2 (br s, 1H, NH), 10.33 (s, 1H), 7.75 (dd, J=1.1, 7.7 Hz, 1H), 7.68 (dd, J=1.4, 7.7 Hz, 1H), 7.50-7.41 (m, 2H), 6.99 (t, J=8.2 Hz, 2H), 3.11-3.07 (m, 2H), 2.53-2.47 (m, 2H), 2.15-2.07 (m, 2H).

MS (ESI) [M+H⁺]: 385

Compound 68:

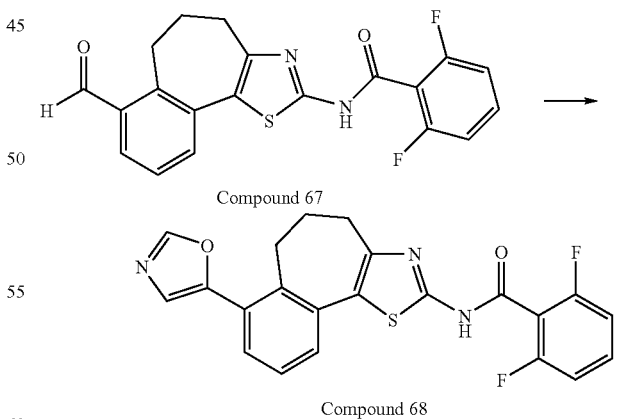

Into the solution of Compound 67 (30 mg, 0.08 mmol) and p-toluenesulfonylmethyl isocyanide (20 mg, 0.1 mmol) in 2 mL of MeOH at room temperature was added K₂CO₃ (28 mg, 0.2 mmol). The mixture was reflux for 1 hour. The mixture was cooled to room temperature, concentrated and redissolved in methylene chloride. The solution was washed with water, dried (Na$_2$SO$_4$), filtered and concentrated under reduced pressure. The residue was purified by column chromatography on silica gel to give Compound 68 (23 mg, 70%).

$^1$H NMR (300 MHz, CDCl$_3$) δ 8.0 (s, 1H), 7.55-7.32 (series of m, 4H), 7.23 (s, 1H), 7.04 (t, J=8.2 Hz, 2H), 2.78-2.70 (m, 4H), 2.28-2.20 (m, 2H).

MS (ESI) [M+H$^+$]: 424

Compound 69:

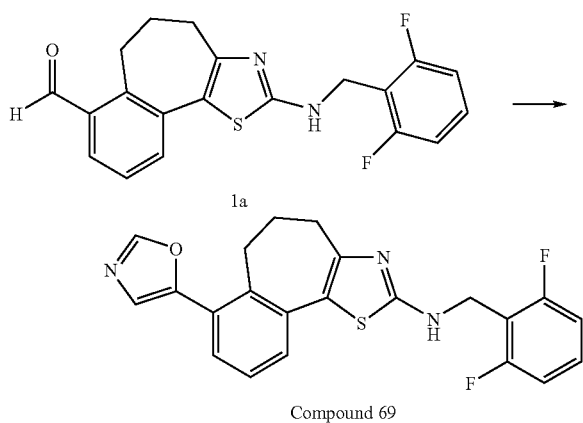

Compound 69

Compound 69 was prepared from 1a similarly as described for the preparation of compound 68.

$^1$H NMR (300 MHz, CDCl$_3$) δ 7.98 (s, 1H), 7.37-7.23 (series of m, 4H), 7.19 (s, 1H), 6.94 (t, J=7.5 Hz, 2H), 4.59 (s, 2H), 2.84-2.78 (m, 4H), 2.26-2.16 (m, 2H).

MS (ESI) [M+H$^+$]: 410

Compound 70:

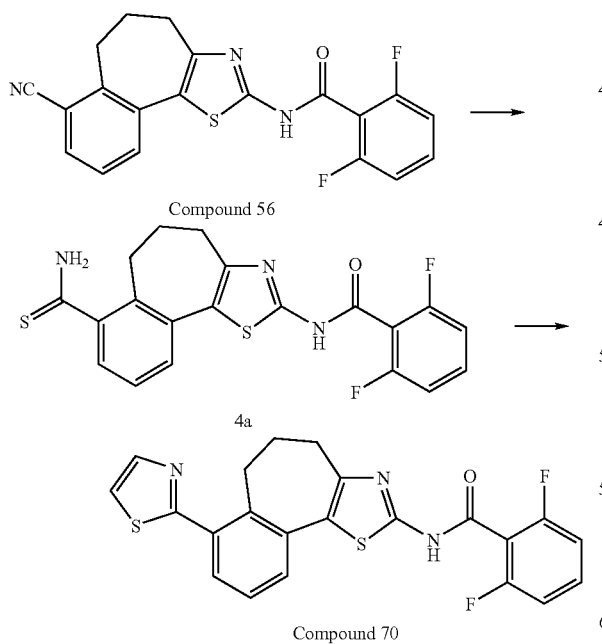

Compound 70

The solution of Compound 56 (38 mg, 0.1 mmol) and (NH$_4$)$_2$S (0.1 mmol, 40 wt. % in H$_2$O) in MeOH (1 mL) was irradiated in a microwave synthesizer at 110° C. for 2 hours. The reaction was cooled to room temperature and the solvent was removed under reduced pressure. The residue was partitioned between EtOAc and H$_2$O. The aqueous layer was further extracted with EtOAc and the organic extracts were combined, washed with brine, dried (Na$_2$SO$_4$) and concentrated under reduced pressure to give crude thioamide 4a (32 mg, 77% yield), which was used for next step without further purification.

MS (ESI) [M+H$^+$]: 416

The solution of 4a (10 mg) and chloroacetaldehyde (45% aqueous solution, 0.1 mL) in 2 mL of CH$_3$CN was heated to 65° C. in a sealed tube for 2 hours. The reaction was cooled to room temperature and the solvent was removed under reduced pressure. The residue was partitioned between CH$_2$Cl$_2$ and H$_2$O. The aqueous layer was further extracted with CH$_2$Cl$_2$ and the organic extracts were combined, washed with brine, dried (Na$_2$SO$_4$), filtered and concentrated under reduced pressure. The residue was purified by column chromatography on silica gel to give compound 70 (3.0 mg) as a white solid.

$^1$H NMR (300 MHz, CDCl$_3$) δ 7.94 (d, J=3.3 Hz, 1H), 7.60-7.31 (series of m, 5H), 7.06 (t, J=8.5 Hz, 2H), 2.90-2.83 (m, 4H), 2.36-2.25 (m, 2H).

MS (ESI) [M+H$^+$]: 440

Compound 71:

Compound 71 was prepared from 4a and 2-chloroacetone similarly as described for the preparation of compound 70).

$^1$H NMR (300 MHz, CDCl$_3$) δ 10.7 (br s, 1H, NH), 7.56-7.40 (series of m, 4H), 7.00 (t, J=8.2 Hz, 2H), 6.98 (s, 1H), 2.84-2.76 (m, 2H), 2.64-2.54 (m, 2H), 2.54 (s, 3H), 2.22-2.12 (m, 2H).

MS (ESI) [M+H$^+$]: 454

Compound 72:

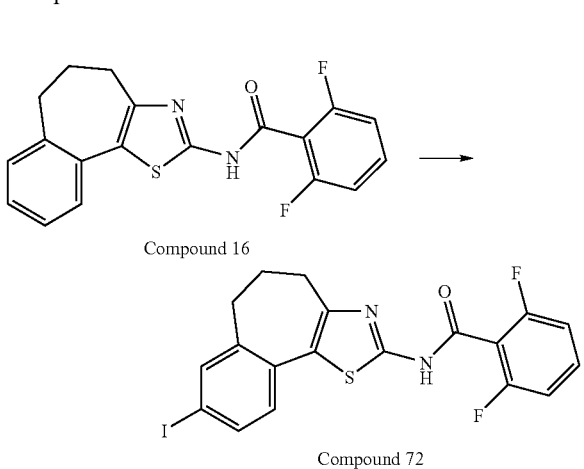

Compound 72

Into a solution of Compound 16 (1.00 g, 2.80 mmol) in concentrated H$_2$SO$_4$ (10.0 mL) at 0° C. was added NIS (0.65 g, 2.80 mmol) slowly over 1 hour. The mixture was stirred at room temperature for 2 hours. The reaction was quenched by addition of ice. The mixture was extracted with CH$_2$Cl$_2$. The extract was washed with water and a solution of saturated NaHCO$_3$, dried (Na$_2$SO$_4$), filtered and concentrated. The residue was purified on silica gel (eluted with 1:9 EtOAc: hexanes, then with 3:7 EtOAc:hexanes) to give compound 72 (670 mg, 50% yield).

$^1$H NMR (300 MHz, CDCl$_3$) δ 7.58-7.40 (m, 3H), 7.06-6.95 (m, 3H), 2.80-2.65 (m, 4H), 2.03-1.93 (m, 2H).

MS (ESI) [M+H$^+$]: 483

Compound 73:

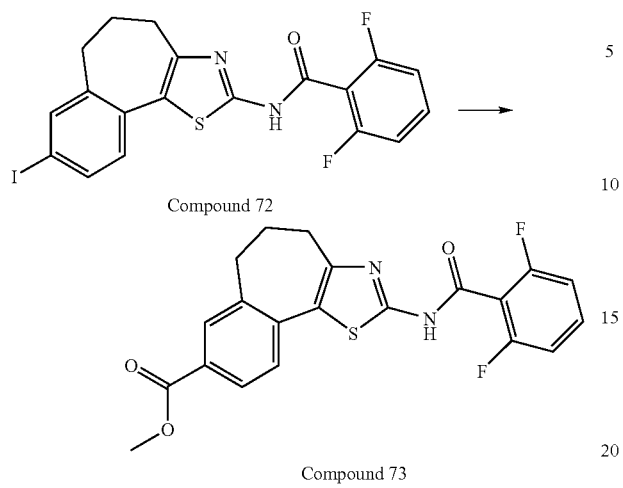

Into a solution of Compound 72 (50.0 mg, 0.10 mmol) and DIEA (26.0 mg, 0.20 mmol) in MeOH (2.0 mL) were added Pd(OAc)$_2$ (5.0 mg, 0.02 mmol) and PPh$_3$ (11 mg, 0.04 mmol). The reaction mixture was purged continuously with a slow bubbling stream of carbon monoxide. After 5 hours at room temperature, the reaction mixture was concentrated under reduced pressure. The residue was purified on silica gel (eluted with 1:9 EtOAc:hexanes, then with CH$_2$Cl$_2$) to give Compound 73 (31 mg).

MS (ESI) [M+H$^+$]: 415

Compound 74:

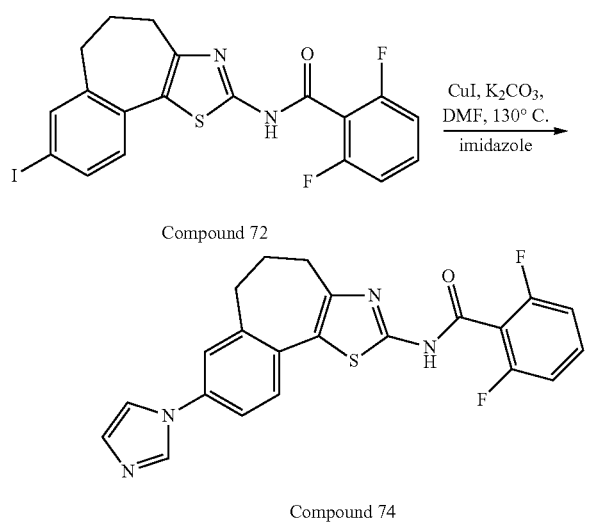

Into the solution of compound 72 (48 mg, 0.1 mmol) in DMF (3 mL) was added copper(I) iodide (19 mg, 0.1 mmol), imidazole (20 mg, 0.3 mmol) and K$_2$CO$_3$ (42 mg, 0.3 mmol). The mixture was heated in a sealed tube under nitrogen at 130° C. for 1 hour. The mixture was cooled and poured into water, and the resulting mixture was extracted with ethyl acetate. The combined organic extracts were washed with water and brine, dried (Na$_2$SO$_4$), filtered and concentrated under reduced pressure. The residue was purified by column chromatography on silica gel to give compound 74 (12 mg, 28% yield)

MS (ESI) [M+H$^+$]: 423

Compound 75:

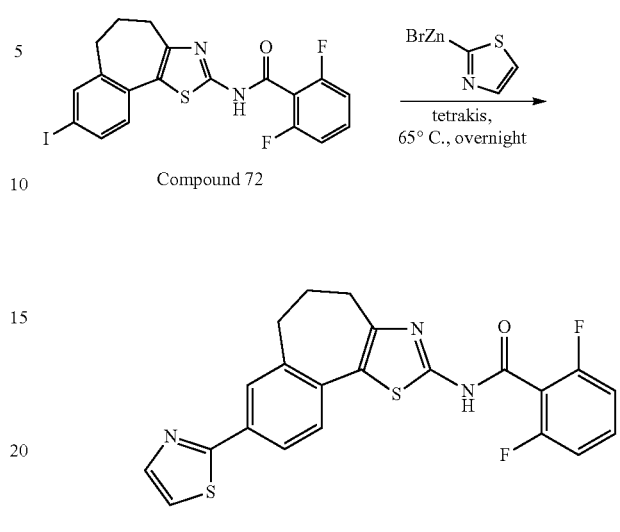

Into the solution of Compound 72 (48 mg, 0.10 mmol) in 2 mL of THF at room temperature was added tetrakis(triphenylphosphine)palladium (23.0 mg, 0.02 mmol) followed by a solution of 0.5M 2-thiazolzinc bromide in THF (0.5 mL, 0.25 mmol). The mixture was degassed by vacuum/N$_2$-fill method (3×). The degassed solution was heated to 65° C. overnight, cooled to room temperature, quenched with ice water, extracted with methylene chloride. The combined extracts were washed with water, dried (Na$_2$SO$_4$), filtered and concentrated under reduced pressure. The residue was purified by column chromatography on silica gel to give compound 75 (16 mg, 36%).

$^1$H NMR (300 MHz, CDCl$_3$) δ 10.6 (br s, 1H, NH), 7.81 (s, 1H), 7.87-7.31 (series of m, 5H), 7.01 (t, J=8.5 Hz, 2H), 2.86-2.71 (m, 4H), 2.06-1.97 (m, 2H).

MS (ESI) [M+H$^+$]: 440

Compound 76:

Compound 76 was prepared from compound 72 and oxazol-2-ylzinc(II) chloride similarly as described for the preparation of compound 75.

$^1$H NMR (300 MHz, CDCl$_3$) δ 10.7 (br s, 1H, NH), 7.91-7.86 (m, 2H), 7.72 (s, 1H), 7.62 (d, J=7.7 Hz, 1H), 7.51-7.42 (m, 1H), 7.28-7.25 (m, 1H), 7.01 (t, J=8.5 Hz, 2H), 2.85-2.74 (m, 4H), 2.04-1.98 (m, 2H).

MS (ESI) [M+H$^+$]: 424

Compound 77:

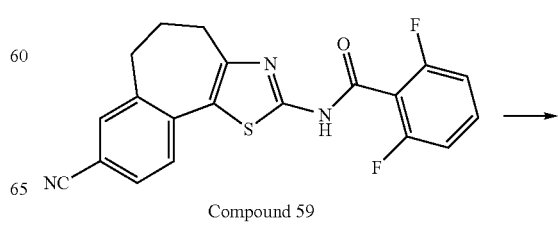

117

-continued

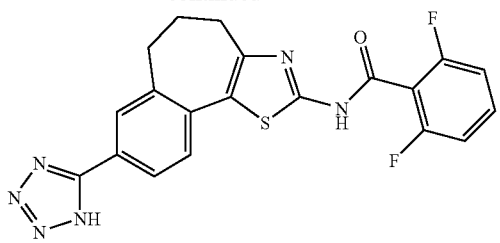

Compound 77

A solution of Compound 59 (50 mg, 0.13 mmol), azidotrimethylsilane (0.1 mL, 0.76 mmol), and ammonium chloride (21 mg, 0.39 mmol) in DMF (2.0 mL) was heated to 90° C. for 3 days. The mixture was cooled to room temperature, diluted with $CH_2Cl_2$, washed with 1N HCl, with water, dried ($Na_2SO_4$), filtered and concentrated. The residue was purified on silica gel (eluted with $CH_2Cl_2$) to give the desired compound 77 (25 mg).

$^1$H NMR (300 MHz, $CDCl_3$) δ 7.96 (s, 1H), 7.93 (d, J=1.6 Hz, 1H), 7.83 (dd, J=8.2, 1.6 Hz, 1H), 7.63 (d, J=8.2 Hz, 1H), 7.52-7.42 (m, 1H), 7.02 (dd, J=8, 8 Hz, 2H), 3.04-3.00 (m, 2H), 2.91-2.85 (m, 2H), 2.16-2.08 (m, 2H).

MS (ESI) [M+H$^+$]: 425

Compound 78:

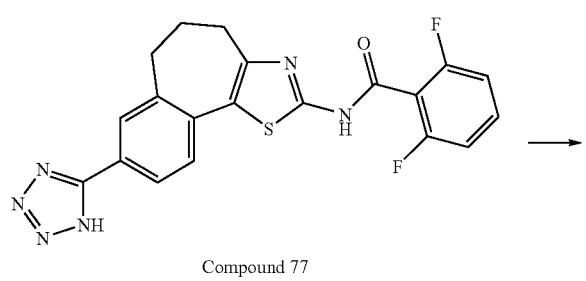

Compound 77

118

-continued

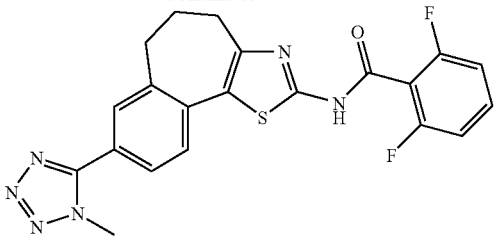

Compound 78

Into a solution of compound 77 (10 mg, 0.024 mmol) in $CH_2Cl_2$ (1.0 mL) at 0° C. was added dropwise a solution of 2M TMSCHN$_2$ in ether (5 drops) in $CH_2Cl_2$ (1.0 mL). The reaction was continuously monitored for completion by TLC (eluted with $CH_2Cl_2$). The solvent was removed under reduced pressure. The residue was purified by eluting through a short plug of silica (eluted with $CH_2Cl_2$) to give the product Compound 78 (9 mg).

$^1$H NMR (300 MHz, $CDCl_3$) δ 8.02-7.99 (m, 2H), 7.65 (d, J=8.5 Hz, 1H), 7.55-7.45 (m, 1H), 7.06 (dd, J=8.5, 8.3 Hz, 2H), 4.41 (s, 3H), 2.96-2.89 (m, 4H), 2.16-2.08 (m, 2H).

MS (ESI) [M+H$^+$]: 439

Compounds 79, 80 and 81:

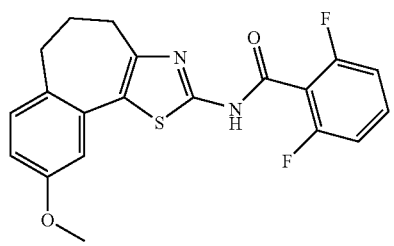

Compound 8

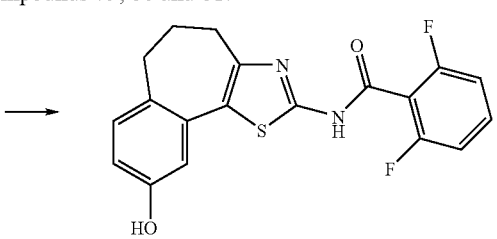

Compound 79

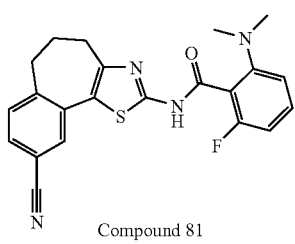

Compound 81

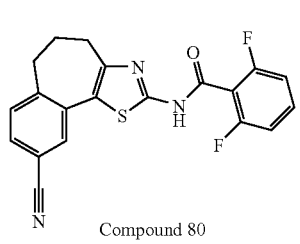

Compound 80

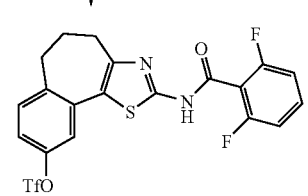

14a

Into a solution of Compound 8 (200 mg, 0.52 mmol) in $CH_2Cl_2$ (4.0 mL) at 0° C. was added a solution of 1M BBr$_3$ (2.0 mL, 1.0 mmol). The mixture was stirred at 0° C. for 30 minutes, then at room temperature for 2 hours. The reaction was quenched by addition of ice. The resulting aqueous solution was extracted with $CH_2Cl_2$. The extract was washed with water, dried ($Na_2SO_4$), filtered and concentrated. The residue can be purified on silica gel (eluted first with $CH_2Cl_2$ then with EtOAc) to give compound 79).

$^1$H NMR (300 MHz, $CDCl_3$) δ 7.57-7.47 (m, 1H), 7.26 (s, 1H), 7.09-6.99 (m, 2H), 6.92 (d, J=2.5 Hz, 1H), 6.71 (dd, J=8.2, 2.5 Hz, 1H) 3.10-3.05 (m, 2H), 2.75-2.72 (m, 2H), 2.15-2.05 (m, 2H).

MS (ESI) [M+H$^+$]: 373

The crude mixture of compound 79, obtained above, was taken up in pyridine (158 mg, 2.0 mmol) and $CH_2Cl_2$ (2.0 mL). The mixture was cooled to 0° C. Into the cooled reaction mixture a solution of trifluoromethanesulfonic acid anhydride (282 mg, 1.0 mmol) in CH₂Cl₂ (1.0 mL) was added. The mixture was stirred at room temperature for 3 hours, diluted with CH₂Cl₂, washed with 1N HCl then with water, dried (Na₂SO₄), filtered and concentrated. The residue was filtered through a short plug of silica gel (eluted with CH₂Cl₂) to give the crude triflate product 14a. The crude 14a was taken up in DMF (1.0 mL). Zn(CN)₂ (60.0 mg, 0.51 mmol) and Pd(PPh₃)₄ (22.0 mg, 0.02 mmol) were added. The mixture was degassed by vacuum/N₂-filled method (4×). The reaction mixture was sealed and heated to 100° C. for 1 day, cooled to room temperature, diluted with CH₂Cl₂, washed with water, dried (Na₂SO₄), filtered and concentrated. The residue was purified on silica gel (eluted with CH₂Cl₂) to give compound 80 (35 mg) and compound 81 (9 mg).

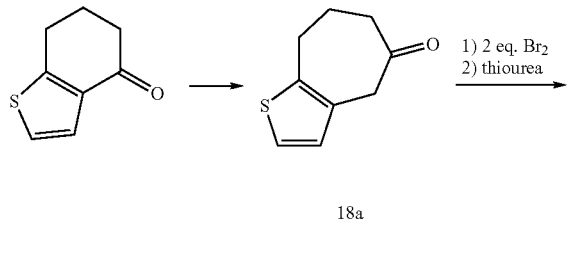

Compound 80: ¹H NMR (300 MHz, CDCl₃) δ 7.78 (bs, 1H), 7.56-7.43 (m, 1H), 7.45 (dd, J=7.7, 1.4 Hz, 1H), 7.27 (d, J=7.7 Hz, 1H), 7.04-6.99 (m, 2H), 2.83-2.65 (m, 4H), 2.05-1.93 (m, 2H).

MS (ESI) [M+H⁺]: 382

Compound 81: MS (ESI) [M+H⁺]: 407

Compound 82:

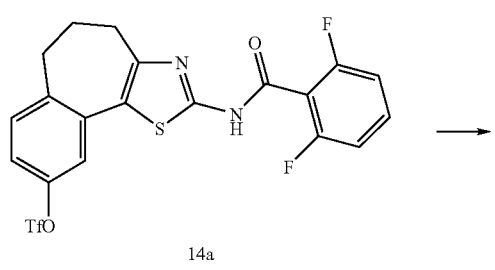

A reaction mixture of 14a (50.0 mg, 0.10 mmol), 0.5M 2-pyridylzinc bromide in THF (1.0 mL, 0.50 mmol), and Pd(Ph₃)₄ (23.0 mg, 0.02 mmol) in THF (0.5 mL) was degassed by vacuum/N₂-filled method (4×). The mixture was heated to 65° C. overnight, cooled to room temperature, concentrated under reduced pressure. The residue was purified on silica gel (eluted with a solution of 1:9 EtOAc:hexanes, then with CH₂Cl₂) to give compound 82 (36 mg).

MS (ESI) [M+H⁺]: 434

Compound 83:

Compound 83 was prepared from 14a as described for the preparation of Compound 82 using a solution of 0.5M 2-thiazolzinc bromide in THF.

MS (ESI) [M+H⁺]: 440

Compounds 84 and 85:

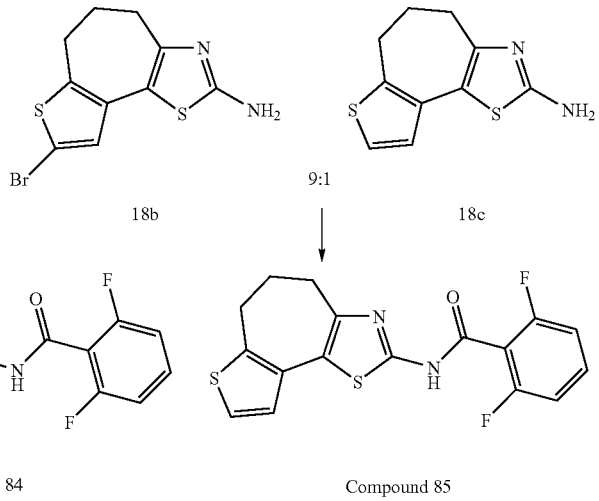

Into a solution of 6,7-dihydrobenzo[b]thiophen-4(5H)-one (0.76 g, 0.50 mmol) in CH₂Cl₂ (20.0 mL) at 0° C. were added a solution of 1M Et₂AlCl in hexanes (5.0 mL, 5.0 mmol). The mixture was stirred at 0° C. for 10 minutes then at room temperature for 20 minutes. The reaction mixture was quenched by ice addition and acidified by addition of a solution of 3N HCl. The resulting mixture was extracted with CH₂Cl₂ (2×). The combined extracts were washed with water, dried (Na₂SO₄), filtered and concentrated to give crude 18a. The crude product was taken up in CH₂Cl₂ (30.0 mL). The mixture was cooled to 0° C. A solution of Br₂ (1.60 g, 10.0 mmol) in CH₂Cl₂ (10.0 mL) was added. The mixture was stirred at 0° C. for 30 minutes, quenched by addition of a solution of 10% NaHSO₃. The organic layer was washed with water, dried (Na₂SO₄), filtered and concentrated. The residue was filtered through a short plug of silica gel (eluted with a solution of 1:9 EtOAc:hexanes then with CH₂Cl₂) to give crude 9:1 mixture of 18b and 18c respectively (255 mg).

18b: MS (ESI) [M+H⁺]: 301

18c: MS (ESI) [M+H⁺]: 223

Into a solution of a 9:1 mixture of 18b and 18c (155 mg, 0.49 mmol) in CH₂Cl₂ (2.0 mL) at room temperature were added DMAP (10 mg, 0.082 mmol), Et₃N (101 mg, 1.0 mmol), and 2,6-difluorobenzoylchloride (176 mg, 1.00 mmol). The mixture was stirred at room temperature overnight. The reaction mixture was concentrated under reduced pressure. The residue was taken up in MeOH (2.0 mL). K₂CO₃ (138 mg, 1.00 mmol) was added. The mixture was stirred at room temperature for 1 hour, diluted with CH₂Cl₂, washed with water, dried (Na₂SO₄), filtered and concentrated. The residue was purified on silica (eluted with a solution of 1:9 EtOAc:hexanes then with a solution of 3:7 EtOAc:

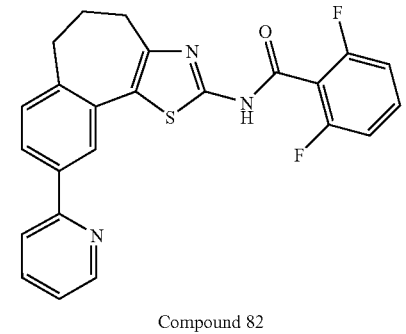

hexanes) to give enriched fractions of compound 84 and 85. Pure Compound 84 (75 mg), and Compound 85 (8 mg) were obtained by recrystallization from ether.

Compound 84: ¹H NMR (300 MHz, CDCl₃) δ 7.50-7.40 (m, 1H), 7.05 (s, 1H), 7.02-6.90 (m, 2H), 2.90-2.80 (m, 2H), 2.78-2.60 (m, 2H), 1.95-1.80 (m, 2H).

MS (ESI) [M+H⁺]: 443

Compound 85: ¹H NMR (300 MHz, CDCl₃) δ 7.43-7.33 (m, 1H), 7.38 (d, J=5.2 Hz), 6.98 (d, J=5.2 Hz), 6.92 (dd, J=8.2, 8.2 Hz, 2H), 3.10-3.05 (m, 4H), 2.16-2.09 (m, 2H).

MS (ESI) [M+H⁺]: 363

Compound 86:

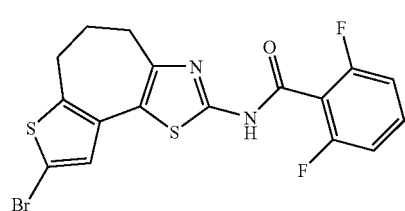

Compound 84

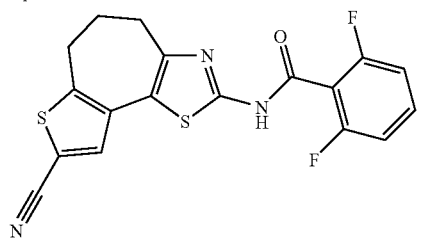

Compound 86

A mixture of Compound 84 (70 mg, 0.16 mmol), Zn(CN)₂ (59 mg, 0.5 mmol) and Pd(PPh₃)₄ (33 mg, 0.03 mmol) in DMF (1.0 mL) was degassed by vacuum/nitrogen-fill method (3×). The resulting mixture was sealed and heated to 100° C. for 1 day, cooled to room temperature, diluted with CH₂Cl₂, washed with water (3×), dried (Na₂SO₄), filtered, and concentrated. The residue was purified on silica gel (eluted with a solution of 1:9 EtOAc:hexanes, then with a solution of 3:7 EtOAc:hexanes) to give compound 86 (21 mg).

¹H NMR (300 MHz, CDCl₃) δ 7.61 (s, 1H), 7.57-7.47 (m, 1H), 7.08-7.05 (m, 2H), 3.09-2.95 (m, 4H), 2.15-2.05 (m, 2H).

MS (ESI) [M+H⁺]: 388

Compound 87:

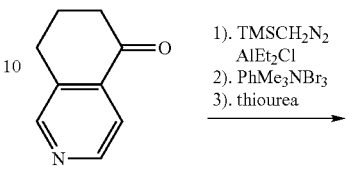

1). TMSCH₂N₂
   AlEt₂Cl
2). PhMe₃NBr₃
3). thiourea

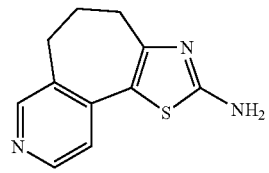

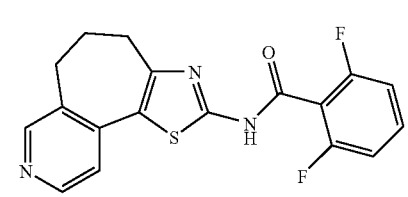

Compound 87

Compound 87 was prepared from 7,8-dihydroisoquinolin-5(6H)-one similarly as described for the preparation of compound 12.

MS (ESI) [M+H⁺]: 358

Compound 88:

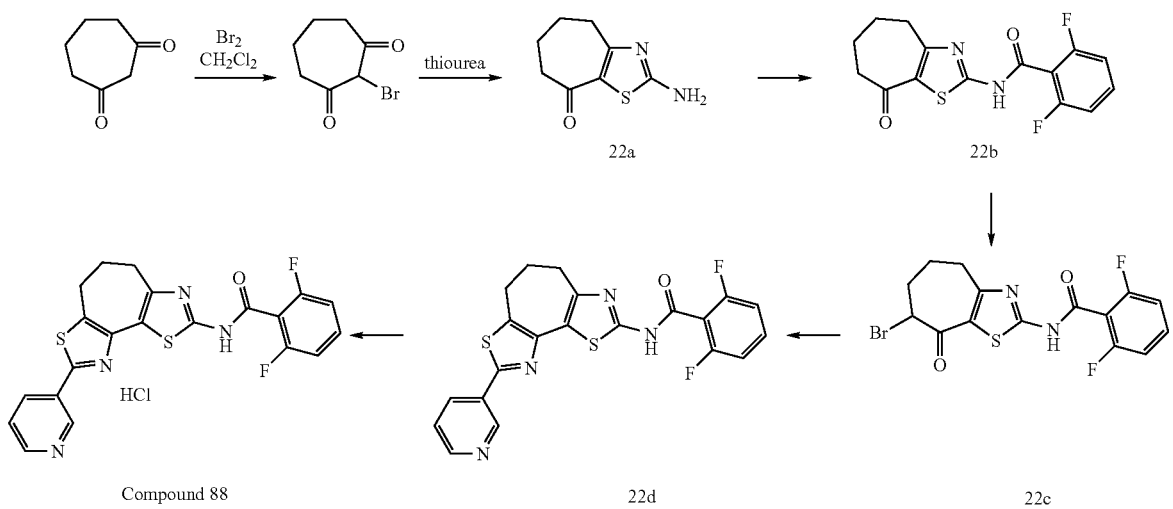

Into the solution of 1,3-cycloheptanedione (252 mg, 2.0 mmol) in 5 mL of CH₂Cl₂ was added a solution of Br₂ (320 mg, 2.0 mmol) in 2 mL of CH₂Cl₂. The mixture was stirred at room temperature for 15 minutes. The white solid was collected, washed with CH$_2$Cl$_2$, and dried to give 2-bromo-1,3-cycloheptanedione (330 mg), which was used for next step with no further purification. Into the solution of 2-bromo-1,3-cycloheptanedione (205 mg, 1 mmol) in 5 mL of MeOH was added thiourea (152 mg, 2 mmol) and K$_2$CO$_3$ (276 mg, 2 mmol). The mixture was stirred at 70° C. for 1 hour, cooled down to room temperature. The solution was concentrated, and the residue was partitioned between EtOAc and H$_2$O. The aqueous layer was washed with EtOAc. The combined organic phases were dried (Na$_2$SO$_4$) and concentrated to give the crude thiazole 22a as a yellow solid.

MS (ESI) [M+H$^+$]: 183

The crude thiazole 22a was suspended in 5 mL of CH$_2$Cl$_2$. To the mixture was added triethylamine (202 mg, 2 mmol), 2,6-difluorobenzoylchloride (176 mg, 1.0 mmol) and catalytic amount of DMAP. The mixture was stirred at room temperature overnight, concentrated under reduced pressure. The residue was purified by column chromatography on silica gel to give 22b (113 mg) as a white solid.

MS (ESI) [M+H$^+$]: 323

Into the solution of 22b (32 mg, 0.1 mmol) in THF (2 mL) at 0° C. was added phenyltrimethylammonium tribromide (38 mg, 0.1 mmol). The mixture was stirred at 0° C. for 1 hour, quenched by ice addition, extracted with CH$_2$Cl$_2$. The extract was dried (Na$_2$SO$_4$), filtered and concentrated to give crude 22c (20 mg) as a solid.

MS (ESI) [M+H$^+$]: 403, 401.

Into the solution of crude 22c (20 mg, 0.05 mmol) in 3 mL of MeOH was added 3-pyridinecarbothioamide (10 mg, 0.07 mmol) and K$_2$CO$_3$ (14 mg, 0.1 mmol). The mixture was stirred at 80° C. in a sealed tube for 2 hours and then cooled to room temperature. The solvent was removed under reduced pressure and the residue was partitioned between EtOAc and H$_2$O. The aqueous layer was washed with EtOAc. The combined organic phases were dried (Na$_2$SO$_4$) and concentrated, The residue was purified by column chromatography on silica gel to give 22d (16 mg) as a yellow solid.

A solution of 22d (5 mg) in 0.5 mL of CH$_2$Cl$_2$ was treated with 0.1 mL of 2 M HCl in Et$_2$O. The precipitate formed was collected and dried to give Compound 88 (5 mg) as a white solid MS (ESI) [M–Cl$^-$]: 441

Compound 89:

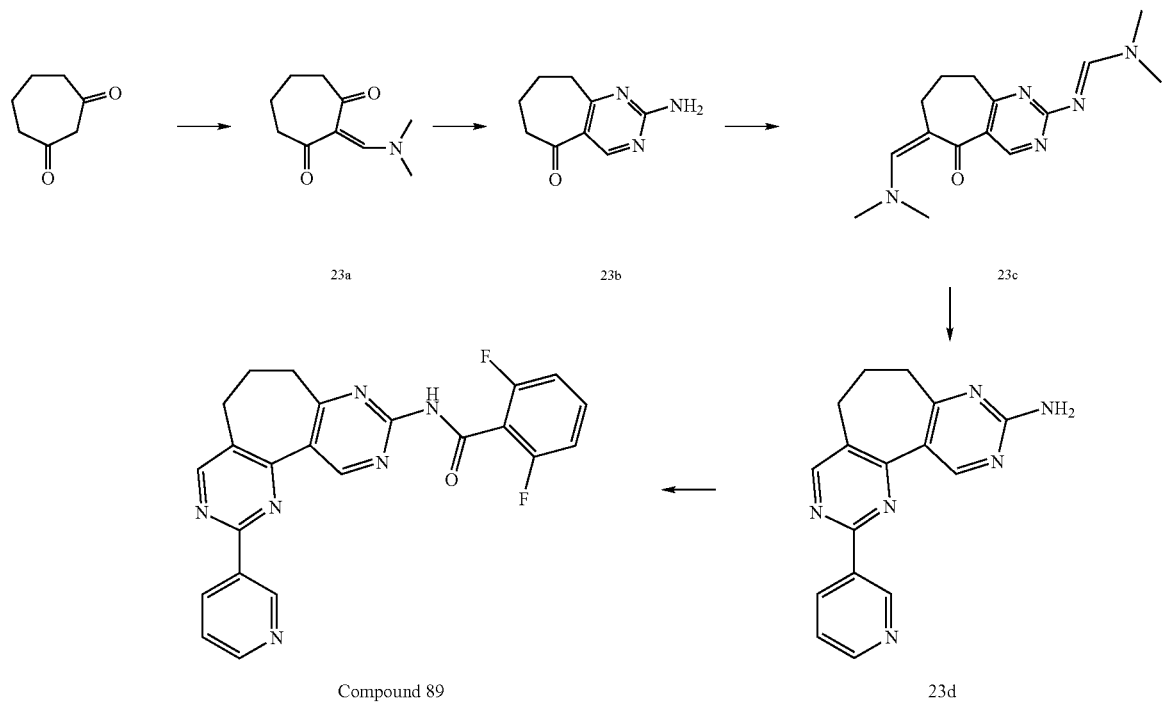

Compound 89

23d

Into a reaction flask with 1,3-cyclohexadione (1.00 g, 7.94 mmol) was added N,N-dimethylformamide dimethyl acetal (7.0 mL, 53.0 mmol). The mixture was stirred at room temperature for 1 hour. The excess reagent was removed under reduced pressure to give crude 23a. The residue was taken up in 2-methoxyethanol (5.0 mL). Guanidine hydrochloride (0.96 g, 10.0 mmol) and K$_2$CO$_3$ (1.38 g, 10.0 mmol) were added. The mixture was heated to 80° C. overnight, cooled to room temperature, diluted with water, extracted with CH$_2$Cl$_2$ (2×). The combined extracted were dried (Na$_2$SO$_4$), filtered and concentrated to give 23b (1.24 g).

MS (ESI) [M+H$^+$]: 178

Into a reaction flask with 23b (400 mg, 2.25 mmol) was added N,N-dimethylformamide dimethyl acetal (3.00 mL, 22.7 mmol). The mixture was stirred at 90° C. overnight, cooled to room temperature, concentrated under reduced pressure to give crude 23c (690 mg).

MS (ESI) [M+H$^+$]: 288

Into a solution of 23c (200 mg, 0.70 mmol) in 2-methoxyethanol (2.0 mL), 3-amidinopyridine hydrochloride (158 mg, 1.00 mmol) and K$_2$CO$_3$ (138 mg, 1.00 mmol) were added. The mixture was heated to 90° C. overnight, cooled to room temperature, acidified with a solution of 2N HCl (4.00 mL). The mixture was stirred at room temperature for 1 hour, neutralized with an aqueous solution of saturated NaHCO$_3$, extracted with CH$_2$Cl$_2$ (2×). The combined extracted were washed with water, dried (Na$_2$SO$_4$), filtered and concentrated to give crude 23d (70% pure, 190 mg).

MS (ESI) [M+H$^+$]: 291

Compound 89 was prepared from 23d and 2,6-difluorobenzoyl chloride as described for the preparation of Compound 8.

MS (ESI) [M+H⁺]: 431

Compound 90:

Compound 90 was prepared from compound 89 as described for the preparation of compound 88

MS (ESI) [M−Cl⁻]: 431

Compound 91:

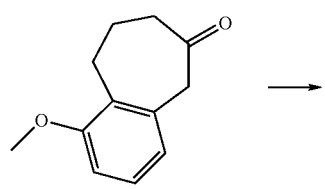

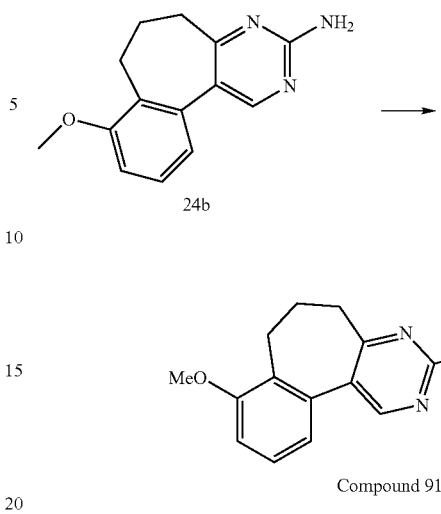

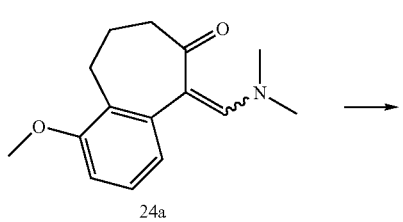

24a

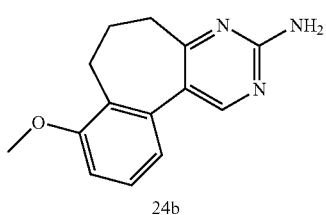

24b

The solution of 5,7,8,9-tetrahydro-1-methoxy-6H-benzocyclohepten-6-one (1.9 g, 10 mmol) in 3 mL of dimethylformamide dimethylacetal was heated in a sealed tube at 90° C. for 6 hours. After cooling to room temperature, the reaction was concentrated under reduced pressure. The residue was purified by column chromatography on silica gel to give 24a (2.30 g, 94% yield) as a pale yellow oil.

MS (ESI) [M+H⁺]: 246

Into the solution of NaOMe (270 mg, 5 mmol) in 50 mL of anhydrous MeOH was added guanidine hydrochloride (480 mg, 5 mmol). The mixture was stirred at room temperature for 0.5 hour. Into the reaction mixture a solution of 24a (1.23 g, 5 mmol) in 10 mL of MeOH was added. The resulting mixture was heated to reflux for 8 hours under nitrogen atmosphere. The solution was then cooled to room temperature, concentrated under reduced pressure. The residue was partitioned between Et₂O and H₂O. The aqueous phase was extracted with ether. The combined organic phases were washed with water, dried (Na₂SO₄), filtered and concentrated under reduced pressure. The residue was purified by column chromatography on silica gel to give 24b (0.93 g, 77% yield) as a white solid.

MS (ESI) [M+H⁺]: 242

Into the solution of 24b (48 mg, 0.2 mmol), triethylamine (41 mg, 0.4 mmol), and a catalytic amount of DMAP in 5 mL of methylene chloride at room temperature was added 2,6-difluorobenzoylchloride (44 mg, 0.25 mmol). The mixture was stirred at room temperature overnight. The solvent was removed under reduced pressure and the residue was taken up in 5 mL of MeOH. The solution was treated with K₂CO₃ (100 mg). The mixture was stirred at room temperature for 1 hour, concentrated under reduced pressure. The residue was partitioned between EtOAc and H₂O, the aqueous phase was extracted with EtOAc. The combined organic phases were washed with water, dried (Na₂SO₄), filtered and concentrated under reduced pressure. The residue was purified by column chromatography on silica gel to give Compound 91 (32 mg, 40% yield) as a white solid.

MS (ESI) [M+H⁺]: 382

Compound 92:

Compound 92 was prepared from 24b and 3-methylisonicotinoyl chloride similarly as described for the preparation of compound 91.

MS (ESI) [M+H⁺]: 361

Compound 93:

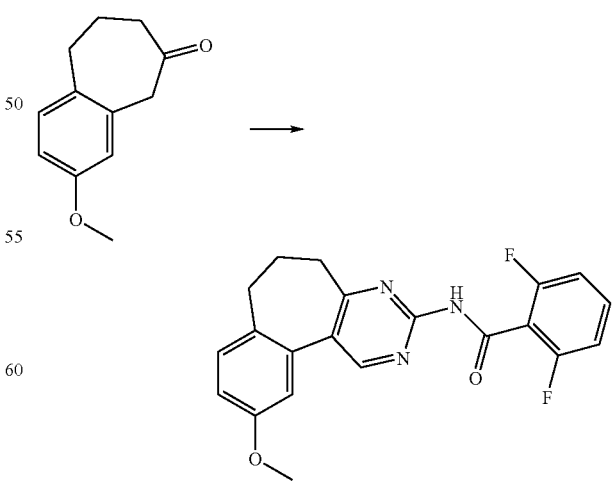

Compound 93 was prepared from 3-methoxy-8,9-dihydro-5H-benzo[7]annulen-6(7H)-one similarly as described for the preparation of compound 91.

¹H NMR (300 MHz, CDCl₃) δ 8.50 (bs, 1H), 7.46-7.37 (m, 1H), 7.18 (d, J=8.0 Hz, 1H), 7.00 (d, J=8.3, 8.0 Hz, 2H), 6.91-6.86 (m, 2H), 2.63-2.52 (m, 2H), 2.50-2.47 (m, 2H), 2.30-2.10 (m, 2H).

MS (ESI) [M+H⁺]: 382

Compound 94:

Compound 94 was prepared from 7-methoxy-2,3-dihydrobenzo[b]oxepin-4(5H)-one similarly as described for the preparation of compound 91.

¹H NMR (300 MHz, CDCl₃) δ 8.94 (bs, 1H), 8.54 (s, 1H), 7.47-7.37 (m, 1H), 7.11 (d, J=8.5 Hz, 1H), 7.02-6.87 (series of m, 4H), 4.59-4.55 (m, 2H), 2.91-2.87 (m, 2H).

MS (ESI) [M+H⁺]: 384

Compound 95:

Compound 95 was prepared similarly as described for the preparation of compound 94 using 3-methylisonicotinoyl chloride.

MS (ESI) [M+H⁺]: 363

Compound 96:

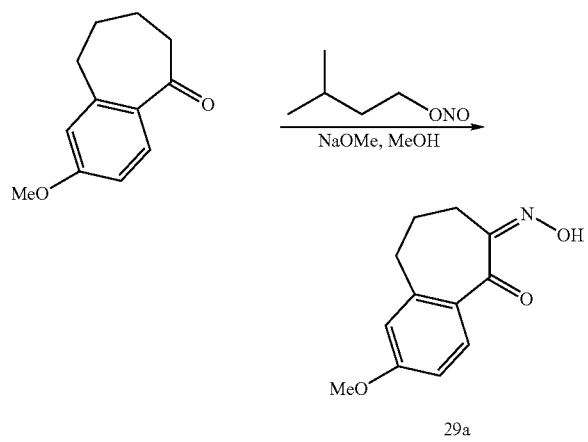

Into the solution of NaOMe (810 mg, 15 mmol) in 50 mL of MeOH was added 7-methoxybenzosuberone (1.90 g, 10 mmol) and isopentyl nitrite (1.48 mL, 11 mmol). The mixture was stirred at room temperature for 48 hours. The reaction mixture was concentrated under reduced pressure. The residue was taken up in methylene chloride, washed with H₂O. The aqueous layer was neutralized with 1N aqueous HCl and extracted with methylene chloride. The combined organic phases were dried (Na₂SO₄), filtered and concentrated. The residue was recrystallized from CH₂Cl₂/hexanes to give 29a (1.6 g, 73%) as a white solid.

MS (ESI) [M+H⁺]: 220

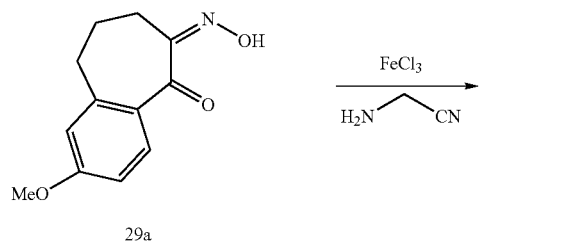

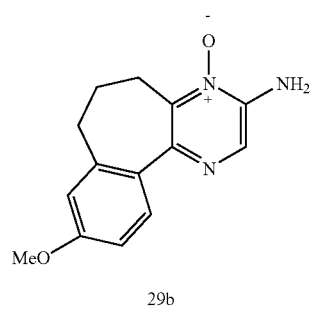

29b

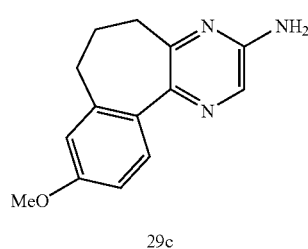

29c

Into the solution of aminoacetonitrile sulfate (720 mg, 5 mmol) in 5 mL of MeOH at room temperature were added 12 N aqueous NaOH (10 mmol), 29a (550 mg, 2.5 mmol) and ferric chloride (407 mg, 2.5 mmol). The resulting mixture was stirred at 50° C. for 2 hours then at reflux for 4 hours. The reaction mixture was cooled to room temperature. The solvent was removed under reduced pressure. The residue was purified by column chromatography on silica gel to give 29b (420 mg, 65% yield) as a white solid.

MS (ESI) [M+H⁺]: 258

Into the solution of 29b (257 mg, 1 mmol) in 10 mL of MeOH was added Pd/C (10% w/w, 150 mg). The mixture was stirred under a pressure of hydrogen (3 atm) at 50° C. for 48 hours. The solid was filtered off and the filtrate was concentrated under reduced pressure. The residue was taken up in EtOAc. The solution was washed with water and the aqueous layer was extracted with EtOAc. The combined organic layers were washed with water, dried (Na₂SO₄), filtered and concentrated. The residue was purified by column chromatography on silica gel to give 29c (150 mg, 63%) as a white solid.

MS (ESI) [M+H⁺]: 242

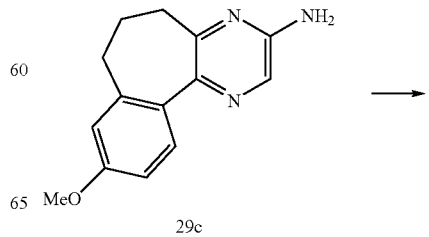

129
-continued

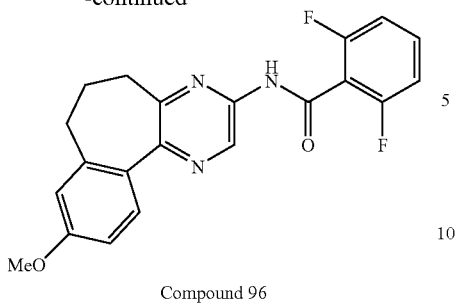
Compound 96

Compound 96 was prepared from 29c similarly as described for the preparation of compound 91.
MS (ESI) [M+H⁺]: 382

Compound 97:
Compound 97 was prepared from 29b similarly as described for the preparation of compound 96.
MS (ESI) [M+H⁺]: 398

Compound 98:

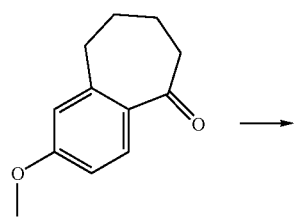

130
-continued

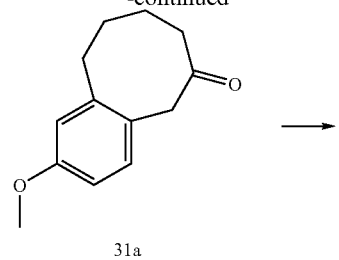
31a

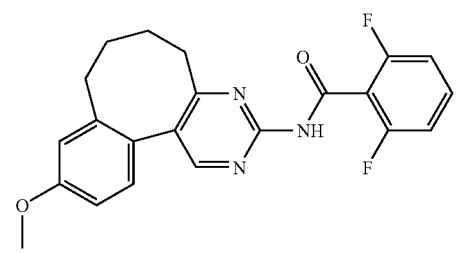
Compound 98

Compound 98 was prepared from 31a as described for the preparation of compound 91. 31a was prepared from 2-methoxy-6,7,8,9-tetrahydro-5H-benzo[7]annulen-5-one by ring-expansion method described in the preparation of Compound 8.
MS (ESI) [M+H⁺]: 396

Compound 99:

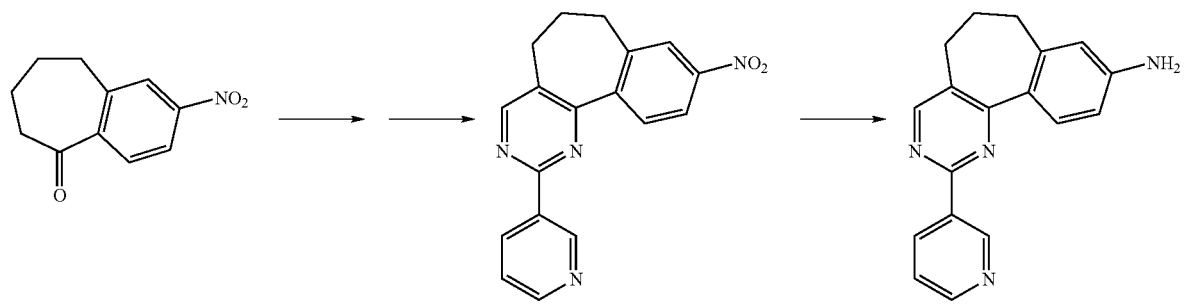

32a     32b

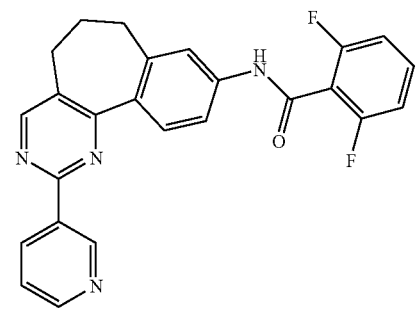
Compound 99

32a was prepared from 2-nitro-6,7,8,9-tetrahydro-5H-benzo[7]annulen-5-one as described for the preparation of 24b.

Into a solution of 32a (400 mg) in ethanol (10.0 mL) at room temperature were added a solution of 2N HCl (1.0 mL) and 10% Pd/C (100 mg). The mixture was stirred under hydrogen gas (1 atm) for 3 hours. The mixture was neutralized with a solution of saturated NaHCO₃, extracted with CH₂Cl₂ (2×). The combined extracts were dried (Na₂SO₄), filtered and concentrated to give 32b (317 mg).

MS (ESI) [M+H⁺]: 289

Compound 99 was prepared from 32b as described for the preparation of compound 91.

MS (ESI) [M+H⁺]: 429

Compound 100:

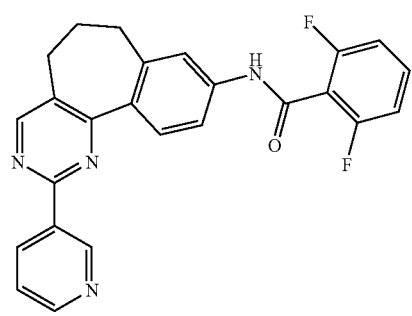

Compound 99

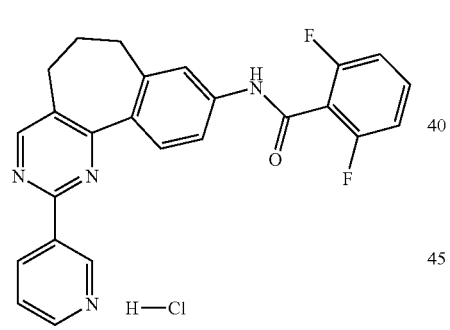

Compound 100

Into a solution of compound 99 (7 mg) in methylene chloride (1.0 mL) at room temperature was added a solution of 4M HCl in 1,4-dioxane (0.1 mL). The solvent and excess reagent were removed under reduced pressure. The residue was washed with ether and dried to give compound 100 (7 mg).

MS (ESI) [M−Cl⁻]: 429

Compound 101:

Compound 101 was prepared from 32b as described for the preparation of compound 92.

MS (ESI) [M+H⁺]: 408

Compound 102:

Compound 102 was prepared from compound 101 as described for the preparation of Compound 100.

MS (ESI) [M−HCl—Cl⁻]: 408

Compounds 103 and 104

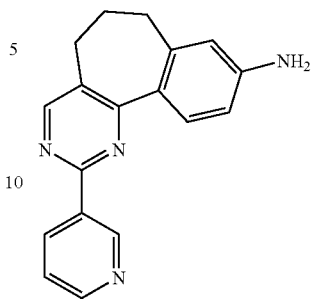

32b

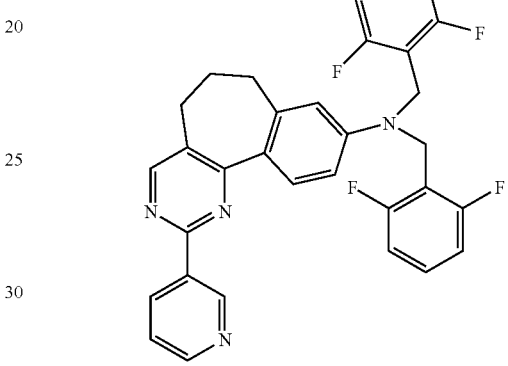

Compound 103

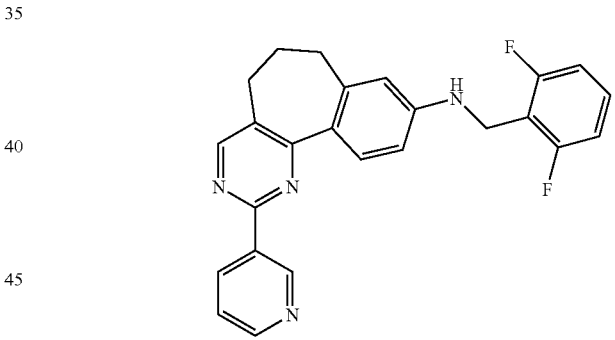

Compound 104

Into a solution of the amine 32b (30 mg, 0.1 mmol) and 2,6-difluorobenzaldehyde (14 mg, 0.1 mmol) in CH₂Cl₂ (1.0 mL) was added TFA (1 drop). The mixture was stirred at room temperature for 30 minutes. Na(OAc)₃BH (42 mg, 0.2 mmol) was added. The mixture was stirred at room temperature overnight, diluted with CH₂Cl₂, washed with a solution of saturated NaHCO₃, dried (Na₂SO₄), filtered and concentrated. The residue was purified on silica gel (eluted with 1:9, EtOAc:hexanes) to give compound 103 (15 mg) and compound 104 (9 mg).

Compound 103: MS (ESI) [M+H⁺]: 541.

Compound 104: MS (ESI) [M+H⁺]: 415.

Compound 105:

Compound 105 was prepared from compound 104 as described for the preparation of Compound 100.

MS (ESI) [M−HCl—Cl⁻]: 415.

133

Compound 106:

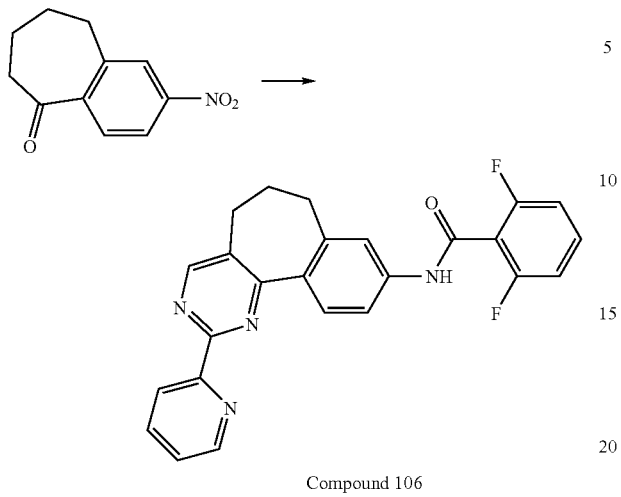

Compound 106

Compound 106 was prepared from 2-nitro-6,7,8,9-tetrahydro-5H-benzo[7]annulen-5-one and 2-amidinopyridine hydrochloride similarly as described for the preparation of compound 99:

MS (ESI) [M+H$^+$]: 429

Compound 107:

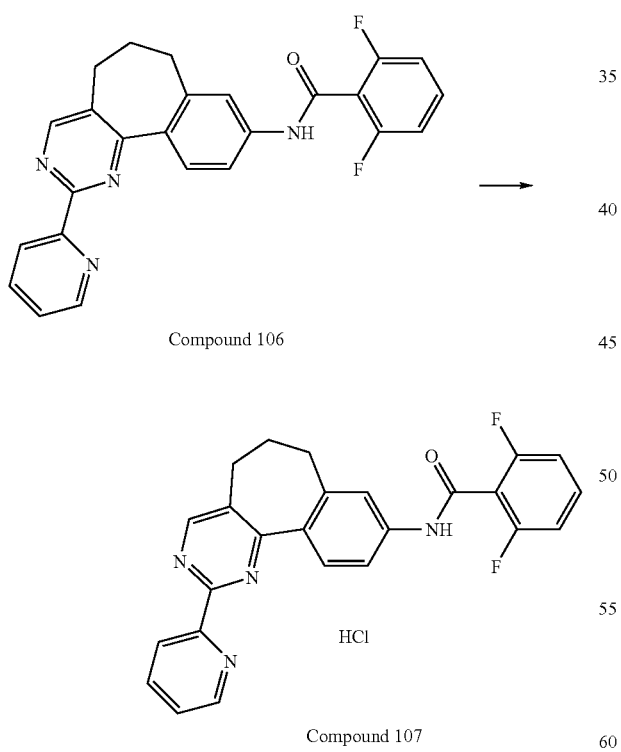

Compound 107

A solution of Compound 106 (10 mg) in 0.5 mL of CH$_2$Cl$_2$ was treated with 0.1 mL of 2 M HCl in Et$_2$O. The precipitate formed was collected and dried to give Compound 107 (10 mg) as a white solid.

MS (ESI) [M−Cl$^−$]: 429

134

Compound 108:

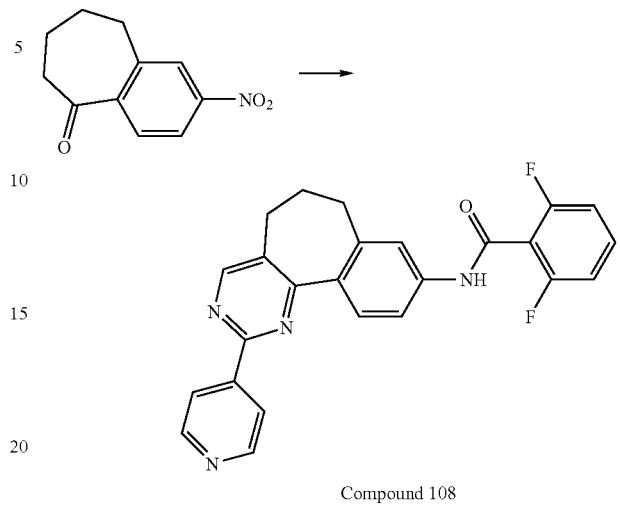

Compound 108

Compound 108 was prepared from 2-nitro-6,7,8,9-tetrahydro-5H-benzo[7]annulen-5-one and 4-amidinopyridine hydrochloride similarly as described for the preparation of compound 99:

MS (ESI) [M+H$^+$]: 429

Compound 109:

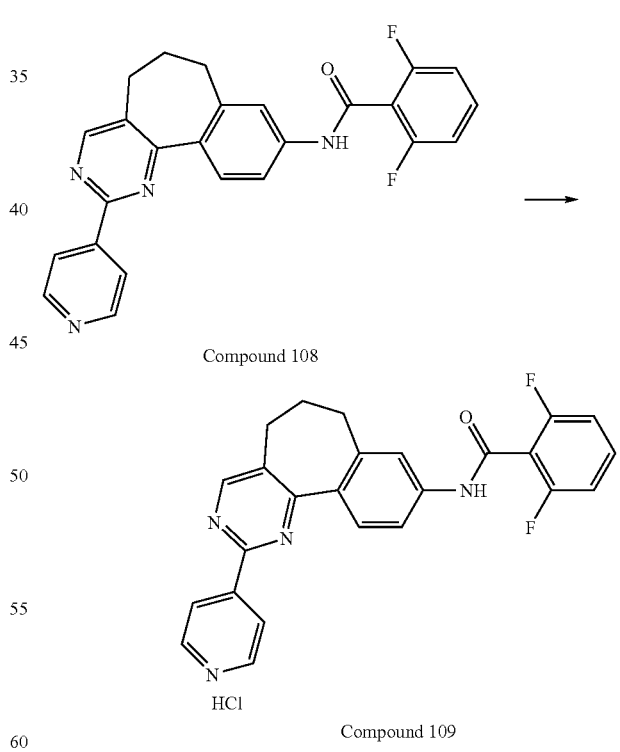

Compound 109

A solution of compound 108 (5 mg) in 0.5 mL of CH$_2$Cl$_2$ was treated with 0.1 mL of 2 M solution of HCl in Et$_2$O. The precipitate formed was collected and dried to give compound 109 (5 mg) as a white solid.

MS (ESI) [M−Cl$^−$]: 429

Compound 110:

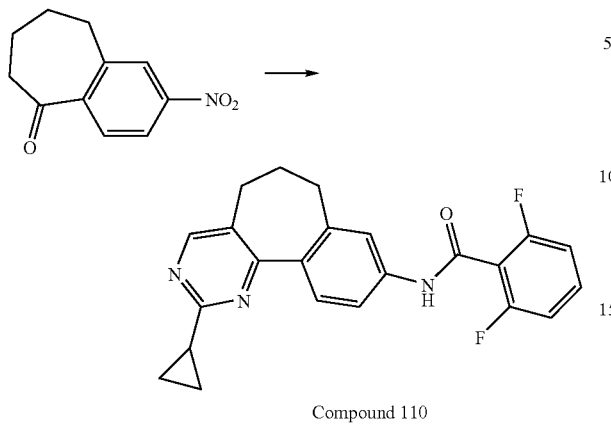

Compound 110

Compound 110 was prepared from 2-nitro-6,7,8,9-tetrahydro-5H-benzo[7]annulen-5-one and cyclopropycarbamidine hydrochloride similarly as described for the preparation of compound 99:

MS (ESI) [M+H⁺]: 392

Compound 111:

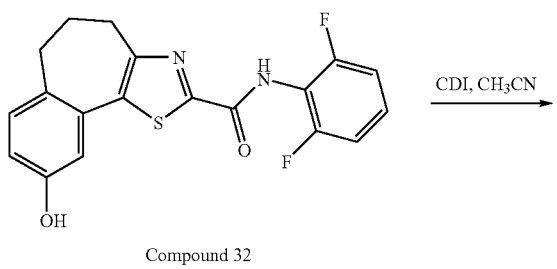

Compound 32

CDI, CH₃CN

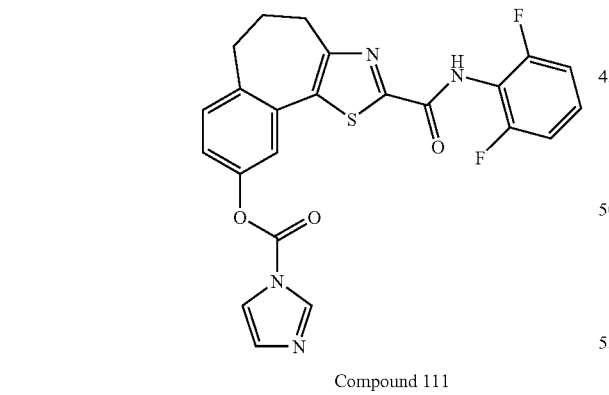

Compound 111

Into the solution of Compound 32 (100 mg, 0.27 mmol) in 4 mL of CH₃CN was added 1,1-carbonylbis-1H-imidazole (150 mg, 0.93 mmol). The mixture was heated to reflux for 30 minutes. The reaction was cooled to room temperature, concentrated under reduced pressure. The residue was purified by column chromatography on silica gel to give compound III (88 mg, 70% yield) as a white solid.

MS (ESI) [M+H⁺]: 467

Compound 112:

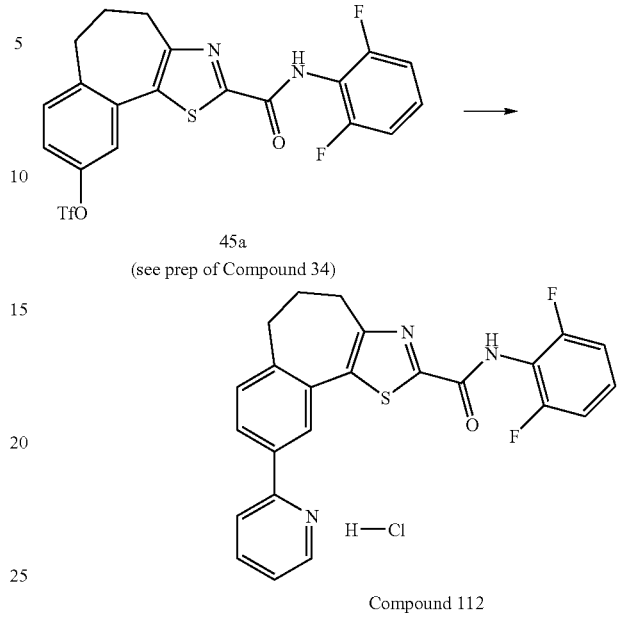

45a
(see prep of Compound 34)

Compound 112

Compound 112 was prepared from the triflate 45a similarly as described for the preparation of compound 82 followed by salt formation as described for the preparation of compound 107.

MS (ESI) [M−Cl⁻]: 434

Compound 113:

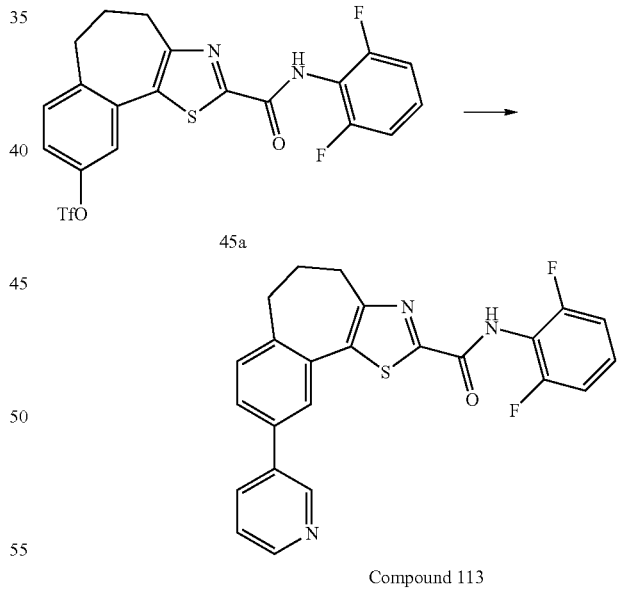

45a

Compound 113

A mixture of 45a (400 mg, 0.79 mmol), pyridin-3-ylboronic acid (185 mg, 1.50 mmol), potassium acetate (196 mg, 2.0 mmol), and Pd(PPh₃)₄ (100 mg, 0.1 mmol) in 10:1 solution of ethanol:water (5.5 mL) was purged with nitrogen for 10 minutes. The mixture was sealed and heated to 85° C. overnight, cooled to room temperature, diluted with water, extracted with CH₂Cl₂ (2×). The combined extracts were dried (Na₂SO₄), filtered and concentrated. The residue was purified on silica gel (eluted with CH₂Cl₂ then with a solution of 4:1 CH₂Cl₂:EtOAc) to give compound 113 (230 mg).

MS (ESI) [M+H⁺]: 434

Compound 114:

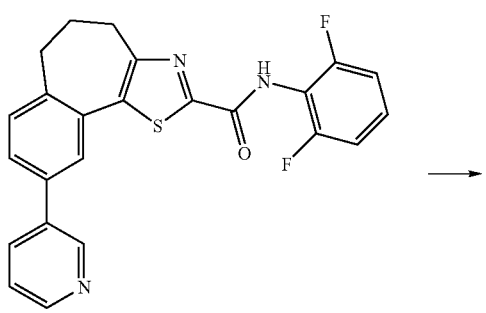
Compound 113

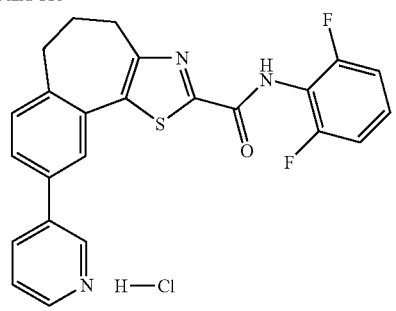
Compound 114

Into a solution of compound 113 (230 mg, 0.53 mmol) in CH$_2$Cl$_2$ (10.0 mL) at room temperature was added a solution of 2M HCl in ether (2.0 mL, 2.0 mmol). The mixture was stirred at room temperature for 10 minutes. Solvent and excess reagent was removed under reduced pressure. The solid was washed with ether to give compound 114 (198 mg).

$^1$H NMR (300 MHz, CD$_3$OD) δ 10.65 (s, 1H), 9.45 (s, 1H), 8.85-8.65 (m, 2H), 8.00 (s, 1H), 7.96-7.18 (series of m, 6H), 3.17-3.11 (m, 2H), 2.89-2.80 (m, 2H), 2.25-2.15 (m, 2H).

MS (ESI) [M−Cl$^-$]: 434

Compound 115:

Compound 115 was prepared as described for the preparation of compound 113 using 2-aminopyridine-5-boronic acid pinacol ester.

MS (ESI) [M+H$^+$]: 449

Compound 116:

Compound 116 was prepared from compound 115 as described for the preparation of compound 114.

MS (ESI) [M−Cl$^-$]: 449

Compound 117:

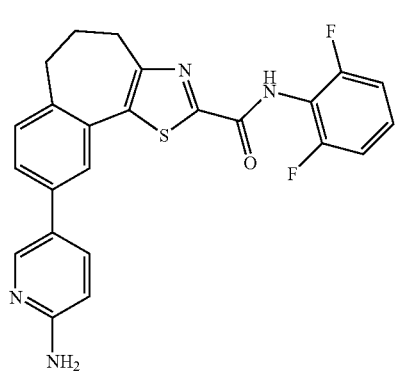
Compound 115

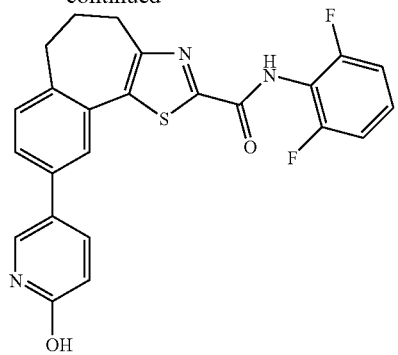
Compound 117

Into a solution of compound 115 (10.0 mg, 0.022 mmol) in acetic acid (1.0 mL) at 0° C. was added NaNO$_2$ (10.0 mg, 0.14 mmol). The mixture was stirred at 0° C. for 1 hour then at room temperature overnight, concentrated under reduced pressure. The residue was taken up in a solution of methanol (0.5 mL) and pyridine (0.5 mL). The mixture was heated to 50° C. for 1 hour, cooled to room temperature, concentrated under reduced pressure. The residue was taken up in water, acidified with acetic acid, extracted with CH$_2$Cl$_2$ (3×). The combined extracts were dried (Na$_2$SO$_4$), filtered and concentrated. The residue was purified on a short plug of silica gel (eluted with CH$_2$Cl$_2$ then with EtOAc) to give compound 117 (8 mg).

MS (ESI) [M+H$^+$]: 450

Compound 118:

Compound 118 was prepared as described for the preparation of compound 113 using 2-fluoropyridine-4-boronic acid.

MS (ESI) [M+H$^+$]: 452

Compound 119:

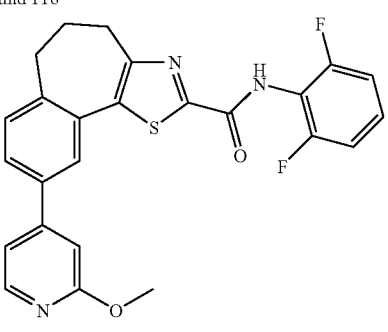
Compound 118

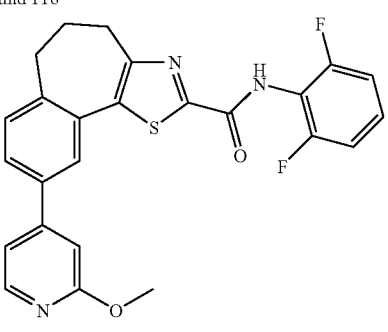
Compound 119

Into a solution of compound 118 (10.0 mg, 0.022 mmol) in methanol (1.0 mL) at room temperature was added a solution of 25% NaOMe in methanol (0.2 mL, 0.88 mmol). The mixture was heated to 50° C. for 1 day, cooled to room temperature, diluted with water, acidified with acetic acid, extracted with CH$_2$Cl$_2$ (2×). The combined extracts were washed with a solution of saturated NaHCO$_3$, dried (Na$_2$SO$_4$), filtered and concentrated. The residue was purified on silica gel to give compound 119 (8 mg).

MS (ESI) [M+H$^+$]: 464

Compound 120:

Compound 120 was prepared as described for the preparation of compound 113 using 6-fluoropyridine-3-boronic acid.

MS (ESI) [M+H$^+$]: 452

Compound 121:

Compound 121 was prepared from compound 120 similarly as described for the preparation of compound 119.

MS (ESI) [M+H$^+$]: 464

Compound 122:

Compound 122 was prepared as described for the preparation of compound 113 using 2-fluoropyridine-3-boronic acid.

MS (ESI) [M+H$^+$]: 452

Compound 123:

Compound 123 was prepared from compound 122 similarly as described for the preparation of compound 119.

MS (ESI) [M+H$^+$]: 464

Compound 124:

Compound 124 was prepared as described for the preparation of compound 113 using pyrimidine-5-boronic acid.

MS (ESI) [M+H$^+$]: 435

Compound 125

Compound 125 was prepared as described for the preparation of compound 113 using pyridine-4-boronic acid.

MS (ESI) [M+H$^+$]: 434

Compound 126:

Compound 126 was prepared from compound 125 as described for the preparation of compound 113.

MS (ESI) [M−Cl$^−$]: 434

Compound 127:

Compound 127 was prepared as described for the preparation of compound 113 using 1-methyl-4-(4,4,5,5-tetramethyl-1,3,2-dioxaborolan-2-yl)-1H-pyrazole.

MS (ESI) [M+H$^+$]: 437

Compound 128:

Compound 128 was prepared as described for the preparation of compound 113 using tert-butyl 4-(4,4,5,5-tetramethyl-1,3,2-dioxaborolan-2-yl)-1H-pyrazole-1-carboxylate. Deprotection occurred in situ to provide compound 128.

MS (ESI) [M+H$^+$]: 423

Compound 129:

45a

Compound 129

Into a solution of 45a (600 mg, 1.19 mmol) and 1-methyl-5-(tributylstannyl)-1H-imidazole (888 mg, 2.38 mmol) in DMF (5.0 mL) was added Pd(PPh$_3$)$_4$ (300 mg, 0.26 mmol). The mixture was degassed by vacuum/nitrogen-filled method. The resulting mixture was sealed and heated to 100° C. overnight, cooled to room temperature, diluted with ethyl acetate, washed with water (3×) then with brine and dried (Na$_2$SO$_4$), filtered and concentrated. The residue was purified on silica gel (eluted with 1:9 MeOH:CH$_2$Cl$_2$ to give compound 129 (245 mg).

MS (ESI) [M+H$^+$]: 437

Compound 130:

Compound 130 was prepared from compound 129 similarly as described for the preparation of compound 114.

MS (ESI) [M−Cl$^−$]: 437

Compound 131:

64a
(see prep of Compound 19)

Compound 131

Into a slurry of 64a (50 mg, 0.13 mmol), toluenesulfonylamide (34 mg, 0.2 mmol) and silica (200 mg) in toluene (4.0 mL) was heated to 80° C. for 4 hours. The mixture was cooled to room temperature, filtered through a short plug of Celite. The filtrate was concentrated under reduced pressure. The residue was taken up in MeOH (1.0 mL) and 1,2-dimethoxyethane (2.0 mL). p-Toluenesulfonylmethyl isocyanide (78 mg, 0.40 mmol) and K$_2$CO$_3$ (138 mg, 1.00 mmol) were added. The mixture was heated to 80° C. for 1 day, cooled to room temperature, diluted with CH$_2$Cl$_2$, washed with water (2×), dried (Na$_2$SO$_4$), filtered and concentrated. The residue was purified on silica gel to give Compound 131 (18 mg).

MS (ESI) [M+H$^+$]: 423

Compound 132:

Compound 132 was prepared from compound 131 similarly as described for the preparation of compound 114.

MS (ESI) [M−Cl$^−$]: 423

Compound 133:

solution of saturated NaHCO$_3$, dried (Na$_2$SO$_4$), filtered and concentrated under reduced pressure to give 66c (895 mg, 95%).

MS (ESI) [M+H$^+$]: 240

Into a solution of 66c (239 mg, 1.00 mmol) in THF at 0° C. was added trimethylphenylammonium tribromide (376 mg, 1.0 mmol). The mixture was stirred at 0° C. for 10 minutes then at room temperature for 2 hours. The mixture was diluted with water, extracted with CH$_2$Cl$_2$. The extract was washed with a solution of 10% NaHSO$_3$, then with water and dried

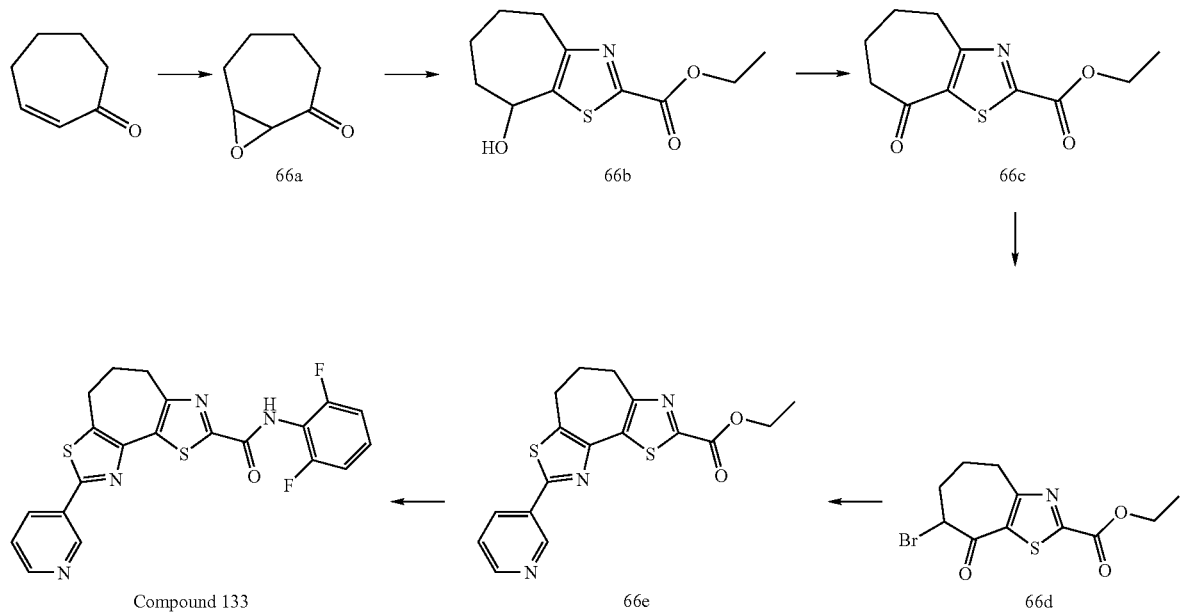

Into a solution of 2,3-cycloheptanone (1.00 g, 0.90 mmol) in THF (10.0 mL) at 0° C. were added 2M NaOH (5.0 mL, 10.0 mmol) followed by a solution of 30% aqueous H$_2$O$_2$ (0.5 mL, 4.3 mmol). The mixture was stirred at room temperature for 1 hour, diluted with water, extracted with CH$_2$Cl$_2$ (4×). The combined extracts were dried (Na$_2$SO$_4$), filtered and concentrated to give the crude epoxide 66a. The crude epoxide 66a obtained was taken up in ethanol (10.0 mL). Into the mixture ethyl thiooxamate (1.33 g, 10.0 mmol) was added. The mixture was heated to 80° C. for 5 days, cooled to room temperature, diluted with water, extracted with CH$_2$Cl$_2$ (3×). The combined extracts were dried (Na$_2$SO$_4$), filtered and concentrated. The residue was purified on silica gel to give 66b (950 mg, 44% for 2 steps).

MS (ESI) [M+H$^+$]: 242

Into a solution of 66b (950 mg, 3.93 mmol) in CH$_2$Cl$_2$ (10.0 mL) at 0° C. was added Dess-Martin reagent (2.12 g, 5.00 mmol). The mixture was stirred at 0° C. for 30 minutes then at room temperature for 2 hours. The reaction mixture was quenched by addition of a solution of 10% NaHSO$_3$. After 10 minutes at room temperature, the reaction mixture was neutralized with a solution of saturated NaHCO$_3$, extracted with CH$_2$Cl$_2$ (3×). The combined extracts were washed with a solution of saturated NaHCO$_3$, dried (Na$_2$SO$_4$), filtered and concentrated under reduced pressure to give 66d (325 mg), which was used without further purification.

Into the crude 66d (325 mg, 1 mmol) in ethanol (5.0 mL) was added pyridine-3-carbothioamide (138 mg, 1.00 mmol). The mixture was stirred at room temperature for 1 day, diluted with a solution of saturated NaHCO$_3$, extracted with CH$_2$Cl$_2$ (2×). The combined extracts were dried (Na$_2$SO$_4$), filtered and concentrated under reduced pressure. The residue was purified by recrystallization form ether to give 66e (185 mg).

MS (ESI) [M+H$^+$]: 358

Into a solution of 66e (22 mg, 0.06 mmol) in toluene (1.0 mL) were added 2,6-difluoroaniline (26 mg, 0.2 mmol) and a solution of 2M trimethylaluminum in hexane (0.1 mL, 0.2 mmol). The mixture was heated to 85° C. for 2 hours, cooled to room temperature, quenched with addition of ice. The mixture was extracted with methylene chloride. The extract was washed with a solution of 1N NaOH, then with water and dried (Na$_2$SO$_4$), filtered and concentrated. The residue was purified on silica to give compound 133 (16 mg).

MS (ESI) [M+H$^+$]: 441

Compound 134:

Compound 134 was prepared from compound 133 similarly as described for the preparation of compound 114.

MS (ESI) [M−Cl$^−$]: 441

Compound 135:

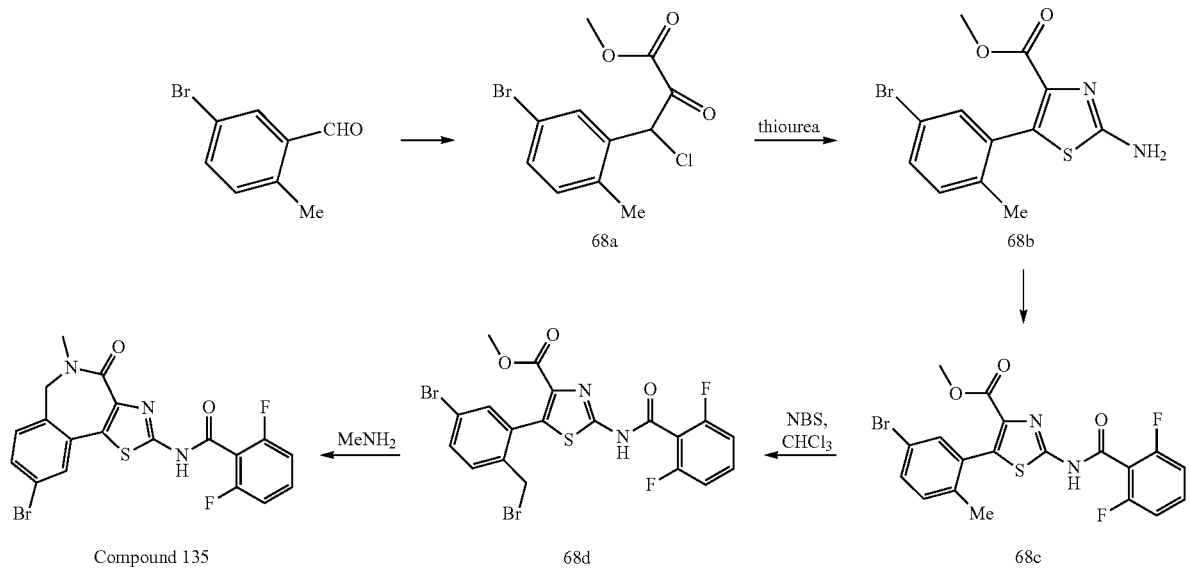

Compound 135

25% NaOMe in MeOH (2.30 mL, 10.0 mmol) was dissolved in 40 mL of THF. The solution was cooled to −78° C. and treated dropwise with a solution of 5-bromo-2-methyl-benzaldehyde (2.0 g, 10 mmol) in 5 mL of THF and methyl 2,2-dichloroacetate (1.43 g, 10.0 mmol). The mixture was stirred at −78° C. for 3 hours, then at room temperature overnight. The reaction was quenched with $H_2O$ and the mixture was extracted with methylene chloride. The combined organic phases were washed with brine, dried ($Na_2SO_4$), filtered and concentrated. The residue was purified by column chromatography on silica gel to give 68a (3.0 g).

Into the solution of 68a (1.5 g, 4.9 mmol) in 20 mL of MeOH was added thiourea (0.76 g, 10.0 mmol) at room temperature. The mixture was stirred 80° C. for 1 hour, cooled to room temperature, concentrated. The residue was partitioned between EtOAc and $H_2O$, the aqueous phase was basified with $NaHCO_3$, extracted with EtOAc. The combined organic phases were washed with water, dried ($Na_2SO_4$), filtered, and concentrated. The residue was purified by column chromatography on silica gel to give 68b (2.0 g, 61% yield) as a solid.

MS (ESI) [M+H$^+$]: 329, 327.

Into the solution of 68b (654 mg, 2.0 mmol), triethylamine (404 mg, 4.0 mmol), and catalytic amount of DMAP in 10 mL of $CH_2Cl_2$ at room temperature was added 2,6-difluorobenzoylchloride (492 mg, 2.8 mmol). The mixture was stirred at room temperature overnight, concentrated under reduced pressure. The residue was purified by column chromatography on silica gel (eluted with methylene chloride) to give 68c (660 mg, 71% yield).

MS (ESI) [M+H$^+$]: 469, 467

Into the solution of 68c (234 mg, 0.5 mmol) in 5 mL of anhydrous $CHCl_3$ was added NBS (90 mg, 0.5 mmol) and benzoyl peroxide (24 mg, 0.1 mmol). The reaction mixture was reflux under nitrogen atmosphere for 3 hours, cooled to room temperature, and diluted with $CH_2Cl_2$. The mixture was washed with aqueous $NaHCO_3$ and $H_2O$. The organic layer was dried ($Na_2SO_4$), filtered and concentrated under reduced pressure. The residue was purified by column chromatography on silica gel to give 68d (223 mg) as a solid.

MS (ESI) [M+H$^+$]: 549, 547, 545.

Into the solution of 68d (55 mg, 0.1 mmol) in 2 mL of MeOH was added 2 M solution of $MeNH_2$ in MeOH (0.2 mL). The resulting solution was stirred at room temperature overnight. The reaction was concentrated and the residue was purified by column chromatography on silica gel to give compound 135 (38 mg) as a white solid.

MS (ESI) [M+H$^+$]: 466, 464.

Compound 136:

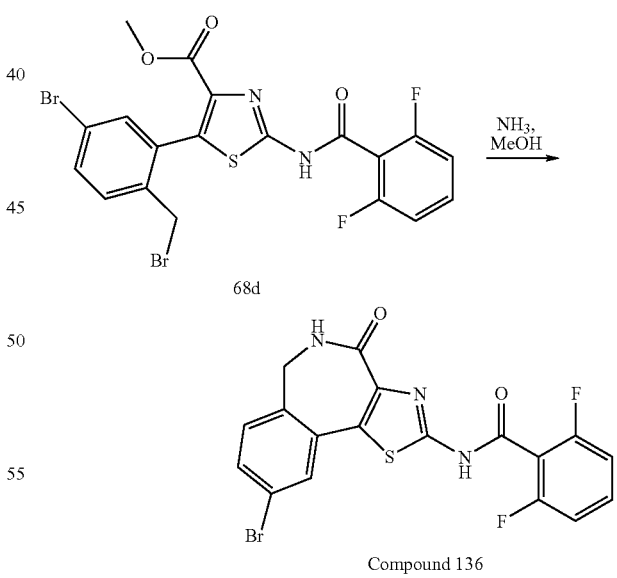

Compound 136

Into the solution of 68d (55 mg, 0.1 mmol) in 2 mL of MeOH was added 2 M solution of ammonia in MeOH (0.5 mL). The resulting solution was stirred at room temperature overnight. The reaction was concentrated and the residue was purified by column chromatography on silica gel to give compound 136 (33 mg) as a white solid.

MS (ESI) [M+H$^+$]: 452, 450

Compound 137:

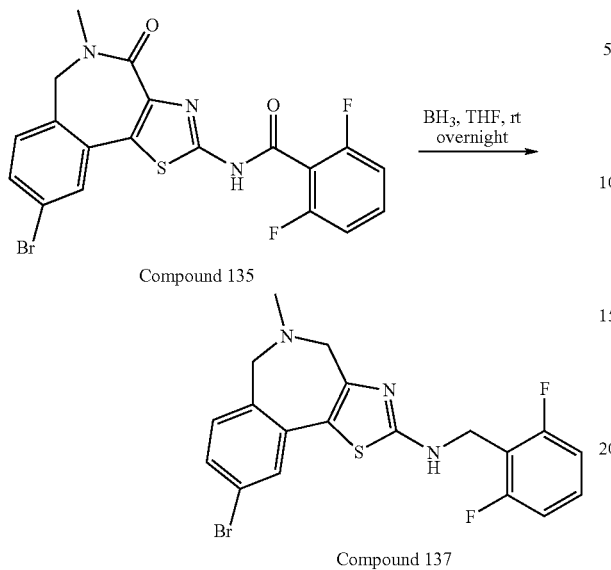

Into solution of compound 135 (23.5 mg, 0.05 mmol) in 2 mL of THF at room temperature was added a 1.0 M solution of BH$_3$-THF in THF (1.0 mL). The mixture was stirred at room temperature overnight, quenched with water and extracted with CH$_2$Cl$_2$. The extracts were dried (Na$_2$SO$_4$), filtered and concentrated. The residue was purified by column chromatography on silica gel to give compound 137 (10 mg) as a yellow solid.

MS (ESI) [M+H$^+$]: 436, 434

Compound 138:

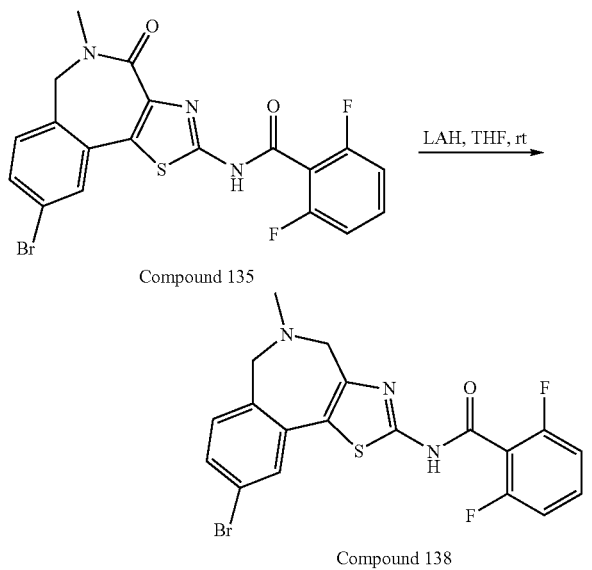

Into solution of compound 135 (23.5 mg, 0.05 mmol) in 2 mL of THF at room temperature was added a 1.0 M solution of Lithium aluminum hydride in THF (0.2 mmol, 0.2 mL). The mixture was stirred at room temperature for 1 hour, cooled to 0° C. and quenched with water followed by 2 M aqueous NaOH. The mixture was extracted with EtOAc, the extracts were washed with water, dried (Na$_2$SO$_4$), concentrated. The residue was purified by column chromatography on silica gel to give compound 138 (8.8 mg) as a yellow solid.

MS (ESI) [M+H$^+$]: 452, 450

Example 139

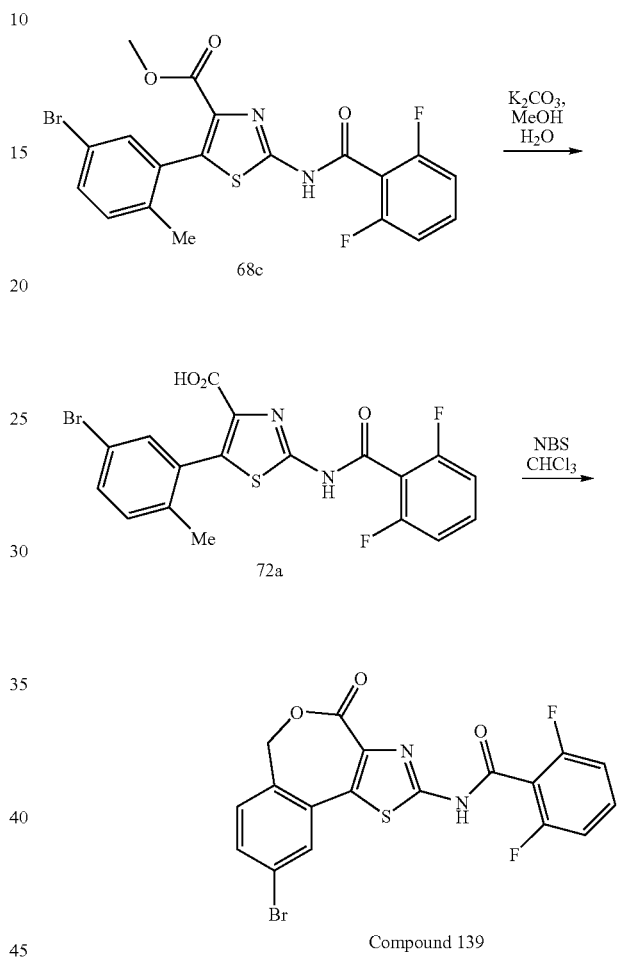

Into the solution of 68c (234 mg, 0.5 mmol) in 2 mL of MeOH/H$_2$O (1:1) was added K$_2$CO$_3$ (100 mg). The solution was heated to reflux for 2 hours and cooled down to room temperature. The reaction was neutralized with 2 M aqueous HCl and extracted with Et$_2$O. The combined extracts were washed with water, dried (Na$_2$SO$_4$), filtered and concentrated to give crude acid 72a which was used for the next step with no further purification.

MS (ESI) [M+H$^+$]: 455, 453

The crude 72a was dissolved in 5 mL of CHCl$_3$. The solution was treated with NBS (90 mg, 0.5 mmol) and benzoyl peroxide (24 mg, 0.1 mmol). The reaction mixture was reflux under nitrogen atmosphere overnight, cooled to room temperature, and diluted with CH$_2$Cl$_2$. The solution was washed with aqueous NaHCO$_3$ and H$_2$O. The organic layer was dried (Na$_2$SO$_4$), concentrated under reduced pressure. The residue was purified by column chromatography on silica gel to give compound 139 (133 mg) as a solid.

MS (ESI) [M+H$^+$]: 453, 451

Compound 140:

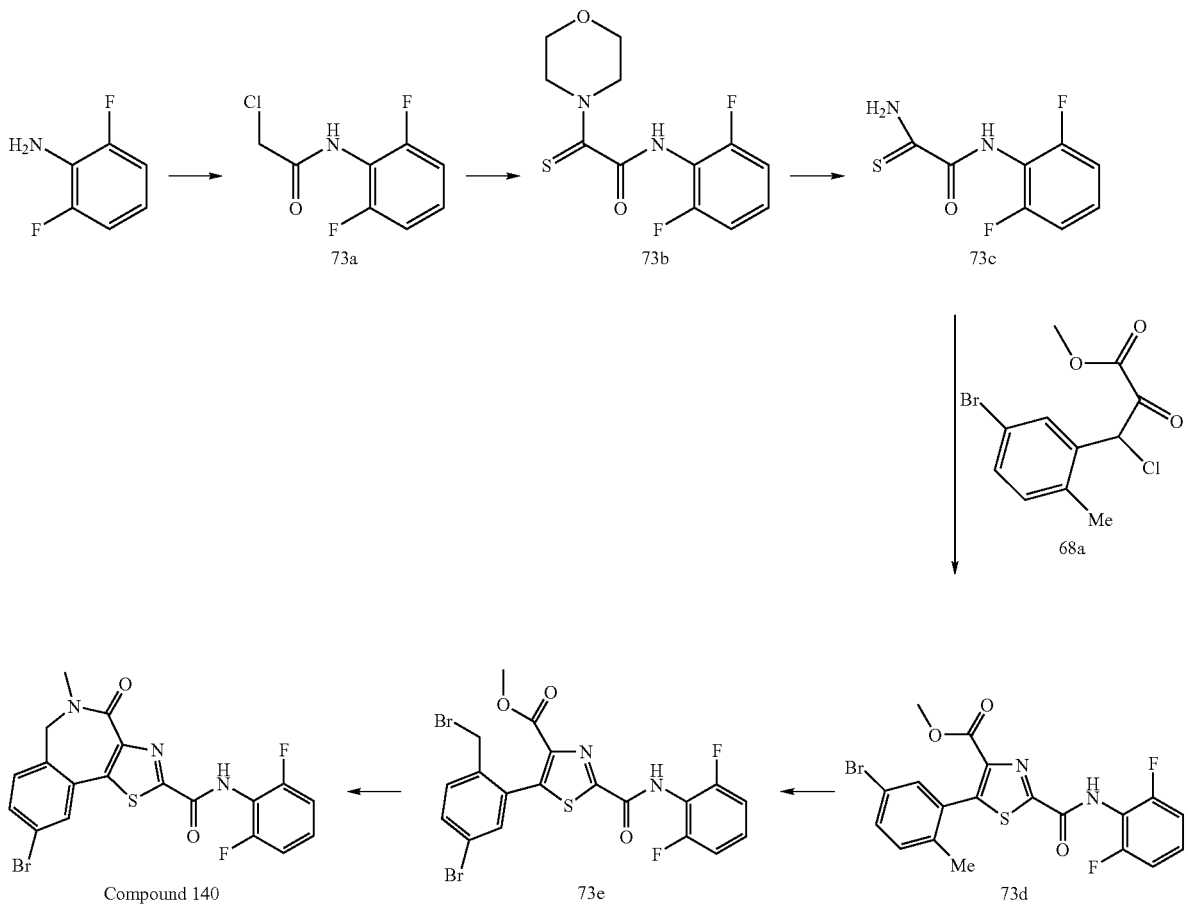

Into a mixture of 1 M aqueous NaOH (98 mL) and 2,6-difluoroaniline (12.9 g, 0.1 mol) in 100 mL of Et$_2$O was added dropwise a solution of 2-chloroacetyl chloride (13.3 g, 117 mmol) in 100 mL of Et$_2$O over 20 minutes at room temperature. The mixture was stirred for 30 minutes at room temperature and the reaction was cooled to 0° C. The white precipitate was collected by filtration to give the first portion of product 73a (12 g). The organic layer of the filtrate was separated and washed with saturated NaHCO$_3$ and brine, dried and concentrated. The residue was recrystallized from EtOAc to give the second portion of 73a (7.5 g) as a white solid.

MS (ESI) [M+H$^+$]: 206

Into the solution of 73a (2.05 g, 10 mmol) in 10 mL of DMF was added morpholine (0.84 g, 11 mmol) and sulfur (1.4 g). The mixture was stirred at room temperature overnight. The reaction mixture was poured into 100 mL of ice water and the white solid formed was collected, dried and recrystallized from EtOH to give 73b (2.2 g, 77% yield) as a pale yellow solid.

MS (ESI) [M+H$^+$]: 287

Into the solution of 73b (1.2 g, 4.2 mmol) in 5 mL of pyridine was slowly past through anhydrous ammonia gas. The reaction was stirred at room temperature and monitored by TLC. When the starting material was totally consumed, ammonia was removed and the reaction was concentrated under reduced pressure to remove pyridine. The residue was purified by column chromatography on silica gel to give 73c (580 mg, 64% yield) as a yellow solid.

The solution of 68a (305 mg, 1 mmol) and 73c (216 mg, 1 mmol) in 10 mL of EtOH was heated to reflux overnight. After cooling to room temperature, the reaction was concentrated under reduced pressure. The residue was purified by flash chromatography on silica gel to give 73d (288 mg, 62% yield) as a pale yellow solid.

MS (ESI) [M+H$^+$]: 469, 467

Into the solution of 73d (234 mg, 0.5 mmol) in 5 mL of anhydrous CHCl$_3$ was added NBS (90 mg, 0.5 mmol) and benzoyl peroxide (24 mg, 0.1 mmol). The reaction mixture was reflux under nitrogen atmosphere for 16 hours, cooled to room temperature, and diluted with CH$_2$Cl$_2$. The mixture was washed with aqueous NaHCO$_3$ and H$_2$O. The organic layer was dried (Na$_2$SO$_4$) and concentrated under reduced pressure. The residue was purified by column chromatography on silica gel to give 73e (200 mg, 73% yield) as a solid.

MS (ESI) [M+H$^+$]: 549, 547, 545

Into the solution of compound 73e (22 mg, 0.04 mmol) in 2 mL of MeOH was added 2 M solution of MeNH$_2$ in MeOH (0.1 mL). The resulting solution was stirred at room temperature overnight. The reaction was concentrated and the residue was purified by column chromatography on silica gel to give compound 140 (14 mg) as a white solid.

MS (ESI) [M+H$^+$]: 466, 464

Compound 141:

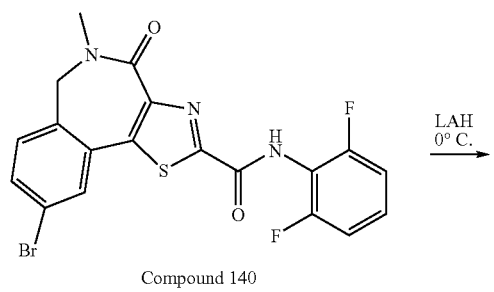

Compound 140

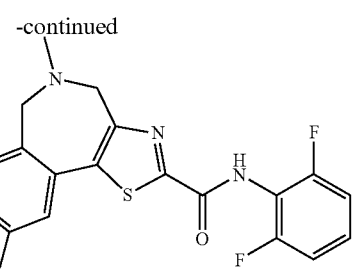

Compound 141

Into solution of compound 140 (10 mg) in 2 mL of THF at 0° C. was added a 1.0 M solution of Lithium aluminum hydride in THF (0.2 mmol, 0.2 mL). The mixture was stirred at 0° C. for 1 hour, and quenched with ice water followed by 2 M NaOH. The mixture was extracted with EtOAc. The extracts were washed with water, dried (Na$_2$SO$_4$), filtered and concentrated under reduced pressure. The residue was purified by column chromatography on silica gel to give compound 141 (5.6 mg) as a yellow solid.

MS (ESI) [M+H$^+$]: 452, 450

Compound 142:

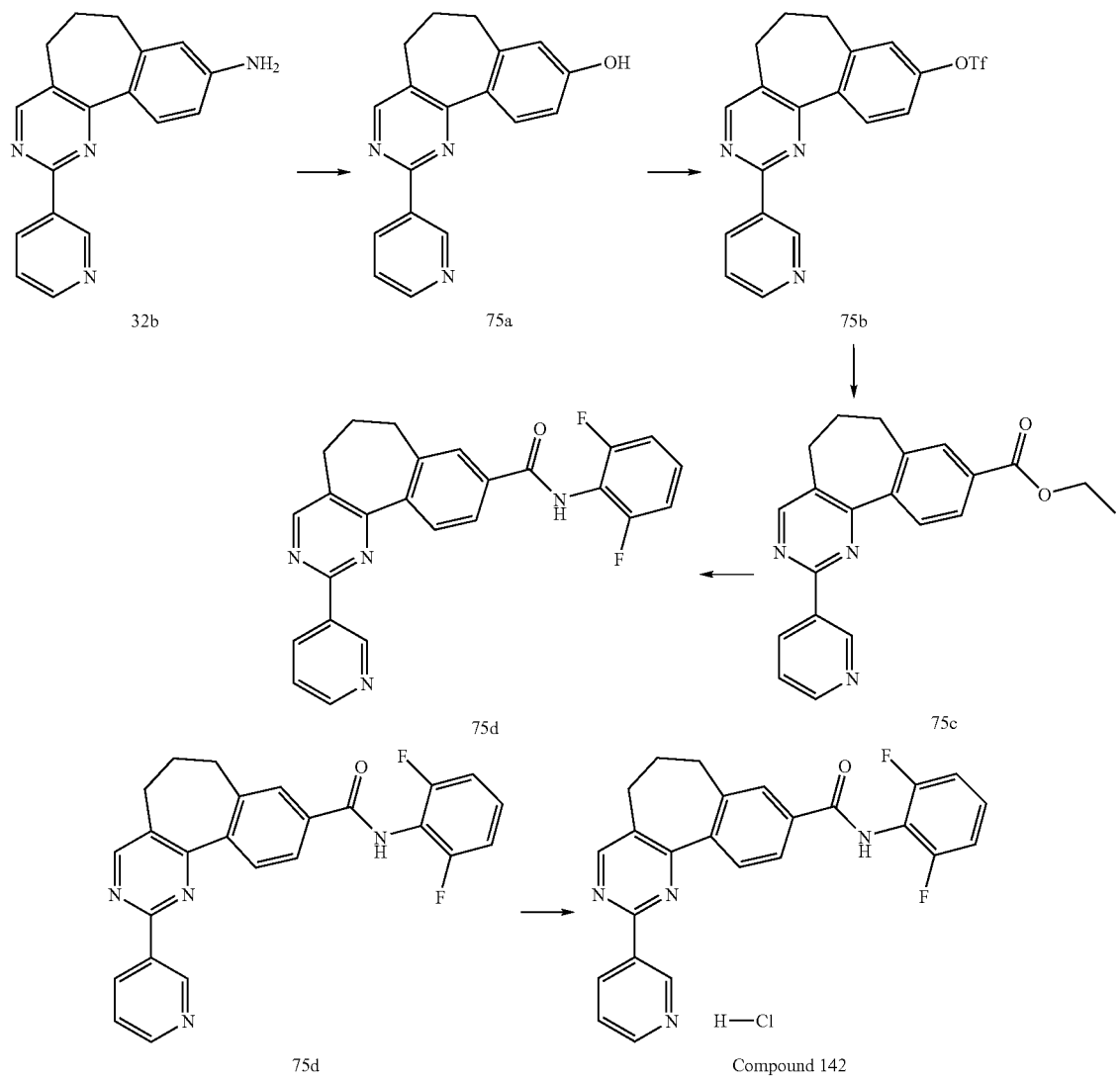

Into a solution of 32b (317 mg, 1.10 mmol) in acetic acid (5.0 mL) at 0° C. was added sodium nitrite (175 mg, 2.50 mmol). The mixture was stirred at room temperature overnight. Another portion of sodium nitrite (175 mg, 2.50 mmol) was added. The mixture was heated to 80° C. for 5 hours, cooled to room temperature, diluted with water, extracted with CH₂Cl₂ (4×). The combined extracts were dried (Na₂SO₄), filtered and concentrated under reduced pressure. The residue was taken up in methanol (2.0 mL). Into the mixture a solution of 2M NaOH (0.2 mL) was added. The mixture was stirred at room temperature for 30 minutes, neutralized with acetic acid, extracted with CH₂Cl₂ (4×). The combined extracts were dried (Na₂SO₄), filtered and concentrated under reduced pressure to give crude 75a. The crude mixture and pyridine (350 mg, 4.4 mmol) were taken in CH₂Cl₂ (2.0 mL). The mixture was cooled to 0° C. A solution of trifluoromethanesulfonic acid anhydride (620 mg, 2.2 mmol) in CH₂Cl₂ (1.0 mL) was added slowly. The mixture was stirred at room temperature overnight, concentrated under reduced pressure. The residue was taken up in CH₂Cl₂, washed with a solution of saturated NaHCO₃, dried (Na₂SO₄), filtered and concentrated under reduced pressure to give crude 75b (340 mg).

MS (ESI) [M+H⁺]: 422.

Into a solution of crude 75b (340 mg) in ethanol (5.0 mL) were added DIEA (0.50 mL), triphenylphosphine (80 mg, 0.30 mmol), and Pd(OAc)₂ (40 mg, 0.18 mmol). Into the mixture slow stream of bubbling carbon monoxide was introduced. The mixture was stirred at room temperature overnight, then concentrated under reduced pressure. The residue was purified on silica gel to give 75c (60% pure, 210 mg).

MS (ESI) [M+H⁺]: 346.

Compound 142 was prepared from 75d similarly as described for the preparation of compound 114.

MS (ESI) [M−Cl⁻]: 429.

Compound 143:

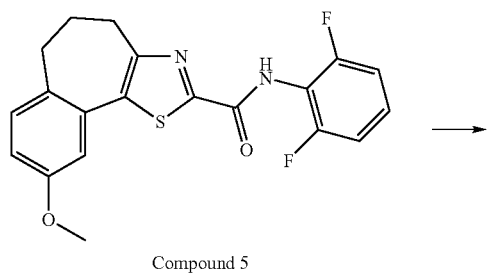

Compound 5

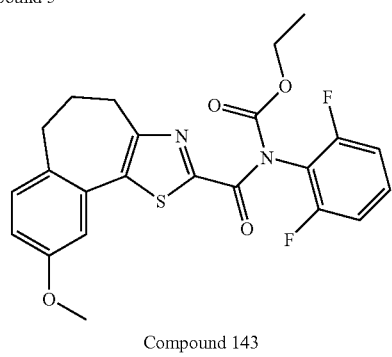

Compound 143

Into a solution of Compound 5 (50 mg, 0.13 mmoL) in THF (2.0 mL) at 0° C. was added NaH (60% pure, 40 mg, 1.0 mmol). The mixture was stirred at 0° C. for 30 minutes. Into the mixture, ethyl chloroformate (70 mg, 0.65 mmol) in THF (1.0 mL) was added. The mixture was stirred at 0° C. for 30 minutes then poured over ice. The mixture was extracted with methylene chloride (2×). The combined extracts were dried (Na₂SO₄), filtered concentrated. The residue was purified on silica gel (eluted with 1:9 EtOAc:hexanes) to give compound 143 (45 mg).

MS (ESI) [M+H⁺]: 459

Compound 144:

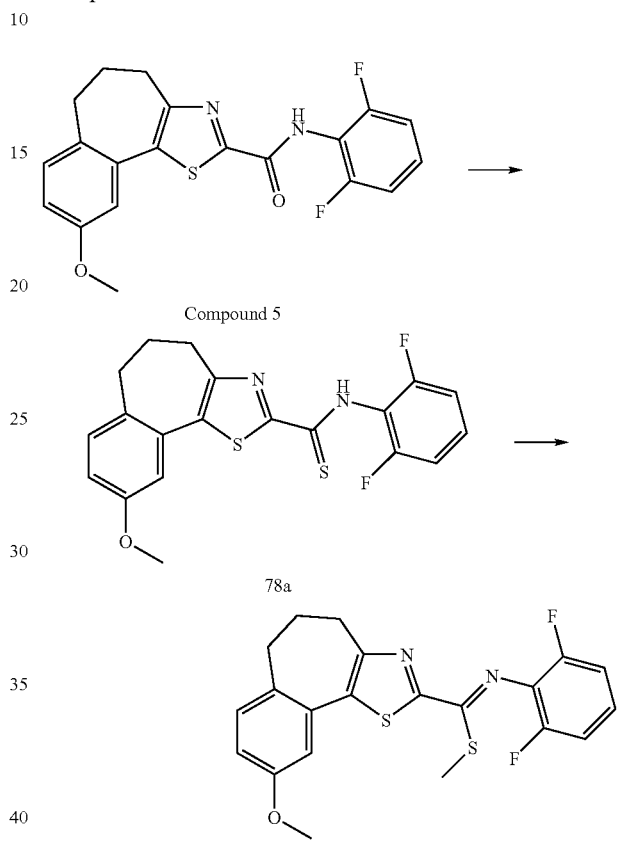

Compound 5

78a

Compound 144

Into a solution of Compound 5 (300 mg, 0.78 mmol) in toluene (10.0 ml) at room temperature was added Lawesson's reagent (600 mg, 1.5 mmol). The mixture was stirred at 100° C. overnight, cooled to room temperature. The solid was removed by filtration an discarded. The filtrate was concentrated. The residue was purified on silica gel (eluted with a solution of 1:9 EtOAc:hexanes) to give a semipure thioamide 78a (415 mg).

MS (ESI) [M+H⁺]: 403

Into a solution of the semipure 78a (415 mg, 1 mmol) in DMF (2.0 mL) at 0° C. was added NaH (60% pure, 120 mg, 3.0 mmol). The mixture was stirred at 0° C. for 30 minutes. Methyl iodide (0.3 mL, 2.0 mmol) in DMF (1.0 mL) was added. After 10 minutes at 0° C., the reaction mixture was quenched by addition of ice. The resulting mixture was extracted with CH₂Cl₂ (2×). The combined extracts were washed with water (3×), dried (Na₂SO₄), filtered concentrated. The residue was purified on silica gel (eluted with 1:19 EtOAc:hexanes) to give 144 (305 mg).

MS (ESI) [M+H⁺]: 417

Compound 145:

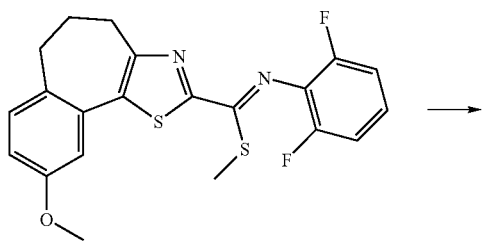

Compound 144

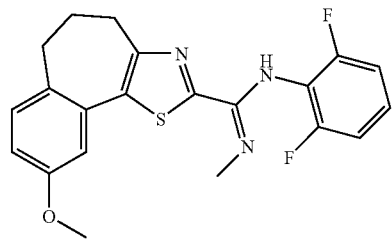

Compound 145

A mixture of Compound 144 (10 mg, 0.024 mmol) in a solution of 1M methylamine in methanol (1.0 mL) was sealed and heated to 65° C. for 1 day. The mixture was cooled to room temperature, concentrated under reduced pressure. The residue was purified on silica gel (eluted initially with 1:9 EtOAc:hexanes then with EtOAc) to give compound 145 (7 mg).

MS (ESI) [M+H$^+$]: 400

Compound 146:

Compound 146 was prepared from compound 145 similarly as described for the preparation of compound 114.

MS (ESI) [M−Cl$^-$]: 400

Compound 147:

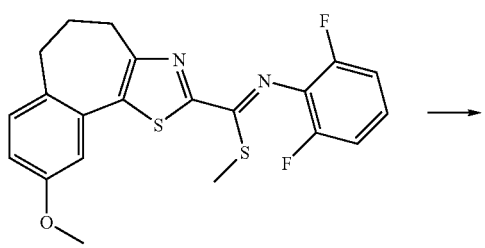

Compound 144

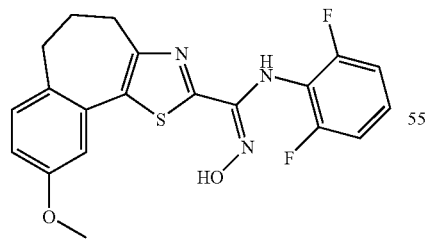

Compound 147

Into a solution of compound 144 (20 mg, 0.048 mmol) in pyridine (1.0 mL) at room temperature was added hydroxylamine hydrochloride (14 mg, 0.2 mmol). The mixture was heated to 80° C. overnight, cooled to room temperature, diluted with CH$_2$Cl$_2$, washed with water, dried (Na$_2$SO$_4$), filtered and concentrated. The residue was purified on silica gel (eluted with 1:9 MeOH:CH$_2$Cl$_2$) to give compound 147 (13 mg).

MS (ESI) [M+H$^+$]: 402

Compound 148:

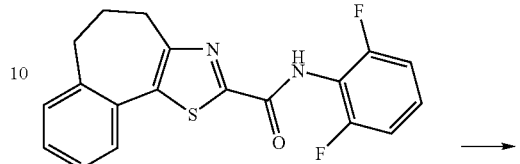

Compound 19

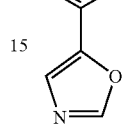

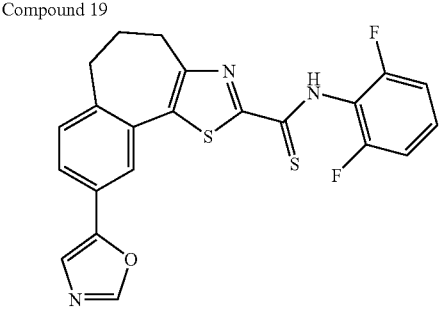

Compound 148

Into a solution of Compound 19 (50.0 mg, 0.12 mmol) in toluene (2.0 mL) at room temperature was added Lawesson's reagent (100 mg, 0.25 mmol). The mixture was heated to 100° C. overnight, cooled to room temperature. The solid was removed by filtration. The filtrate was concentrated under reduced pressure. The residue was purified on silica gel (eluted with a solution of 1:19 EtOAc:hexanes) to give compound 148 (32 mg).

MS (ESI) [M+H$^+$]: 440

Compound 149:

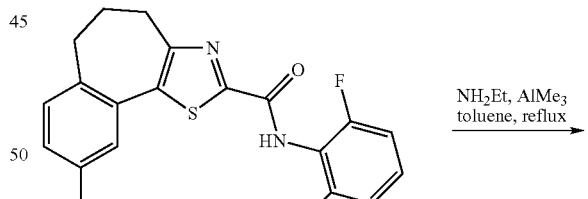

Compound 5

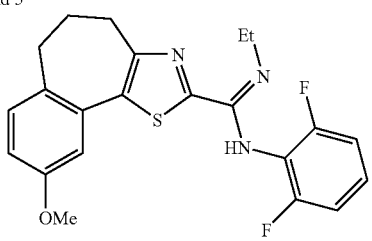

Compound 149

Into the solution of Compound 5 (50 mg, 0.13 mmol) and ethylamine hydrochloride (40 mg) in 5 mL of toluene at room temperature was added a 2 M solution of trimethylaluminum in hexanes (0.2 mL, 0.40 mmol). The mixture was heated to reflux for 3 hours and then cooled to room temperature. The reaction was poured over ice water and basified with 2N NaOH. The mixture was extracted with methylene chloride (2×). The combined extracts were washed with water, dried ($Na_2SO_4$), filtered and concentrated under reduced pressure. The residue was purified by column chromatography on silica gel to give compound 149 (41 mg, 77% yield).

MS (ESI) [M+H$^+$]: 414

Compound 150:

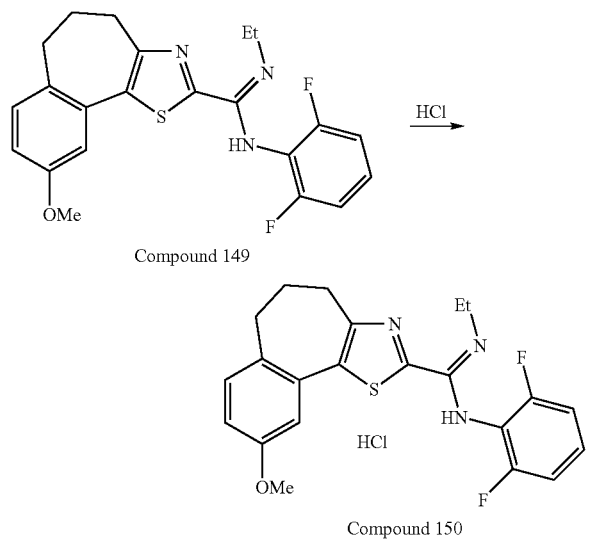

A solution of compound 149 (10 mg) in 0.5 mL of $Et_2O$ was treated with 0.1 mL of 2 M HCl in $Et_2O$. The precipitate formed was collected and dried to give compound 150 (10 mg) as a white solid.

MS (ESI) [M−Cl$^-$]: 414

Compound 151:

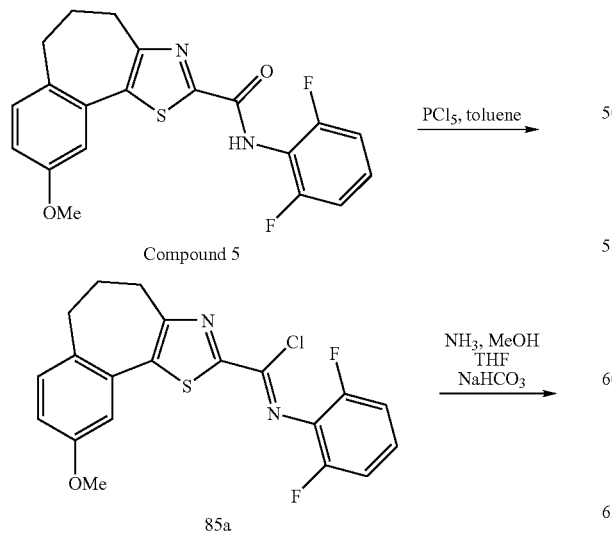

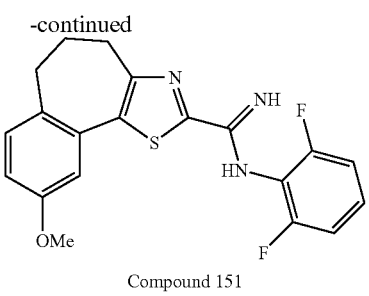

Compound 151

The solution of Compound 5 (50 mg) and $PCl_5$ (100 mg) in 2 mL of toluene was stirred at room temperature overnight. The solution was concentrated under reduced pressure. The residue was partitioned between EtOAc and $H_2O$. The aqueous layer was extracted with EtOAc and the organic extracts were combined, washed with brine, dried ($Na_2SO_4$), filtered and concentrated. The residue was purified by column chromatography on silica gel to give 85a (41 mg) as a white solid.

MS (ESI) [M+H$^+$]: 405

Into the solution of 85a (20 mg) in 2 mL of THF was added $NaHCO_3$ (100 mg) and $NH_3$ (2.0 M solution in EtOH, 0.2 mL). The mixture was stirred at room temperature overnight. The solution was concentrated under reduced pressure. The residue was partitioned between EtOAc and $H_2O$. The aqueous layer was extracted with EtOAc. The organic extracts were combined, washed with brine, dried ($Na_2SO_4$) and concentrated. The residue was purified by column chromatography on silica gel to give compound 151 (17 mg) as a white solid.

MS (ESI) [M+H$^+$]: 386

Compound 152:

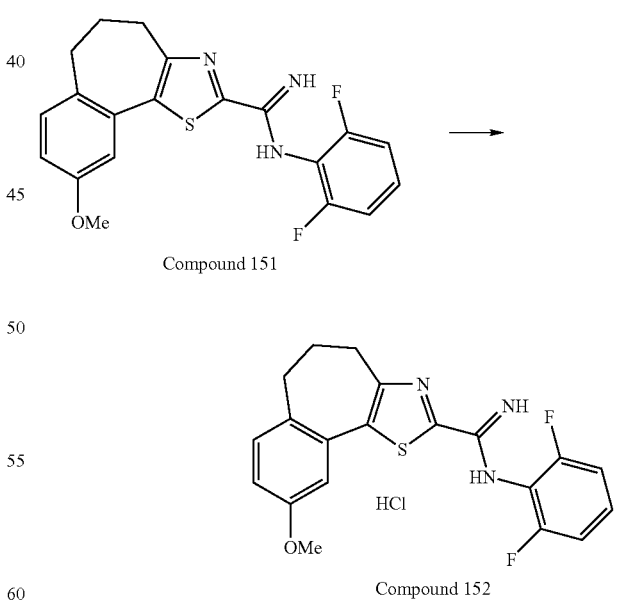

A solution of compound 151 (5 mg) in 0.5 mL of $CH_2Cl_2$ was treated with 0.1 mL of 2 M HCl in $Et_2O$. The precipitate formed was collected and dried to give compound 152 as a white solid.

MS (ESI) [M−Cl$^-$]: 386

Compound 153:

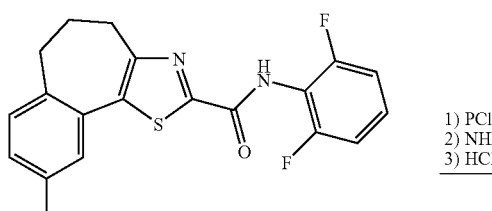

Compound 19

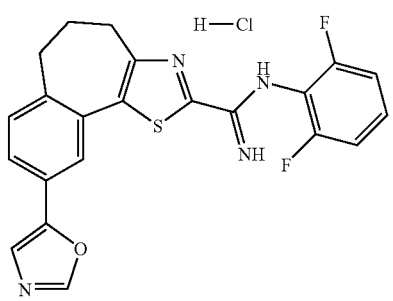

Compound 153

Compound 153 was prepared in 3 steps from Compound 19 similarly as described for the preparation of compound 152.

MS (ESI) [M−Cl⁻]: 423

Compound 154:

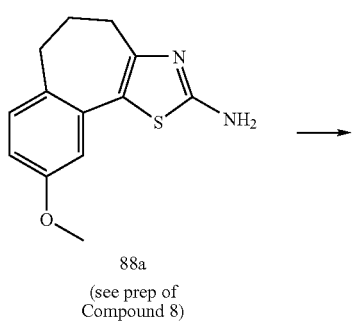

88a
(see prep of Compound 8)

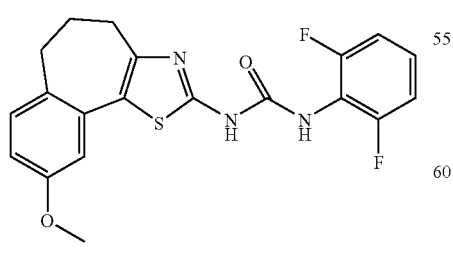

Compound 154

Into a solution of compound 88a (50 mg, 0.2 mmol) in methylene chloride (2.0 mL) at 0° C. was added a solution of 1,3-difluoro-2-isocyanatobenzene (29 mg, 0.2 mmol) in methylene chloride (0.5 mL). The mixture was stirred at room temperature for 30 minutes, diluted with methylene chloride, washed with a solution of saturated NaHCO₃, dried (Na₂SO₄), filtered and concentrated. The residue was purified on silica gel to give compound 154 (57 mg).

MS (ESI) [M−Cl⁻]: 402.

Example 155

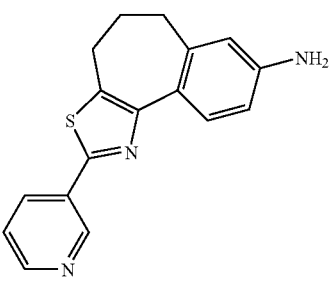

155a

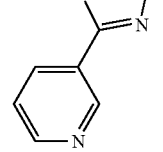

155b

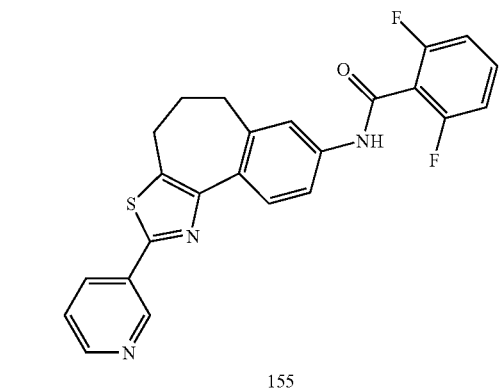

155

Compound 155a was prepared from 2-nitro-6,7,8,9-tetrahydro-5H-benzo[7]annulen-5-one as described for the preparation of compound 66e. Nitro reduction to give 155b followed by acylation as described for the preparation of compound 99 to give compound 155.

MS (ESI) [M+H⁺]: 434

Example 156

Compound 156 was prepared from compound 155b as described for the preparation of compound 104.
MS (ESI) [M+H$^+$]: 420.

Example 157

Compound 157 was prepared from compound 156 as described for the preparation of Compound 152.
MS (ESI) [M–H$^+$-2Cl$^-$]: 420.

Example 158

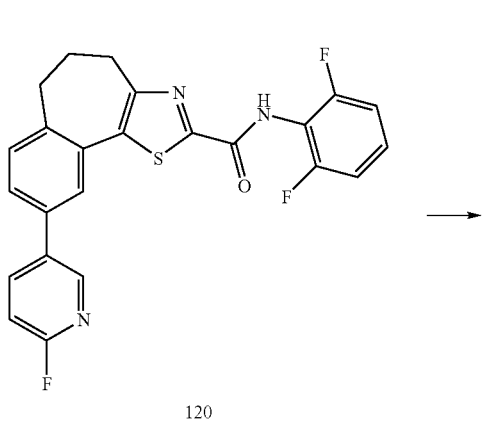

120

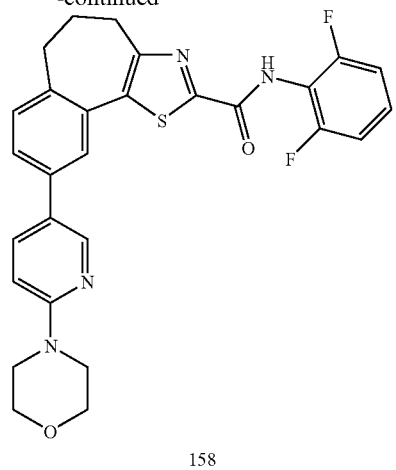

158

A mixture of compound 120 (10.0 mg, 0.022 mmol) in morpholine (0.1 mL) was heated to 120° C. overnight, cooled to room temperature, taken up in methylene chloride, washed with a solution of saturated NaHCO$_3$, dried (Na$_2$SO$_4$), filtered and concentrated. The residue was purified on silica gel to give compound 158.
MS (ESI) [M+H$^+$]: 519.

Example 159

Compound 159 was prepared from compound 120 and piperazine as described for the preparation of compound 158.
MS (ESI) [M+H$^+$]: 518.

Example 160

Compound 160 was prepared from compound 120 and 2-methoxyethanamine as described for the preparation of compound 158.
MS (ESI) [M+H$^+$]: 507.

Example 161

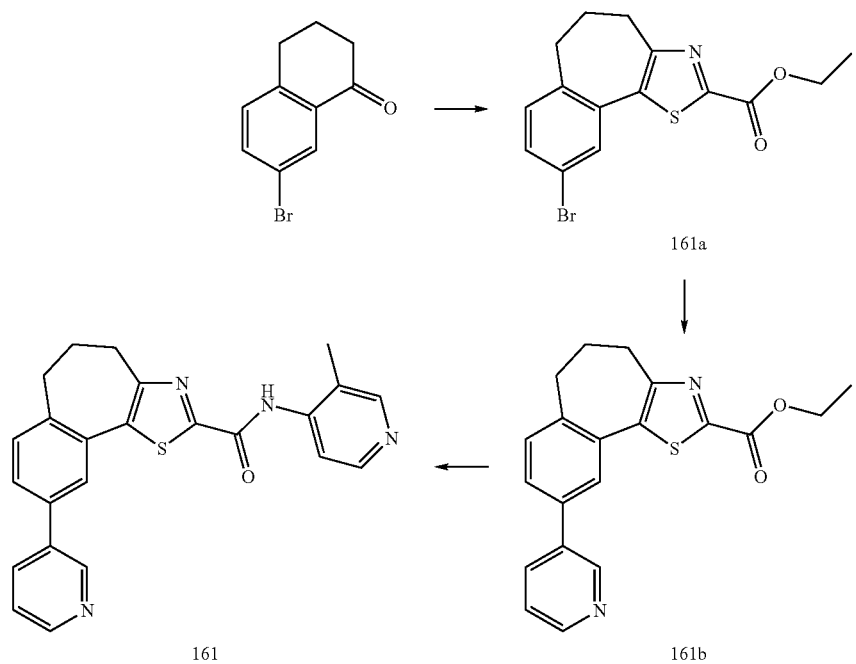

Into a solution of 7-bromo-3,4-dihydronaphthalen-1(2H)-one (4.50 g, 20.0 mmol) in methylene chloride (200 mL) at 0° C. was added a solution of 1M diethylaluminum chloride in hexane (22.0 mL, 22.0 mmol). Into the reaction mixture a solution of 2.0M trimethylsilyldiazomethane (11.0 mL, 22.0 mmol) was added slowly. The mixture was stirred at 0° C. for 15 minutes then at room temperature for 10 minutes. Ice was added. The resulting mixture was acidified with a solution of 3N HCl, extracted with methylene chloride (2×). The combined extracts were washed with a solution of saturated NaHCO₃, dried (Na₂SO₄), filtered and concentrated. The residue was taken in THF (100 mL). The mixture was cooled to 0° C. Into the reaction mixture, phenyltrimethylammonium tribromide (7.52 g, 20.0 mmol) was added. The mixture was stirred at 0° C. for 15 minutes then at room temperature for 1 hour. The reaction mixture was quenched by addition of a solution of 10% NaHSO₃, stirred at room temperature for 10 minutes, extracted with methylene chloride. The extract was washed with water, dried (Na₂SO₄), filtered and concentrated. The residue was taken in ethanol (20.0 mL). Into the mixture, ethyl thiooxamate (2.66 g, 20.0 mmol) was added. The mixture was stirred at room temperature overnight, neutralized with a solution of saturated NaHCO₃, extracted with methylene chloride (2×). The combined extracts were dried (Na₂SO₄), filtered and concentrated. The residue was purified on silica gel to give 161a (3.45 g).

MS (ESI) [M+H⁺]: 354, 352.

A slurry solution of 161a (2.00 g, 5.71 mmol), pyridin-3-ylboronic acid (0.91 g, 7.4 mmol), potassium acetate (1.45 g, 14.8 mmol), and palladium tetrakistriphenylphosphine (628 mg, 0.57 mmol) in 90% aqueous ethanol (20.0 mL) was purged with nitrogen for 20 minutes. The mixture was sealed and heated to 90° C. overnight, cooled to room temperature, taken up in methylene chloride, washed with water, dried (Na₂SO₄), filtered and concentrated. The residue was purified on silica gel to give 161b (1.45 g).

MS (ESI) [M+H⁺]: 351.

Compound 161 was prepared from 161b and 3-methylpyridin-4-amine as described for the preparation of compound 5.

MS (ESI) [M+H⁺]: 413.

Example 162

Compound 162 was prepared from 161b and 2,4-difluoroaniline as described for the preparation of compound 5.
MS (ESI) [M+H⁺]: 434.

Example 163

Compound 163 was prepared from 161b and 2-aminopyrimidine as described for the preparation of compound 5.
MS (ESI) [M+H⁺]: 400.

Example 164

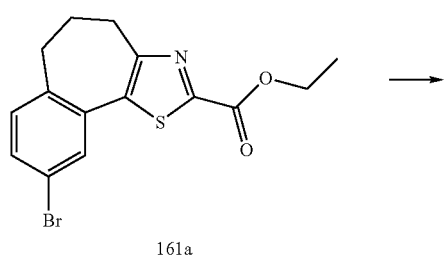

161a

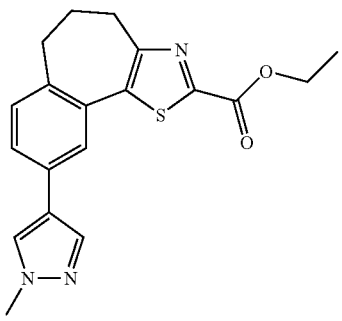

164a

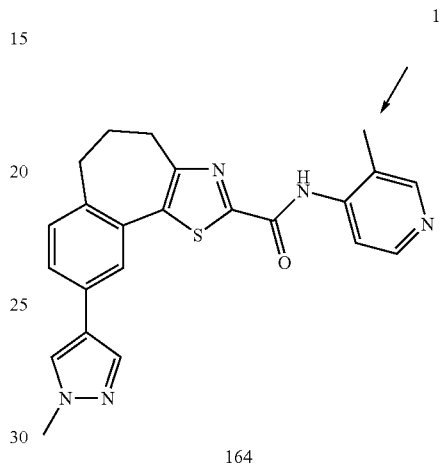

164

Compound 164a was prepared from 161a and 1-methyl-4-(4,4,5,5-tetramethyl-1,3,2-dioxaborolan-2-yl)-1H-pyrazole as described for the preparation of 161b.

MS (ESI) [M+H⁺]: 354.

Compound 164 was prepared from 164a and 3-methylpyridin-4-amine as described for the preparation of compound 5.

Example 165

Compound 165 was prepared from 164a and 2,4-difluoroaniline as described for the preparation of compound 5.

MS (ESI) [M+H⁺]: 437.

Example 166

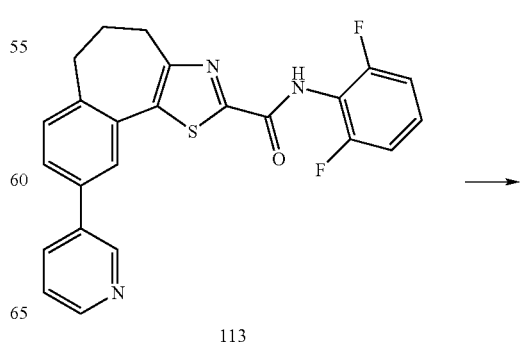

113

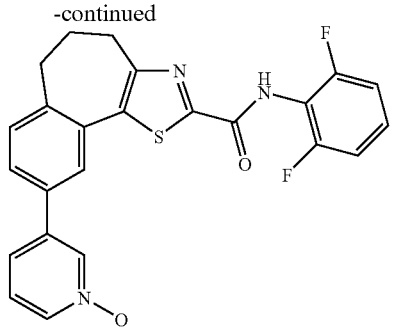

166

Into a solution of 113 (14.0 mg, 0.032 mmol) in methylene chloride (1.0 mL) at room temperature was added mCPBA (77% pure, 9.0 mg, 0.04 mmol). The mixture was stirred at room temperature overnight. Solvent was removed under reduced pressure. The residue was purified on silica gel to provide 166 (12.0 mg).

MS (ESI) [M+H⁺]: 450.

Example 167

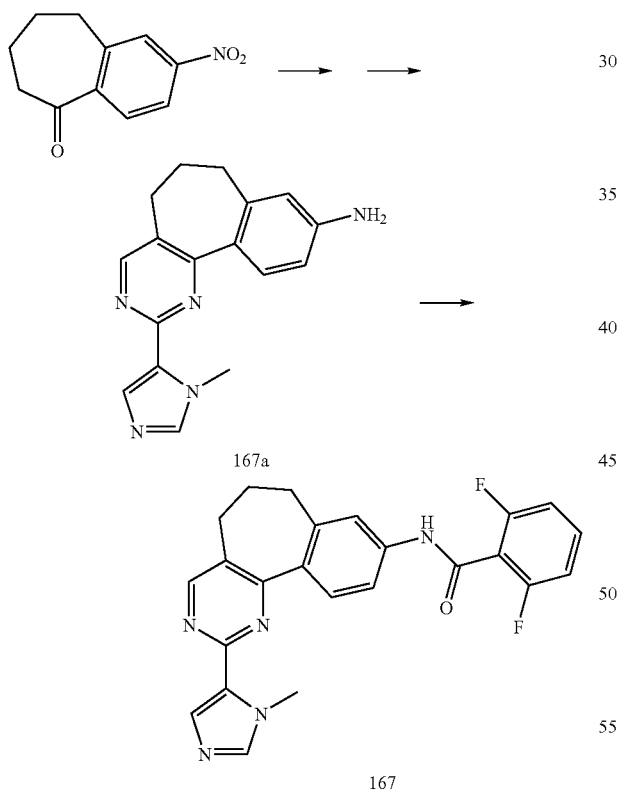

167a

167

Compound 101a was prepared from 2-nitro-6,7,8,9-tetrahydro-5H-benzo[7]annulen-5-one and 1-methyl-1H-imidazole-5-carboximidamide as described for the preparation of 32b.

MS (ESI) [MH⁺]: 292

Compound 167 was prepared from 167a as described for the preparation of compound 91.

MS (ESI) [M+H⁺]: 432

Example 168

Compound 168 was prepared from compound 135 as described for the preparation of compound 113.

MS (ESI) [M+H⁺]: 463

¹H NMR (300 MHz, CDCl₃) δ 9.10 (s, 1H), 8.96 (s, 1H), 8.73 (d, 1H), 8.20 (br d, 1H), 7.83 (s, 1H), 7.75 (dd, J=2.0, 8.0 Hz, 1H), 7.69 (m, 1H), 7.63 (d, J=8.0 Hz, 1H), 7.31 (m, 1H), 7.03 (t, J=8.0 Hz, 2H), 4.44 (br s, 2H), 3.30 (s, 3H).

Example 169

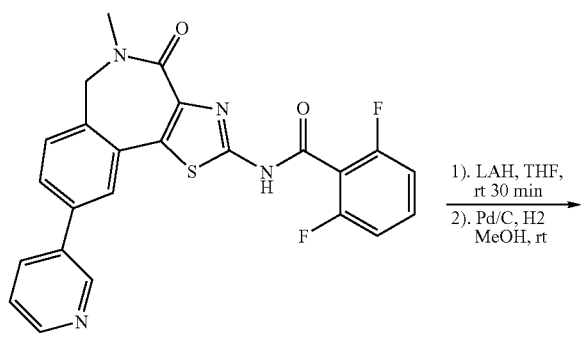

168

169

Into solution of compound 168 (10 mg) in 2 mL of THF at 0° C. was added a 1.0 M solution of Lithium aluminum hydride in THF (0.2 mmol, 0.2 mL). The mixture was stirred at rt for 1 hour, and quenched with ice water followed by 2 M NaOH. The mixture was extracted with EtOAc. The extracts were concentrated and redissolved in 2 mL of MeOH. To the solution was added 10 mg of Pd/C (10% w/w) and the mixture was stirred at rt under H₂ gas overnight. The catalyst was removed and the filtrate was concentrated and purified by column chromatography on silica gel to give compound 169 (2.3 mg) as a yellow solid.

MS (ESI) [M+H⁺]: 449

Example 170

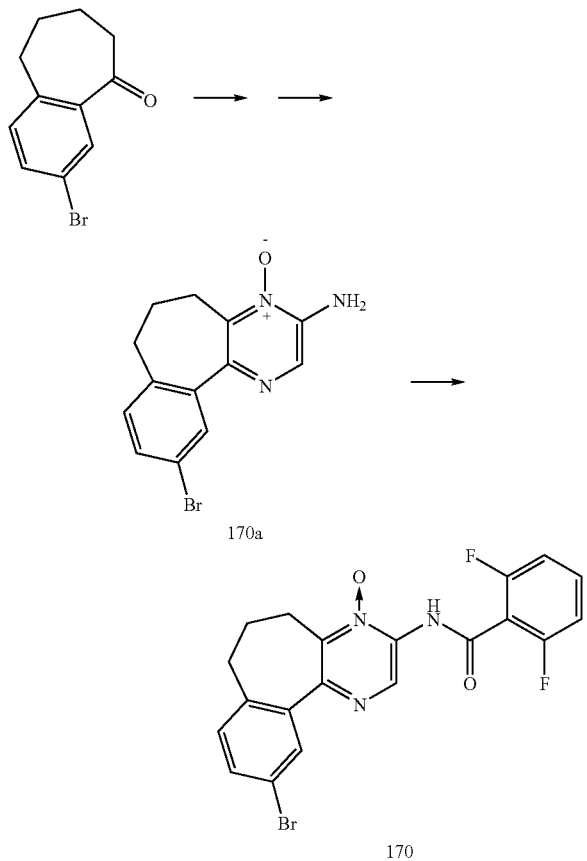

Compound 170a was prepared from 8-bromo-1-benzosuberone as described for the preparation of compound 29b.

MS (ESI) [M+H$^+$]: 306, 308

Compound 170 was prepared from 170a as described for the preparation of compound 91.

MS (ESI) [M+H$^+$]: 446, 448

$^1$H NMR (300 MHz, CDCl$_3$) δ 10.39 (brs, 1H), 9.78 (s, 1H), 7.92 (d, J=2.1 Hz, 1H), 7.56-7.49 (m, 2H), 7.17 (d, J=8.0 Hz, 1H), 7.08 (t, J=8.0 Hz, 2H), 3.07 (t, J=7.1 Hz, 2H), 2.59 (t, J=7.0 Hz, 2H), 2.41-2.34 (m, 2H).

Example 171

Compound 171 was prepared from 170 as described for the preparation of compound 113.

MS (ESI) [M+H$^+$]: 445

$^1$H NMR (300 MHz, CDCl$_3$) δ 10.42 (brs, 1H, NH), 9.81 (s, 1H), 8.92 (d, J=2.4 Hz, 1H), 8.61 (dd, J=4.9, 2.2 Hz, 1H), 8.01-7.96 (m, 2H), 7.70-7.38 (m, 4H), 7.08 (t, J=8.0 Hz, 2H), 3.13 (dd, J=7.3, 6.7 Hz, 2H), 2.69 (dd, J=7.3, 6.7 Hz, 2H), 2.51-2.37 (m, 2H).

Example 172

Compound 172 was prepared from 171 as described for the preparation of compound 29c.

MS (ESI) [M+H$^+$]: 429

$^1$H NMR (300 MHz, CDCl$_3$) δ 9.67 (s, 1H), 8.92 (s, 1H), 8.60 (d, J=4.9 Hz, 1H), 8.40 (s, 1H), 7.97 (m, 2H), 7.61 (d, J=8.0 Hz, 1H), 7.51-7.34 (m, 4H), 7.06 (t, J=8.0 Hz, 2H), 2.73 (t, J=7.0 Hz, 2H), 2.67 (t, J=7.0 Hz, 2H), 2.41 (m, 2H).

Example 2

Inhibition of IL-2 Production

Jurkat cells were placed in a 96 well plate (0.5 million cells per well in 1% FBS medium) then a test compound of this invention was added at different concentrations. After 10 minutes, the cells were activated with PHA (final concentration 2.5 µg/mL) and incubated for 20 hours at 37° C. under CO$_2$. The final volume was 200 µL. Following incubation, the cells were centrifuged and the supernatants collected and stored at −70° C. prior to assaying for IL-2 production. A commercial ELISA kit (IL-2 Eli-pair, Diaclone Research, Besancon, France) was used to detect production of IL-2, from which dose response curves were obtained. The IC$_{50}$ value was calculated as the concentration at which 50% of maximum IL-2 production after stimulation was inhibited versus a non-stimulation control.

Inhibition of other cytokines, such as IL-4, IL-5, IL-13, GM-CSF, TNF-α, and INF-γ, can be tested in a similar manner using a commercially available ELISA kit for each cytokine.

| Compound # | IC$_{50}$ (nM) |
| --- | --- |
| 5, 12, 19, 34, 37, 38, 39, 78, 114, 122, 123, 127, 129, 130 | ≤30 |
| 8, 13, 18, 32, 51, 59, 60, 72, 73, 76, 87, 99, 100, 102, 108, 109, 112, 115, 116, 124, 125, 126, 133, 134, 148, 155 | 30 < IC$_{50}$ ≤ 100 |
| 14, 33, 35, 70, 74, 75, 83, 91, 113, 117, 118, 119, 128, 142, 143, 149 | 100 < IC$_{50}$ ≤ 250 |
| 6, 10, 16, 41, 69, 71, 79, 96, 101, 107, 110, 111, 120, 121, 132, 138, 153 | 250 < IC$_{50}$ ≤ 500 |
| 36, 67, 81, 88, 89, 93, 97, 106, 131, 147, 152, 154 | 500 < IC$_{50}$ ≤ 1000 |
| 1, 2, 3, 4, 7, 9, 11, 15, 17, 31, 40, 42, 77, 80, 82, 84, 85, 86, 90, 92, 94, 95, 98, 013, 104, 105, 135, 136, 137, 139, 140, 144, 145, 146, 151 | >1000 |

Example 3

Patch Clamp Studies of Inhibition of I$_{CRAC}$ Current in RBL Cells, Jurkat Cells, and Primary T Cells In general, a whole cell patch clamp method is used to examine the effects of a compound of the invention on a channel that mediates I$_{crac}$. In such experiments, a baseline measurement is established for a patched cell. Then a compound to be tested is perfused (or puffed) to cells in the external solution and the effect of the compound on I$_{crac}$ is measured. A compound that modulates I$_{crac}$ (e.g., inhibits) is a compound that is useful in the invention for modulating CRAC ion channel activity.

1) RBL Cells

Cells

Rat basophilic leukemia cells (RBL-2H3) are grown in DMEM media supplemented with 10% fetal bovine serum in an atmosphere of 95% air/5% CO$_2$. Cells are seeded on glass coverslips 1-3 days before use.

Recording Conditions

Membrane currents of individual cells are recorded using the whole-cell configuration of the patch clamp technique with an EPC10 (HEKA Electronik, Lambrecht, Germany).

Electrodes (2-5 MΩ in resistance) are fashioned from borosilicate glass capillary tubes (Sutter Instruments, Novato, Calif.). The recordings are done at room temperature.

Intracellular Pipette Solution

The intracellular pipette solution contains Cs-Glutamate 120 mM; CsCl 20 mM; CsBAPTA 10 mM; CsHEPES 10 mM; NaCl 8 mM; MgCl$_2$ 1 mM; IP3 0.02 mM; pH=7.4 adjusted with CsOH. The solution is kept on ice and shielded from light before the experiment is preformed.

Extracellular Solution

The extracellular solution contains NaCl 138 mM; NaHEPES, 10 mM; CsCl 10 mM; CaCl$_2$ 10 mM; Glucose 5.5 mM; KCl 5.4 mM; KH$_2$PO$_4$ 0.4 mM; Na$_2$HPO$_4$.H$_2$O 0.3 mM at pH=7.4 adjusted with NaOH.

Compound Treatment

Each compound is diluted from a 10 mM stock in series using DMSO. The final DMSO concentration is always kept at 0.11%.

Experimental Procedure $I_{CRAC}$ currents are monitored every 2 seconds using a 50 msec protocol, where the voltage is ramped from −100 mV to +100 mV. The membrane potential is held at 0 mV between the test ramps. In a typical experiment, the peak inward currents will develop within 50-100 seconds. Once the $I_{CRAC}$ currents are stabilized, the cells are perfused with a test compound in the extracellular solution. At the end of an experiment, the remaining $I_{CRAC}$ currents are then challenged with a control compound (SKF96365, 10 µM) to ensure that the current can still be inhibited.

Data Analysis

The $I_{CRAC}$ current level is determined by measuring the inward current amplitude at −80 mV of the voltage ramp in an off-line analysis using MATLAB. The $I_{CRAC}$ current inhibition for each concentration is calculated using peak amplitude in the beginning of the experiment from the same cell. The IC$_{50}$ value and Hill coefficient for each compound is estimated by fitting all the individual data points to a single Hill equation.

2) Jurkat Cells

Cells

Jurkat T cells are grown on glass coverslips, transferred to the recording chamber and kept in a standard modified Ringer's solution of the following composition: NaCl 145 mM, KCl 2.8 mM, CsCl 10 mM, CaCl$_2$ 10 mM, MgCl$_2$ 2 mM, glucose 10 mM, HEPES.NaOH 10 mM, pH 7.2.

Extracellular Solution

The external solution contains 10 mM CaNaR, 11.5 mM glucose and a test compound at various concentrations.

Intracellular Pipette Solution

The standard intracellular pipette solution contains: Cs-glutamate 145 mM, NaCl 8 mM, MgCl$_2$ 1 mM, ATP 0.5 mM, GTP 0.3 mM, pH 7.2 adjusted with CsOH. The solution is supplemented with a mixture of 10 mM Cs-BAPTA and 4.3-5.3 mM CaCl$_2$ to buffer [Ca$^{2+}$]i to resting levels of 100-150 nM.

Patch-Clamp Recordings

Patch-clamp experiments are performed in the tight-seal whole-cell configuration at 21-25° C. High-resolution current recordings are acquired by a computer-based patch-clamp amplifier system (EPC-9, HEKA, Lambrecht, Germany). Sylgard®-coated patch pipettes have resistances between 2-4 MΩ after filling with the standard intracellular solution. Immediately following establishment of the whole-cell configuration, voltage ramps of 50 ms duration spanning the voltage range of −100 to +100 mV are delivered from a holding potential of 0 mV at a rate of 0.5 Hz over a period of 300 to 400 seconds. All voltages are corrected for a liquid junction potential of 10 mV between external and internal solutions. Currents are filtered at 2.3 kHz and digitized at 100 µs intervals. Capacitive currents and series resistance are determined and corrected before each voltage ramp using the automatic capacitance compensation of the EPC-9.

Data Analysis

The very first ramps before activation of $I_{CRAC}$ (usually 1 to 3) are digitally filtered at 2 kHz, pooled and used for leak-subtraction of all subsequent current records. The low-resolution temporal development of inward currents is extracted from the leak-corrected individual ramp current records by measuring the current amplitude at −80 mV or a voltage of choice.

3) Primary T Cells

Preparation of Primary T Cells

Primary T cells are obtained from human whole blood samples by adding 100 µL of RosetteSep® human T cell enrichment cocktail to 2 mL of whole blood. The mixture is incubated for 20 minutes at room temperature, then diluted with an equal volume of PBS containing 2% FBS. The mixture is layered on top of RosetteSep® DM-L density medium and then centrifuged for 20 minutes at 1200 g at room temperature. The enriched T cells are recovered from the plasma/density medium interface, then washed with PBS containing 2% FBS twice, and used in patch clamp experiments following the procedure described for RBL cells.

Example 4

Inhibition of Multiple Cytokines in Primary Human PBMCs

Peripheral blood mononuclear cells (PBMCs) are stimulated with phytohemagglutinin (PHA) in the presence of varying concentrations of compounds of the invention or cyclosporine A (CsA), a known inhibitor of cytokine production. Cytokine production is measured using commercially available human ELISA assay kits (from Cell Science, Inc.) following the manufacturers instructions.

The compounds of the invention are expected to be potent inhibitors of IL-2, IL-4, IL-5, IL-13, GM-CSF, INF-α and TNF-γ in primary human PBM cells. In addition, compounds of the invention are not expected to inhibit the anti-inflammatory cytokine, IL-10.

Example 5

Inhibition of Degranulation in RBL Cells

Procedure:

The day before the assay is performed, RBL cells, that have been grown to confluence in a 96 well plate, are incubated at 37° C. for at least 2 hours. The medium is replaced in each well with 100 µL of fresh medium containing 2 µLg/mL of anti-DNP IgE.

On the following day, the cells are washed once with PRS (2.6 mM glucose and 0.1% BSA) and 160 µL of PRS is added to each well. A test compound is added to a well in a 20 µL solution at 10× of the desired concentration and incubated for 20 to 40 minutes at 37° C. 20 µL of 10× mouse anti-IgE (10 µL/mL) is added. Maximum degranulation occurs between 15 to 40 minutes after addition of anti-IgE.

Compounds of the invention are expected to inhibit degranulation.

Example 6

Inhibition of Chemotaxis in T Cells

T-Cell Isolation:

Twenty ml aliquots of heparinized whole blood (2 pig, 1 human) are subjected to density gradient centrifugation on Ficoll Hypaque. The buffy coat layers representing peripheral blood mononuclear cells (PBMCs) containing lymphocytes and monocytes are washed once, resuspended in 12 ml of incomplete RPMI 1640 and then placed in gelatin-coated T75 culture flasks for 1 hr at 37° C. The non-adherent cells, representing peripheral blood lymphocytes (PBLs) depleted of monocytes, are resuspended in complete RPMI media and placed in loosely packed activated nylon wool columns that have been equilibrated with warm media. After 1 hr at 37° C., the non-adherent T cell populations are eluted by washing of the columns with additional media. The T cell preparations are centrifuged, resuspended in 5 ml of incomplete RPMI, and counted using a hemocytometer.

Cell Migration Assay:

Aliquots of each T cell preparation are labeled with Calcien AM (TefLabs) and suspended at a concentration of $2.4 \times 10^6$/ml in HEPES-buffered Hank's Balanced Salt Solution containing 1.83 mM $CaCl_2$ and 0.8 mM $MgCl_2$, pH 7.4 (HHBSS). An equal volume of HHBSS containing 0, 20 nM, 200 nM or 2000 nM of compound 1 or 20 nM EDTA is then added and the cells incubated for 30 min at 37° C. Fifty µl aliquots of the cell suspensions (60,000 cells) are placed on the membrane (pore size 5 µm) of a Neuroprobe ChemoTx 96 well chemotaxis unit that have been affixed over wells containing 10 ng/ml MIP-1α in HHBSS. The T cells are allowed to migrate for 2 hr at 37° C., after which the apical surface of the membrane is wiped clean of cells. The chemotaxis units are then placed in a CytoFlour 4000 (PerSeptive BioSystems) and the fluorescence of each well measured (excitation and emission wavelengths of 450 and 530 nm, respectively). The number of migrating cells in each well is determined from a standard curve generated from measuring the fluorescence of serial two-fold dilutions of the labeled cells placed in the lower wells of the chemotaxis unit prior to affixing the membrane.

Compounds of the invention are expected to inhibit chemotactic response of T cells.

All publications, patent applications, patents, and other documents cited herein are incorporated by reference in their entirety. In case of conflict, the present specification, including definitions, will control. In addition, the materials, methods, and examples are illustrative only and not intended to be limiting in any way.

We claim:

1. A compound represented by formula (X):

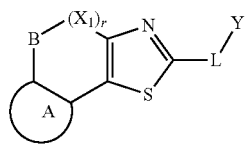

(X)

wherein:

Ring A is a 6 membered aryl ring wherein the members of the ring are independently —CZ;

Y is an aryl optionally substituted with one to two substituents independently selected from lower alkyl and halo; or an optionally substituted heteroaryl provided that when the heteroaryl is a five-membered ring it is selected from the group consisting of furyl, thienyl, pyrrolyl, oxazolyl, thiazolyl, isoxazolyl, pyrazolyl, isothiazolyl, triazolyl, thiadiazolyl, isothiazolyl and tetrazolyl;

B is —C($R^a$)$_2$—, —C(O)—, —O—, —S—, or —N($R^b$)—;

each $X_1$ is independently —C($R^a$)$_2$—, —C(O)—, —O—, —S—, or —N($R^b$)—;

Z is a substituent selected from the group consisting of hydrogen, alkyl, alkoxy, alkyl sulfanyl, alkylamino, dialkylamino, alkenyl, alkynyl, cycloalkyl, cycloalkenyl, heterocyclyl, aryl, heteroaryl, aralkyl, heteraralkyl, haloalkyl, —C(O)NR$_{13}$R$_{14}$, —NR$_{15}$C(O)R$_{16}$, halo, —OR$_{15}$, cyano, nitro, haloalkoxy, —C(O)R$_{15}$, —NR$_{13}$R$_{14}$, —SR$_{15}$, —C(O)OR$_{15}$, —OC(O)R$_{15}$, —NR$_{15}$C(O)NR$_{13}$R$_{14}$, —OC(O)NR$_{13}$R$_{14}$, —NR$_{15}$C(O)OR$_{16}$, —S(O)$_p$R$_{15}$, and —S(O)$_p$NR$_{13}$R$_{14}$; wherein R$_{13}$ and R$_{14}$, for each occurrence are, independently, H, optionally substituted alkyl, optionally substituted alkenyl, optionally substituted alkynyl, optionally substituted cycloalkyl, optionally substituted cycloalkenyl, optionally substituted heterocyclyl, optionally substituted aryl, optionally substituted heteroaryl, optionally substituted aralkyl, or optionally substituted heteraralkyl; or R$_{13}$ and R$_{14}$, taken together with the nitrogen to which they are attached is optionally substituted heterocyclyl or optionally substituted heteroaryl; and R$_{15}$ and R$_{16}$, for each occurrence are, independently, H, optionally substituted alkyl, optionally substituted alkenyl, optionally substituted alkynyl, optionally substituted cycloalkyl, optionally substituted cycloalkenyl, optionally substituted heterocyclyl, optionally substituted aryl, optionally substituted heteroaryl, optionally substituted aralkyl, or optionally substituted heteraralkyl;

L is —NRCH$_2$—, —CH$_2$NR—, —NR—C(O)—, or —C(O)—NR—, wherein R, for each occurrence, is independently —H, alkyl, —C(O)—R$_7$, or —C(O)OR$_7$; and R$_7$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

each $R^a$ is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —SR$_4$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_p$NR$_1$R$_2$;

each $R^b$ is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, halo, —C(O)NR$_1$R$_2$, —C(O)R$_4$, or —C(O)OR$_4$;

R$_1$ and R$_2$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_1$ and R$_2$ taken together with the nitrogen to which they are attached is optionally substituted heterocyclyl or optionally substituted heteroaryl;

R$_4$ and R$_5$, for each occurrence is, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

r is 1, 2, 3, or 4;

p is 0, 1, or 2; and provided that when r is 1, X$_1$ is C(O) and L is —NHC(O)—, Y is not phenyl or methylphenyl;

or a pharmaceutically acceptable salt or prodrug thereof.

2. The compound of claim 1, wherein the compound is represented by formula (I):

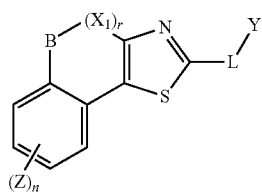

(I)

wherein:

Y is an aryl optionally substituted with one to two substituents independently selected from lower alkyl and halo; or an optionally substituted heteroaryl provided that when the heteroaryl is a five-membered ring it is selected from the group consisting of furyl, thienyl, pyrrolyl, oxazolyl, thiazolyl, isoxazolyl, pyrazolyl, isothiazolyl, triazolyl, thiadiazolyl, isothiazolyl and tetrazolyl;

B is —C(R$^a$)$_2$—, —C(O)—, —O—, —S—, or —N(R$^b$)—;

each X$_1$ is independently —C(R$^a$)$_2$—, —C(O)—, —O—, —S—, or —N(R$^b$)—;

Z is a substituent selected from the group consisting of alkyl, alkoxy, alkyl sulfanyl, alkylamino, dialkylamino, alkenyl, alkynyl, cycloalkyl, cycloalkenyl, heterocyclyl, aryl, heteroaryl, aralkyl, heteraralkyl, haloalkyl, —C(O)NR$_{13}$R$_{14}$, —NR$_{15}$C(O)R$_{16}$, halo, —OR$_{15}$, cyano, nitro, haloalkoxy, —C(O)R$_{15}$, —NR$_{13}$R$_{14}$, —SR$_{15}$, —C(O)OR$_{15}$, —OC(O)R$_{15}$, —NR$_{15}$C(O)NR$_{13}$R$_{14}$, —OC(O)NR$_{13}$R$_{14}$, —NR$_{15}$C(O)OR$_{16}$, —S(O)$_p$R$_{15}$, and —S(O)$_p$NR$_{13}$R$_{14}$; wherein R$_{13}$ and R$_{14}$, for each occurrence are, independently, H, optionally substituted alkyl, optionally substituted alkenyl, optionally substituted alkynyl, optionally substituted cycloalkyl, optionally substituted cycloalkenyl, optionally substituted heterocyclyl, optionally substituted aryl, optionally substituted heteroaryl, optionally substituted aralkyl, or optionally substituted heteraralkyl; or R$_{13}$ and R$_{14}$, taken together with the nitrogen to which they are attached is optionally substituted heterocyclyl or optionally substituted heteroaryl; and R$_{15}$ and R$_{16}$, for each occurrence are, independently, H, optionally substituted alkyl, optionally substituted alkenyl, optionally substituted alkynyl, optionally substituted cycloalkyl, optionally substituted cycloalkenyl, optionally substituted heterocyclyl, optionally substituted aryl, optionally substituted heteroaryl, optionally substituted aralkyl, or optionally substituted heteraralkyl;

L is —NRCH$_2$—, —CH$_2$NR—, —NR—C(O)—, or —C(O)—NR—;

each R$^a$ is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —SR$_4$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_p$NR$_1$R$_2$;

each R$^b$ is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, halo, —C(O)NR$_1$R$_2$, —C(O)R$_4$, or —C(O)OR$_4$;

R$_1$ and R$_2$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_1$ and R$_2$ taken together with the nitrogen to which they are attached is optionally substituted heterocyclyl or optionally substituted heteroaryl;

R$_4$ and R$_5$, for each occurrence is, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

r is 1, 2, 3, or 4;

n is 0, 1, 2, 3 or 4; and p is 0, 1, or 2.

3. The compound of claim 2, wherein

Y is a phenyl optionally substituted with one to two substituents independently selected from lower alkyl and halo, an optionally substituted oxazolyl, an optionally substituted furanyl, an optionally substituted pyrazolyl, an optionally substituted pyridinyl, an optionally substituted pyridazinyl, an optionally substituted thiadiazolyl, or an optionally substituted thiophenyl;

Z is a phenyl, an oxazolyl, a thiazolyl, an imidazolyl, a-pyridinyl, a pyrazolyl, a pyrrolyl, a thiophenyl, a furanyl, a thiadiazolyl, an oxadiazolyl, or a tetrazolyl;

B is —C($R^a$)$_2$— or —O— and each $X_1$ is —C($R^a$)$_2$—;

R, for each occurrence, is independently —H, alkyl, —C(O)—$R_7$, or —C(O)O$R_7$; and $R_7$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl.

4. The compound of claim 3, wherein R is —H.

5. The compound of claim 4, wherein Y is a phenyl optionally substituted with one to two substituents independently selected from lower alkyl and halo, or an optionally substituted pyridinyl.

6. The compound of claim 5, wherein Y is a difluorophenyl.

7. The compound of claim 6, wherein Z is an oxazolyl, a thiazolyl, a pyridinyl, or a tetrazolyl.

8. A compound represented by formula (III):

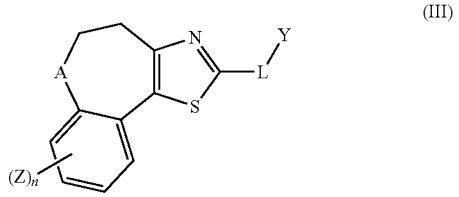

(III)

wherein:

Y is an optionally substituted aryl or an optionally substituted heteroaryl provided that when the heteroaryl is a five-membered ring it is selected from the group consisting of furyl, thienyl, pyrrolyl, oxazolyl, thiazolyl, isoxazolyl, pyrazolyl, isothiazolyl, triazolyl, thiadiazolyl, isothiazolyl and tetrazolyl;

A is —C($R^a$)$_2$— or —O—;

Z is a substituent selected from the group consisting of alkyl, alkoxy, alkyl sulfanyl, alkylamino, dialkylamino, alkenyl, alkynyl, cycloalkyl, cycloalkenyl, heterocyclyl, aryl, heteroaryl, aralkyl, heteraralkyl, haloalkyl, —C(O)NR$_{13}$R$_{14}$, —NR$_{15}$C(O)R$_{16}$, halo, —OR$_{15}$, cyano, nitro, haloalkoxy, —C(O)R$_{15}$, —NR$_{13}$R$_{14}$, —SR$_{15}$, —C(O)OR$_{15}$, —OC(O)R$_{15}$, —NR$_{15}$C(O)NR$_{13}$R$_{14}$, —OC(O)NR$_{13}$R$_{14}$, —NR$_{15}$C(O)OR$_{16}$, —S(O)$_p$R$_{15}$, and —S(O)$_p$NR$_{13}$R$_{14}$; wherein R$_{13}$ and R$_{14}$, for each occurrence are, independently, H, optionally substituted alkyl, optionally substituted alkenyl, optionally substituted alkynyl, optionally substituted cycloalkyl, optionally substituted cycloalkenyl, optionally substituted heterocyclyl, optionally substituted aryl, optionally substituted heteroaryl, optionally substituted aralkyl, or optionally substituted heteraralkyl; or R$_{13}$ and R$_{14}$, taken together with the nitrogen to which they are attached is optionally substituted heterocyclyl or optionally substituted heteroaryl; and R$_{15}$ and R$_{16}$, for each occurrence are, independently, H, optionally substituted alkyl, optionally substituted alkenyl, optionally substituted alkynyl, optionally substituted cycloalkyl, optionally substituted cycloalkenyl, optionally substituted heterocyclyl, optionally substituted aryl, optionally substituted heteroaryl, optionally substituted aralkyl, or optionally substituted heteraralkyl;

L is —NRCH$_2$—, —CH$_2$NR—, —NR—C(O)—, or —C(O)—NR—, wherein R, for each occurrence, is independently —H, alkyl, —C(O)—R$_7$, or —C(O)OR$_7$; and R$_7$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

each $R^a$ is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —SR$_4$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_p$NR$_1$R$_2$;

R$_1$ and R$_2$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_1$ and R$_2$ taken together with the nitrogen to which they are attached is optionally substituted heterocyclyl or optionally substituted heteroaryl;

R$_4$ and R$_5$, for each occurrence is, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

n is 0, 1, 2, 3 or 4; and p is 0, 1, or 2;

or a pharmaceutically acceptable salt or prodrug thereof.

9. The compound of claim 8, wherein the compound is represented by formula (IV):

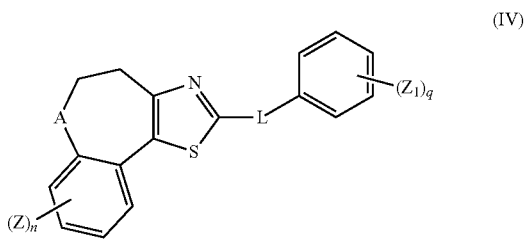

(IV)

wherein:

$Z_1$ is a substituent selected from the group consisting of alkyl, alkoxy, alkyl sulfanyl, alkylamino, dialkylamino, alkenyl, alkynyl, cycloalkyl, cycloalkenyl, heterocyclyl, aryl, heteroaryl, aralkyl, heteraralkyl, haloalkyl, —C(O)

$NR_{13}R_{14}$, $-NR_{15}C(O)R_{16}$, halo, $-OR_{15}$, cyano, nitro, haloalkoxy, $-C(O)R_{15}$, $-NR_{13}R_{14}$, $-SR_{15}$, $-C(O)OR_{15}$, $-OC(O)R_{15}$, $-NR_{15}C(O)NR_{13}R_{14}$, $-OC(O)NR_{13}R_{14}$, $-NR_{15}C(O)OR_{16}$, $-S(O)_pR_{15}$, and $-S(O)_pNR_{13}R_{14}$; wherein $R_{13}$ and $R_{14}$, for each occurrence are, independently, H, optionally substituted alkyl, optionally substituted alkenyl, optionally substituted alkynyl, optionally substituted cycloalkyl, optionally substituted cycloalkenyl, optionally substituted heterocyclyl, optionally substituted aryl, optionally substituted heteroaryl, optionally substituted aralkyl, or optionally substituted heteraralkyl; or $R_{13}$ and $R_{14}$, taken together with the nitrogen to which they are attached is optionally substituted heterocyclyl or optionally substituted heteroaryl; and $R_{15}$ and $R_{16}$, for each occurrence are, independently, H, optionally substituted alkyl, optionally substituted alkenyl, optionally substituted alkynyl, optionally substituted cycloalkyl, optionally substituted cycloalkenyl, optionally substituted heterocyclyl, optionally substituted aryl, optionally substituted heteroaryl, optionally substituted aralkyl, or optionally substituted heteraralkyl; and q is 0, 1, 2, 3, 4, or 5.

10. The compound of claim 9, wherein
Z is a phenyl, an oxazolyl, a thiazolyl, an imidazolyl, a pyridinyl, a pyrazolyl, a pyrrolyl, a thiophenyl, a furanyl, a thiadiazolyl, an oxadiazolyl, or tetrazolyl; and
$Z_1$ is an alkyl, an alkenyl, an alkynyl, a cycloalkyl, a cycloalkenyl, a heterocyclyl, an aryl, a heteroaryl, an aralkyl, a heteraralkyl, halo, $-NO_2$, $-C(O)NR_1R_2$, $-NR_4C(O)R_5$, $-OR_4$, haloalkoxy, $-C(O)R_4$, $-NR_1R_2$, $-SR_4$, $-C(O)OR_4$, $-OC(O)R_4$, $-NR_4C(O)NR_1R_2$, $-OC(O)NR_1R_2$, $-NR_4C(O)OR_5$, $-S(O)_pR_4$, or $-S(O)_pNR_1R_2$.

11. The compound of claim 10, wherein R is —H.

12. The compound of claim 11, wherein Z is an oxazolyl, a thiazolyl, a pyridinyl, or a tetrazolyl.

13. The compound of claim 12, wherein $Z_1$ is halo.

14. The compound of claim 8, wherein the compound is represented by formula (V):

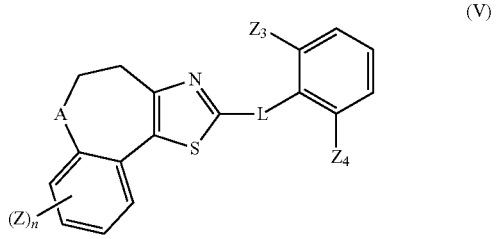

(V)

wherein:
$Z_3$ and $Z_4$ are each independently substituents selected from the group consisting of alkyl, alkoxy, alkyl sulfanyl, alkylamino, dialkylamino, alkenyl, alkynyl, cycloalkyl, cycloalkenyl, heterocyclyl, aryl, heteroaryl, aralkyl, heteraralkyl, haloalkyl, $-C(O)NR_{13}R_{14}$, $-NR_{15}C(O)R_{16}$, halo, $-OR_{15}$, cyano, nitro, haloalkoxy, $-C(O)R_{15}$, $-NR_{13}R_{14}$, $-SR_{15}$, $-C(O)OR_{15}$, $-OC(O)R_{15}$, $-NR_{15}C(O)NR_{13}R_{14}$, $-OC(O)NR_{13}R_{14}$, $-NR_{15}C(O)OR_{16}$, $-S(O)_pR_{15}$, and $-S(O)_pNR_{13}R_{14}$; wherein $R_{13}$ and $R_{14}$, for each occurrence are, independently, H, optionally substituted alkyl, optionally substituted alkenyl, optionally substituted alkynyl, optionally substituted cycloalkyl, optionally substituted cycloalkenyl, optionally substituted heterocyclyl, optionally substituted aryl, optionally substituted heteroaryl, optionally substituted aralkyl, or optionally substituted heteraralkyl; or $R_{13}$ and $R_{14}$, taken together with the nitrogen to which they are attached is optionally substituted heterocyclyl or optionally substituted heteroaryl; and $R_{15}$ and $R_{16}$, for each occurrence are, independently, H, optionally substituted alkyl, optionally substituted alkenyl, optionally substituted alkynyl, optionally substituted cycloalkyl, optionally substituted cycloalkenyl, optionally substituted heterocyclyl, optionally substituted aryl, optionally substituted heteroaryl, optionally substituted aralkyl, or optionally substituted heteraralkyl.

15. The compound of claim 14, wherein
Z is a phenyl, an oxazolyl, a thiazolyl, an imidazolyl, a pyridinyl, a pyrazolyl, a pyrrolyl, a thiophenyl, a furanyl, a thiadiazolyl, an oxadiazolyl, or a tetrazolyl;
$Z_3$ and $Z_4$ are each independently an alkyl, an alkenyl, an alkynyl, a cycloalkyl, a cycloalkenyl, a heterocyclyl, an aryl, a heteroaryl, an aralkyl, a heteraralkyl, halo, $-C(O)NR_{13}R_{14}$, $-NR_{15}C(O)R_{16}$, $-OR_{15}$, haloalkoxy, $-C(O)R_{15}$, $-NR_{13}R_{14}$, $-SR_{15}$, $-C(O)OR_{15}$, $-OC(O)R_{15}$, $-NR_{15}C(O)NR_{13}R_{14}$, $-OC(O)NR_{13}R_{14}$, $-NR_{15}C(O)OR_{16}$, $-S(O)_pR_{15}$, or $-S(O)_pNR_{13}R_{14}$; and
wherein A is $-CH_2-$.

16. The compound of claim 15, wherein R is —H.

17. The compound of claim 16, wherein Z is an oxazolyl, a thiazolyl, a pyridinyl, or a tetrazolyl.

18. The compound of claim 17, wherein $Z_3$ and $Z_4$ are each —F.

19. The compound of claim 8, wherein the compound is represented by formula (VI):

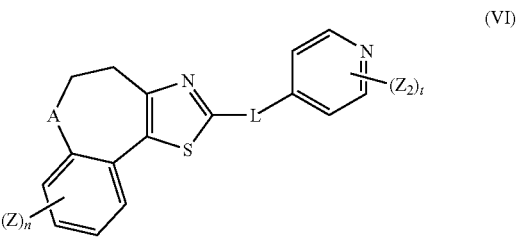

(VI)

wherein
$Z_2$ is a substituent; and
t is 0, 1, 2, 3 or 4.

20. The compound of claim 19, wherein
L is $-NRCH_2-$, $-CH_2NR-$, $-NR-C(O)-$, or $-C(O)-NR-$;
Z is a phenyl, an oxazolyl, a thiazolyl, an imidazolyl, a pyridinyl, a pyrazolyl, a pyrrolyl, a thiophenyl, a furanyl, a thiadiazolyl, an oxadiazolyl, or a tetrazolyl; and
$Z_2$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, $-C(O)NR_1R_2$, $-NR_4C(O)R_5$, $-OR_4$, haloalkoxy, $-C(O)R_4$, $-NR_1R_2$, $-SR_4$, $-C(O)OR_4$, $-OC(O)R_4$, $-NR_4C(O)NR_1R_2$, $-OC(O)NR_1R_2$, $-NR_4C(O)OR_5$, $-S(O)_pR_4$, or $-S(O)_pNR_1R_2$.

21. The compound of claim 20, wherein
R is —H;
Z is an oxazolyl, a thiazolyl, a pyridinyl, or a tetrazolyl; and
$Z_2$ is halo or lower alkyl.

22. A compound represented by formula (VII):

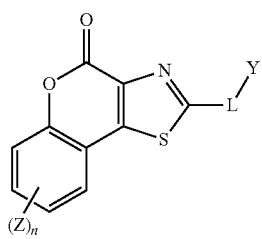

(VII)

wherein:
- Y is an optionally substituted aryl or an optionally substituted heteroaryl;
- Z is selected from the group consisting of an optionally substituted phenyl, an optionally substituted oxazolyl, an optionally substituted thiazolyl, an optionally substituted imidazolyl, an optionally substituted pyridinyl, an optionally substituted pyrazolyl, an optionally substituted pyrrolyl, an optionally substituted thiophenyl, an optionally substituted furanyl, an optionally substituted thiadiazolyl, an optionally substituted oxadiazolyl, or an optionally substituted tetrazolyl;
- L is selected from the group consisting of —NRCH$_2$—, —CH$_2$NR—, —NR—C(O)—, or —C(O)—NR—, wherein R, for each occurrence, is independently —H, alkyl, —C(O)—R$_7$, or —C(O)OR$_7$; and R$_7$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;
- each R$^a$ is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —SR$_4$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_p$NR$_1$R$_2$;
- R$_1$ and R$_2$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_1$ and R$_2$ taken together with the nitrogen to which they are attached is optionally substituted heterocyclyl or optionally substituted heteroaryl;
- R$_4$ and R$_5$, for each occurrence is, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;
- n is 0, 1, 2, 3 or 4; and
- p is 0, 1, or 2;
- provided that when L is —NHC(O)—, Y is not phenyl or methylphenyl;
- provided that when n is 0, L is not —NH—;
- or a pharmaceutically acceptable salt or prodrug thereof.

23. The compound of claim 22, wherein the compound is represented by formula (VIII):

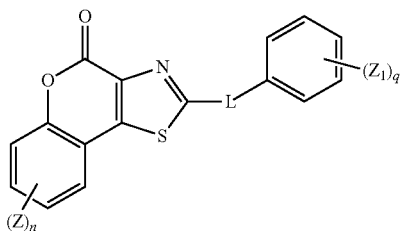

(VIII)

wherein:
- $Z_1$ is a substituent selected from the group consisting of alkyl, alkoxy, alkyl sulfanyl, alkylamino, dialkylamino, alkenyl, alkynyl, cycloalkyl, cycloalkenyl, heterocyclyl, aryl, heteroaryl, aralkyl, heteraralkyl, haloalkyl, —C(O)NR$_{13}$R$_{14}$, —NR$_{15}$C(O)R$_{16}$, halo, —OR$_{15}$, cyano, nitro, haloalkoxy, —C(O)R$_{15}$, —NR$_{13}$R$_{14}$, —SR$_{15}$, —C(O)OR$_{15}$, —OC(O)R$_{15}$, —NR$_{15}$C(O)NR$_{13}$R$_{14}$, —OC(O)NR$_{13}$R$_{14}$, —NR$_{15}$C(O)OR$_{16}$, —S(O)$_p$R$_{15}$, and —S(O)$_p$NR$_{13}$R$_{14}$; wherein R$_{13}$ and R$_{14}$, for each occurrence are, independently, H, optionally substituted alkyl, optionally substituted alkenyl, optionally substituted alkynyl, optionally substituted cycloalkyl, optionally substituted cycloalkenyl, optionally substituted heterocyclyl, optionally substituted aryl, optionally substituted heteroaryl, optionally substituted aralkyl, or optionally substituted heteraralkyl; or R$_{13}$ and R$_{14}$, taken together with the nitrogen to which they are attached is optionally substituted heterocyclyl or optionally substituted heteroaryl; and R$_{15}$ and R$_{16}$, for each occurrence are, independently, H, optionally substituted alkyl, optionally substituted alkenyl, optionally substituted alkynyl, optionally substituted cycloalkyl, optionally substituted cycloalkenyl, optionally substituted heterocyclyl, optionally substituted aryl, optionally substituted heteroaryl, optionally substituted aralkyl, or optionally substituted heteraralkyl; and
- q is 0, 1, 2, 3, 4, or 5.

24. The compound of claim 23, wherein
L is —NRCH$_2$—, —CH$_2$NR—, —NR—C(O)—, or —C(O)—NR—; Z is an optionally substituted phenyl, an optionally substituted oxazolyl, an optionally substituted thiazolyl, an optionally substituted imidazolyl, an optionally substituted pyridinyl, an optionally substituted pyrazolyl, an optionally substituted pyrrolyl, an optionally substituted thiophenyl, an optionally substituted furanyl, an optionally substituted thiadiazolyl, an optionally substituted oxadiazolyl, or an optionally substituted tetrazolyl;

$Z_1$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, —C(O)NR$_1$R$_2$, —NR$_4$C(O)R$_5$, —OR$_4$, haloalkoxy, —C(O)R$_4$, —NR$_1$R$_2$, —SR$_4$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_p$NR$_1$R$_2$;

R, for each occurrence, is independently —H, alkyl, —C(O)—R$_7$, or —C(O)OR$_7$; and R$_7$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl.

25. The compound of claim 24, wherein
R is —H;
Z is an optionally substituted oxazolyl, an optionally substituted thiazolyl, an optionally substituted pyridinyl, or an optionally substituted tetrazolyl; and
$Z_1$ is halo.

26. The compound of claim 22, wherein the compound is represented by formula (IX):

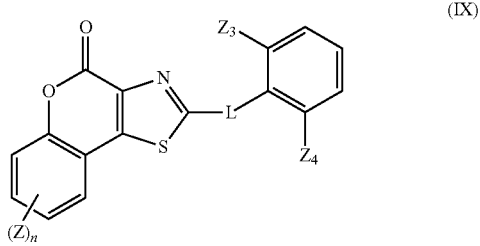

(IX)

wherein:
$Z_3$ and $Z_4$ are each independently substituents selected from the group consisting of alkyl, alkoxy, alkyl sulfanyl, alkylamino, dialkylamino, alkenyl, alkynyl, cycloalkyl, cycloalkenyl, heterocyclyl, aryl, heteroaryl, aralkyl, heteraralkyl, haloalkyl, —C(O)NR$_{13}$R$_{14}$, —NR$_{15}$C(O)R$_{16}$, halo, —OR$_{15}$, cyano, nitro, haloalkoxy, —C(O)R$_{15}$, —NR$_{13}$R$_{14}$, —SR$_{15}$, —C(O)OR$_{15}$, —OC(O)R$_{15}$, —NR$_{15}$C(O)NR$_{13}$R$_{14}$, —OC(O)NR$_{13}$R$_{14}$, —NR$_{15}$C(O)OR$_{16}$, —S(O)$_p$R$_{15}$, and —S(O)$_p$NR$_{13}$R$_{14}$; wherein R$_{13}$ and R$_{14}$, for each occurrence are, independently, H, optionally substituted alkyl, optionally substituted alkenyl, optionally substituted alkynyl, optionally substituted cycloalkyl, optionally substituted cycloalkenyl, optionally substituted heterocyclyl, optionally substituted aryl, optionally substituted heteroaryl, optionally substituted aralkyl, or optionally substituted heteraralkyl; or R$_{13}$ and R$_{14}$, taken together with the nitrogen to which they are attached is optionally substituted heterocyclyl or optionally substituted heteroaryl; and R$_{15}$ and R$_{16}$, for each occurrence are, independently, H, optionally substituted alkyl, optionally substituted alkenyl, optionally substituted alkynyl, optionally substituted cycloalkyl, optionally substituted cycloalkenyl, optionally substituted heterocyclyl, optionally substituted aryl, optionally substituted heteroaryl, optionally substituted aralkyl, or optionally substituted heteraralkyl.

27. The compound of claim 26, wherein
L is —NRCH$_2$—, —CH$_2$NR—, —NR—C(O)—, or —C(O)—NR—;
Z is an optionally substituted phenyl, an optionally substituted oxazolyl, an optionally substituted thiazolyl, an optionally substituted imidazolyl, an optionally substituted pyridinyl, an optionally substituted pyrazolyl, an optionally substituted pyrrolyl, an optionally substituted thiophenyl, an optionally substituted furanyl, an optionally substituted thiadiazolyl, an optionally substituted oxadiazolyl, or an optionally substituted tetrazolyl;
$Z_3$ and $Z_4$ are each independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, —C(O)NR$_1$R$_2$, —NR$_4$C(O)R$_5$, —OR$_4$, haloalkoxy, —C(O)R$_4$, —NR$_1$R$_2$, —SR$_4$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_p$NR$_1$R$_2$;

R, for each occurrence, is independently —H, alkyl, —C(O)—R$_7$, or —C(O)OR$_7$; and R$_7$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl.

28. The compound of claim 27, wherein
R is —H;
Z is an optionally substituted oxazolyl, an optionally substituted thiazolyl, an optionally substituted pyridinyl, or an optionally substituted tetrazolyl; and
$Z_3$ and $Z_4$ are each —F.

29. A pharmaceutical composition, comprising a pharmaceutically acceptable carrier and a compound of claim 1.

* * * * *